United States Patent
van Mierlo et al.

(10) Patent No.: US 12,419,328 B2
(45) Date of Patent: Sep. 23, 2025

(54) **PHAGE COCKTAIL AGAINST *E. coli* O157**

(71) Applicant: Micreos Food Safety B.V., Wageningen (NL)

(72) Inventors: Joël Thomas van Mierlo, Wageningen (NL); Sander Witte, Wageningen (NL); Steven Hagens, Wageningen (NL)

(73) Assignee: Micreos Food Safety B.V., Wageningen (NL)

( * ) Notice: Subject to any disclaimer, the term of this patent is extended or adjusted under 35 U.S.C. 154(b) by 634 days.

(21) Appl. No.: 17/059,507

(22) PCT Filed: May 28, 2019

(86) PCT No.: PCT/EP2019/063858
§ 371 (c)(1),
(2) Date: Nov. 30, 2020

(87) PCT Pub. No.: WO2019/229079
PCT Pub. Date: Dec. 5, 2019

(65) Prior Publication Data
US 2021/0204551 A1 Jul. 8, 2021

(30) Foreign Application Priority Data
Jun. 1, 2018 (EP) .................................... 18175523

(51) Int. Cl.
| | |
|---|---|
| *A23K 10/16* | (2016.01) |
| *A01N 63/40* | (2020.01) |
| *A23B 4/22* | (2006.01) |
| *A23B 7/155* | (2006.01) |
| *A23K 20/195* | (2016.01) |
| *A23L 13/40* | (2023.01) |
| *A23L 19/00* | (2016.01) |
| *C12N 7/00* | (2006.01) |

(52) U.S. Cl.
CPC .............. *A23K 10/16* (2016.05); *A01N 63/40* (2020.01); *A23B 4/22* (2013.01); *A23B 7/155* (2013.01); *A23K 20/195* (2016.05); *A23L 13/42* (2016.08); *A23L 19/03* (2016.08); *C12N 7/00* (2013.01); *A23V 2002/00* (2013.01); *C12N 2795/00021* (2013.01); *C12N 2795/00031* (2013.01)

(58) Field of Classification Search
None
See application file for complete search history.

(56) References Cited

U.S. PATENT DOCUMENTS 7,625,741 B2 12/2009 Pasternack et al.

FOREIGN PATENT DOCUMENTS

WO WO2016/003307 A1 1/2016

OTHER PUBLICATIONS

Anonymous: 2015.014aB, May 17, 2015 (May 2015), pp. 1-7, XP055525315, Retrieved from the Internet: URL:https://talk.ictvonline.org/ictv/proposals/2015.014aB.A.v3.Phieco32virus_4sp.pdf p. 2.
Anonymous: Uni Parc—UPI0003ED1D45, Apr. 16, 2014, pp. 1-3, XP055525295, Retrieved from the Internet: URL:https://www.uniprot.org/uniparc/UPI0003ED1D45 [retrieved on Nov. 20, 2018].
Anonymous: "Global Alignment between EP335 and KBNP17711 (NC_023593.1)", https://WWW.ebi.ac.uk/Tools/psa/emboss_stretcher/, Jul. 30, 2019, pp. 1-110, XP055609565, Retrieved from the Internet: URL:https://WWW.ebi.ac.uk/Tools/psa/embossstretcher/ [retrieved on Jul. 30, 2019].
Anonymous: "UPI0003ED1D45", Jul. 30, 2019 (Jul. 30, 2019), XP055609580, Retrieved from the Internet: URL:https://WWW.uniprot.org/uniparc/UPI0003ED1D45 [retrieved on Jul. 30, 2019].
Steven Hagens: GRAS notification of the bacteriophage cocktail PhageGuard E(TM) for bio-control of *E. coli* O157 on beef Jan. 23, 2018, p. 1, XP055525285.
S. S. Shahrbabak et al: "Isolation, characterization and complete genome sequence of Phaxl: a phage of *Escherichia coli* O157 : H7", Journal of General Microbiology, vol. 159, No. Pt_8, May 15, 2013, pp. 1629-1638,.
Seo, Jina, et al. "Inhibiting the growth of *Escherichia coli* O157: H7 in beef, pork, and chicken meat using a bacteriophage." Korean journal for food science of animal resources 36.2 (2016): 186.
Carter, Chandi D., et al. "Bacteriophage cocktail significantly reduces *Escherichia coli* O157: H7 contamination of lettuce and beef, but does not protect against recontamination." Bacteriophage 2.3 (2012): 178-185.
O'flynn, G., et al. "Evaluation of a cocktail of three bacteriophages for biocontrol of *Escherichia coli* O157: H7." Applied and environmental microbiology 70.6 (2004): 3417-3424.
Morita, Masatomo, et al. "Characterization of a virulent bacteriophage specific for *Escherichia coli* O157: H7 and analysis of its cellular receptor and two tail fiber genes." FEMS microbiology letters 211.1 (2002): 77-83.

*Primary Examiner* — Nicole Kinsey White
(74) *Attorney, Agent, or Firm* — B.V. Nederlandsch Octrooibureau

(57) ABSTRACT

The invention relates to the field of microbiology, specifically to an antimicrobial composition comprising a first and a second bacteriophage, wherein the composition has lytic activity against *E. coli* O157. The invention further relates to a use of the antimicrobial composition for controlling bacterial contamination in a food- or feed environment on or in food- or feed processing equipment or food- or feed containers or in a food- or feed product.

14 Claims, 4 Drawing Sheets
Specification includes a Sequence Listing.

PHAGE COCKTAIL AGAINST E. coli O157

FIELD OF THE INVENTION

The invention relates to the field of microbiology, specifically to a bacteriophage or a combination of bacteriophages, to a composition comprising said bacteriophage or said combination of bacteriophages preferably for preventing, treating or controlling contamination with and/or growth of *Escherichia coli* O157. The invention further relates to an antimicrobial agent, preferably a food preservative or a disinfectant for controlling bacterial contamination in a food- or feed environment on or in food- or feed processing equipment or food- or feed containers, wherein said antimicrobial agent comprises a bacteriophage or a combination of bacteriophages according to the invention.

BACKGROUND ART

*Escherichia coli* (*E. coli*) bacteria are short Gram-negative rods that are part of the normal flora of the intestines of most warm-blooded animals. These organisms are the most common facultative anaerobe in the large bowel and provide protection against colonization by other harmful microbes. However, shiga toxin-producing strains of *E. coli* (STECs), such as *E. coli* O157 are responsible for most severe cases of food poisoning. The toxin produced by *E. coli* O157 in the intestines can cause anything from a mild diarrhea to severe hemorrhagic colitis, where the cells of the intestinal lining are damaged, allowing blood to pass into stool.

*E. coli* O157 is found regularly in the feces of healthy cattle, and is transmitted to humans through contaminated food, water, and direct contact with infected people or animals. During the slaughter process, intestinal fluid or feces of infected cattle can drip onto the surface of the meat, contaminating it. Other foods that are often found to be contaminated with *E. coli* bacteria include unpasteurized milk and cheese, unpasteurized juices, alfalfa and radish sprouts, lettuce, spinach, and water. However, any food is at risk of becoming contaminated with *E. coli* through cross-contamination.

A variety of treatment strategies are currently employed to eliminate or significantly reduce *E. coli* O157 contamination, ranging from simple washing of foods to chemical or physical decontamination of foods. Efforts to reduce or prevent *E. coli* outbreaks and control the growth of *E.coli* on foodstuff have been made. For example, Seo et al (Korean J. Food Sci. An. Vol. 36, No. 2, pp. 186~193 2016) describes inhibiting the growth of *E. coli* O157 in meat using bacteriophage BPECO19. Carter et al (Bacteriophage 2:3, 178-185; 2012) describe that a bacterial phage cocktail containing ECML-4, ECML-117, and ECML-134 could be used to reduce levels of *E. coli* O157:H7 in lettuce and beef but that this method could not protect against recontamination. U.S. Pat. Nos. 7,625,741 7,635,584, and 7,625,556 describes bacteriophages using ECML-4, ECTA-47, ECML-84, ECML-117, ECML-119, ECML-122 and ECML-134 for the treatment of foodstuff and food equipment and containers to prevent or control the growth of *E. coli* O157.

However despite the efforts described above there remains a need for novel bacteriophages to treat food products and food processing facilities or containers to reduce, eliminate or prevent colonization with pathogens such as *E. coli* O157. In particular, there remains a need to develop antimicrobial agents capable of specifically targeting a broad range of *E. coli* O157 (clinical) isolates without affecting other *E. coli* strains.

SUMMARY OF THE INVENTION

In one aspect, the invention provides for a composition comprising a first bacteriophage and a second bacteriophage, wherein:
  the first bacteriophage has a genome with at least 70% sequence identity with SEQ ID NO: 1 over the entire length of SEQ ID NO: 1, or has at least 70% sequence identity with the genome of bacteriophage EP75 over the entire length of the genome of bacteriophage EP75, deposited under number CBS 143858, and
  the second bacteriophage has a genome with at least 70% sequence identity with SEQ ID NO: 2 over the entire length of SEQ ID NO: 2, or has at least 70% sequence identity with the genome of bacteriophage EP335 over the entire length of the genome of bacteriophage EP335, deposited under number CBS 143859,
wherein the composition has lytic activity against *E. coli* O157.

The invention further provides for a composition that comprises the progeny of the first bacteriophage as described herein, and/or the second bacteriophage as described herein.

In another aspect, the invention provides the use of a composition according to the invention, preferably as an antimicrobial agent, more preferably as a food preservative or disinfectant, preferably for controlling a bacterium, preferably by lysing said bacterium, preferably a bacterium of the species *E. coli*, more preferably *E. coli* O157.

In yet another aspect, the invention relates to a method for controlling bacterial contamination in a food- or feed environment, on and/or in food- or feed processing equipment, on and/or in food- or feed containers comprising contacting a composition according to the invention with the food- or feed processing equipment and/or the food- or feed containers.

In a further aspect, the invention provides a method of controlling bacterial contamination in a food- or feed product comprising administering to the food product an effective amount of a composition according to the invention to reduce the number of a pathogenic bacterium in said food product. The invention also provides for a food product obtainable the methods according to the invention.

In an another aspect, the invention provides for a composition comprising a bacteriophage, wherein the bacteriophage has a genome with at least 70% sequence identity with SEQ ID NO: 1 over the entire length of SEQ ID NO: 1, or has at least 70% sequence identity with the genome of bacteriophage EP75 over the entire length of the genome of bacteriophage EP75, deposited under number CBS 143858, and wherein the composition has lytic activity against *E. coli* O157.

In yet another aspect, the invention provides for a composition comprising a bacteriophage, wherein the bacteriophage has a genome with at least 70% sequence identity with SEQ ID NO: 2 over the entire length of SEQ ID NO: 2, or has at least 70% sequence identity with the genome of bacteriophage EP335 over the entire length of the genome of bacteriophage EP335, deposited under number CBS 143859, and wherein the composition has lytic activity against *E. coli* O157.

DESCRIPTION OF THE INVENTION

Provided here are newly isolated bacteriophages named EP75 and EP335 and compositions comprising EP75 and/or EP335. The inventors surprisingly found that compositions comprising EP75 and/or EP335 are very specifically active against a broad range of *E. coli* O157 strains and clinical isolates.

Sequence analysis revealed that EP75 contains two open reading frames (ORF) 169.1 and ORF167 that have little to no homology with any of the known *Escherichia* phages. ORF167 is a tailspike protein of 754 Amino acids in length. ORF167 is homologous to the N-terminal region spanning approximately the first 180 amino acids in several *Escherichia* phages (Phaxl and ECML-4), yet no homology is found against the C-terminal region of about 570 amino acids in these *Escherichia* phages. In contrast, homology to the C-terminal region of EP75 ORF167 was found in phages that share no significant sequence homology to the rest of the EP75 genome (K1ind1 and HK620). Therefore, it is hypothesized that EP75 ORF167 acquired the C-terminal domain of ORF167 from another phage, like K1ind1 or HK620, forming an ORF167 protein which seems to be unique in combining these two protein domain sequences. It is suggested that the N-terminal domain of this tailspike protein connects the tailspike to the baseplate of the bacteriophage, while the C-terminal domain provides a specific enzymatic activity to bind and degrade sugar molecules on the bacterial cell. Therefore, the inventors conclude that EP75 contains a tailspike protein (ORF167) which is not found to date in combination with the rest of the genome sequence and structure of EP75. Likely ORF167 contributes to the O157 specific hostrange of phage EP75. ORF 169.1 of phage EP75 is a putative tailspike protein of 708 amino acids in length. Upon a blast search with the complete protein sequence of ORF169.1, homologous proteins with a sequence coverage of more than 50% exclusively originate from *Salmonella* phages, while no homologs are found in *Escherichia* phages. However, high homology to *Escherichia* phage proteins is found in the first 160 to 200 amino acids of ORF169.1. This aligns with the general structure of a tailspike protein, in which the N-terminal part binds to the baseplate of the bacteriophage, in this case an *Escherichia* phage. Therefore, the inventors hypothesized that EP75 acquired the C-terminal region of tailspike ORF 169.1 from a *Salmonella* phage, in its tailspike protein, a combination which seems to be unique.

Sequences analysis revealed that the EP335 genome shares homology with several described *Escherichia* phages. However, the C-terminal 450 amino acids of ORF12 and the C-terminal 260 amino acids of ORF13 share only little homology with corresponding tail fiber proteins of other *Escherichia* phages. Other differences in the genomic nucleotide sequence are made in regions which contain hypothetical proteins of which we do not know the function yet. These proteins appear to provide a crucial difference between EP335 and the mentioned phages.

The inventors found that the host range of these novel EP75 and EP335 bacteriophages is surprisingly very specifically active against a broad range of *E. coli* O157 isolates without affecting other *E. coli* strains.

In a first aspect, the invention provides for a composition comprising a first bacteriophage and/or a second bacteriophage, wherein:
the first bacteriophage has a genome with at least 70% sequence identity with SEQ ID NO: 1, or has at least 70% sequence identity with the genome of bacteriophage EP75, deposited under number CBS 143858, and
the second bacteriophage has a genome with at least 70% sequence identity with SEQ ID NO: 2, or has at least 70% sequence identity with the genome of bacteriophage EP335, deposited under number CBS 143859, wherein the composition has lytic activity against *E. coli* O157. The composition and the first and second bacteriophage are herein referred to as a composition according to the invention and a bacteriophage according to the invention.

Bacteriophage EP75 has been deposited under number CBS 143858 under the regulations of the Budapest Treaty at the Westerdijk Fungal Biodiversity Institute (CBS), Uppsalalaan 8, 3508AD Utrecht, The Netherlands.

Bacteriophage EP335 has been deposited under number CBS 143859 under the regulations of the Budapest Treaty at the Westerdijk Fungal Biodiversity Institute (CBS), Uppsalalaan 8, 3508AD Utrecht, The Netherlands.

Preferably, the first bacteriophage according to the invention has a genome comprising at least one polynucleotide encoding a polypeptide with an amino acid sequence having preferably at least 70, 75, 80, 81, 82, 83, 84, 85, 86, 87, 88, 89, 90, 91, 92, 93, 94, 95, 96, 97, 98, at least 99 or 100% sequence identity with SEQ ID NO:1 over the entire length of SEQ ID NO: 1. Preferably, the first bacteriophage according to the invention has a genome that has at least 70, 75, 80, 81, 82, 83, 84, 85, 86, 87, 88, 89, 90, 91, 92, 93, 94, 95, 96, 97, 98, at least 99 or 100% sequence identity with the genome of bacteriophage EP75 over the entire length of the genome of bacteriophage EP75, deposited under number CBS 143858 and represented herein by SEQ ID NO: 1.

Preferably, the second bacteriophage according to the invention has a genome comprising at least one polynucleotide encoding a polypeptide with an amino acid sequence having preferably at least 70, 75, 80, 81, 82, 83, 84, 85, 86, 87, 88, 89, 90, 91, 92, 93, 94, 95, 96, 97, 98, 99 or 100% sequence identity with SEQ ID NO:2 over the entire length of SEQ ID NO: 2. Preferably, the first bacteriophage according to the invention has a genome that has at least 70, 75, 80, 81, 82, 83, 84, 85, 86, 87, 88, 89, 90, 91, 92, 93, 94, 95, 96, 97, 98, 99 or 100% sequence identity with the genome of bacteriophage EP335 over the entire length of the genome of bacteriophage EP335, deposited under number CBS 143859 and represented herein by SEQ ID NO: 2.

The first and second bacteriophages of the invention may be mutant, chimeric and/or recombinant bacteriophages. The person skilled in the art may construct a bacteriophage starting from either EP75 or EP335 by placing mutations in the genome and/or deleting and/or inserting coding sequences or parts thereof into the genome using methods known in the art.

Most preferably, a composition according to the invention comprises EP75 and EP335 as deposited at the CBS Fungal Biodiversity Centre under numbers CBS 143858 and CBS 143859.

The composition comprising the first and second bacteriophage according to the invention has lytic activity against *E. coli* O157. Lytic activity can be assessed by any suitable method known by the person skilled in the art. In an embodiment, lytic activity can be assessed spectrophotometrically by measuring a decrease in turbidity of substrate cell suspensions. Turbidity is assessed by measuring optical density at a wavelength of 600 nm, typically a culture is turbid when it exhibits an optical density of at least 0.3 OD at a wavelength of 600 nm. Preferably, lytic activity can be assessed spectrophotometrically measuring a decrease in turbidity of an *E. coli* suspension, wherein turbidity is quantified by measuring OD600 spectrophotometrically (Libra S22, Biochrom). More preferably, 1 ul of a composition according to the invention is incubated together with an *E.*

*coli* suspension having an initial OD600 of 1±0.05, as assessed spectrophotometrically (Libra S22, Biochrom), in PBS buffer pH 7.4, 120 mM sodium chloride for 30 min at 37° C. The decrease in turbidity is calculated by subtracting the OD600 after 30 min of incubation from the OD600 before 30 min of incubation. Within the context of the invention, a bacteriophage according to the invention is said to have lytic activity when using this assay a drop in turbidity of at least 10, 20, 30, 40, 50 or 60% is detected. Preferably, a drop of at least 70% is detected.

In an embodiment, the first bacteriophage of the composition according to the invention comprises: —a tailspike protein that has at least 70, 75, 80, 81, 82, 83, 84, 85, 86, 87, 88, 89, 90, 91, 92, 93, 94, 95, 96, 97, 98, at least 99 or 100% sequence identity with SEQ ID NO: 3 over the entire length of SEQ ID NO: 3, or SEQ ID NO: 4 over the entire length of SEQ ID NO: 4, and/or a tailspike protein that has at least 70, 75, 80, 81, 82, 83, 84, 85, 86, 87, 88, 89, 90, 91, 92, 93, 94, 95, 96, 97, 98, at least 99 or 100% sequence identity with SEQ ID NO: 5 over the entire length of SEQ ID NO: 5.

In another embodiment, which can be combined with the previous embodiment, the second bacteriophage of the composition according to the invention comprises:

a tail fiber protein that has at least 70, 75, 80, 81, 82, 83, 84, 85, 86, 87, 88, 89, 90, 91, 92, 93, 94, 95, 96, 97, 98, at least 99 or 100% sequence identity with SEQ ID NO: 6 over the entire length of SEQ ID NO: 6, SEQ ID NO: 7 over the entire length of SEQ ID NO: 7, and/or a tail fiber protein that has at least 70, 75, 80, 81, 82, 83, 84, 85, 86, 87, 88, 89, 90, 91, 92, 93, 94, 95, 96, 97, 98, at least 99 or 100% sequence identity with SEQ ID NO: 8 over the entire length of SEQ ID NO: 8 or SEQ ID NO: 9 over the entire length of SEQ ID NO: 9.

In a second aspect, the invention provides for a composition that comprises progeny of the first bacteriophage as described herein, and/or the second bacteriophage as described herein. Preferably, said progeny has the same phenotypic features and the same lytic activity against *E. coli* O157 as the respective first and second bacteriophage. The invention thus provides for the progeny of the bacteriophages described herein, said progeny is described as having minor variation(s) in the genomic sequence and polypeptides encoded thereby while retaining the same general genotypic and/or phenotypic characteristics as the bacteriophages described herein. In particular these progeny are the result of successive passaging of the bacteriophages described herein where the variants accumulate silent mutations, conservative mutations, minor deletions, and/or minor replications of genetic material. The progeny retains the phenotypic characteristics of bacteriophages according to the invention, in a preferred embodiment, the progeny retain lytic activity against *E. coli* O157. Preferably, the progeny has at least 90, 91, 92, 93, 94, 95, 96, 97, 98 or at least 99% sequence identity with the genome of the parent bacteriophage over the entire length of the genome of the parent bacteriophage.

In a third aspect of the invention, the composition according to the invention preferably is an aqueous liquid or a lyophilized aqueous liquid. Preferably, the composition according to the invention comprises $1 \times 10^7$ PFU/ml to $1 \times 10^{13}$ PFU/ml of bacteriophage. In an embodiment, the composition according to the invention comprises $1 \times 10^{10}$ PFU/ml, $1 \times 10^{11}$ PFU/ml, $1 \times 10^{12}$ PFU/ml or $1 \times 10^{13}$ PFU/ml of bacteriophage. Preferably, the composition according to the invention comprises at least $1 \times 10^{10}$ PFU/ml of bacteriophage, more preferably at least $1 \times 10^{11}$ PFU/ml. Preferably, when comprising two bacteriophages, the bacteriophages are present in a ratio of 50/50 (±20%) in the composition according to the invention. In an embodiment, $1 \times 10^{11}$ PFU/ml of bacteriophage EP75 and $1 \times 10^{11}$ PFU/ml are present in a composition according to the invention. Plaque Forming Unit (PFU) is a term known in the art and is a standard unit for depicting the concentration of bacteriophages. The concentration can be assessed by any assay known in the art, typically by a plaque assay.

In an embodiment, a composition according to the invention further comprises an additional active ingredient, preferably in a concentration known to be effective. Preferably said active ingredient is present in a concentration known in the art to result in a significantly reduced number, such as one, two or three logs, of foodborne pathogens that would otherwise be present. Preferably, said one or more additional active ingredients are selected from the group consisting of a further bacteriophage, a bacteriostatic agent, a bactericidal agent, an antibiotic, a surfactant and/or an enzyme. An antibiotic can be any antibiotic known in the art including antibiotics and chemotherapeutic agents, and including but not limited to vancomycin, nisin, danofloxacin and neomycin. An enzyme useful in a composition of the invention includes but is not limited to enzymes that aid in breaking up biofilms (e.g. biofilms found in food processing equipment) such as but not limited to polysaccharide depolymerise enzymes and protease. A surfactant useful in a composition of the invention helps to wet the surface so that bacteriophages are properly distributed over the various surfaces, and to solubilise and remove dirt so that the *E. coli* are accessible to the bacteriophage. Suitable surfactants include but are not limited to polysorbate (tween) 80, 20 and 81 and Dobanols (Shell Chemical Co. RTM). An antimicrobial disinfectant composition of the invention may further comprise surface disinfectants known in the art such as but not limited to benzoic acid and PBT, preferably disinfectants with which a bacteriophage of the invention is compatible. A further bacteriophage in a composition according to the invention can be any phage known in literature, other than the bacteriophage of the invention. Preferably, such a further bacteriophage includes, but is not limited to, a tailed phage of the order of Caurdovirales, consisting of Myoviridae, Siphoviridae and Podoviridae. Preferably, the composition according to the invention is buffered. An additional active ingredient of the composition according to the invention may be an inorganic salt, preferably selected from the group consisting of lactic acid, preferably L-lactic acid, acetic acid, propionic acid and mixtures thereof. The salt of the organic acid according to the invention is preferably selected from the group consisting of the sodium salt, potassium salt, ammonium salt and mixtures thereof, preferably K-(L)lactate, Na-(L)lactate, K-acetate, Na-acetate, K-diacetate, Na-diacetate, K-propionate, Na-propionate and mixtures thereof.

Preferably, the organic acid in the composition according to the invention is acetic acid in a buffered aqueous solution, preferably comprising 2% to 30% acetate, more preferably comprising 5% to 20% acetate, more preferably comprising 10% to 20% acetate, more preferably comprising 15% to 20% acetate, more preferably comprising 15, 16, 17, 18, 19 or 20% acetate, most preferably comprising 17% acetate. The preferred pH of the acetic acid in a buffered aqueous solution is 2 to 7, more preferably 5 to 6.5 and most preferably to 5.7 to 6.3. Preferred buffering is performed using sodium acetate, acetic acid, sodium hydroxide, sodium carbonate and/or sodium bicarbonate.

Preferably, the salt of the organic acid in the composition according to the invention is in an aqueous solution comprising a mixture of K-(L)lactate and Na-diacetate, preferably comprising 50% to 80% K-(L)lactate and 2% to 10% Na-diacetate, more preferably comprising 60% to 80% K-(L)lactate and 3% to 10% Na-diacetate, more preferably comprising 70% to 75% K-(L)lactate and 4% to 6% Na-diacetate, most preferably comprising 72.8% K-(L)lactate and 5.2% Na-diacetate. The aqueous solution may be buffered as described here above.

In a fourth aspect, the invention provides for a use of a composition according to the invention. Preferably, the composition is used as an antimicrobial agent, more preferably as a food preservative or disinfectant, preferably for controlling a bacterium, preferably by lysing said bacterium, preferably a bacterium of the species $E.$ $coli$, more preferably $E.$ $coli$ O157. Preferably, a composition according to the invention, is used to reduce the counts of $E.$ $coli$ O157 bacteria and/or to prevent their growth in the first place, in food products as well as in food processing plants in which the food products are being processed such as on processing equipment and other sites in food industry facilities, e.g. food storage container.

Preferably, a composition according to the invention is used as an antimicrobial agent, preferably a food preservative or a disinfectant. Preferably said antimicrobial agent is for killing a bacterium, preferably a bacterium of the species $E.$ $coli$, more $E.$ $coli$ O157. Preferably, the composition according to the invention exhibits a broad host range $E.$ $coli$ O157 infection property and has lytic activity as defined herein.

In a fifth aspect, the invention relates to a method for controlling bacterial contamination in a food- or feed environment, on and/or in food- or feed processing equipment, on and/or in food- or feed containers comprising contacting a composition according to the invention with the food- or feed processing equipment and/or the food- or feed containers. Preferably said method is for controlling a bacterium of the species $E.$ $coli$, more preferably $E.$ $coli$ O157. Preferably, said method of controlling includes the reduction of counts of $E.$ $coli$ O157 bacteria and/or the prevention of their growth in the first place, in food products as well as in food processing plants in which the food products are being processed, such as on processing equipment and other sites in food industry facilities, e.g. food storage containers. A method of the invention encompasses the application of a composition according to the invention on or into food products, and/or into various physical sites within the food processing plants on or in food processing equipment, by a number of means including, but not limited to, admixing, spraying or directly applying said composition. The applications according to the invention significantly reduce the numbers of $E.$ $coli$ bacteria that would otherwise be present.

In a sixth aspect, the invention provides a method of controlling bacterial contamination in a food- or feed product comprising administering to the food product an effective amount of a composition according to the invention to reduce the number of a pathogenic bacterium in said food product. In an embodiment, the food product is a processed, non-processed, cured or uncured food product. Preferably, the food product is selected from the group consisting of meat, fish, shellfish, pastry, dairy products, vegetables, fruit and mixtures thereof. More preferably, the food product is selected from the group consisting of beef, pork, lamb, fruit, vegetables, including but not limited to lettuce, leafy greens, baby leafy greens, sprouts.

In an embodiment, the method for controlling bacterial growth and/or bacterial contamination on a food- or feed product, a food- or feed environment, on and/or in food- or feed processing equipment, on and/or in food- or feed containers is a method for controlling the bacterial growth and/or bacterial contamination of a pathogenic bacterium. Preferably, the pathogenic bacterium is a species of $E.$ $coli$. More preferably the species of $E.$ $coli$ is $E.$ $coli$ O157.

In an embodiment, the method of controlling bacterial contamination in a food- or feed product comprises contacting the food- or feed product with the composition according to the invention wherein the contacting is done by spraying or misting the composition to the food product or by dipping or soaking the food product into the composition.

In an seventh aspect the invention provides for a food product obtainable or obtained by a method according the fifth or sixth aspect of the invention. In an embodiment, the food product obtainable or obtained by a method according to the invention comprises at least $1\times10^3$ PFU, or at least $1\times10^3$ PFU equivalents of a first bacteriophage according to the invention and/or a second bacteriophage according to the invention, per average gram of food product. Preferably, the food product according to the invention contains at least $1\times10^4$ PFU, $1\times10^5$ PFU, $1\times10^6$ PFU, $1\times10^7$ PFU, $1\times10^8$ PFU or PFU equivalents, per average gram of food product. More preferably, the food product contains at least $1\times10^9$ PFU, or at least $1\times10^9$ PFU equivalents, per average gram of food product.

In an eight aspect, the composition according to the invention may comprise a bacteriophage with the features as defined previously herein that has a genome with at least 70% sequence identity with SEQ ID NO: 1 over the entire length of SEQ ID NO: 1, or has at least 70% sequence identity with the genome of bacteriophage EP75 over the entire length of the genome of bacteriophage EP75, deposited under number CBS 143858, and wherein the composition has lytic activity against $E.$ $coli$ O157. Preferably, the bacteriophage comprises:

a tail spike protein that has at least 70% sequence identity with SEQ ID NO: 3 over the entire length of SEQ ID NO: 3 or has at least 70% sequence identity with SEQ ID NO: 4 over the entire length of SEQ ID NO: 4, and/or, a tail spike protein that has at least 70% sequence identity with SEQ ID NO: 5 over the entire length of SEQ ID NO: 5.

In an ninth aspect, the composition according to the invention may comprise a bacteriophage with the features as defined previously herein that has a genome with at least 70% sequence identity with SEQ ID NO: 2 over the entire length of SEQ ID NO: 2, or has at least 70% sequence identity with the genome of bacteriophage EP335 over the entire length of the genome of bacteriophage EP335, deposited under number CBS 143859, and wherein the composition has lytic activity against $E.$ $coli$ O157. Preferably, the bacteriophage comprises:

a tail fiber protein that has at least 70% sequence identity with SEQ ID NO: 6 over the entire length of SEQ ID NO: 6 or has at least 70% sequence identity with SEQ ID NO: 7 over the entire length of SEQ ID NO: 7, and/or a tail fiber protein that has at least 70% sequence identity with SEQ ID NO: 8 over the entire length of SEQ ID NO: 8 or has at least 70% sequence identity with SEQ ID NO: 9 over the entire length of SEQ ID NO: 9.

Sequence table

| SEQ ID NO | Name {GenBank accession number} | Organism |
|---|---|---|
| 1 | genomic DNA sequence {MG748547} | Phage EP75 |
| 2 | genomic DNA sequence MG748548} | Phage EP335 |
| 3 | tail spike protein (ORF 167:754aa) | Phage EP75 |
| 4 | tail spike protein (the 570aa C-terminal part of ORF167) | Phage EP75 |
| 5 | tail spike protein (ORF169.1) | Phage EP75 |
| 6 | tail fiber protein (ORF 12) | Phage EP335 |
| 7 | tail fiber protein (the C-terminal 450aa of ORF 12) | Phage EP335 |
| 8 | tail fiber protein (ORF 13) | Phage EP335 |
| 9 | tail fiber protein (the C-terminal 450a of ORF 13) | Phage EP335 |

Where applicable, the Genbank accession number is given between brackets { } in column two.

Definitions

The terms "homology", "sequence identity" and the like are used interchangeably herein. Sequence identity is herein defined as a relationship between two or more amino acid (polypeptide or protein) sequences or two or more nucleic acid (polynucleotide) sequences, as determined by comparing the sequences. In the art, "identity" also means the degree of sequence relatedness between amino acid or nucleic acid sequences, as the case may be, as determined by the match between strings of such sequences. "Similarity" between two amino acid sequences is determined by comparing the amino acid sequence and its conserved amino acid substitutes of one polypeptide to the sequence of a second polypeptide. "Identity" and "similarity" can be readily calculated by known methods.

"Sequence identity" and "sequence similarity" can be determined by alignment of two peptide or two nucleotide sequences using global or local alignment algorithms, depending on the length of the two sequences. Sequences of similar lengths are preferably aligned using a global alignment algorithms (e.g. Needleman Wunsch) which aligns the sequences optimally over the entire length, while sequences of substantially different lengths are preferably aligned using a local alignment algorithm (e.g. Smith Waterman). Sequence identity" and "sequence similarity" are preferably expressed as the sequence identity or sequence similarity in view of the entire length of the subject sequence. E.g. when a sequence of 30 amino acids is identical over said 30 amino acids with a part of a sequence according to the invention SEQ ID NO: X of 300 amino acids, the sequence identity in view of SEQ ID NO: X is 10%. Sequences may be referred to as "substantially identical" or "essentially similar" when they (when optimally aligned by for example the programs GAP or BESTFIT using default parameters) share at least a certain minimal percentage of sequence identity (as defined below). GAP uses the Needleman and Wunsch global alignment algorithm to align two sequences over their entire length (full length), maximizing the number of matches and minimizing the number of gaps. A global alignment is suitably used to determine sequence identity when the two sequences have similar lengths. Generally, the GAP default parameters are used, with a gap creation penalty=50 (nucleotides)/8 (proteins) and gap extension penalty=3 (nucleotides)/2 (proteins). For nucleotides the default scoring matrix used is nwsgapdna and for proteins the default scoring matrix is Blosum62 (Henikoff & Henikoff, 1992, PNAS 89, 915-919).

Sequence alignments and scores for percentage sequence identity may be determined using computer programs, such as the GCG Wisconsin Package, Version 10.3, available from Accelrys Inc., 9685 Scranton Road, San Diego, CA 92121-3752 USA, or using open source software, such as the program "needle" (using the global Needleman Wunsch algorithm) or "water" (using the local Smith Waterman algorithm) in EmbossWIN version 2.10.0, using the same parameters as for GAP above, or using the default settings (both for 'needle' and for 'water' and both for protein and for DNA alignments, the default Gap opening penalty is 10.0 and the default gap extension penalty is 0.5; default scoring matrices are Blossum62 for proteins and DNAFull for DNA). When sequences have a substantially different overall lengths, local alignments, such as those using the Smith Waterman algorithm, are preferred.

Alternatively percentage similarity or identity may be determined by searching against public databases, using algorithms such as FASTA, BLAST, etc. Thus, the nucleic acid and protein sequences of the invention can further be used as a "query sequence" to perform a search against public databases to, for example, identify other family members or related sequences. Such searches can be performed using the BLASTn and BLASTx programs (version 2.0) of Altschul, et aL. (1990) J. Mol. Biol. 215:403-10. BLAST nucleotide searches can be performed with the NBLAST program, score=100, wordlength=12 to obtain nucleotide sequences homologous to oxidoreductase nucleic acid molecules of the invention. BLAST protein searches can be performed with the BLASTx program, score=50, wordlength=3 to obtain amino acid sequences homologous to protein molecules of the invention. To obtain gapped alignments for comparison purposes, Gapped BLAST can be utilized as described in Altschul et al., (1997) Nucleic Acids Res. 25(17): 3389-3402. When utilizing BLAST and Gapped BLAST programs, the default parameters of the respective programs (e.g., BLASTx and BLASTn) can be used. See the homepage of the National Center for Biotechnology Information at www.ncbi.nlm.nih.gov/.

Optionally, in determining the degree of amino acid similarity, the skilled person may also take into account so-called "conservative" amino acid substitutions, as will be clear to the skilled person. Conservative amino acid substitutions refer to the interchangeability of residues having similar side chains. Examples of classes of amino acid residues for conservative substitutions are given in the Tables below.

The term "homologous" when used to indicate the relation between a given (recombinant) nucleic acid or polypeptide molecule and a given host organism or host cell, is understood to mean that in nature the nucleic acid or polypeptide molecule is produced by a host cell or organisms of the same species, preferably of the same variety or strain. If homologous to a host cell, a nucleic acid sequence encoding a polypeptide will typically (but not necessarily) be operably linked to another (heterologous) promoter sequence and, if applicable, another (heterologous) secretory signal sequence and/or terminator sequence than in its natural environment. It is understood that the regulatory sequences, signal sequences, terminator sequences, etc. may also be homologous to the host cell. When used to indicate the relatedness of two nucleic acid sequences the term "homologous" means that one single-stranded nucleic acid sequence may hybridize to a complementary single-stranded nucleic acid sequence. The degree of hybridization may depend on a number of factors including the amount of identity between the sequences and the hybridization conditions such as temperature and salt concentration as discussed later.

The term "heterologous" when used with respect to a nucleic acid (DNA or RNA) or protein refers to a nucleic acid or protein that does not occur naturally as part of the organism, cell, genome or DNA or RNA sequence in which it is present, or that is found in a cell or location or locations in the genome or DNA or RNA sequence that differ from that in which it is found in nature. Heterologous nucleic acids or proteins are not endogenous to the cell into which it is introduced, but has been obtained from another cell or synthetically or recombinantly produced. Generally, though not necessarily, such nucleic acids encode proteins that are not normally produced by the cell in which the DNA is transcribed or expressed. Similarly exogenous RNA encodes for proteins not normally expressed in the cell in which the exogenous RNA is present. Heterologous nucleic acids and proteins may also be referred to as foreign nucleic acids or proteins. Any nucleic acid or protein that one of skill in the art would recognize as heterologous or foreign to the cell in which it is expressed is herein encompassed by the term heterologous nucleic acid or protein. The term heterologous also applies to non-natural combinations of nucleic acid or amino acid sequences, i.e. combinations where at least two of the combined sequences are foreign with respect to each other.

Any reference to nucleotide or amino acid sequences accessible in public sequence databases herein refers to the version of the sequence entry as available on the filing date of this document.

As used herein, "progeny" shall mean all bacteriophages, including descendants of EP75 or EP335 created by serial passage of EP75 or EP335 or by other means known in the art, that have a substantive sequence identity with the sequences of EP75 or EP335. Substantive sequence identity is herein defined as at least 95%, 96%, 97%, 98%, or at least 99% sequence identity. Alternatively, the term progeny includes descendants of EP75 or EP335 created by serial passage of EP75 or EP335 or by other means well known in the art whose RFLP profiles are substantially equivalent to the RFLP profile of EP75 or EP335 in accordance with the standards advanced by Tenover et al. from the United States Centers for Disease Control and Prevention (Tenover, F. C. et al. (1995) Interpreting Chromosomal DNA Restriction Patterns Produced by Pulsed-Field Gel Electrophoresis: Criteria for Bacterial Strain Typing. J. Clin. Microbiol. 33:2233-2239). Tenover et al. teaches the acceptable levels of variation that may be seen when the genomes identical propagated organisms are electrophoretically analyzed following restriction enzyme digestion.

In this document and in its claims, the verb "to comprise" and its conjugations is used in its non-limiting sense to mean that items following the word are included, but items not specifically mentioned are not excluded. In addition the verb "to consist" may be replaced by "to consist essentially of" meaning that a product or a composition may comprise additional component(s) than the ones specifically identified; said additional component(s) not altering the unique characteristic of the invention. In addition, reference to an element by the indefinite article "a" or "an" does not exclude the possibility that more than one of the elements is present, unless the context clearly requires that there be one and only one of the elements. The indefinite article "a" or "an" thus usually means "at least one".

All patent and literature references cited in the specification are hereby incorporated by reference in their entirety.

The following examples are offered for illustrative purposes only, and are not intended to limit the scope of the invention in any way.

EXAMPLES

The inventors developed a composition named PHAGEGUARD E™ which comprises two bacteriophages named EP75 and EP335. Both bacteriophages have a high specificity for E. coli O157 bacteria and a broad host range spectrum within the E. coli O157 group.

Example 1

Challenge Study I: PhageGuard E™ Efficacy on Meat Samples Inoculated with a Single Stx(-)) E. coli O157 Isolate.

Material and Methods

Bacterial Overnight Cultures

One colony of the respective E. coli O157 Stx(-) strain was inoculated in 5 ml LB broth and incubated overnight at 37° C. shaking.

Preparation of Samples

Beef sample pieces of 3×3 (×1) cm were prepared to achieve a 5 $cm^2$ surface to be contaminated (Acon) and a surface of 9 $cm^2$ to be treated with phages (Atreated). Samples were placed and stored in sterile petri dishes.

Artificial Contamination of Beef Samples

An appropriate dilution of the overnight culture is prepared in PBS buffer to allow the contamination of the samples with a final concentration of approximately $1 \times 10^5$ $cfu/cm^2$ (5 µL liquid/$cm^2$). In the laminar flow hood 5 µl/$cm^2$ of the dilution is transferred to each sample and rubbed in evenly with the pipette tip.

To allow the treatment of the beef samples with a final concentration of 3×107 or 3×108 pfu/$cm^2$, dilutions of PHAGEGUARD E™ were prepared. In the fume hood, 10 µl/$cm^2$ was transferred onto the samples. The liquid was distributed with the pipette tip. The petri dishes were closed and incubated at 4° C. for 24 hours, before bacterial enumeration. Bacteria were retrieved by stomaching the beef samples with 20 ml of retrieval buffer for 180 seconds. Dilutions of retrieved sample were plated on LB agar plates. Bacteria were enumerated on two different beef samples per treatment at 0 hours and 24 hours after treatment.

Results

Figure 1:
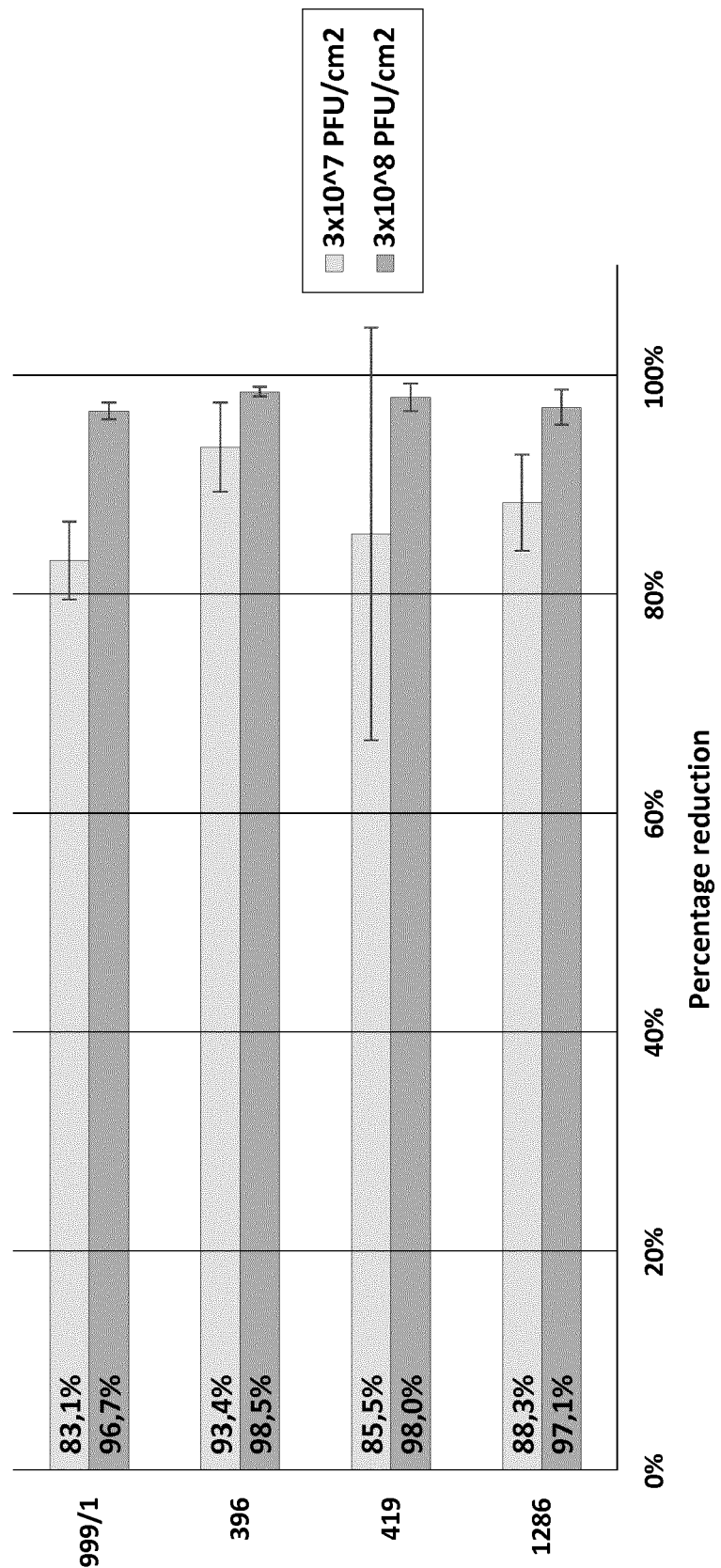
FIG. 1. Efficacy after 24 h of PHAGEGUARD E™ (composition comprising $E.$ $coli$ O157) on cold fresh beef contaminated with a single Stx (−) $E.$ $coli$ O157 isolate. Data presented is the average of three independent experiments of which each experiment consisted of a duplo sample. Error bars represent the standard deviation.

FIG. 1 shows the reduction levels achieved by two different phage concentrations on chilled beef samples after incubation of 24 hours at refrigeration temperature. Between 84% and 98% reduction can be achieved on all of the Stx(-) E. coli O157 cultures depending on concentration.

Example 2

Challenge Study II: PHAGEGUARD E™ Efficacy on Meat Samples Inoculated with Three Different E. coli O157 Mixes, Each Mix Consisting of Four Different Stx(+) E. coli O157 Isolates Next, the efficacy of PHAGEGUARD E™ was tested on meat samples inoculated with three different E. coli mixes. Sample and bacterial culture preparation was performed as described in Example 1. Likewise contamination and treatment was performed as described in Example 1. Contamination of the samples took place with three different E. coli O157 mixes, each mix consisting of four different Stx(+) E. coli O157 isolates. The E. coli mixes used are described in table 1.

TABLE 1

Overview of E. coli O157 strains used in presented challenge studies on roast beef

| Mix# | Database | ID number | Isolation source |
|---|---|---|---|
| E. coli O157 mix 1 | USDA* | 38 | Human (1991 cider outbreak) |
| | USDA* | 39 | Human (Salami outbreak) |
| | Unknown | 40 | Human |
| | Unknown | 45 | Human |
| E. coli O157 mix 2 | OARDC** | EC 260 | Bovine (dairy cattle, Creston, Ohio) |
| | OARDC** | EC 274 | Bovine (dairy cattle, Wooster, Ohio) |
| | OARDC** | EC 280 | Bovine (dairy cattle, Minerva, Ohio) |
| | OARDC** | EC 302 | Bovine (dairy cattle, Millersburg, Ohio) |
| E. coli O157 mix 3 | OARDC** | EC 1787 | Bovine (Beef feedlot, Kansas) |
| | OARDC** | EC 1805 | Bovine (Beef feedlot, Kansas) |
| | OARDC** | EC 1828 | Bovine (Beef feedlot, Kansas) |
| | OARDC** | EC 1890 | Bovine (Beef feedlot, Missouri) |
| | NENT*** | 999/1 | unknown |
| | NENT*** | 396 | unknown |
| | NENT*** | 419 | unknown |
| | NENT*** | 1286 | unknown |

*United States Department of Agriculture
**Ohio Agricultural Research and Development Center
***National Reference Centre for Enteropathogenic Bacteria and Listeria

Results

Figure 2:
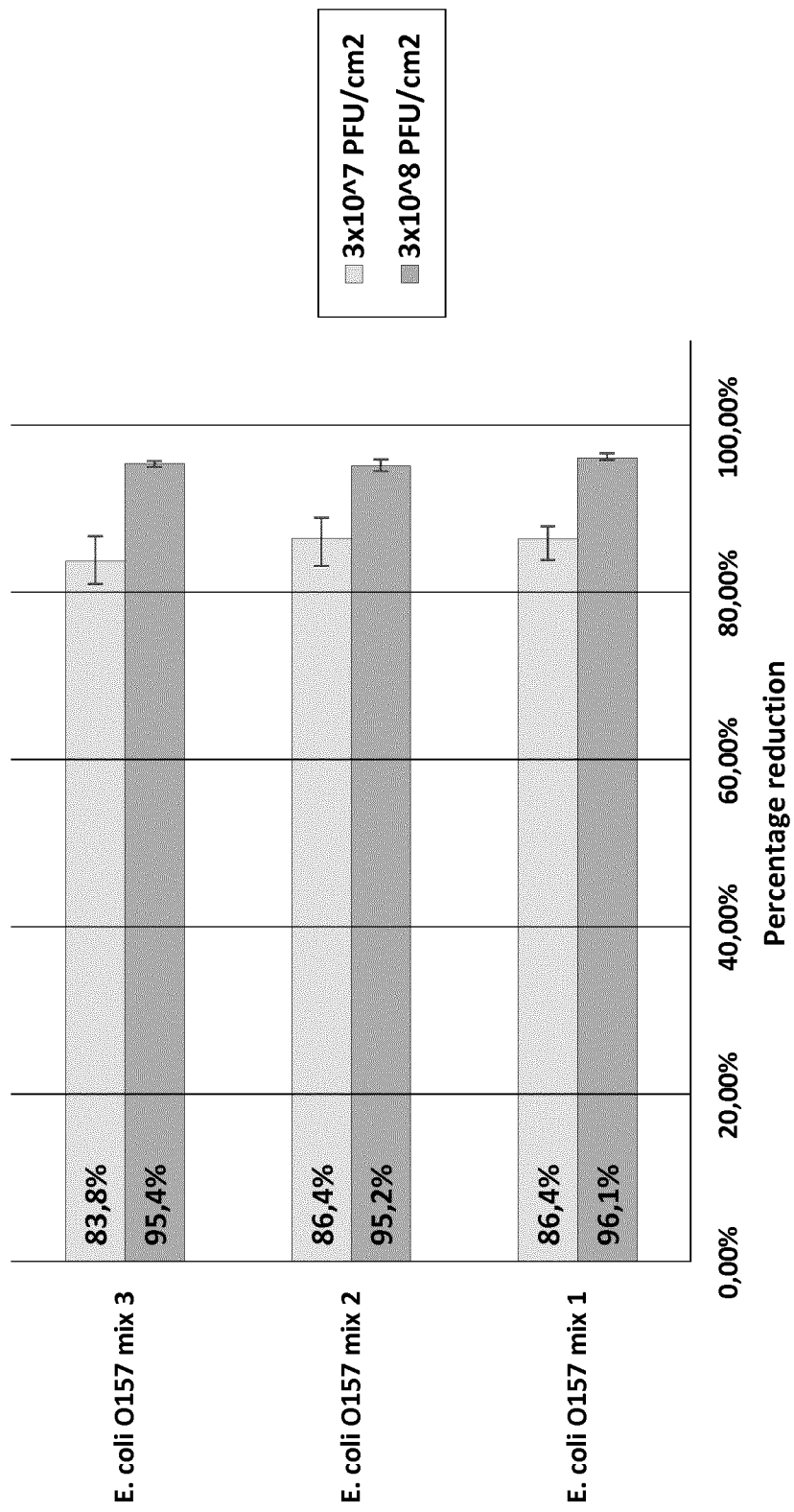
FIG. 2. Efficacy after 24 h of PHAGEGUARD E™ on cold fresh beef contaminated with three different $E.$ $coli$ O157mixes, each mix consisting of four different Stx(+) $E.$ $coli$ O157 isolate. Data presented is the average reduction of duplicate samples in a single experiment. Range bars indicate the minimum and maximum reduction obtained for each treatment on the respective $E.$ $coli$ O157 mix.

FIG. 2 shows the reduction levels achieved by two different phage concentrations on chilled beef samples after incubation of 24 hours at refrigeration temperature. Between 84% and 96% reduction can be achieved on all mixes of Stx(+) E. coli O157 cultures depending on concentration.

Example 3

Host Range Analysis

Materials and Methods

Host range analysis of PHAGEGUARD E™ was performed using the spot-on-the-lawn methods. In brief, dry LB agar plates (1.5% agar) were flooded with 4 ml of soft agar (0.4% agar) containing 100 µL of an overnight E. coli culture. The soft agar containing the E. coli cells was allowed to solidify after which 5-10 µl of phage dilutions 10-2, 10-4, 10-6, and 10-7 of the respective phage stocks ($1*10^{10}$ to $1*10^{11}$ PFU/ml) were spotted onto the plates. After the spot plates were incubated overnight at 20° C., all the spots were scored for formation of a confluent lysis zone or single plaques.

Results

PHAGEGUARD E™ infection was tested on 88 E. coli O157 clinical isolates and on 56 other E. coli strains (table 2). PHAGEGUARD E™ is able to lyse all but 5 of the clinical E. coli O157 isolates when spotted. The other E. coli strains were not found to be sensitive for PHAGEGUARD E™. Thus, PHAGEGUARD E™ has been proven to be very specifically active against E. coli O157.

Table 2: Host range analysis PHAGEGUARD E™"

TABLE 2

| | Host range analysis-PHAGEGUARD E ™ | | | | |
| --- | --- | --- | --- | --- | --- |
| | | | | PhageGuard ™ (EP75 + EP335) | |
| Source | Organism | Serogroup | STRAIN # | Lysis in spots | Single plaques |
| 4 | E. coli | K12 | C600 | − | − |
| 5 | E. coli | O157 | PARC 37 | ++ | + |
| 5 | E. coli | O157 | PARC 38 | ++ | + |
| 5 | E. coli | O157 | PARC 39 | ++ | + |
| 5 | E. coli | O157 | PARC 40 | ++ | + |
| 5 | E. coli | O157 | PARC 43 | ++ | + |
| 5 | E. coli | O157 | PARC 44 | ++ | + |
| 5 | E. coli | O157 | PARC 45 | ++ | + |
| 5 | E. coli | O157 | PARC 46 | ++ | + |
| 5 | E. coli | O157 | PARC 51 | ++ | + |
| 5 | E. coli | O157 | PARC 54 | ++ | + |
| 5 | E. coli | O157 | PARC 66 | ++ | + |
| 5 | E. coli | O157 | PARC 273 | ++ | + |
| 5 | E. coli | O157 | PARC 275 | ++ | + |
| 5 | E. coli | O157 | PARC 276 | ++ | + |
| 5 | E. coli | O157 | PARC 277 | − | − |
| 5 | E. coli | O157 | PARC 443 | ++ | + |
| 5 | E. coli | O157 | EC 66 | ++ | + |
| 5 | E. coli | O157 | EC 260 | ++ | + |
| 5 | E. coli | O157 | EC 274 | ++ | + |
| 5 | E. coli | O157 | EC 280 | ++ | + |
| 5 | E. coli | O157 | EC 285 | ++ | + |
| 5 | E. coli | O157 | EC 302 | ++ | + |
| 5 | E. coli | O157 | EC 306 | ++ | + |
| 5 | E. coli | O157 | EC 317 | ++ | + |
| 5 | E. coli | O157 | EC 338 | ++ | + |
| 5 | E. coli | O157 | EC 565 | ++ | + |
| 5 | E. coli | O157 | EC 617 | ++ | + |
| 5 | E. coli | O157 | EC 1082 | ++ | + |
| 5 | E. coli | O157 | EC 1486 | ++ | + |
| 5 | E. coli | O157 | EC 1649 | ++ | + |
| 5 | E. coli | O157 | EC 1784 | − | − |
| 5 | E. coli | O157 | EC 1785 | ++ | + |
| 5 | E. coli | O157 | EC 1787 | ++ | + |
| 5 | E. coli | O157 | EC 1794 | ++ | + |
| 5 | E. coli | O157 | EC 1805 | ++ | + |
| 5 | E. coli | O157 | EC 1818 | ++ | + |
| 5 | E. coli | O157 | EC 1828 | ++ | + |
| 5 | E. coli | O157 | EC 1839 | ++ | + |
| 5 | E. coli | O157 | EC 1890 | ++ | + |
| 5 | E. coli | O157 | EC 1894 | ++ | + |
| 5 | E. coli | O157 | EC 1912 | ++ | + |
| 5 | E. coli | O157 | EC 1949 | ++ | + |
| 5 | E. coli | O157 | EC 1969 | ++ | + |
| 5 | E. coli | O157 | EC 1971 | ++ | + |
| 5 | E. coli | O157 | EC 2004 | ++ | + |
| 5 | E. coli | O157 | EC 2063 | ++ | + |
| 5 | E. coli | O157 | EC 2064 | ++ | + |
| 5 | E. coli | O157 | EC 2065 | ++ | + |
| 5 | E. coli | O157 | EC 2067 | ++ | + |
| 5 | E. coli | O157 | EC 2068 | ++ | + |
| 5 | E. coli | O157 | EC 2070 | ++ | + |
| 5 | E. coli | O157 | EC 2071 | ++ | + |
| 5 | E. coli | O157 | EC 2074 | ++ | + |
| 5 | E. coli | O157 | EC 2079 | ++ | + |
| 5 | E. coli | O157 | EC 2080 | ++ | + |
| 5 | E. coli | O157 | EC 2081 | ++ | + |
| 2 | E. coli | O157 | NC13128 | ++ | + |
| 2 | E. coli | O157 | NC13125 | ++ | + |
| 2 | E. coli | O157 | NC13126 | ++ | + |
| 2 | E. coli | O157 | NC13127 | ++ | + |
| 3 | E. coli | O157 | 777/1 | − | − |
| 3 | E. coli | O157 | 2905 | + | − |
| 3 | E. coli | O157 | 264 | + | − |
| 3 | E. coli | O157 | 332 | ++ | + |
| 3 | E. coli | O157 | 584 | + | − |
| 3 | E. coli | O157 | 877 | ++ | + |
| 3 | E. coli | O157 | 2929 | ++ | + |
| 3 | E. coli | O157 | 419 | ++ | + |
| 3 | E. coli | O157 | 922 | ++ | + |
| 3 | E. coli | O157 | 396 | ++ | + |
| 3 | E. coli | O157 | 999/1 | ++ | + |

TABLE 2-continued

Host range analysis-PHAGEGUARD E ™

PhageGuard ™ (EP75 + EP335)

| Source | Organism | Serogroup | STRAIN # | Lysis in spots | Single plaques |
|---|---|---|---|---|---|
| 3 | E. coli | O157 | 261 | ++ | + |
| 3 | E. coli | O157 | 740/1 | ++ | + |
| 1 | E. coli | O157 | TW07496 | ++ | + |
| 1 | E. coli | O157 | TW07793 | ++ | + |
| 1 | E. coli | O157 | TW07794 | ++ | + |
| 1 | E. coli | O157 | TW07796 | + | − |
| 1 | E. coli | O157 | TW07797 | ++ | + |
| 1 | E. coli | O157 | TW07798 | + | − |
| 1 | E. coli | O157 | TW04583 | − | − |
| 1 | E. coli | O157 | TW07492 | ++ | + |
| 1 | E. coli | O157 | TW07493 | ++ | + |
| 1 | E. coli | O157 | TW07494 | ++ | + |
| 1 | E. coli | O157 | TW07495 | ++ | + |
| 1 | E. coli | O157 | TW00018 | ++ | + |
| 1 | E. coli | O157 | TW01286 | ++ | + |
| 1 | E. coli | O157 | TW01289 | ++ | + |
| 1 | E. coli | O157 | TW01292 | ++ | + |
| 1 | E. coli | — | ECOR-01 | − | − |
| 1 | E. coli | — | ECOR-02 | − | − |
| 1 | E. coli | 1 | ECOR-03 | − | − |
| 1 | E. coli | — | ECOR-04 | − | − |
| 1 | E. coli | 79 | ECOR-05 | − | − |
| 1 | E. coli | — | ECOR-06 | − | − |
| 1 | E. coli | 85 | ECOR-07 | − | − |
| 1 | E. coli | 6 | ECOR-10 | + | − |
| 1 | E. coli | 6 | ECOR-11 | − | − |
| 1 | E. coli | 7 | ECOR-12 | − | − |
| 1 | E. coli | — | ECOR-13 | − | − |
| 1 | E. coli | 25 | ECOR-15 | − | − |
| 1 | E. coli | — | ECOR-16 | − | − |
| 1 | E. coli | 106 | ECOR-17 | − | − |
| 1 | E. coli | 5 | ECOR-19 | + | − |
| 1 | E. coli | 89 | ECOR-20 | − | − |
| 1 | E. coli | 121 | ECOR-21 | − | − |
| 1 | E. coli | — | ECOR-22 | − | − |
| 1 | E. coli | 15 | ECOR-24 | − | − |
| 1 | E. coli | — | ECOR-25 | − | − |
| 1 | E. coli | 104 | ECOR-26 | − | − |
| 1 | E. coli | 150 | ECOR-29 | − | − |
| 1 | E. coli | 113 | ECOR-30 | − | − |
| 1 | E. coli | 79 | ECOR-31 | − | − |
| 1 | E. coli | 7 | ECOR-32 | − | − |
| 1 | E. coli | 7 | ECOR-33 | + | − |
| 1 | E. coli | 88 | ECOR-34 | ++ | + |
| 1 | E. coli | 1 | ECOR-35 | − | − |
| 1 | E. coli | 79 | ECOR-36 | − | − |
| 1 | E. coli | — | ECOR-37 | − | − |
| 1 | E. coli | 7 | ECOR-38 | − | − |
| 1 | E. coli | 7 | ECOR-39 | − | − |
| 1 | E. coli | 7 | ECOR-40 | + | − |
| 1 | E. coli | 7 | ECOR-41 | − | − |
| 1 | E. coli | — | ECOR-42 | − | − |
| 1 | E. coli | — | ECOR-43 | − | − |
| 1 | E. coli | — | ECOR-47 | − | − |
| 1 | E. coli | 2 | ECOR-49 | − | − |
| 1 | E. coli | 2 | ECOR-50 | + | − |
| 1 | E. coli | 25 | ECOR-51 | + | − |
| 1 | E. coli | 25 | ECOR-52 | − | − |
| 1 | E. coli | 25 | ECOR-54 | − | − |
| 1 | E. coli | 25 | ECOR-55 | − | − |
| 1 | E. coli | 6 | ECOR-56 | − | − |
| 1 | E. coli | — | ECOR-57 | − | − |
| 1 | E. coli | 4 | ECOR-59 | ++ | + |
| 1 | E. coli | 4 | ECOR-60 | ++ | + |
| 1 | E. coli | 2 | ECOR-62 | − | − |
| 1 | E. coli | — | ECOR-63 | − | − |
| 1 | E. coli | — | ECOR-65 | ++ | − |
| 1 | E. coli | 4 | ECOR-66 | − | − |
| 1 | E. coli | — | ECOR-68 | − | − |
| 1 | E. coli | — | ECOR-69 | ++ | − |
| 1 | E. coli | 78 | ECOR-71 | − | − |
| 1 | E. coli | 144 | ECOR-72 | − | − |

Source 1 STEC center at Michigan state University (www.shigatox.net)
Source 2 Public Health of England (PHE)
Source 3 National Reference Centre for Enteropathogenic Bacteria and Listeria (NENT)
Source 4 Prof. Dr. Richard Calendar (University of California, Berkeley)
Source 5 Ohio Agricultural Research and Development Center (OARDC)/Food Animal Health Research Program (FAHRP)

Example 4

Host Range Analysis Single Phages.

Materials and Methods

Host range analysis of phages EP75 and EP335 was performed using the spot-on-the-lawn methods. In brief, dry LB agar plates (1.5% agar) were flooded with 4 ml of soft agar (0.4% agar) containing 100 uL of an overnight *E. coli* culture. The soft agar containing the *E. coli* cells was allowed to solidify after which 5-10 μl of phage dilutions 10-2, 10-4, 10-6, and 10-7 of the respective phage stocks ($1*10^{10}$ to $1*10^{11}$ PFU/ml) were spotted onto the plates. After the spot plates were incubated overnight at 20° C., all the spots were scored for formation of a confluent lysis zone or single plaques.

Results

EP75 and EP335 infection was tested on 88 *E. coli* O157 clinical isolates and on 56 other *E. coli* strains (table 3).

TABLE 3

Host range analysis EP75 and EP335

| | | | EP75 | | EP335 | |
|---|---|---|---|---|---|---|
| Source | Organism | Serogroup | Lysis in spots | Single plaques | Lysis in spots | Single plaques |
| 4 | E. coli | – | – | – | – | – |
| 5 | E. coli | O157 | ++ | + | ++ | + |
| 5 | E. coli | O157 | ++ | + | ++ | + |
| 5 | E. coli | O157 | ++ | + | ++ | + |
| 5 | E. coli | O157 | ++ | + | ++ | + |
| 5 | E. coli | O157 | ++ | + | ++ | + |
| 5 | E. coli | O157 | ++ | + | ++ | + |
| 5 | E. coli | O157 | ++ | + | ++ | + |
| 5 | E. coli | O157 | ++ | + | ++ | + |
| 5 | E. coli | O157 | ++ | + | – | – |
| 5 | E. coli | O157 | ++ | + | ++ | + |
| 5 | E. coli | O157 | ++ | + | ++ | + |
| 5 | E. coli | O157 | ++ | + | ++ | + |
| 5 | E. coli | O157 | – | – | – | – |
| 5 | E. coli | O157 | ++ | + | ++ | + |
| 5 | E. coli | O157 | ++ | + | ++ | + |
| 5 | E. coli | O157 | ++ | + | ++ | + |
| 5 | E. coli | O157 | ++ | + | ++ | + |
| 5 | E. coli | O157 | + | – | ++ | + |
| 5 | E. coli | O157 | ++ | + | ++ | + |
| 5 | E. coli | O157 | + | – | ++ | + |
| 5 | E. coli | O157 | ++ | + | ++ | + |
| 5 | E. coli | O157 | ++ | ++ | ++ | + |
| 5 | E. coli | O157 | ++ | + | ++ | + |
| 5 | E. coli | O157 | ++ | + | ++ | + |
| 5 | E. coli | O157 | ++ | + | ++ | + |
| 5 | E. coli | O157 | ++ | + | ++ | + |

TABLE 3-continued

Host range analysis EP75 and EP335

| | | | EP75 | | EP335 | |
|---|---|---|---|---|---|---|
| Source | Organism | Serogroup | Lysis in spots | Single plaques | Lysis in spots | Single plaques |
| 5 | E. coli | O157 | – | – | – | – |
| 5 | E. coli | O157 | ++ | + | ++ | + |
| 5 | E. coli | O157 | ++ | + | ++ | + |
| 5 | E. coli | O157 | ++ | + | ++ | + |
| 5 | E. coli | O157 | ++ | + | ++ | + |
| 5 | E. coli | O157 | ++ | + | ++ | + |
| 5 | E. coli | O157 | ++ | + | ++ | + |
| 5 | E. coli | O157 | ++ | + | ++ | + |
| 5 | E. coli | O157 | ++ | + | ++ | + |
| 5 | E. coli | O157 | ++ | + | ++ | + |
| 5 | E. coli | O157 | ++ | + | ++ | + |
| 5 | E. coli | O157 | ++ | + | ++ | + |
| 5 | E. coli | O157 | ++ | + | ++ | + |
| 5 | E. coli | O157 | ++ | + | ++ | + |
| 5 | E. coli | O157 | ++ | + | ++ | + |
| 5 | E. coli | O157 | ++ | + | ++ | + |
| 5 | E. coli | O157 | ++ | + | ++ | + |
| 5 | E. coli | O157 | ++ | + | ++ | + |
| 5 | E. coli | O157 | ++ | + | ++ | + |
| 5 | E. coli | O157 | ++ | + | ++ | + |
| 2 | E. coli | O157 | ++ | + | ++ | + |
| 2 | E. coli | O157 | ++ | + | ++ | + |
| 2 | E. coli | O157 | ++ | + | ++ | + |
| 3 | E. coli | O157 | + | – | – | – |
| 3 | E. coli | O157 | + | – | + | – |
| 3 | E. coli | O157 | – | – | + | – |
| 3 | E. coli | O157 | – | – | ++ | + |
| 3 | E. coli | O157 | + | – | + | – |
| 3 | E. coli | O157 | ++ | + | ++ | + |
| 3 | E. coli | O157 | ++ | + | ++ | + |
| 3 | E. coli | O157 | ++ | + | ++ | + |
| 3 | E. coli | O157 | ++ | + | + | – |
| 3 | E. coli | O157 | – | – | ++ | + |
| 3 | E. coli | O157 | ++ | + | + | – |
| 3 | E. coli | O157 | ++ | + | ++ | + |
| 3 | E. coli | O157 | ++ | – | ++ | + |
| 1 | E. coli | O157 | ++ | + | ++ | + |
| 1 | E. coli | O157 | ++ | + | ++ | + |
| 1 | E. coli | O157 | ++ | + | ++ | + |
| 1 | E. coli | O157 | + | – | + | – |
| 1 | E. coli | O157 | + | – | ++ | + |
| 1 | E. coli | O157 | + | – | + | – |
| 1 | E. coli | O157 | – | – | – | – |
| 1 | E. coli | O157 | ++ | + | ++ | + |
| 1 | E. coli | O157 | ++ | + | ++ | + |
| 1 | E. coli | O157 | ++ | + | ++ | + |
| 1 | E. coli | O157 | ++ | + | ++ | + |
| 1 | E. coli | O157 | ++ | + | ++ | + |
| 1 | E. coli | O157 | ++ | + | ++ | + |
| 1 | E. coli | O157 | ++ | + | ++ | + |
| 1 | E. coli | O157 | ++ | + | ++ | + |
| 1 | E. coli | – | – | – | – | – |
| 1 | E. coli | – | – | – | – | – |
| 1 | E. coli | 1 | – | – | – | – |
| 1 | E. coli | – | – | – | – | – |
| 1 | E. coli | 79 | – | – | – | – |
| 1 | E. coli | – | – | – | – | – |
| 1 | E. coli | 85 | – | – | – | – |
| 1 | E. coli | 6 | – | – | + | – |
| 1 | E. coli | 6 | – | – | – | – |
| 1 | E. coli | 7 | – | – | – | – |
| 1 | E. coli | – | – | – | – | – |
| 1 | E. coli | 25 | – | – | – | – |
| 1 | E. coli | – | – | – | – | – |
| 1 | E. coli | 106 | – | – | – | – |
| 1 | E. coli | 5 | – | – | + | – |

TABLE 3-continued

Host range analysis EP75 and EP335

| | | | EP75 | | EP335 | |
|---|---|---|---|---|---|---|
| Source | Organism | Serogroup | Lysis in spots | Single plaques | Lysis in spots | Single plaques |
| 1 | E. coli | 89 | – | – | – | – |
| 1 | E. coli | 121 | – | – | – | – |
| 1 | E. coli | – | – | – | – | – |
| 1 | E. coli | 15 | – | – | – | – |
| 1 | E. coli | – | – | – | – | – |
| 1 | E. coli | 104 | – | – | – | – |
| 1 | E. coli | 150 | – | – | – | – |
| 1 | E. coli | 113 | – | – | – | – |
| 1 | E. coli | 79 | – | – | – | – |
| 1 | E. coli | 7 | – | – | – | – |
| 1 | E. coli | 7 | – | – | + | – |
| 1 | E. coli | 88 | – | – | ++ | + |
| 1 | E. coli | 1 | – | – | – | – |
| 1 | E. coli | 79 | – | – | – | – |
| 1 | E. coli | – | – | – | – | – |
| 1 | E. coli | 7 | – | – | – | – |
| 1 | E. coli | 7 | – | – | – | – |
| 1 | E. coli | 7 | – | – | + | – |
| 1 | E. coli | 7 | – | – | – | – |
| 1 | E. coli | – | – | – | – | – |
| 1 | E. coli | – | – | – | – | – |
| 1 | E. coli | – | – | – | – | – |
| 1 | E. coli | 2 | – | – | – | – |
| 1 | E. coli | 2 | – | – | + | – |
| 1 | E. coli | 25 | – | – | + | – |
| 1 | E. coli | 25 | – | – | – | – |
| 1 | E. coli | 25 | – | – | – | – |
| 1 | E. coli | 25 | – | – | – | – |
| 1 | E. coli | 6 | – | – | – | – |
| 1 | E. coli | – | – | – | – | – |
| 1 | E. coli | 4 | – | – | ++ | + |
| 1 | E. coli | 4 | – | – | ++ | + |
| 1 | E. coli | 2 | – | – | – | – |
| 1 | E. coli | – | – | – | – | – |
| 1 | E. coli | – | – | – | ++ | – |
| 1 | E. coli | 4 | – | – | – | – |
| 1 | E. coli | – | – | – | – | – |
| 1 | E. coli | – | – | – | ++ | – |
| 1 | E. coli | 78 | – | – | – | – |
| 1 | E. coli | 144 | – | – | – | – |

Source 1 STEC center at Michigan state University (www.shigatox.net)

Source 2 Public Health of England (PHE)

Source 3 National Reference Centre for Enteropathogenic Bacteria and Listeria (NENT)

Source 4 Prof. Dr. Richard Calendar (University of California, Berkeley)

Source 5 Ohio Agricultural Research and Development Center (OARDC)/Food Animal Health Research Program (FAHRP)

Example 5

Effectivity of PHAGEGUARD E™ on Vegetables

Introduction

Efficacy of the bacteriophage product PHAGEGUARD E™ was performed on vegetable samples in the laboratory.

Material and Methods

Bacterial Overnight Cultures

One colony of each E. coli O157 strain (see Table 5) was inoculated in LB broth and incubated overnight at 37° C. shaking.

Preparation of Samples

Vegetable sample pieces of 6×3 cm were prepared to achieve a 10 cm² surface to be contaminated ($A_{con}$) and a surface of 18 cm² to be treated with phages ($A_{treated}$). Samples were placed and stored in sterile petri dishes.

Artificial Contamination of Vegetable Samples

An appropriate dilution of the overnight culture were prepared in PBS buffer to allow the contamination of the samples with a final concentration of approximately $5 \times 10^5$ cfu/cm² E. coli O157 (2.5 µL liquid/cm²). In a laminar flow hood, 2.5 µl/cm² of the dilution was transferred to each sample and rubbed in evenly with the pipette tip.

Treatment with PHAGEGUARD E™

To allow treatment of the vegetable samples with a final concentration of $3 \times 10^7$ or $3 \times 10^8$ pfu/cm², dilutions of PHAGEGUARD E™ were prepared. Vegetable samples were treated by hand spraying the respective PHAGEGUARD E™ onto the sample surface to achieve 5 µl/cm². The petri dishes were closed and incubated at 4° C. for the indicated time periods, before bacterial enumeration. Bacteria were retrieved by stomaching the vegetable samples with 40 ml of retrieval buffer for 180 seconds.

Dilutions of retrieved sample were plated on LB agar plates, which were supplemented with 500 µg/mL Streptomycin for the time trial experiments. Bacteria were enumerated on two different vegetable samples per treatment at the indicated time points after phage treatment.

TABLE 5

Overview of E. coli O157 strains used in presented challenge studies on vegetables

| Database | ID number | Isolation source |
|---|---|---|
| NENT* | 999/1 | unknown |
| NENT* | 396 | unknown |
| NENT* | 1286 | unknown |
| PHE** | NCTC13127 | Human diarrhea-stool |

*National Reference Centre for Enteropathogenic Bacteria and Listeria
**Public Health of England Results Challenge Study 1: PHAGEGUARD E™ Efficacy on Shiga Toxin Negative (Stx(−)) E. Coli O157 Inoculated Romaine Lettuce 24 Hours Post Phage Treatment.

Figure 3:
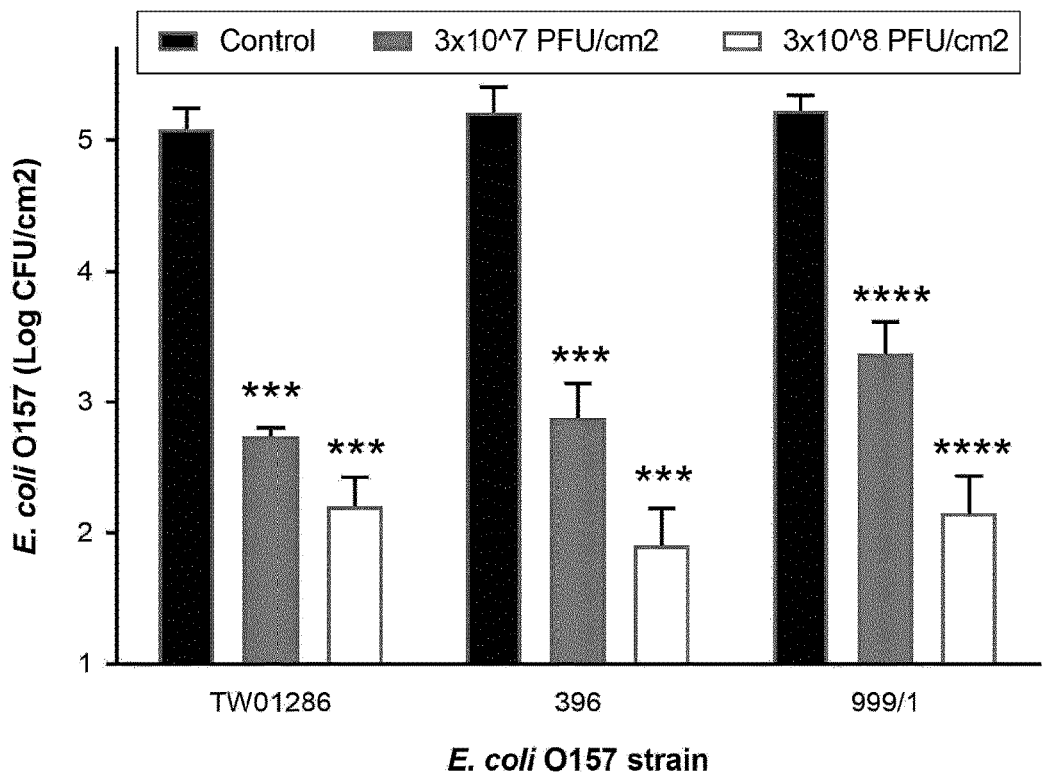
FIG. 3. $E.$ $coli$ O157 load on non-treated (control) and treated ($3 \times 10^7$ and $3 \times 10^8$ PFU/cm2) romaine lettuce samples. The data presented is an average of three independent experiments containing two samples per treatment. Error bars represent the standard deviation. Asterisks indicate statistical significance according to two-way ANOVA (Tukey's multiple comparisons test) (* P<0.001, ** P<0.0001).

It is evident from FIG. 3 that PHAGEGUARD E™ reduces E. coli O157 on refrigerated romaine lettuce. Romaine lettuce samples contaminated with E. coli strains 1286, 396, or 999/1 were treated with either 3×107 or 3×108 PFU/cm2 of PHAGEGUARD E™ or with tap water (Control). After storage of the samples at 4° C. for 24 hours, microbial loads were determined. The two different phage treatments both achieved significant (P<0.001) E. coli O157 reductions of 2.1 to 3.4 log CFU/cm², respectively, after incubation of 24 hours at refrigeration temperature.

Figure 4A:
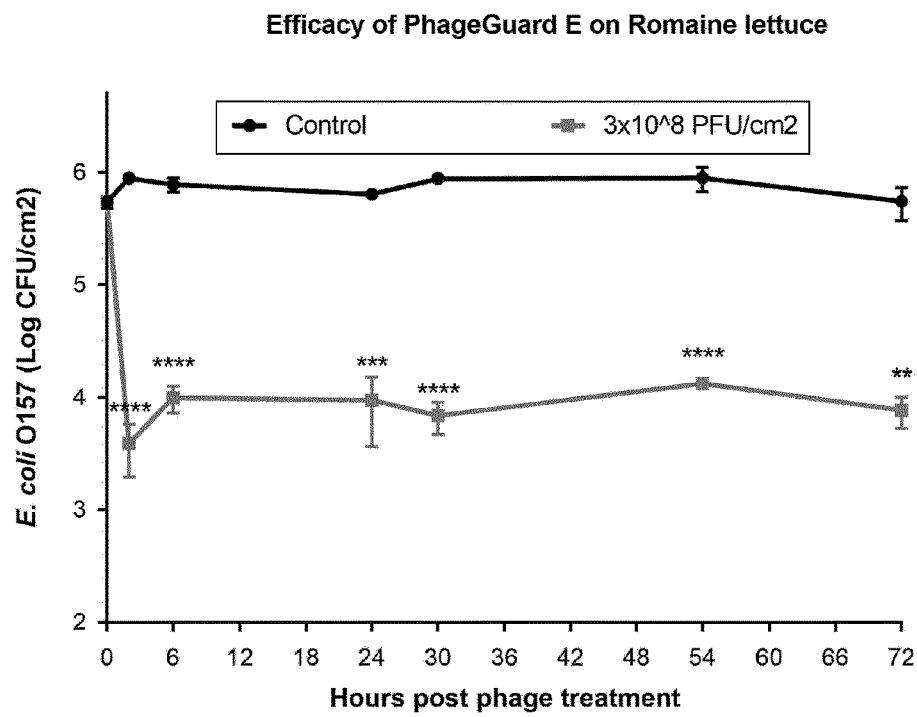
FIG. 4. Time trial with PHAGEGUARD E™ on romaine lettuce (A), spinach (B), and zucchini (C). Samples of all vegetable types were contaminated with $E.$ $coli$ strain NCTC13127 and subsequently treated with either $3 \times 10^8$ PFU/cm2 of PHAGEGUARD E™ or tap water (Control). The data presented is an average of three independent experiments containing two samples per treatment and per time point. Error bars represent the standard error of the mean. Asterisks indicate statistical significance according to two-way ANOVA (Sidak's multiple comparisons test, * P<0.05,  P<0.01, * P<0.001, **** P<0.0001).
Figure 4B:
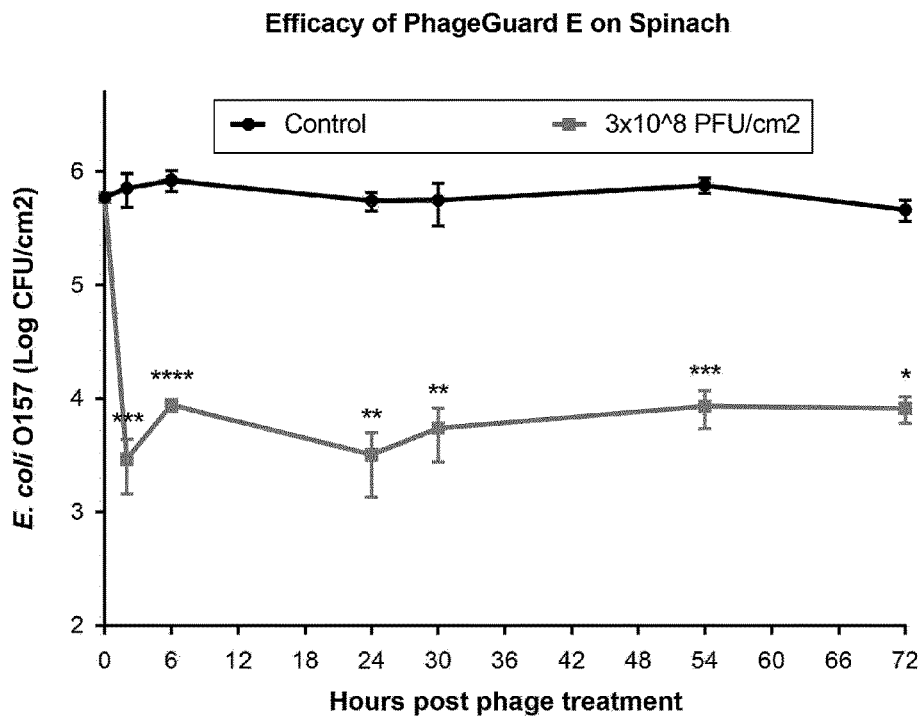
Figure 4C:
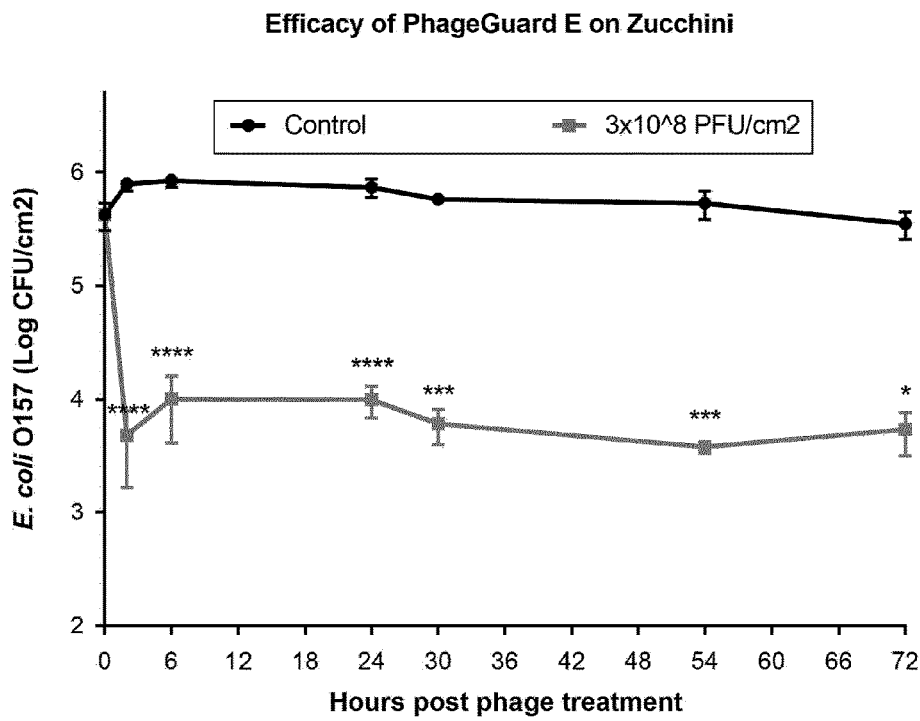

Challenge Study 2: PHAGEGUARD E™ Efficacy Time Trial on Shiga Toxin Negative (Stx(−)) E. Coli O157 Inoculated Romaine Lettuce, Spinach, and Zucchini It is evident from FIG. 4 that PHAGEGUARD E™ reduces E. coli O157 on refrigerated romaine lettuce, spinach, and zucchini over time. Romaine lettuce, spinach, and zucchini samples were artificially contaminated with the streptomycin resistant *E. coli* O157 strain NC13127, after which half of the samples were treated with tap water (control), while the other half were treated with 3×10⁸ PFU/cm2 of PHAGEGUARD E™ Subsequently, the *E. coli* O157 loads were determined at 2, 6, 24, 30, 54, and 72 hours post treatment for both the control and phage treated samples. For romaine lettuce, spinach, and zucchini reductions of at least 1.8 log CFU/cm$^2$ were observed at all time points ($P<0.05$), with no marked difference in microbial reductions between the time points, as can be observed in FIG. 4.

The invention claimed is:

1. A method of controlling bacterial contamination in a food- or feed environment or in food- or feed processing equipment or food- or feed containers or in a food- or feed product comprising contacting a composition with the food- or feed environment or the food- or feed processing equipment or the food- or feed containers or the food- or feed product, wherein the composition has lytic activity against E.coli O157 and comprises a first bacteriophage and a second bacteriophage, wherein:
the first bacteriophage has a genome with at least 98% sequence identity with SEQ ID NO: 1 over the entire length of SEQ ID NO: 1, or
the second bacteriophage has a genome with at least 98% sequence identity with SEQ ID NO: 2 over the entire length of SEQ ID NO: 2,
and wherein the first bacteriophage comprises:
a tail spike protein that has at least 97% sequence identity with SEQ ID NO: 3 over the entire length of SEQ ID NO: 3 or has at least 97% sequence identity with SEQ ID NO: 4 over the entire length of SEQ ID NO: 4, and
a tail spike protein that has at least 97% sequence identity with SEQ ID NO: 5 over the entire length of SEQ ID NO: 5.

2. The method according to claim 1, wherein the food product is a processed, non processed, cured or uncured food product selected from the group consisting of meat, fish, shellfish, pastry, dairy products, vegetables, fruit and mixtures thereof.

3. The method according to claim 1, wherein the food product is selected from the group consisting of beef, pork, lamb, fruit, and vegetables.

4. The method according to claim 1, wherein the composition is administered by spraying or misting the composition to the food product or by dipping or soaking the food product into the composition.

5. The method according to claim 1, wherein the composition is an aqueous liquid or a lyophilized aqueous liquid.

6. The method according to claim 1, wherein the composition comprises $1 \times 10^7$ PFU/ml to $1 \times 10^{13}$ PFU/ml of bacteriophage.

7. The method according to claim 1, wherein the composition further comprises an additional active ingredient selected from the group consisting of: a further bacteriophage, a bacteriostatic agent, a bactericide agent, an antibiotic, a surfactant and an enzyme.

8. A food product comprising at least $1 \times 10^3$ PFU, or at least $1 \times 10^3$ PFU equivalents, of the first bacteriophage, the second bacteriophage or the first and second bacteriophage as defined in claim 1 per average gram of food product.

9. The food product according to claim 8, wherein the food product is a processed, non-processed, cured or uncured food product selected from the group consisting of meat, fish, shellfish, pastry, dairy products, vegetables, fruit and mixtures thereof.

10. The food product according to claim 8, wherein the food product is selected from the group consisting of beef, pork, lamb, fruit, and vegetables.

11. The method according to claim 3, wherein the vegetables include lettuce, leafy greens, baby leafy greens, a sprouts.

12. The food product according to claim 10, wherein the vegetables include lettuce, leafy greens, baby leafy greens, and sprouts.

13. The method according to claim 1, wherein:
the first bacteriophage has a genome with at least 99% sequence identity with SEQ ID NO: 1 over the entire length of SEQ ID NO: 1, or the second bacteriophage has a genome with at least 99% sequence identity with SEQ ID NO: 2 over the entire length of SEQ ID NO: 2.

14. The method according to claim 1, wherein:
the first bacteriophage has a genome with 100% sequence identity with SEQ ID NO: 1 over the entire length of SEQ ID NO: 1, or
the second bacteriophage has a genome with 100% sequence identity with SEQ ID NO: 2 over the entire length of SEQ ID NO: 2.

* * * * *

SEQUENCE LISTING

```
<160> NUMBER OF SEQ ID NOS: 9

<210> SEQ ID NO 1
<211> LENGTH: 158143
<212> TYPE: DNA
<213> ORGANISM: Unknown
<220> FEATURE:
<223> OTHER INFORMATION: E.coli bacteriophage EP75

<400> SEQUENCE: 1
ggggcactgt gagttctatg aagaaatatg tcgtgctcat cacaggttcc cgctcaataa      60
ccgagcggga taaaatcttc gccaaactgg atgaactgtt agatccccac gagatcgaaa     120
cttttataga aggtgaagcg gctggtgtgg acttgatatc tcgtgattgg tgtgaaatca     180
attatgtcca tgttacacca atggagatcc ctaagaatta tcacacgata tatgggaaag     240
gcgcaggaaa ccaacgtaac aaagatatgt tagacaaagc tacaaccctg gccaaacaaa     300
aaggtcttga ggtctttgga attgcattat gggatggttc gtctactggg acgcaagaca     360
tgattacccg catgaaaaaa gcaggagtca atgttaatat cactctcatg ggcaaaccca     420
aaaccaaacg attgttataa atatgtttgc cttcacaccc atatggagtt agctatgctg     480
caattaattt tgattctttg cgtcgctttt accatgtact ttctggcgcg aatcagttat     540
atcacactaa atgatctgaa aaatacacca cgcgaaccta aatttatatt tctaaagaaa     600
tacaccaaaa agttctgcga gaattttatc tatcatcttc catgattata aatacccca      660 aaattggggg tatttatgaa cgcacaaatc tacgatgtcc tttcctctgg taacgcattt     720
agcaacccgc ttccgtccct ctccggtccc tcacaggatt taatcaccag tggtagtacc     780
aatataccat tgataactgc caacgcgact ccggaaatgc aggtggctat gtcagcaggt     840
ggattaacac cagataaact tacagcagcc acaaacatgt atagctctgc caacacgggg     900
ttaacgacac tgaacacata tggcgaccag agcataaatg aagcgtattc aagaattggg     960
acttccgttt catataaatc aggtttgaaa agtatatcac gggaaccaaa caattgtgac    1020
ctgatcaaca aagcattcgg tgttgttcag gatctaggcc gccaatggtt aaacgctatg    1080
gaaggcgctc tccagactgt gactaacaag atatcggaat tgtatgacat gattatggaa    1140
ggtgcctcag aaggtatggc aaaactacag caattggctg ctgaagtaac agggtatatc    1200
aatgaggcaa taaccgccgt caatggagtt ataaatgata tcaccgatgg gatagctgca    1260
gaacttgctc atattgaaag tatgatcaaa gaatgtctaa acttctcttt tgcgaatgtt    1320
cttggagaat gggccaaaga tctctgtgct ggaggcgtta ttgataaaat agggactcca    1380
gaattaaaag agtccctgaa ataatcaatg tctagcgggg agaactccca ctggttcgat    1440
accttccatc accagggagt tcaccccaac atcactcatt cgaatccata ctttaccgcc    1500
tggtcttatt tcatagatgt tcatttcatt acccacagca gatccattaa cgaaaacacc    1560
ctgagtggca attcggatcg gagatttggt gttattaact atctgaaatg atattgcaac    1620
gtctctggtg atttctacgc cccttgcttg agtattcctt ctgagtttgt caaagaaaga    1680
aggattgaaa gtcgctatga tgctattatt ctgagagtaa taaatacttg cggatagata    1740
```

```
tgggatcttt ccttcgtcac cttccctcaa taggggaatc gtggttttcc agtatggtct    1800
cagtgaatgg ttgttatcat caaaacaacc aacagcttga agagtctgga agttctgaaa    1860
atcagatact acttgattca gaatattttt attgcattta tcaatgtcgg ctgagatgtt    1920
aacaggtatg gttctgattt caggatccca gaggtcggtt acagaaatga cggacgtgac    1980
aaagatacgg caacttgtga gtgcaagcac cattatcatc gtcatgatcc attttctgaa    2040
tccgcgtgtc aggaacacta aaacgttctc cacagcaaag gtgctaacat gacaggtgta    2100
caattcaaaa acgaaaatcc taatttcgcg gcttccgata aatggcgctt aactatcgga    2160
gacctgatat tgcttactcg ttcaatacat gacttcagta ttcctggagt gtattctgaa    2220
ggtatcgagg gaccatcccc tggtgatgtg ctcaactcca taccttcaga acgtctcacg    2280
tatgacccca tcgtatttac gttcgttatc gatgagagtt ggtacaactg gaacagatt    2340
tacaattgga ttgcgtctaa tgctggatct gatttagctg ttagccgcga catcaccatc    2400
gaccttcttg ataacatgaa tcgaccatt ggtctacaat tgttgttgga agaagcccgt    2460
cccacagctt tggataacgt attggtggat gtggatgctg cggttcccca actggtcacg    2520
actgttacgt tcaaatattt gaaactgact ccgactcgcg tcacccgcga aattgataaa    2580
caataagtta taatacagag agttgaaaca gcagggaata aatcatgagc gaaacaaaac    2640
ttgaaacgat gaaaaccgaa gatataatgg cagaattgga acctcttatt tcggtaaatc    2700
ctgaagacat gaacttggac caaatgtcat tgaaaattgg tcgttcgtgg atgactgtgc    2760
aacgccatta tattcgtgaa ggaagatatc tggagtatct aactggcaaa ttccgccaaa    2820
tagatctcta tttacgccga ttttatgcag gggaattgcc gcccaacgtt tatgttgaac    2880
gcccattaaa agttcgaccc ctgaaatctg atatagatgt atgggtaaaa gcagatgatg    2940
attatatcga attgtctagc atgcttcaag agcagaaagc caaagtcaag ttcatcgaaa    3000
gttgcttaga tcgtttgaac aaactcggat atgaagtgaa gaatgctatt gattggcgaa    3060
aatatttgga tgggatgtaa tggtttctct acaggctttg cgcaaactta atgactttga    3120
aaatcgtcat catacatttc agcaatattc cttgccgttt aaggaactga cttgcgtaac    3180
tactgaaaat ggtcgtcact atgtttctcc cactggagtc aaactgactt cagtgacgac    3240
catgttaggg cgtactggtg accacacatg gttagaagcc tggcgggaca agttggggca    3300
tgaagctgct gatatagaaa cacatcgttg cgcagaccgt ggggaaaaac ttcatttggc    3360
ttgtgagttg tatctcaaaa acagaccaat gaaagaagtt ctggaagctg caggggaata    3420
cgtgtttatg ttcaaacagg ttttcccta ccttaacaaa atgagcaaga tatatgcaca    3480
agagattcca ttatatagcg aagtcctggg tcttgctggt cgtgttgacc tcatcggggt    3540
ttacgaagga attccaagca taatcgattt caaaacatcc aacaccctaa aaactcgaag    3600
catgatagaa gattatagta ttcaattgtg tctatactca gtcatgtttc aacaaatgtt    3660
taatgtcaag atagagcgtt taatcaatat tatatccaac gaaaatgccc ttgttcccac    3720
cataatcgaa ttcgatcgca aagacgttat ttctaaaatg tttgaccgtg tccgtctgta    3780
tcacaaaatg gacaaagaac agaaaggaat ctgggcggat cgctaaatac tccataatat    3840
tgggggaaat tagtgatgtc tgagatccaa atagtcaaag tgaacgaagt tagaatgcgg    3900
atccttgccg aggattatat ccgtgaagaa ctcaacgatt acttcaaatt tgaagatcct    3960
aatttccaac cgaatccgtt cagtaaatgg acggcgtag tgcggttgtt cacaagagt    4020
tctgggctta tcgacatcgg cctgttattt gaggtgttca aattctgtaa gatgaacggt    4080
tacaccatca aattagatcc ggccttaaaa tatattcaag atattccgga tgaagaaatt    4140
```

```
catgcgttca tcgatacatt gaatgcggtg taccgagacg aaaacaaaca atatcaaaaa    4200
gcgattgtcc gcgattatca atttgattcc gttaccacag caatacgcca aagcagatgt    4260
gtcctcgaag ctgccacgag tgctggcaaa tcctttattt tgtacatcat ggcgcgttac    4320
tacaggcaac gcagagatgc cctcgaaagt aatctgagga cgttaatcgt tgtaccatcc    4380
attcatttgg tgactcagtt gtatgacaac ttcgaagaat atagccacgg gacagaatgg    4440
aaaccattga tgaatgtcca gacaatatac gaaggggcaa cgaaagagat tttcaaaccc    4500
atagttattt caacttggca aggtatccag aaccaaccca agagtggtt ccatcaattt      4560 ggagatatcg tcatcgacga agtacataca tcaaaatcag ataaattgtc ttacatcttg    4620
aacaactgta ttaacgctga tcaacgtttg ggagtaaccg gaaccctggc gaatacaaag    4680
gtcgcggggt tacaagtcgt tgctcacttt ggcgcatatc ataaaattat tacagcgcgc    4740
gatttaatcg atctaggata tgcggcagac atcaatgtta atatgattga agtcatacat    4800
cctgtggcag actgtattga aatgcacggt gctgagtatc aaaaggaaat agaattcctc    4860
attgctaacg aacgccgcaa tgaattgata gctcgaatgg ctctgtcttt gaaagggaac    4920
gtcgcagtaa tgttcgaacg tatcgatgca cacatgatgt tggtttatga aatgctatcg    4980
gcagtcaaga aaaacgtatt cgtcatcaac ggggaagtca agacagaagt tcgtaaacag    5040
attcaggctg ctatggaaga aggggaagat ataacactgt tggcatcata tggtactatg    5100
caacagggcg tatctatcaa aaaactccat catctgatat tggcccatcc cagcaaatct    5160
tatatccgtg ttatacagac attggggcgt ttgatgcgcc agcattcctc taaggatgtt    5220
gcgcgaatct gggacctggt agacaacctg cgttacaacg gttcctacaa ccatgctctc    5280
aggcattctc atgagagata taaattttat cttatggagc gccaccctgt taaaatgaaa    5340
aaagtggcgc tctaaccatt tcaaatatct tgattcacat aggcgggggt tgcctcgcct    5400
tctttgttgg atccaaataa acagtcgatc gtgccaatac attgttgtag cactttcggc    5460
tcaagaatct gagaaaacaa ttcttcatta gatgccagca gtggaacaac tttcacttcc    5520
cgcgcctggc cttgttgaat aatgccaaca tacagacctt tgttatttgg gagtaatggt    5580
atcaccaaca tcggtgacac aataaacccc gatgtacaga aaaggctttg taaataaacg    5640
ccttttaatg acggacgttg ttctgctatg gaaagaatta cttcttggtc tttccctact    5700
gcgtataaac caacaaattg cttcatatat tatttctcac gtgttagcaa acttgactac    5760
ataataatgt catgctctgt ttagaccaaa taaaatattt tacttgttga ataaaaatcg    5820 cttttcttgtt gaacaatccg tgcgtaatat acgagttgtg agctttgcga gcaacgagta    5880
ttatcacgag caaagcgagt agactgataa agaaaggttt tattaaaaca gaatattata    5940
aatgccgtca ggcatttatt tatcgcgcgt agggcaattt atcacttgtt ctataactac    6000
aaacacgcga tactaatttg cgtcaaatat gacttgaacc ccactatatt ttgaggatac    6060
aactaatgca agagatcact cttttccgaac gcactttaca actgctggct aactttgaaa    6120
ccatctgccc ctctatcgtt ctggcacctg gtaaaaagtt gcgcactgtt aacgattcca    6180
gtacagttat cgctattgcc gacattgacg aagacttccc gttcgaattc ccgattctgg    6240
atctgaccaa attgctggca atccagcgtc tgccgagttt taaggtggt aaaattgaaa      6300 tgtcggaaga ccacattttg ctgaaaggtg aaaactccca actgcaattc tggcgttccg    6360
ctaaagaact gactgtcgtt ccggcagaca gcatcgatct tccgtctgta gaatttgaag    6420
caacagtcac tcctgaaaaa atgaaagagc tgactcgcgc ctgttctact ctgggccaca    6480
```

```
aaactgtacg cctggtggcc agcggcggta aaactcgtct ggtgggcacg accactacta   6540
tcgacaattc caacgattac actgttgagt tgggtgaaac aactctgggt gattttgcta   6600
tgcctgttga tgtggtcaac ctgaaaatga tcgaaggcaa ctatgtgatc cgcgcctgtg   6660
ccgaaatgca actggttaac ttccaatccg cagatggcac catcaactat tacgtcggca   6720
tgcagctgga ttaatcaata acgattcggc gctttattat cggtggcggg gtttccccgc   6780
cctttgaaac gttttatcta agaggctgc aatgtctaac atcactatcg tcacagatca   6840
atacgcgtgg gaaaacaaat atcgccctga caatctggat gagatcgtcc tcccttcaga   6900
cgtccgtgca aaaatccatg gctatgttac atcaggcaat ggaaacatcc cctcaatgct   6960
gttctattcc cctcagcctg gtacgggcaa gactacttct gctctggctg tttgcaacga   7020
aatcggttgt atcaaaccgt tgatgatcaa tgcgtcactg gataacagca ttgatgtcat   7080
ccgtgaccgt gttattcaat acgcaactgg cgtcagtgtt ttcggtggcc gtaaagtcgt   7140
tatccttgat gaagttgagc gactttctat ggcggcacag gaatccctga aaggcatcgt   7200
agagaaagtc tccaaaaact gctccttcat cctgacgact aatgcgaaac agcgcgttaa   7260
cgaacctctg cgttcccgct gtcgtgaaat tgatttatc tggtctgaaa aggaagcaga   7320
tgaagttaaa cttcaattca tgcgtcgttg cgccactatc ctgacggaag aaggtatccc   7380
atacgaagct ggtgttattg catcgattgt caaatcttat ttccctgaca accgcaagat   7440
tatgggaacc cttcaggata atgccaccac gtttggtaaa atcgatgaac gtgctttggc   7500
tcaggtgaaa gcaggtgaat tccaggcgct ggtcgatttc ttaaaggcca atgattgggc   7560
tggcatgaag caatgggtga ctgacaacca aaactatatt acagaggact tctactctcg   7620
tttcttccat ttctgtgtcc cacagaacaa agagaagact cctttgattc agaacgaatc   7680
tatcccagat ttggtctgcg tttgtggtca gtcacagatt gaacatcgtt cagttggaga   7740
cgtctggtta cacggcgttt acttcctgac caacgtcatg ctcaacatca agtggaagtg   7800
atattatggc cgctccgtca ctgttcgatt acctgggtgc tctgaacagc accaaagaga   7860
atctgttgtt gaccgaagac cccgaaatca gaaaggcatt tgatcctttc atgactcggc   7920
gcggccttgc ccagagtaaa gacacgttgg tggttgcaga acgaatgaac cactttcatg   7980
ccattactcc ttggatgcaa tggaaccttg cgtttcatag cattccggcg aaacgccgtt   8040
atgataaatg gtctaagaaa ggagccatgg accctgatgt aaaattgatt tccgagtatt   8100
actacatcag tcctgaaaag gcttctgaat atgttcgatt cctgccgaaa gaagtcctgg   8160
ctgaaatcaa ggcgaaggtc gaacgttcta acagcaacga aaaagctaaa ccgcgcaagg   8220
ctaagtaatt caaattattg ttaaagggt acgagtcatg gcgcgtaata cgctggacat   8280
cttgaaactt tcagccgtta acgatgaggc cagcatcgtt gattgtatgg ttgaagttca   8340
attaaaccaa gataaaccag gaattttct gggtatcaag gaaactctga gccggatagg   8400
ggttaacact cgtcaagagc cgaataccct gtatcaaaca tgtcatatcc tgcataaatt   8460
tggcagatat cacatcgtgc acttcaagca tcttttcatg ctggatgggc attacaacgg   8520
ctttacgcgt gaagatgtcc tgcgtatgaa tcggattatt cggcttttgg agcagtggaa   8580
tatggttaaa atactgcatc cggaacagat taccgaagtt gctgatatgt ctcgaatcaa   8640
agttgtaaaa catgaccaag tttctgattg gaaactggtt ccaaaatata ccatccgccc   8700
gagtcgggca aaaagcgaat aactggagtc gctatattat gacaactaca tttaataaaa   8760
acgtgagact gaatctggct tttggtaatg ctgcagggga cgtgaccgcc cccgacttta   8820
gcaaaattcg caatcaggca aaactcgttc tggaagaaac taaagaactt ctggaagcgg   8880
```

```
cgttctttga tcatcaagtg gttctaacat tagaattgaa cccttgtgaa agtgagatcc   8940
caaccactat cgaagaccgc atgaaagcca tcatggatgc ccagggtgat atcactactg   9000
tcaacgacgg cgtggcgcat atcgcgggtt ttaatggtga tgagtgctta cagcgcgtgt   9060
ttgcctccaa catgagcaag tttatccgct ctgaagatga agtcggtccg gctctggact   9120
attactattc tcgcggtttc cctgatgggc aattgcgcgt ggaaggcgaa ttccctcagg   9180
cgtgcatcaa agttaatgaa actgttgttt ggaatggcaa agaatatcct aaaggaaaat   9240
tccttaaaaa catggccgtt ttccaagagc ctgatttttc tgacatgctg actaaaactc   9300
cttcccgtca gatcaacgat atcgttgcca gcatggcgat tgaagaaggc caggtgttta   9360
tcgatgatct caatggtgtg gcgttggtat ccccgaacac attgggtgta attctttcca   9420
tggctgttga aaaaacttct caacctgtag agatcgacgg gcaaattgaa agctatgtgc   9480
ccgcgttcat cgtggatgat accaatatgc ctaagctgtg tggggtgtgg ggttctaatg   9540
ttcgtgttta tgcgagcact ccagtgcaga acacggtaac acacctttcc cgtattgatt   9600
aatataaacc gttattcatt aaacaacaga ggctataatg gcctctgttt ttgtattcta   9660
gagaggatac catgaaagat aaaccgtgtg acattcctta ttgcggtgtt cgagaagcca   9720
aaattaaatc tgcacatccc atgttaagtc catttcataa acaactcgca tacgaatgga   9780
tgagtgagcg ctataagatc cacgtgagaa aggacgtaca gcgtcttcct gctccttgga   9840
cggataatcc catactacgg caggtcaagt tctgcaacgt ccggagagag cacgacaggc   9900
agtctcttaa cctgatcaac aatatcgtca agaacgacgc tctgagcatg ctgacaagaa   9960
tgttcaattg tgttctgttt cgcatgttca atctctggga cccgatcaag gtggcgctcg  10020
agggtgctat gacgatttca gacttcgcta aaatcaacct cgacgagacc cgcgcccgtc  10080
ttcagaagtt tgaatcagaa ggtggtaaga tattcaccaa tgcattcaac acaggtggtc  10140
taaaacaatg cctggcgttc cctgaacttg ttgtcaacca caaggagcag cgctttggtg  10200
gtatgatggt taaggtacac cgtgttggtc agggtatcgt tgatgaattg gattacaagg  10260
tcgccaagaa gctggttgaa gagaatcctg gggagtacac gatcgagggc tgggagccgt  10320
acatgccgat gcgtgttatc cgttccctga aggcatttgt caacaagtat cctgattact  10380
tcaatgatct tttacgtctt gactctccga tgaaagtcta ccagcgcatg tatgaagaca  10440
ttgaagggct tggaccattc ctggcttatc agatctgggt agacttcacg tacatccctg  10500
aatatccatt cagcgagaac catttcacta tcgctggccc aggttgtcgc gcgggtattg  10560
acctgatgtt cctggataag gacggcatga ctcatgaaga atgcatcttc tgggttcgag  10620
atcaccagta tcaattgttt gcccagtatg gttatgtcca agagcagttc tggtcagccg  10680
aagcaccgga agatcagtgc atgaatgtca tgcagctgga gaatatgttc tgtgaattga  10740
gcaagtacac ccgctgtgtg caggctgttg agagagggga aaagcccgt ggcaaggtcg  10800 gttacgatgg aggcggggaa tacaaaaagc ggtgcgatga agttgtcctc aatcgcggat  10860
cggtcaattt gttagatcgt ttgaagaaac ctgaataaag aatcgcttta cttcattctt  10920
caataacccc ctttcaacgt atattgacct cactttaacg acgcgcccat ttagggcgct  10980
caatttgaac tgaaacagga agactacacc atggcagaat ttaaaccttt cgcaacggct  11040
gttaatgata acgtgctggc gatgtccgca actggtctgt tcatgaccaa cgttgataaa  11100
gatgctctgt gggatttgta tttggcatcc ttcccagctg gtaccaaccc gatgtaccgc  11160
gaacgcactg aacacgactg cacctgctgt aaacaattca tccgtaatat cggcggcgtt  11220
```

```
gtgactatcg atgctgacct gaacgttatc tcgatttggg acaacattga gttgggtaac    11280
gaatacgacg tggtcgctgc ggcgctgtcg accttcgtta acaacacgc aatcgtcgac     11340 gtgtatttta acgattctgc taaagtcggc ctgtctcata accacgaatc tggtgtagac    11400
ggtaaaatcc gcacgtataa ccatttccat accgaactgc tcggcagcta tgtcctgcgt    11460
tctgatgcta tcgcatctaa aaaaggtgaa atccgtcagg ctatcgaatt atttgaacgc    11520
ggtctgcgtg aaattactct ggaatcagca gaaatcgttc tggaattgat tgatcagaat    11580
tctttgtatc gcggtgctga acataaagct gcggtgatgg gcttcgtagt agccaagacg    11640
gcatatgaag aaatcccaga atctaaccgt tctctgtggg catggcgcac tggttatcgt    11700
tcaaacaatc atgttccaca tggcattcgc aacaccgtta tcggtactct gttgactgat    11760
atcagtgaag gcgtggaact ggaaaaggcc gttaagtcgt ttgaaaccaa agttgcccca    11820
gcgaactaca aacgcccgac ggctctggtc tccaagtcca tgatcgaaaa cgctcagaaa    11880
gaagtgattg ctctcggtct ggaagattcg ctggcgcgtc gttatgcagt ttatgacgac    11940
ctgacgatca ataacgttct gtttgcagac ctggctgctc aaaaagcgat ggatccattc    12000
gctcaactgg ccgccgaagt gaaaacgccg accaagtcgc tggataaagt tgaagagatc    12060
ggcattgacg acttcctgag caatatcctg ccgaaagcgc attcaatgga agtgctggtt    12120
gaaaactcgc atacaggaaa cctgatgtct ctggtcgctc cggctatcgc aggtgctcct    12180
aaccttttca aatggggcaa cggtttctca tggtcataca acggcgaagt gaccgactcc    12240
atcaaagagc gtgtgaaagc ggctggtggt aaagtcgacg ggttcctccg tgtgtctttg    12300
gcttggcaca caacgatga cctcgacctg catatgttct ttaacaatat ggaacatgtg    12360
tacttccgcg atcgtcgttc aatgactggt gctcatctcg atatcgacat gaacggtatg    12420
gacggcatca cccgaaccg ctctccggta gaaaacatca tcttcactga tgaaagaaag    12480
ttgcgtgacg gtgaatatcg ttttgagatt cacaactaca accaacgtga aagatcgac    12540 gaagggtttg aaattgaagt tgaatacaaa ggcactacgc aacgtttcag ccacaatggg    12600
ttaaaagacc aggggcgcat cactgccgtc gttctgactg ttaaagacaa acaagtcgtt    12660
agcatcaagt ccgagctggc gaatgttgat aaatccaaag aaatttgggg cattaagaca    12720
gcgaccttcc agaaggtaca actggtcctg aactcaccga accattggga tggtgaacaa    12780
actggcaaca gcacgtcttc cttcatcctg gaaggttgtg caaatcctga aggtactcgt    12840
ggtttctaca acgaatatct gaagccggaa ctggataaac atcgtaaggt tttgaaatg    12900 ctgggtagta aaatgaaagt acagcccaac gaaaaccaac tgtctggtct ggggttctca    12960
acgacgcaac gcaatcatgt gttcatcaaa gtgtccggtg cgtttaaccg tactgtaaaa    13020
gtcatttcct aattgatttg acaacaactt cgtaataagg aacaaagaaa tgtttgatca    13080
agcaacccgt ttaaaactgc gttttaactc taacaaaggt ctgctgtctg ttgagcaggt    13140
ttgggatctg aatctgaacg cattgaatga gatggcgaaa gatctcagcc gtcaggtgaa    13200
ggaagccgcc agcgatgaag aagatttcat cggcgtgaaa agcgcagtcg actctcagtt    13260
acaactgcgt ttcgatatcg tgaaagcgat catcggtgtt aaactgaaag aacgtgacga    13320
aagcgcaacc gccgccgaac gtaaagcgaa taaccaggcg atcatggaac tgatccagcg    13380
taagaaacag caggaactgg aaggtctctc tgttgaagaa ctggaaaaac tcctgaaata    13440
atctgtcggc tccggcctga gcaaccccgc cgtgtgcggg gtttcttta ggtaaagaat     13500 atgaaacctg tcgtctgtga ttactgcggt caacctgctc aatacgtcgg gggcgatgct    13560
gtataccccc accgcccaga cctccgcaat ctgaagttct gggtatgcac tccatgtgac    13620
```

```
gctcgtgtgg gttgccatac ccatggggat ggaaagaccc ctctgggaag gatggcgaat    13680
gccgctctcc gtgctgctaa gcaggaagct cataggtcgt ttgaccctat ctggaaaagt    13740
gggcagagga gcaggagtga tgcttacagc tggctggctc ataatctggg gatcaagaag    13800
cgcgattgcc atatcggctt gttcgatatc gtcatgtgcc gtaaagtagt ggaggtctgt    13860
aaacaaatat cataggataa cacatgacaa ctcgtactgg catcaaactc actcctgaag    13920
tcctgaagtc acatatcgct gaggtgattt acgaagaccg cgaagtcggc ggtcaccggg    13980
ctatcacttg tcatttcaag atggataacg gcttcgtcgt tcacggcacc aagcccagca    14040
catccataga cccggccaac ttcgatgaag ccctgggcaa agagatttcc tacaataaca    14100
ccttcgacca gctgtggcag ctggaggcgt accgggcgct tgttgaacaa gatctgttgg    14160
ccaaagccac ggaaacggca gagatccgga tcgatcaata cgctgttgaa cgtagcgccc    14220
tctgtccggc ctatcaccct ggcttcaatg tgatgattca ggacgtgatg ttcagagcgg    14280
aaaatggcga gcgcttcttg gcgtctttcg tttgtgggcc ggatgacatg gaacttgttg    14340
ttgactctca caacgccaaa tctcgtaagg ctgttagtga tttcctgtgc gccaactcca    14400
aactcgatct cacttattcg ccattggttc tgcgcatcgc caagatttgt catgaagcca    14460
accgcgcata ctgcaagtct gttggtgacg actctcaact gccttgggaa caatctccgg    14520
cctggcagcg tgagagcgct tgcaaaggtg ttatcttcca tctcactggt gatcgtaagc    14580
ccagcgaatc gcatgagagc tggatggcgg agaaggaggc tgagggatgg gtgtatggcc    14640
cagtcaaaga ccctcagacc aagcaacacc cttgcatggt tccgtatgga gaactcccgg    14700
tacaacaacg ctccaaagat tatattttca aatccattgt agactccttt aaataagctc    14760
tgaataatat ttcaacctgt caataatata atgcccggtt atattcaatc gggcatttta    14820
ttatattaat tggcatcaat accgcctgtc gtaatataat agtcccatgt tgaaatagtt    14880
gggaaatata actcacgaga gcctgatgac cgacaacaaa ttaaaacgcg ccggacttga    14940
ttgtcttgac aattcattcc gtcccagtga tgttctggtc gcccaaatgg aaaacaaccg    15000
ggatttcatt gaaactatgc tggagaacgc cgacgcgaac tccaaacact ccaaagccca    15060
aaaaggtcaa aacgatgatt gaatcattaa catttaagaa tgcggttgcg actgtcgcgc    15120
cgtctaacca tgtaatcgtt gtggatatct ccggttccat gtatcgttca cttccagaag    15180
ttcgtaagca tctgaaggag aacctgcctt ccctggtgaa accggaagat actgtgagca    15240
tcctttactt ttcatctcgc ggtgatttcg gaacggtatt tgccggacgt cagattaaca    15300
gtgcaactga tctcactgag atcaataatc taattgaccg cttcctgcaa ccgtcggat    15360 gtacgggatt tgtagaacct ctgaaattgg ctgctgaaac cgcgttgagt ctgaacaaac    15420
ctggttatgt caataacctg cgcttcatga ccgacggtta tgacaactgc tggcgctcta    15480
atgaaattct ggcagcagct gaagtactgc ccaaagcgtt tgataacatt accttcatcg    15540
aatacggttg gtattgtaat cgcgaactgc tggctctgat gtccgagcgt tctggcgcga    15600
cccacgtgtt tgccgaaggt cagactgaat atcagaccga actggaaaac gtactgaaat    15660
catctacgcc gaaagtggtt gttgatgttc ccctggttta cactcatgcc atctacgttg    15720
aaaacggcgt ggcaactgtg ctagccatac agccagatga agaacacccg attggccacg    15780
tgagcattcc tgaaagcgtt tctcagctgt gggttgtaaa ccccaacatg atcgaccagc    15840
tggacaatct ggccgacatc caggcggcat acgtgctggc attttatggc gtgtatacca    15900
tggatgccga tctggtttgg gctgcgctga agaagacagg cgacgtccgc ttcatcaaac    15960
```

```
aatacagcaa ctgtttcacc aagcaggact attccaacat caaagtcgac ctgacccagg    16020
ctatcgtgga tgaaactctg cgcggcgtag atggtatcga ttacaacatg gttccagctg    16080
aagatgcgac gaccattgtt gatgtcttga cctatctggc cgaagccgac gtctctgttg    16140
tcactaagca tccgttgttc tcttacaaca gcatcggtcg cggaactgtg cagaaagttg    16200
atgacacaga agacaagctg gctgaacaaa tcgccgaagc caaaaccaaa gcagagcgta    16260
aagcgctggc tcttaaactg gccgagcacg aagattggac gccggaattt actccggttg    16320
acgacaaagg gattgtccca attagcaatc tggtctacaa ttcagagcgc cctaacatca    16380
gcattcagac cgttcagcac gggacggttg ttgtgccgga gttcgtacag aagaaatatg    16440
aacttcctga agaactggga acctggcgtt atcgtaatta ccaccatcgtc aaagatggca    16500 tcatcaacct gaagacgatg ccgattactg ctgaatctcc gattgtccga gctaaggttg    16560
tccaagattt gaccgccatg ggcgttaatg tgtttggtgg tccggaaatc tttatcgtta    16620
atttagaaag cgttccaatg gtcaaccgcg ccatgaccaa gaatatcagt gctgccgaat    16680
tcttcgccga caacgttcgt cgcgaagcgc tgaaggcaaa acagaaagtt ctgaaattct    16740
atcgtgatga actggttggc aaaggtaatg caacaggcct ggcgtctaaa tatggtaaag    16800
aagccgccga tttcttgtca gcaaatggca ttcgtgacta cgggttctca ccgaaaacta    16860
cttctgtgga atcaaccgac gtctacatga gtcgtgaact gaacgtgaaa atcaaaggtg    16920
cttcgtcgct gccgagtatt gcgtctgttg ttaaaaagca agcagacggt aaaaaactga    16980
atgtcgctga tcagttgatt gctaatgctc tggccgaata caacgctttt gttaaatctc    17040
caatgatcac cagcgtacct gaagagactc agaaaaagct gattgaaagt tggattggcg    17100
acgcagcaaa agcagccatc aacgaagtcc gcgccctgaa caaaacgctg tctaaagtag    17160
tttacggcat cgtcgctggt catggttggt tcactgattt ggatctggaa gagtctacga    17220
tggatgtaga agttgatggg gtgaaataca ccgtcactgc cgaactggcc gaaaaagaaa    17280
tcaagatcta atctaattg gcggggccaa cccgccttac tttcaggaaa tgaatatgag    17340
caacaaaccg acttatgttg atgtaatgcg cgttttggcc caatacgcgt gtgacaatct    17400
aaacatggaa acttggcgcg acggcgacca taaagaaaag ttcgataata tcgacgacaa    17460
cattgatgcg ttggctcctc ttcgggccaa gagcgatctc ggtggtgatg atcttgacat    17520
gattgaactc atcatggaag ttgaagaaca atatgatgtt gaaatcagcg atgaatgggt    17580
aggcaaacat ggtgatgacc ccacgctcgg cgcattggct gaattggtag ttgccctcag    17640
caagtaacca aaagaatccc caataaaata ttggggattt ttactttag gggtttactt    17700 cctctaaaga atgtcctatt attcaataac tggctaacgt ggggttggct agaaaaagga    17760
gatacaaaat gaaactacca ggtcacattg aagtttatat gcggttatac aaagaaggta    17820
acgccgctgc taagaacta cacgaactga ttttgtcata cggcgttaag tctgttacag    17880
gagtaaagaa caaaaaaata gacggcgaat atgtgtcaat caatgggcgt ggtctgaaaa    17940
ccaacccaac atattttgtg ggtgtccatt tagacacagg gaaagaagtc gtggagatcg    18000
tggcataatg tctaataaga aagttgaaac gacagtagaa attgatcgta attggggatt    18060
actccgcgct aaaggttttc gtcgcgttta tgaccaagaa gtttatg ttcagcggcg    18120 cgacgttatt atcagcaaga aaggtaaaga atgggttgct gaagaagttg acattgaaac    18180
aggtgtcgtg ggcaaagtaa aagcgaaggc ggctattttg tttgctcttc tgaagcatat    18240
caattaattc tataatttac ggcggggtat gattaccccg cctatttgaa attgcaggaa    18300
ctatatcatg acagatcaaa gaagtattgc tcgttcggaa atcaaagata ttatacagag    18360
```

```
caagaccaac gaaactcatg ctcaatccag aatgctatct cgatttgttg aaattaagtt    18420
cgacattgaa gagaataaca atcggagagc gctggaggga atgttggcga ttatcttggg    18480
ccatgtcacc aattcagcat atgacatgga tgatttaact cgtttgttga acgcccagaa    18540
taacgttggg aattctgttc gtgaattgct gtttaagtcc gaatgaacta actaagggat    18600
aaccctatat cccgaggtgt gacatgttcc ttacatcctt tattgactgg atgaatatca    18660
taaatggcct gaggatccct gttgggaacc tcgggctttc tcgttcttct atgccgcaaa    18720
tagatgccga caaacaagaa gattttcaca aatatcttga agacaacggt gtgtccatag    18780
atgctgcgca agtgcccatc aaaatgcttc gtcttaccca gaacgaaatc aataaaatga    18840
aggtctggaa gatcatgaag caaatcagaa ataagaaacc tatgggtcga gtttgggtgt    18900
cttctgacaa ttacgttgtt gacgttctc accgatttgt cgctgcgttg aacatggatg    18960
gtaaacagcg aatgaaggtc tacaaagttg atttacccgc gatggaattc gtaaaactcg    19020
ccaaacaatt tcagggtgtg cggtacagaa cggtcagtga tacccgtttc tgaatacgat    19080
agtttattga aaccctttac tcaacatggt gagccgacta tcattttatc caatgaaata    19140
aggagaatca ccatgaaaca tttaatcctc ggggttgtgc tggcaggtct ggcattaccc    19200
gccgccgcca agctgaactc cacaggtgag aaactgtggt ctgatctttc ctactgtgct    19260
gggttctccc aggcggtcgc tatcgacaag tccggttcca tagagaattt tgctgaactt    19320
tggaacacgg gtaacgtctc cactgctgtt gttaatgctg ggattgagtt caaccgttac    19380
aaacagggag cctacaactt gaaaggctac ctgaatgacg atgaatttaa ccgaggaggc    19440
atggaggctg gcgatctcat catgactggc cgtatgggca cacaaggccg tatgactgta    19500
aggcaatgcc gttctctccc ctctccggca ttacagaagg gtgtgcaaat cgggcgtcga    19560
catctggatc tgatcaatga tggcaaccaa tgcatcaagg tgtttgaata tagtgccgac    19620
caagaatcag atcgacgttt gaaaaaggaa tggcggacac gcgcccttgg attgagagca    19680
tggctcgtag aaaacgatta ttactacgag gatcgtgttc agaacggatt gaaagatctt    19740
tctactaatt tgtctgtcaa tctagacgac ccaaggcttt cgcgtgaact caagcaaaca    19800
cggattgact gcgacaatat gatgaaggag aacgaaagat gagaaacata atattcttgt    19860
tattcttttc tatgttagca tcattccaag ttatggcaac tccggccagc aaattgaata    19920
tatgtgcggc ctggttgtct acttatcaac aatttcaccc tgatgataaa gatacatcca    19980 tcctttatc agattatgaa ggtgagttga acgccttga tctctacagc gtggatcaaa    20040
tagagaatgc tttagatttg ccaatgatgg agtccgctgc cgataatagc aaacagacga    20100
tcaaagatct gactatgtgt cgggaaatag cgactaattt cgttggaaat caaagataat    20160
tttcaggtta aaatttaact tccattgaac tgaaaggaaa tacttcgtga tgattattac    20220
taaaaagatc gccgaatcga tcgttgaaaa gaataagatg ttcgcgccca caaagcaaa    20280 ggtcattctg attcacgaag acgggcgcgt catcttcgct gagaagtttg agcagggttg    20340
tgctttctgg ttcgcagata ctatgcgcga aagcaagctg cagggcatca tctataaatt    20400
aaccctggtt gccaagcgca atgatcaggg tgattgggtt acggtctgcg atttcagctc    20460
taaggtagaa gctaaaccca aaactcgcca agaaaggatt ttagaggctc aggaaaaact    20520
tcgggttgct cgcacatcat ccgcggagaa gccggaaata aaaccagccg ttattcctgt    20580
caccaataat ccgctcccac ctgtgggtca aaaggctttc gaacaatatg ttgaaaagag    20640
aaaagaagaa tctatgaaga ctccggtaga aaataatgat gagtctgaat ttatttcaat    20700
```

```
acgacagttg tgcccgcaag aacaacgtta ttcttctcca aatgatttat ttgtgtcatt   20760
ccgatgcaac ggaaagatca tattgtgtaa aactctgcgt gaacaactac catggcctaa   20820
catcaatatg atggtgagtc gcaattttaa acgatttgct attagtgaag ggaacgatta   20880
tcccgtaaac aagagcggaa cgtatgccaa caaacatatg tgtggtaagt tgtcttccc    20940 taacgattcc ggaaccatcc gcgttcgttt agaatgggat gaaaccctga acatgtatgt   21000
tggtgatata aataattca ataacattag ggcggttatt attaaaccgc cttttatttg    21060
agagatctat attatgaata agaagagtcg tatcatcatc ggcgcggatc agggaaatct   21120
gtattttgat acaactggtg ctattgccca cgccatcctt ccaacaggta tttctgttta   21180
ttgtgtcgaa catccagatc cagcgatcaa acgactttgt tacatccatc gtgaaaaggg   21240
attgattgta ttaccggaag cgcaattat gcgcgctcgt tcttggccga tcgattttaa    21300
ttccatgacc gccagagaga ttgacgcccg tttcttcgca tacaatatga atcgaacttt   21360
aaggaacgaa actcaaagag ttgcccattt cgataatgaa acatataccg tgacattaga   21420
atttcgcgtt cttggtgaag ctcttcaggt aaagaaaacg agttgggcaa ccgaagggac   21480
gtttaccaat gattatgctc ttatcgatag attgtgtaat cggttccgaa ttagcctgac   21540
tgcgaatgaa gatttgggag aatatgtatc atggacagct cgttctccac atatgaatgg   21600
gatcatgatg gagagcggga ctcgtaatcg tgctgttctt cagctgctgt tgttagatgc   21660
gtattctcgc aatcctctgg aatatttgtc tcgagagcaa atcgacaacg ctctttccca   21720
ttgcaatcgt ctggaggtgt aatatgtccg gcgtatggtg tgatgtatta ttagtgagat   21780
tttcaaacgg gatggataac cagattattt cattcttta tcctgttccc ttttcttcta    21840
tgggtctgac tgtcaagcgc gttcttgaca tagaagaaaa actcaacgcc atgccgtata   21900
tggcgcgacc acacgtgctg ggttgtgaac tgttaaacga aatgatgatc gatgagaatc   21960
ttgttgaaac aattatcacg cgtgaacaga tgaaaccat actggctcag ggagaacccc    22020
atgtcgaata aaccgtttga acttaaattt cgcgtttggc atattcccca ggttcctggg   22080
atcgcttttc atgttgaggt tccaacattt gaagaagcgc agcgcctgaa gaatgctctg   22140
ggtgattatg atttgttcca gttcaacaac aatatcaagc cggattattg caatgcttcg   22200
ggcattcaga tttatcaaca tgatctgacc gatgatgatc ttaatgatat gggtctggat   22260
gatcgttggg ttgatatgga agatgttgac gaactcaacg attatttcga gcatctgcgc   22320
agtacagggt gggaaatatg atttcaaaat atattgtaaa gcctggggat actctgtcca   22380
gcatcgctct aaaattatat ggtgatgccc aacagtatat caaattagcc agattcaaca   22440
atatccaaaa cccaggccat atcgcggttg gtcaggttat ttgtttaccc acacctgtcg   22500
aagacaaaga acacattatg attccggttc aaccgactca gaagtgtttg gatgcgatag   22560
ctggtttatt tcggccaggt ttttgtgatg gaactattga acgtcacatt tatcaagcaa   22620
ttgtggaaaa cgcaggtgta aaatgatcgg attaattcgt tacctgttca tattcgtaat   22680
ttcaacattc attttatttt tcttttcaa atacttgaaa gagactaaaa tctaccgaag    22740
taaacgttgg cgcaaacggg tgagggcaac tttcctgctg ctgatttctt cggttacaat   22800
aaccgcactc acattgggtg cttatatcta cattttgaa ggggtacatt gatgttcaag    22860
aaactggtgt tcggtgcaat tatggttctg gctgcaagtc tactttctgg ttgtggtggc   22920
gttatcgatg aaggtaacgt cggcgttcgt acccaatggg gtgaagtaga catgaaccct   22980
gtaacggcgg ggatctacac cagctttgtt tcaagcgtgg atgtttacac gaccaaagaa   23040
gccgttgtga gtcttactaa aatgactcca aaggcgaaag acaacctgac tctggaagac   23100
```

```
ttggatgtag atgtttatta cacacccaac gtcgcaaagg ttccgtggtt ccataccaaa   23160
tttgctggcc agagcgctga actcgatgat ggcacgatag cggtgggttt caatctggtt   23220
aaaactgctg catcatcttc ttcaatggac gccgtttctt ctcttgattc tatgacaatt   23280
cacacccaac gtgctgaatt ggagaagatg attaaagatc gcactcagca acaattagaa   23340
actgctgcgc ctggtatgtt cacaattaca cgcgtgttag tgaaaaaggc gctgacagat   23400
ccttctattg agcagtctat ccgtgataat gttatggcgg acaaacgatt ggatacggca   23460
agaaagaacg ttgaaattcg cgagcaagaa gcccaagcga accaaaaact gaccacctcg   23520
ctgacgcctg aatatctaca acatgaatat aacatggtgt tacaatcatg cgccaacagt   23580
ggaaaatgta ctctgatcgt tgacggatcc ggctcaggta aaatgctgaa cgtcggcaaa   23640
taaacgcttt attcaataat atttgttagg taagctgtag tcctcttgta gtgaaacatt   23700
gtaaacaact aactggagta atccgaatga accgtactga ttttatcgct cacatcgccc   23760
agactcaggg tatgaccaaa ggcgaagcag agaagatcgt ggcatctttt atcaacggcg   23820
taaaaactgc agtcgcagct ggccaatctg tccaattcgt cggcttcggc gcgtttgaag   23880
ttaaacatca ggaagcgcgc actggccgca acccgctgaa cgggcaagcg attcagatcg   23940
aagcgaaaaa tgttgttaaa ttcaaagtcg gcgaaggtct gaaagctgct gccaacggcc   24000
agtaatcaca tccagagcgg gcgtgcctag cacagcgtgt taggctaaaa gagaaagccg   24060
aggcattaac ctcggctttt tcgttgctgg aattcgggta aactataaca gaacccaaag   24120
gaggaacaac gtgacagcat ttaatcaata ccgaaaggcg attgacgcca taggccgtaa   24180
ggttcctata gaagaaatag aaagccttgc caaaaacgaa tttccatatg acaaggcgaa   24240
cccaggccag atggaatgta tcgttgaagc tgttgatgca ctggtcaaca aaaaggtcaa   24300
acatgtgatc atcgaagccc caactggcgt ggggaaatct ttgatcggaa caacgattca   24360
taaagttatt cgccatttgg ttttacatgc cgatccttat gggcaattcc gcacgtctat   24420
cagtacaccc accaaaggtc tacaagacca atatgctgct gaaaaggcgg tggcgataga   24480
catcctgaaa ggcaagaaga actatcgttg ccacgtacac ccagatgtgt attataacgc   24540
tgtgcaatgc cgtatagcat gccgagacgg gcattgtagt aaacgccgtt gtccatatgt   24600
acaagcacgt aatttgtgga cggacatttc atcattgcgt tgcactaatg cagctatgat   24660
gattgagatg tgcaccacca tatgtatgaa gcctgaaaac cgctccgaca tgctgatctt   24720
agacgagtgc cataagatgc cctccacgct cctagagcac acgataatgg aatacaatac   24780
aaaggctgtg gatgggctgc gaactatccc cgaaggaaag gagatagtct ccatcattgc   24840
cgatattgta gaccgcacta agactatgt cttgggcaaa ttgtattctt tgtctggtga   24900
aatgcattcg atgttcgaag acctccatct taaagtggga tctttgttgg aagttcttga   24960
agaattggtt gaagatgacc gcctgagtga agccaggtg atgaaactcg ctgacattat   25020
agatgtgcta cacaatctga gtgattattg tggtattatg tctcagacaa aggccagcac   25080
ctttatcgta caggaaaagg gagatgactt tatccggttc aaacccgtca tgccttctga   25140
tgtaagtgaa tttggtttgt tcaggaaagc cgattaccat gttcatatgt cggcaacaat   25200
ctgtgggatc gattcatatg cccgttcctt gggtatccgc caggggatt atcattcaat   25260 acagattgga aatccaatcc caattgaaaa tcgtaaagtc aactatatgc ccattgttaa   25320
gatgaccaac aacatgggcg attatgaaat gaaaaggctg acggaataca tcgatgaaat   25380
aatcgcgttt catccagggc aatctggtat tatacacacg gtgagttatg atcgtgcatt   25440
```

```
ggcgatacaa aaattcagca aataccagaa ttttatccat gtgccccgca ctcgaaaggc   25500
gttgatggat attatggaaa atgcattcag gacaaagacg ccttgtgtca ttgccagtcc   25560
ggctatggaa gaaggatatg acttcaaagg tgattacagc cgattccaga tactgatcaa   25620
agttccttac gattatctgg gtgatcctct aattgcacat atcaactcag tagatccgtc   25680
agcgtacttc cgcaatgcgg tactgaggat tgtacaaatg tgcggacgct cggtcagggg   25740
tgtcgatgac tgggctgcaa catacataat tgattcttcc tttgaatctc ttatgatgcg   25800
caacccagag ttcttcccaa cctggttcac cgatgcagta tttgaagttt aataacctgc   25860
aataaacgat aaatggcact tgatatttgg ttcaagtgtc gttatcgtga tgatcatatt   25920
atccacatct tggctgaaag atatatttgc aatcggtttg gtttgcacat gattatacag   25980
actgtaaatc aaatcttcac cgcgataacc tactttgcca tcagtgtctt gccaatggcc   26040
taacgtggat tcatgagcat gtactcggaa ttctatcata tggaacaatg cttttgggat   26100
tgttttcagt atgctggttc cgacaacagg gatatcaata gcagagtcgt tggaattgcc   26160
ctcatatact gacgcccaac caaaagttgg atctcctccc gctactggag ttctcttcca   26220
atattggaat tccggatttc cagcagcatt cttttgaaga aggattactt caccgccttc   26280
aaaattggat gtgtctatgt catcacgtgc taataaatca gctggagaac caataaattt   26340
ccaggtttcg cgatctaaaa tagacttata ataatcggtg aatacgttgc tgtcgttagc   26400
tgcattgatt gcgtctttaa gaccttcacc tgtgaccatc tcattgagtt ttagccacat   26460 gttttttgaca gctgacgcag ctgcgacctg accttcagtc ccacccgccg tgtagtcata   26520
tacgatgtcc agcttttgga tggagtcgtt tatggacaag agcaaacgct caatttctgg   26580
ggcggtcaga ctgaaacgat atgcgcgttc tgacatgatt cgttcctcat cgataaaacc   26640
agtttgggat acttatacat gattgaaata tacactgacg gggcatcatc ccctcagaag   26700
acaagagctg ctggttgggc atttgccatc agtccaatca ctggagagca atggaaagtg   26760
ttttatgggt atttacccccc gccgtcaacg aacaatatag ctgagttact cggggttata   26820
aacgcgatga agatcctatg gaaattctct aattgtggtg aacgctgcat tcccccagcc   26880
cgcattatat ccgacagcca atatgttatc aatagtgttt tggagtggcg tagaaaatgg   26940
gaatatgaag ggatgccgcc taagaacaca gaacttctgc tcgagttgtt cgattattat   27000
gacaaagttt gttcaatttg tgaacttgaa ttaaaatggg tgaaaggtca tgcaggaacg   27060
atgggcaacg aaattgcgga tcagtggagc gttagagcca agaagatag ttcaatggtt    27120 cttgaaaata accgtttctc ggtcaagaaa gtcgttggtt cttttcaatga attcattggt   27180 atttgaggat tatcacgatg ggtatgaatt ttatagacag gggtgataac gtcaccaaat   27240
atttcacaga cgaagataat gaccgtgttg ttggaatatt gagagattgg attccggctc   27300
gcaaaaaggc tttggccgaa ggaacacccc taccaagaat ccccaattat gtggccatga   27360
atgttcagat gattattaag aacatgagta tgcgctacaa ctatcgtgat tatccatacc   27420
gcgaagacat ggtcagtgag gccgttgtca acatccttcg ttacctccat acatttgatg   27480
tcagtcatat cggcaagaaa ggaaaaatca attttttctc ttgggtaacg atgtgcgccg   27540
accgttcatt cgccaagaaa ctcaccagtg aagaagaaca caattatatc aagttgcgtt   27600
catttgaaga agcaggtggg ttcgctgcat tatcggatga cccagacttc caacaacaaa   27660
ccttcgttga tagcactggg ataacgatgg acttccgtga gcgtatcgga aattttgaaa   27720
ctaagaagaa agcccagcgc gaaaaggaac gccaaaagca aatcgccatc aaagaagagg   27780
aaaagaataa gaaaattcct cgcggtatac ttcaatgtct tacgaagagt gaaaatacca   27840
```

```
ttaccgctga cgccgaagat aattcagata atgacttcgg ctctactcaa tttagtcttg   27900
aagatataat ggacagcccc acattgttag ccgaatcagt tggagaaaag aataatggcg   27960
attgctaaaa ttggcgattt acacatcggg agccgcaatg gttcccgtta cgttcgtgaa   28020
ttcataaaga attatctcat caactatttt attcccgaat tggtagatgc agacattaaa   28080
gaagtttggc aatttggtga tacgtttgat gttcgcaaat tcatgtatgg gcgcgataaa   28140
gattggttga aagatgaatt aacgccagcc ctgagaaagg cgggtatcaa atggaatggc   28200
atcgttggaa accatgatat caccttagaa gaatctaacc gtatcaactg ccatcctat    28260 ctgaatgaat tagcgccaga cgtctatcat tattacagtg aacccactga agtattgatt   28320
gaaggtgtca agactctcct actgccgtgg atcaataaag agaattatga tgcatctgtt   28380
aaagcgatac aagatacaga cgccaagtac tgtttttgcgc atctggagtt ggcagggttc   28440
aaaatgtacc agtcctctgt atgtgataaa ggtcagatcg acgtggcgct cctttccaag   28500
ttcgagcgcg tggataccgg acatttccat acccgttcga tggaaggtaa cattcagtat   28560
attgggactc cttatcacct tacctgggaa gaccataaag acgggacgaa ccgaggattc   28620
tatgtagacg acatgaatgg cggggaattg tttatcccca caacgaaca acaaacgttg    28680 ttccgattca tagaatacga ctacacccaa atgtcttccg catcgaagg aaactggatt    28740 gacccagatt ggctaaacaa tggtttgggt attgaagggc aaatcgttaa ggtgattgta   28800
cagaaccgcg ataatgccaa gcattatgaa aagttctgcg acgcattgaa gcgctgtaaa   28860
tgcatcgatt acaacttcat cgatcggacg attactgttg cttccgagaa ggtagaagtc   28920
actgaagaga tggtggctac tgatgcggtg gaagtcttga agaaagatat ccgcgccgcc   28980
aataatatcc agcgccctga aaatgtttgc aaattagcag aacaattcta taatgctgcc   29040
caacaacgcc tgaacacatt ggatgcataa taatgagcaa tgtagaccta ttatcaaaat   29100
ttggttcgct gttgaaagaa gcggacactc ctgtttctgt tgaagtacca tttgaaattc   29160
gtggggaaat tacccacaaa ctgactttcc atcgcggtcg cgctaaaaac ttccgttcta   29220
tcggtaatga attcatgaaa attgattacc aacgcaattc ggcaaccttg gttacatccg   29280
atgacaatgg cgctggtaaa tccaccatgc ttgtctggct gctgttcttc gttctgtaca   29340
acgacacgta cagcaagaaa gagaagaaag ccggattggt taactctcaa aacaaaaaag   29400
aatgcgtggg tgaagttgag ttctcaactc gcggtagtga atggaaagtc cgtcgcggta   29460
tcaaaccaga ttttgtagaa gtttatcaga tggtggaagg agagtggaag caagtcgtga   29520
acgatgcggc caaagctgat atgaacaagt acatcgtgaa tctcatcggc gtggaccaga   29580
agatgtttga gaactccctg gttctaggca aagagaagtt catcccattc acggaaatgt   29640
acactgccga ccgtcgcgct atggtagaga caatctggga tttggggttc ttcagtctga   29700
tgaatgaaga tgtaaaagca tctatcaaga cagtaacaaa tgaactcacg acggtcacca   29760
atgattacgc ctttcatgat gtaaatttaa aaggccagca agcgcagttg aacagatca    29820 ataattccaa tgcgatgatc cagcaacaat ctgctgatat ccttgtccaa gagaaggaac   29880
gtctgaatag tttgaattca gatatcggcg cagtgcagga caactgaca gagtcccgtg    29940 ctcaagactc taaattggaa tcagaattat cagaagtccg taatcgcctg aatgccgaaa   30000
tgaaagggga tatcgatgcc atcaatgaag agtatgcggc caaaatccaa gcagttcagg   30060
atgaagccga taccaaggct gaagattatg aacgcataga agtatccgac ggcgaaaggt   30120
cgttacaaga aatccgcgaa agaatggcgg tggtcgcaga acgcaaaaac gatctggtca   30180
```

```
gccaacggaa tgctaatctc gacgaactga ataaagcgtt ggcgcggcgt caacagggag   30240
agaacttccg tttcaaattc gtcacagaaa tggaaggcca tgaatctgcc atcaaacgtt   30300
tccacgatat gggcacttgc cctacgtgta cgcaattagt gtcggacgat accaaatcac   30360
gcattgaaag tcaatattat ccacaaatca gtgaactgac tgacaagatt cttcaggttg   30420
atacagccct agaagaagtg aattccctga ttgagaatta caatgtcaga gattcagaat   30480
tatcttctca gatttcggtt attgacaaag aactggatgc tttgcgcaat gaaatccgag   30540
aagcggaatc agcgatcgcg gctttaaagc gcgatatcca ggggttctac gaggttgcgg   30600
cggttgagaa agcatcttta cagcgagaac aacaatctaa agttaatgat atcctcagag   30660
cagtagatgt ccgttatgaa gatatcacaa cttctattcg ccaagcccgt gatcagctct   30720
ctaagagcat caatgacact gctgataaac tcacgagcat gaaatcgcgt cgtgctcctc   30780
tggaggcatc tattgccgat ttagaacgta aattggctgt taagccgacg cctaccgatg   30840
ctctcgaaga agagatcacc cgcatcacgg agttaatgga tggcttgaac acaagacgtg   30900
tggaattgga tgaaaaattg caagatctga accatctgtt gttcttcctg aaagatgacc   30960
agaccaaagc gcgcattatc agtctgtact tgccttttcct caatagcaag ataaacgagt   31020
atcttgaagc actcaatatg ttcttggata ttgcggttga tgatacattt gaaatcacta   31080
tgagcgctgc tggtcgtaaa gggcaaagca tattctccct gtctacagga caacgcagcc   31140
gactcaatct ggcggtgaca ttagccctgc gggacgtcgc taacctgaag gcgtctgtac   31200
aatgtaacct cttcgtgtta gatgagatac tcgaaaacat gagtgagcgt ggggttcaag   31260
aatccgtcga gatgttgaaa cataaattt gtgggaacaa tctgtttgtc atcagtcagc   31320
gtgaacagga gttccaagaa tatttccaac ataacattcg ttatggtctg cgtaatggca   31380
tgaccgaagt gattaagaag gattgatcat gactaatgtt ctgattgcca cgttttttct   31440
aattgcttct ataaccacgt tcatcttagg ttacaggcgt gtatttcagg ctgatattat   31500
cactggcctg atgtatatcg cgctgggttc atttctggcg ttcggcttct ctgggtttac   31560
gttagaatga aagttgtcca cttcaagaag gagccatacg acgtctacat tggtcgccct   31620
ggtaaatggg gaaacccgtt cgaggtcaaa gaccacgggc ggggaaactg tattgagttg   31680
tttgaagacg acttgtatgt gcgcctgatt gaagggggata tcgccgaaga tgaactcctt   31740
gaattagatg gaaagacctt gggatgctgg tgtaagccgc gcccatgtca tggagatgtt   31800
tatgtcaaag tgatcggtcg tattaaacta ttccgtaagt tgggtaaatc ttttactgaa   31860
tatttgagac aaacatatgc gaaaagttct tgtaaaactt gattgccatc catatttccc   31920
agacatttgg ttcactaaca gtcgcatact cttttttacaa caattatcta aaataaggga   31980
tgaaggtatc atacatgatt tagaagatac tatcggtatg gttagttccg atgaaagtcg   32040
tggaaagatg gtggtcggag tattcatttc agattcaggt gtgttggtac atgaactgag   32100
ccatgcggta ataaacatat ttgaagccgt caatatggta gctaacactc acaccacgga   32160
agcatttgcc tacctgttag agagtctgta taaccaatgt aatcaccatc tgaacttatg   32220
gagttctttt gatgagccga gatgaaattc agattgcttg cgatatcgct gtcgagttat   32280
ggaatcagca aaacaaacat tatcaggtga cgttgacacc aaaacgttac ctagagcaag   32340
gtgggttgat cgttgttgac gccgtcttgg gtttcaacaa gtacacagat atgcaaatcc   32400
tccaagggga tttcatagtg gcatcaaaat cagcttggga tgatcctatg gaatttgtct   32460
acggttggtt ggaatgcatc gaggaatcat accatctgat ctacgaataa ggtgaagggc   32520
actaaatatc acgtgcccctt tatctttttaa ccctgtcagg aggctccagc gagctgcaag   32580
```

```
tcgacaaaca cataaggaac gccatcatga cgatgacaac gttgaaggcc atggccttgt  32640
ccgtgacctt taccattgcc agcgggagtg tgcacgcttc ccaaagtacc acccaatgtg  32700
attatgagtt ttctgatcaa caactttcaa ccatggccac agcctatcac gtgggcaaac  32760
aacaagacct tggtttcacc ctcgccgcaa tatcatggag ggaaagccgc gccggagaag  32820
atgttgtatc catgcggaat aacctgaaat cggctaatat ggggggcattt caaaatcgcg  32880 tccaaaccgt cgggaaacgg gagggatgca aaacacagaa gtgttacgcc aatgttgcga  32940
tcaaattact ggtcaatcaa gaatatgctg ccaatgctgc ccttgatgaa atgaatttct  33000
ggctagaata tcataaccaa aacatccgca aatccctttc ctcttacaat gctgggttca  33060
atcgtaacca gaaatccaat tcttatgcag ccgacgtcgt gaagaaggct aaatatcttc  33120
aacgatgtgt gtcttcaaa ggcatggcaa taaacccaaa ggtcgaccca ggagtgatcg  33180
ccatgaataa gcgcacgatt gagaaactca agaggaccag ataatgaata tcactccatc  33240
tcagaccgga tatgaacaca taatggtatt tctggctatt cagggcgcga aggaagggat  33300
cattacttca gaatattccg gtacaatgcg ccttgcggat tatgtcgcgc ctgaagcatt  33360
catcaagaaa tgcattgacg cttggtgcct ttatgcgctc ggcacgtatc catcacctcc  33420
tgctggtgag ttattgtttg ccataccgac tccggcaact ggtgacacag acgcgatatt  33480
cgctgatatg ctgtcaaagg ttatctgac atatgacagt gctcacggcg tgtatgattt  33540
ttctgcgctg aatcgtatct tcggattcac cataacttct gaagccaata ttcctgatta  33600
tggaatacta gcatggggcg tcgacggttt ggggcaaca tatgcatctt cggatgtcgg  33660
tcctgtgttg atagacccag gggtgacgat ggagcaatac atgtcacaat tccctcaaca  33720
taatgtaacc ggaagcgata tcattattgt ctatcctggt tctaacgcgt tgtcccgcct  33780
ggtggacggc tggaagcctc agctgaagga cattgtctct ggaatcaggt tccatattcc  33840
cgttgtcaat ccaacacctt aaaatattca ataaaagggg caaaagcccc tttacttctt  33900
caataaccca cgtataattc taaacataag cagtacgaca ccaacttgaa aagcaggaac  33960
tacattatga aaatcatcct cgacgcatat atccgttacg gcagcaaatg gttgatggcc  34020
aaagtttacg acggtgaaga attagtccac gcccaaaccg ccccttctga caattgcgt  34080 gaaattatga acgcgattt tcctactgtt gaaatgattg aacctgccaa ccaaaccgaa  34140
gttgacaaag aatgggaacg cgaatggagt ccggcggcgt tggcacaatt tgataagaat  34200
tacaacaatc gccaaaacgc gtctcgcccg ttccgtcgtt aagaataaag gggtgttagc  34260
atccctttct tttcgctaat taagggaaac cgcaccgatt ttataatcag gagaattaca  34320
atggccatcc catctttctt gaactttctt gaagagtcta acaattaga cgaagcgttt  34380 aactcatccc cgtatgaatt gacattcggt aagaagaacg ctggtgacat tttcttcaca  34440
tttgttgatg aagacgaaaa agaattccgc atccaatttt atacccgca ggggctgggc  34500 aagaacgttc gtcaggtctt cataggccag aaacgtggtt cgacctatcc agacgcaatc  34560
ggtcgtttca aaaacccaat gcgtgtcatc gcatccatga tcgaagcaac aaagcaattc  34620
atggcgacgc ctttggggaa aaccattgac ggctttgcaa ttaacttctc caagaaagca  34680
ttggaacgtg gtgttaccct cctgccgaag atcatccgtc agtccggcct gaagcagaag  34740
ctcaatgtca tggacctgac gtataccccct atccctgatc gtgcattcgt atgggttgtg  34800
cgtaaaggta aggatcctgc tcaggtattc gatggtccga aaatgaaagg cgtgacttgg  34860
gacgacccag acaaagtcgg cgacgttcct gaccaggctg ctcgtgacgc cgcactacaa  34920
```

```
ggtgacatag atgatttgag ccaagccata aatgccgatt ctcgctggat tctgaccaag   34980
gctgatcata ctcagcctat gctggtctgg tctggtaaag aacgtgggcg gactattacc   35040
gccaatatcg cacctcacgc gaatgaacct ggtgtgtatg ctggtagtat catgaacgag   35100
aaacggatcc gcgctcaatc cccagacgct attgtacgcc aactgggatt accgcagatc   35160
cctgtgaata ttctgaatga tttcaccaag cagtcgtcca tcttctggaa agagatgacg   35220
ggagattctg gaaaaataga catgcagact ttgccaaaaa caggatctgt ggatgactta   35280
cgaaatcagg gttatattgc tcgccttctg gggattgtag acacatatgc tccacaacag   35340
gtcggtatgt atgcaggtga aaaactaaca cgaatcggcg cgggcaaata tcgtacttcg   35400
ggtggtctgg acattcaggt ttatttctgg ggaattgtca acgaaaaact ttctgtagaa   35460
gtagtatcag atttgtctgg tcattaccaa cttatgctgg aaggagacgt gaaaaacgcc   35520
gcttatgaaa tagtgggcgc aatctcccgt gcagccgatt tcaatttgc gggagaagta   35580 gaatgccgtg tggttcctat caatggtgcc ccatatccga ttcaaaaaat ttcccgttct   35640
cagggatatt cttacgttga ttgtggttct ttcacattga agatcgctga cgctctgctg   35700
aatcggttta ccttgggcaa ggcggtcaaa cttgatctga tgaaagagtt tcctcgtaca   35760
acattcaaag tccgctatga ttggcgtgga aaagatactc tgttggttca atcttccgac   35820
gagcgtacta tctttggtga aatcaacacc aattccagtg aaaatgcagt gatcactgca   35880
aacatcaaag taccaagcaa cgctaaattt tttggtgaaa ccgttcatgg cttctctgta   35940
gcgtgggatt tccagttccc tgctggtagc aagttgcaag ccgcaagatt cgttaccaac   36000
gtaacttacg attttgatcg aaataaagcc aacatcacca ccatgttgac tgaaaatggt   36060
cgaaatgtgg tagacagcaa tggatatgat atttcgttgt ctgtcaaatc agtgcaagat   36120
gcattggatg agatttctcg acgcctgaaa gacgcggctt cgcaactgag ccatctcagt   36180
tcatcaaact ataaccctaa caatctgttc ctgaatgaca tcactgtcag taaatttggc   36240
gcgattatgt tccaagacaa agatttggca cagtccagga accgcacggc agtcattgat   36300
gctttggctc gggctaaaga tcaggctgct ggaggtaaga atgcaggtga tctggccacc   36360
tatgccgaat ccattcgtga cagcgctcct aatggacgag atctggattg cagagtatac   36420
acagccagta atggtacagt tctgaatgtt gcttgggata tcacttttccg tcgcaatacg   36480 accgaaggag catatcgtga attcaaggat cagatcaacc gtgccaacca atacctgcaa   36540
acggtataca acgacgcgaa atctaaaggc tataatccta ccgagccaaa tctcatgact   36600
cttgaacgcg ctcgccaatc cgacgaatgg gctatgagta atggtgatag tgcatacagt   36660
gaatatgaac aatcgctggg tggtaatctt cagattagtc tgaaataagt catagcccct   36720 tcggggcta aatacatcaa aatccttagg agatccacga tgaaaccgtt tatagaatat   36780
tttaaagaac aagctcaaca accgcaaact catggcggca tacaaggcaa aagtgtaacc   36840
atcaccaaac aggccgacgg aacccaatgg tgtactggtg ccaccgtgac ccagatcact   36900
ccagataatc aggccgacat ctataatctg gaattgacta cggcaacac caccaaagta   36960 aaactcacac cggaccaggt tcatgcagtt tctgtcggta agatgtggt tgccgttcat   37020 gacggttttg agttcttctt tgggaaagat gccagcaaag gtcaggtcac agaatcctat   37080
gcccaagaat tggcgaacat ggataagatg atcggtaaag cgctgggcgt tggcaaatct   37140
cgtaaaagcg gtcgtacaga gtttgaatat tccggtattc ctggtattgg aaaacctgtc   37200
gcaatcgact tcgcggagagaga agacgatcca tatgtaattg tcacagtcgc tggcaaacag   37260
catgacatca gtaagggaaa aaccctagct gcggacattg ccaaatatat cggcgttaaa   37320
```

```
cctgtctaag gaggttgtat gaaaggattc caggacttcc tcttgaagga agcaaaggtt   37380
gaccatcgcc gtcttggaca gcagggcatg tatgacatca ccgacgttgg ccgccctaac   37440
aaaggcgatc tgattgatta ctatgatcgc aacggggata acatcaggg gaaagtgaag    37500 tctgtgaacg cacagaacat tatgaccctg acgaacacca gcacgggtga aaccgtcaag   37560
ctgactttga tcaagccttg atgcaatcc ccctaaatac aggggatt ctttttctga      37620 ggaaacaatc atggttaacg cgagtatatt catcaaccgt ggactgcttg ctatagccca   37680
ctctcatgcc ctccacttcg ttacaacgtc ctatgccaag cacaaggcac tcggggagtt   37740
ctacgggaaa ctggaggact tgctggacac ctttacggaa gcgtatattg gtgcgggtgg   37800
tatatacatt ccaggattcg agaacatcaa attatacaat cctgaaccga tatcgtatat   37860
caacagcgtg gtcatcgacg ttaatgggat ctacaatcag tgtgatagcc atttacaaaa   37920
cacgcttgac gaaatcaaaa ctttgtgcta tcaaacgatt tacaaactga agcaattgtc   37980
ctaactcaat aggatcatca tcaggttata attttgccca ttcgtcatca ataggataca   38040
gataacaatg ggcaaaatct ttataccttc tcactcagaa ggttgtcaaa tcgctgcaaa   38100
atttctacac aaacaaatga attgtggtgc tgtgttcgta gaaccaaatt cattcgataa   38160
tcgtgaatcc cctgacgcca tcgggttcag acctggaggt tgttctatat taatggaagt   38220
taaagtctcc cgcgccgact tcctgacaga caaaaagaaa cctcatcgca tgaatccttc   38280
cataggcatg ggagcatatc gtttctatgt ttgcccagca gatgttatta aaattgaaga   38340
cctccctccc aagtgggggtt tgttgtactt caccccctaga aaatctttga agcccgttca  38400
cgttccaaat atgcaatatt cctctttgtc ttcaccggaa cattatgcat catatttgtc   38460
taaatctttg gacaaaagaa gacctacaga tatccctcct tatctattag ggtacaaaca   38520
gatgctggaa gaattcgccc actttgaacg caatcaggtt gcggaacaaa atattctgta   38580
tggggcttgg cgacagcttt gcatagctca aagtcgcggg gtggattata atgtgacaga   38640
agtgttccag aggccaaata tctaatgaaa ttcttggacg aacaatacat caatttttctc  38700 gcccccccgac ttgataaatt cagttgggaa cgtgttggcg ctgtcgccaa atttcgttgc   38760
ccattatgtg gggattctaa gaagagtgcc aacaagcgtc gtggtcactt cttttatgat   38820
cgtgatgacg atgtgtttcg tttcaagtgc cacaactgta atgaaatgag cggttgggcg   38880
tttgaattct ggttgaagaa gtttgacgag cgtctgtata tgaatacaa ccttgaaaaa    38940 ttcaggatca tgggggatac cagttcccgc ccgttacaaa aactcaaacc attacagcgc   39000
ctgacccaga cagcacgtat cggttctcag gtcgccaaac gggatgaaga gcaccttggg   39060
aatatgatac gccttgatct tcttgaccgt gatcatatcg cccgtcgtta cgttgaaggc   39120
aggggaatgc cggagagcgc gttatctctt ttgtattaca gcaagaactt ccgcgaggat   39180
cttttgaatt ttgaaacaga cgttgaaaaa cagaagaaga tccctgaaga tgaacggttg   39240
gttatcccat tctggactca agacggtcgc atgaagatcg ttcaggggcg cgcattcggt   39300
gataaccttc ctgataatgt gttgcggtac gccactgtca aacccaaaaa cgaggatact   39360
aaaatctatg gggaagagcg catcatatgg aataagacca aattggtcgt tgaaggtcca   39420
attgatagcc tgttcctccc gaattgttta gcaactgcgg atgccgacct tctgagcgcc   39480
aagggggata tctatatccc tgacaaccaa tatcgaaaca aacaagtttg tgatggtata   39540
cagaaaatga tagacagcgg agtcaaagtc gttctgttcc caccagaaat tccatggaag   39600
gatatcaacg atatggtcca tccggataag gggaacatcc ctattcgtga tttgcttcag   39660
```

| | |
|---|---|
| atcatagcca agaacgtgta tcaggggttg gcagcgtccc tgaggttttc agatttgagg | 39720 |
| aagatataag aactgaccta aaactttta actcaaaata tttccctcca ggcctcgttc | 39780 |
| tatgaggcct cttaaaatac ttcaaaaata tttaaaaat ttattgaaaa agactttact | 39840 |
| cttcaataat gacgcactat tatagttcac atagggcggt acacaacacc ccgccgaatg | 39900 |
| aaaagtgaaa cgaaccaact acattatgag gaattacatc atggctacta ccaaaactct | 39960 |
| gatcaccaac ggcaccatct cttttgaact gaacactgaa gttgcaaaag ttgaaatgtt | 40020 |
| ccgcatcgct caggcagctg gcttcactgg tggcaaaact tccttcatga acctgctgaa | 40080 |
| cggcaaagtc aaagcgacca acggcttcac cctggttgag caggttgtgg ttgacaaagc | 40140 |
| agtcgtcgca aaaccgctg acaaagttgg catgctgaaa ggcctggggc acgacatcca | 40200 |
| cgttgttgaa gctacgaccg aaacttacg caccatcact gtcggaaagg ggcgcatcca | 40260 |
| gctgaacccg ctgaataacg gaaccttctc tgtgatggta ttcccgaaaa aaggttacga | 40320 |
| caacagcgat atcgtgaaag ccgctggcgg tgaagcaaaa tcccaatatg tcaaaatggg | 40380 |
| taaactgagc gccgacgccg ttgaaactct ggtaagcaaa ctggcataag tcacaagggg | 40440 |
| aggcaactcc cctccttatt cagaattttg gtaggagatt atcatgggac gtccgattat | 40500 |
| ccacgtttca gaaggcgcga tttgggttat gacccgcatc cctaatgttc attttcctca | 40560 |
| gttccaagag gaaatcgagc aagcaatgct aacgatcctg gaaaaatacg ggtacgacac | 40620 |
| tgaagtccgt gaatccttca acgaaattat gcctgtggtg gttgcgcgat gaccctgacc | 40680 |
| ctcgaacaaa tcggcgaagc aacctgtcac ctcctgaagg aaaagacagg caagcagtgg | 40740 |
| aagcatcagt tgtacaaaga tcaccctgat ggcgtagggg cgatcatgat tgatagcgaa | 40800 |
| gagtcaacag ccgtcctctt ctattggcaa gacactggcc gctggtcggc tcagacttat | 40860 |
| ggtgggaata agcaatctaa ctccgtgcct tcaccagtgg aggcatatga agtctgaag | 40920 |
| agaggcattc aaatgcagat cgctaatcta aacactctct tgtcaactat ctaacatagc | 40980 |
| agttcctcaa gtcagttcac tttcactta aatacctctg caatcactgc ggaggtattt | 41040 |
| tcttatggcc attctaaaac ttggcaaccg aggttctgaa gtcaaatcac ttcagcaaag | 41100 |
| cctcaataaa atcgggttct ctcttatagc tgatggcata tttggtaagg cgaccgagaa | 41160 |
| tgctgtcaaa tccgttcagg caggtgccgg actggtgatt gatggtattg caggtccaaa | 41220 |
| aaccttctat gctatccgta atgccggaga cgctcatcag gaacatctta ccgaagccga | 41280 |
| cttagttgac gcagcgcgtg aacttggtgt cgaactggcc agcatgaaag ctgttaacca | 41340 |
| ggtcgaatct cggggtactg gtttcaccaa aacaggtaag atcaaaactc tgttcgagcg | 41400 |
| ccacatcatg tataagaaag tggcggctaa attcggacaa gcaagagcca atgctctgta | 41460 |
| ccaactttac ccaacattgg ttaaccccaa ttctggtggc tatatcggcg gagacgcgga | 41520 |
| gttggaacgc cttcagggtg caatcgccct tgatgaggac tgcgcgtacg agagtgcgtc | 41580 |
| ctacggctta ttccagatca tgggggttcaa ttgccagata tgtggttatc cgaacgccaa | 41640 |
| agaaatgttc acagattttc tgactggtga acgtgcacat cttctggcat ttgtgaaatt | 41700 |
| catcaaagct gacgccaata tgtggaaagc attgaagaac aaaaattggg ctgagttcgc | 41760 |
| ccgtcggtac aatggtccag catatgccaa gaaccagtat gacaccaaac tagcggcggc | 41820 |
| atacaagagt ttctgttaac aaaaggccgg aaacggcctt tttcttattc taacatacag | 41880 |
| gtatgctggg cacgtcgctt aattaaaggt gtcgacaacc cctgtagata taggaaggtt | 41940 |
| caacatgcaa tctgcgtcta aagttgtatc catgaagcca gcgaagacaa aatctgctcg | 42000 |
| taagaaagac accatccaga aggaagaaga ctggatgaag ttttccaaag gcgatttcaa | 42060 |

```
aattgctccg ttcaatggcc tctcagaaaa tcagaacctc gcatatcaat ccgcactcaa   42120
tgaacatctc actatcgcta tcggtccggc aggtacaggc aaatcctatt gtggtgcgtc   42180
cgctgctgcc aagcatctga ttgacaaaac catcaacaag attatcatca cgcgttctcc   42240
tttaccgact ggaaccacag cggggttccg gcctggtgac acatatgaaa agctgatgcc   42300
ttatttgatg ccgctcatac agacattcaa aaaggttctc aaaacagata cgggttccga   42360
cggtttcttc aactatctgt gggagaaacg catcatagaa attcaagacc ttgaaactgt   42420
gaaggggatg actttcgatg attgtttcct gattatcgaa gaggcgcagg aatgcgatat   42480
ggagcaactg aaaaacttat tgactcgtgc ttcagattct tcgtacatct tcgtgaatgg   42540
agatatcaaa cagtctaaca agcgactgcg tgatagtgcg ttacagacgt atgtggattc   42600
ctttaaagac ttcaacaaca agctggaaac aggttctttg caaattgacg gtgtagaaat   42660
cggagatgaa tatcctgagt gggttcagcc attcagcatc atcgaattcg ataagtctga   42720
tcgtaatggt cgcggtaact tcacccgcct gatgttagaa attaacgacc tgtacaacat   42780
ttaaatacca cacgaacttc cccgtcgcct tcaatccatg gaggcgacgt ataataacag   42840
cctgcattaa cacaaaccga ggatcgctat gattaacatc ataaagcggg acggatcttc   42900
tgtccccttt gacattgaaa aactccacac tgttcttgaa cgtgcctgtg aaggattaga   42960
aggagtttcg gtgtctgagg tggaagcagc atcgaagatt cagttcacag acaatatgaa   43020
aaccgaacgc attcaggata ttatcatcca agcggcggct acattgattt ctgtagaaaa   43080
acccaactac caatatgttg ctgcccgcct gaaatcgtat gacctgcgca agtcgtcta   43140 tgggcgatac aagccacctc acttgcttga tatattcgct aaaaacatca agcagggcgt   43200
ttatgatcgt gaattcctcg aactctatac gaaagaagaa tttgaagaac tgaacacggt   43260
catcaatcac aaacgcgaca agaattttac ttgggcggct atgggccagc tcacgcaaaa   43320
atatcttttg cgcgatcgct cagcagacag caaagtatat tacgaaacgc ctcaagtcat   43380
gtatatggcg atcgcgatgg ctctgttctc tgcatgggat aaagaaactc gcctgacgat   43440
ggtgaagaaa ttttatgaat acgccagtac aggtaaattc agtcttccaa cacccatcat   43500
gtccggcgtt cgtaccccaa cccgccaatt cagttcttgt gttcttatca aaaccggtga   43560
cactttggac tcaatcaatg ctacagccaa aagtattgtt gattatgtat ccaaacgcgc   43620
tgggatcgga tttgatgtcg gagcaattcg tggcatcggt agcccatcc gaaaggtga   43680 aatggtgcac acaggtctgg ttcctttcat aaaatatctg actggggcat taaagtcttg   43740
ctctcaaggc ggtattcgtg gcggatcagc aacttgctat atccctatct ggcattatca   43800
atttgatgat gttgtggtcc tgaagaacaa ccgtggtctt gaagagaacc gtgaacgccg   43860
tatcgactat ggtattcaga tcaaccgcgt catgttcgaa cgtctggtga caaacaacc   43920 cctgtatttg ttcgatccga agacaaccg cgatatgtac gaagcgtttt cgcagatgt   43980 cgataagttc cgtaccctgt acgacaacat ggtcaaagct gctgatgctg gtttggttcg   44040
tgccaagaag atgaatgcgg aagaagtatt ccagatgttg ttggatcagc gttcagatac   44100
aggccgcatc tacatcgcgt ttgtcgacca catgaaccag tacagtccat tcaatctaga   44160
cacaatctat agttctaatc tgtgtctgga gattgcgctt cctactcgtg agttccaaca   44220
gtatgatgat gaagatggtc gcattgccct gtgtacactc gcatcattta acctgacggc   44280
gtttgaagat ccaacagaaa tggaagatgt tgctttcgtt ctggtttcag ctttggatat   44340
gttgttggaa tatcaggact acccagctcg ccaagcccgt ttggctgtag aagaatatcg   44400
```

```
tcctctgggt atcggtatcg tcaacgtcgc gcatttcctg gccaagaact tcacgggtta   44460
tggatcgcct gtcggattag aacttctaga caagtggatg gcacatcttc atttctactt   44520
ggtcaaagcg tccaaccgtc tggccatgcg tttcggatct tgtaagaagt caactatcca   44580
tgattctgga tttgtgacag cagaccttca gcctctcccg ctagacatcc tacccaatgg   44640
caaaaagcct gttgggcaag cctatggtct tgactgggaa ggtctgaagc agaacctatc   44700
cgagtatggg atccgtaacg ccacgttgtt agccgtagca ccaactgaaa gctcctctca   44760
ggtgctgaac gcaacgaacg gtatagaacc accaaaaggt ctcatcagca tcaaaggcag   44820
caaggacggc gtctataaac agatcgttcc ggatgtagaa acccttggtc ctctatatga   44880
cctgaaatgg aatttggatt gtattgaata cctgaagacg gctgcggtca tacaacgttg   44940
ggtagatcaa tctatcagca ccaacacatg gtatgaccca gagaaatatc cagaaggcaa   45000
gatcccgcgc tctcttatga tgcaggatat tctgtctttc tacatgtggg gtggtaaaac   45060
tctgtattac aacaccaaca aagactccaa ggaagacgag gagttgtctc aggctgttgt   45120
tgaatgtgac acctgtgttg tttgattagg tctatacaac acaaacgttt aatatcaggg   45180
gtgattcgtc accccttatt catcaggaaa gaaatatgaa cgaacaaaag caattttcag   45240
tatttgaccc atcttcagat aatacaggtt taccgttctt tggcgaccct gtgagcatcc   45300
aacgttatga caaagtcgca tggccttttg tgcagaaatg gtatgaaaaa ggtcttagtc   45360
aattctggcg tccggaagaa gtagacgtga ctaaagacaa agccgacttt gccacactct   45420
ccgcagcaga acaacacatt tacttcagca atctgaaacg gcagaccatg ctggattcta   45480
ttcagggtgc cgcccctgac gaggcgttca aggtgtggac ttcaacgcct gaaatgcagt   45540
tcgctgtaca ggaatggtgt cgtcaggaat ctattcactc cctgtcgtac acgcacatcc   45600
tgcgcaatac ggtgaacgac cctggcatcg tgtttgacca cctcctggac gatgccgaaa   45660
tcgtagactg tgccaagcag atcagcacct actacgacga tatggtgcgt tatagcggaa   45720
tgcgcatggg gggacgtttg tttacccgtg atgatatcat gaacgccaag cgtgcattct   45780
ggcgtgctct atttgccgcc aactccctcg aaggcgtccg tttctatgtt tcatttgcgt   45840
gttcttgggc tttcatgcaa ttcctcaaca aaatggaagg caacgctaaa atcatccgtc   45900
agattgctcg tgatgagcaa gaccatttga tcctcaccca aacactgctg aaccgtctac   45960
cactgatgga ccctgatttt gccattatca gagaagaact gcgtggcgaa atgacccaga   46020
tgtatgtgga tgtggtcaac caagagaaag agtgggcgaa ctatctgttc aaagacggat   46080
ccatgctggg tctgaacgca aatatcttac accaaatggt tgattggcta gcaacacatc   46140
gtatgggcgc gattggccac ccgtaccctg ggcaagcccg taaagacaat ccggttccat   46200
ggataaatga gtggctagat aataaaacaa tgcaatacgc attacaggaa gcggaagccc   46260
ctgattatct gactggtgtc cttactggat cagtctccga cggtctgaaa tttgtttaaa   46320
ggtgagaaat gattacgatc tattccaaac aaggttgtgc gcagtgttta caagccgaaa   46380
acatctgccg cattcgcggt attgaacaca agattctgaa acttgataaa gattacaagc   46440
tggaagaatt acagaaaatc actggtaaac agcgcatgtc tatgcccgtg attgtcctgg   46500
ctgatcaaac cgtgaccgat gttactggac tcgccgcaag tttaaaacgt tgatatttca   46560
aagcccctga tccaggggct ttacttttga aaccttcccg cctatacttc ccagtaattc   46620
attggcaaac gccacaaatt gaacagcagg aactatatca tgaccaattc tgaaatatat   46680
catgcttcta tgcattatca tgacctacgc gcccgtccag gacacgccaa acaaaaagca   46740
ttctgggtag cagaactcag attacgccgt gctgtcgtta accaccaaat aatcatgaat   46800
```

```
cggaaaaacg acaaatcacc gttgttggca gattcttatc ttgaactccg cacagcctat    46860
gaacaagcca aacagcacgt aataggagca taatatgtcc aacaaattac tcaccaaccc    46920
ccgccacaac tttggttata tccaattacc agaagtgata gacacgttgt ttgctgaaga    46980
caaggaagaa gtttgttggg caccaacgac tcttattgaa cgtgaaattt tcaaatctga    47040
agtggatgtg atgttccgca tcggttcatt cggagacctt cattatttgg gaaaagtgac    47100
tgagttaaag acctgtcacg ctcaaagatt tttgcgcatt gacaccactc aatgtgaaga    47160
catttcattc agcattctgc gtgaatatgt tcaggtcaat cgccctgtgt accagcaccg    47220
cccttacctg acgtctatgc atatagacaa ttatatttct gacattcatt tacgtgcatc    47280
aactatccat gaagaagatt ctggtatcgc ggttgataca gtactcaata tgatcgtcat    47340
tactttggtg ccgtgatatg tacaaattcc cgatattaga aacggtgtac tctgttcaca    47400
aaaaggaagg tccattattt gaaaatttgg atattctgtt aaaggaaaat gtccgtatcc    47460
ctctggttct aaagggaaag caaataggat atagccatga ctgccaaata atgcgttctg    47520
aaggcatcga cgtcttacgc atccgtctaa catttgtgtt gacaggtgat ctggacggta    47580
tggtggttaa tctgaaacca accaccatag tccacagaac gggtgggaaa atattatatc    47640
gtttattaac tcattttgag atagtgacaa aatgttctgc caccgacgtt ctttgatcaa    47700
tttgtccgtt tcaaccatat ggtatctgtt atcggctctg ggttgttaac cacataaaaa    47760
gttatggtta cgcccagaga atgataatcg tcagacaatg acacatcaac tgattgtatc    47820
tccgctctcg gttcaaataa agcaatcgcg tcttcaactt tgtttttaac gtcaacctga    47880
attgtggggt ttgtattttc ccccagcatg gtatacagcc cagctccgat acttgggtat    47940
gtcggccaat ccccaacagt cgacatcacg atattccgca cggattgcaa cacggcataa    48000
acacctgttt tcttagtgac atctttggtg accggatgca tgccaaactt caggtcaatg    48060
tccttgtact ctttcatgtt aaacccctttt ggatattgcc tctccggcac gagagggcaa    48120
tatctgccct cgccagtgta atcatgcgtc tttaccacca aagttgccgc cattatcctc    48180
tagttccggt tttatatcaa ttggaccagg accagaagta gatactggag ttgccccagc    48240
gcgtgatgca gcacgaccag caccttcagc atatttgatg ttgccttcaa tagtctgcgc    48300
caccgacaac ttatcacaaa ctatttcact agccagtatt ttaggcactt tcaaagtatt    48360
ggaaacttcc aacatctcgc agatgatacg catcacgttt tgcgcttgaa tttcggccag    48420
ctgtgaaaat ttcaacagcg ccgtgccagc aaccacattg gaatagttcg atgaatgtag    48480
atgatagacc tcacctgtct tgcgctgaac ttcagtccca ccaatggtca ggttgtgatc    48540
acgaccaaca tagtaacgtt tgtcaaacat cgtcagatca tagtgatctt taactgattt    48600
attgaccacg tccccgtcag gaagcatctg cttataagac cccgaggagt gcatccaatg    48660
gagacgttcc ccgcctggtg tgtcatcaac ctccataata tgtcccgaac gagatgccat    48720
gacattgttg taaggataac gagacccgcc agcagaagga accgcacct ctcctgtgtt    48780 atcaatatct tgaacacgcc cagaaggagg cggagtttcc tgaacttttg gtgtacgatc    48840
agggattggc tcagaccatt taccatttg ttgtgtagga gccgccgatg ctgtcgtagc    48900
aggaccaggc caacgataac ccaacacaga tgagcggctg aagcgactca ccttcacaga    48960
atctgattgg ttgcctccaa tacaccaaac ataattggca tcgaatttct gcacgaacgc    49020
aacgtgtccg aatgttgggt tgttgccacg ccggaataca acaacagcgc cgtagcgggg    49080
ttccgacaaa ggggaacccc attgcaaata tgaacgagcc aaagccgagc gcgttgaagt    49140
```

```
gtatcctgct tggatcaaca cccatcccac aaatgatgca caccagctga cttcatcttc   49200
cgaagcgccc aaagatgttg tcttgtgata ttccaaaatc cttgggttat tattgaattt   49260
accagaatat tctttgacac ctaattcacc acgagccact gtcatccatt tctcaggatc   49320
ataaccgtcc acaggaggtt gaggttctgg ttgaggttcg tcttcaatct tgacaggaac   49380
attttcaacg gcgttatatt tctgcctttc tatagattga acgacctggc ccagcgccaa   49440
cgggtttgtg tctgaaccat ctgttggtgt cgccgctggc caaacccagg cgatacgaat   49500
attttggtat gcttcatcca aagcaaaacc cataacatcc gacccgactg taatacccgt   49560
tggagaccag cctaaacctg ccgaggaggc gttagatgct ggcatgagca ttttaccccca   49620 aggcaataat tcggtaggta agagagtggt atcttccgtg tgtacaccat agatgcgcac   49680
agcgacgcgc ccgttctggt cgggatcatt cacgtcttca acgcgcccgt aaaaccaacg   49740
caagttgtct aacatattga aacccattag tcaattagaa tcatgggtta tttatggcgg   49800
ggatttgaaa tctgtcgaat agtaatatta taggaagctc tgcttccgtt caactttatt   49860
cttttcattt ctactcgctg aagctcgtaa caccgccttg acaggcagtc ccattccaat   49920
gccatggagg cataaaggcg aggaaaatac tgtacacctc agaacatgcg tagaaaagga   49980
ttatttttgc ttcaaaacaa attcaaaccc caatttacac aacacttact tcagcaacaa   50040
cggttttata gcaatttaag gttaaacgtt cctgtcttaa cctataaaac agttaagcaa   50100
agaaaacccc acattacgtg ggggttggaag atttcttaga caatcggatc ttcagtgtct   50160
ctgttagcaa atcaagatgc caaggcatcg actcgcttat ttcaaatatg ctatagccat   50220
gtgcctttaa ttcgtcacac atcacaaagt aggagagtaa atcaatttca aaaattaaat   50280
gaaaatttca gtgacactgt taaatttgac ttcgtgttct ttcccacacg aaggacattt   50340
aattttcgtc gcgtaacgga tacgaggaat cttttttaaag aaatcgtcgg atatatcttg   50400
aacaatctca gattcaatat tttcccccac ccatttaatg aattcatcct tgacacgttg   50460 acgttctttta gcaacatcgg gagatatgcc aggctctgct ggattctcta ctttccaaac   50520
ctgaccatca tcgtcataca aacaatcaat aaaggtcgcg atcatttgct ccacagatga   50580
tgcttcgttg agcactgagg cgtccgagaa ggacggttga cgcatcttga tgtgatagcc   50640
accagggagg tcaaatgttt ccctgaagcc ttctggggac acgcatttca cttggttgag   50700
ggggatcggt aaaacaagtt cttgaccgca ttctttaagg ccagaaactg gttcttcgcc   50760
ttcatctgtg gcagctggaa cttttgttgtt gcatttgtaa cgtatcttca tgatctcacc   50820
gatagatata cagcgcatct ttaaaaatac ttccttcagta acaccgatcg gcagtttact   50880
aaagggaacc ccagcgtcaa cacaactatc aaatagttgc tccagcgtcg ccacacgttc   50940
actcatagga gtgttcggat cagcaacctg aagtaacatg gtctgttgcc ctgctgtgaa   51000
ggcgcggtat ttgatcacag tcggccagaa atcactttta tgtgttctct cagttttggg   51060
caatgatggg aaattcataa tgtatctcca cggtatattg taattgtatt tataacgagg   51120
actgaaaatg cacgcgttct gtttcagtaa agtgggggag caactcgcaa ttaattatcc   51180
ggatgcaaac acggactttt ttgtattact cacagatttt gcaaataaat tggggataaa   51240
gaatgtcgcc atgaccgtgt ccgatatgaa attcgggtgg ctgggagtta aagatttatt   51300
gaattatggt ttcaatgtga ttatcgttga tccaacgtac agcccaattg aagaggatga   51360
tgttattccg gtttgggtgc aacgagatat taacaccctg gacaaacact atccggattg   51420
tatcatcatc ggtgaattaa taccgtattt tcataaacgt cgtcggcttg aatcaattaa   51480
aagttatttt caagatagcg atgacggata taaaatggat gtccttacga gcggttgggt   51540
```

```
tgtgaagaat accacaggca acgccgaccg aattacttct cgtctttatg aatatgttaa   51600
agaacgggat tatgaactgg agaacaataa tgccaaacgt agaacgcgct gatatccagc   51660
aagtacaaaa agttatcctt caacgcctcc gtgctgttat cacaaatgaa aagggagaaa   51720
ttgcgccagg gtttgaaggc gcattcgacg gtttcgttgc cgatgatcag gggaacccccg  51780
ttgtacaaac gatcgctggc atgattatgc tgaatagcga atttatggct gatggtaaaa   51840
tccattattc tcccaatctc agtgttgacg gagaatcttt ggcttccgaa gtggttgatt   51900
taacggttgc cgttggtgag ttgggttatg ttttgatggt ttgcaccgcg cattatgtgg   51960
acgccaacgg ccatgtgtcg tatggtgatg aggcgcgagg gatcaaacgt catgtggaca   52020
cttctgcatt actgcaacag atacgtcaga tgcaagaaga aatggactcc aaacctcgcc   52080
tgattttacc ggaaagcaaa atcgtcacca gataatccgg tctaaatacc cataacacaa   52140
tgaaacttcg ttatgggtat ttttatgaaa ttttgcggaa tcgactattc ttacggctgt   52200
ccagccatgt gcttctggga cgacaaagat cctctggatt tgatcatct tcatttctat   52260
gcacatcata ccgttgagaa gcactgtcgt caagtgcgac acaatattct tattttacgt   52320
caacccaaat atgaatcccc cgaagaacgg ttttataaca tttccaaatg ggctgaagcc   52380
gtacttctta cagagaagcc ggatttcatc accctagaag gctatgctat ggggaattca   52440
aaaaactcca acaacatatg ccaaaccgcc gagaacacat ctctattgaa acaagcgatg   52500
cgccgtaaca atatggaatt tcagattgtt accccgtctt ttgttaagaa acattttttgt 52560
ggtaaaggaa atgccgacaa attggtcatg atagatcact ttgagaagct gttcaacgtt   52620
aagatgcgtg gtataatgga catgttggac gtgaaggatc caaagcctat cgatgatctt   52680
gtagactcat tcgcaaacat ggtgtctgga ccttacttca tagaaaaatta tcccgatttc  52740
aatagaggtg taagaaatga ttaattactg gctgttggca gacatactgc ttttcgcctt   52800
gctgttgata acggcatttta tttgggttaa gggattcttg acattccttc attcattaag   52860
tgccatggta tctttctatg cggtttcgcc acatagtgac gtcaatgtaa gagctgcaaa   52920
tcaatctgat atgttggccg aatatgtttt gctgcgtgac aaagcaatca ggattgtcct   52980
gttttctacg ctggtgggag cagttattat atttctgcga cacgtattgg aggcgattca   53040
tgccgtttta tgattatgcc tgtacaggtt gtggaaattc gtttagtgct cgaaaatctt   53100
gtgctgaacg tcatacacct gaattagagc catgttctga atgtggcggt gaaataaaaa   53160
tgattattgg agcaccaaag atcgtatctg gtgttcgtgg tcctcagtcc gcgcctgatg   53220
gcttcaaaga cgttttgcgt catattaaga agcaatcagg gaagggaat acaatcgatg    53280
tctgatcaac aaatagcaca agtgctcaca ccagattctt tttccgaatt ggtgttgatg   53340
agagcaagcc aacgcaagga atcaatcctt gaaacgatgg ccagtgtttg tgaagagtat   53400
gacatcgaag aagcaaaggt caaaaaattg atcacgcctc tcttctgtc aaggctaaca   53460
gctgaatgtt ctgatgctcg gttgttgaag ggtgaattga aatctaaaaa actcatttaa   53520
ggttgtaaca tgagcaaaga gcaaatctat aaaatgttga aggcgcaaga gtatctgcca   53580
ggttctatcc gctggcggca cggtagcctc aatgaacatg ctgatgatat ggatcgtgta   53640
cgttacacga cgccggaagg taatcctat gtcatcgaat accatacatt cttggaaggg    53700
cacaaaacct tctcagatgt gtacgatatt attgaaatag acccagcaaa acaaatgatt   53760
gcgggttaac tcaatagcaa aacgcagtat aattacaccg tcggaataat tgacaaatac   53820
atttacagaa tagcccgaag gggcggatta tagaggaata ttaaaatggg taatttattt   53880
```

```
gatcgtctta aacaatctcg tggccaacaa gccgaagcta tgcaacagcg actcgctcag    53940
caaggccagc gtgttggtgg cggtcgtgac ccacgcatct ggaagtggac ctggaatgac    54000
aagggtactt ctgaaaacat cattcgtttc ctgccgatcc ctttggtgga catgaaggct    54060
caagaagaag gcaccatccc tgaagatgct gtgttaactc cgtgtgccat gatcatgaaa    54120
cacgcattcc agggcgctgg tggttggtat atcgaaaact ctccacagac tttcggtaac    54180
gatgatcctg ttcgtgacca tgaccgtcct cgtgggcac aacagaaaga acgaatgat    54240 gaaaagctga aaacagttct caaaaaacgt ctgccggaca ccaaatacta cgccaacatc    54300
ctggtgatca agatggcaa caatccggaa acaacggca aggtcttctt gcttgagttc    54360
ggtaatgccg tcaagaaaat cctggattcg gctcagaatc ctaagttctc aactgaccct    54420
aaattcgacc cgttcgatat gtgggaaggc gcgaacctga ttctgaacct ctttggcgaa    54480
gagaaagagt tcggcaactg gaaggtctg gtggccaact tcaccaatgt gaagtgggat    54540
actccggcac ctttggggac agacgaatac attgaagaga tctgggaaaa agagcacagc    54600
ttgtttgagt tctttaatcc ggccaacttc aaatcgtacg aagatctgga aaaacgtttg    54660
cgcaaagttc tggccatccc tgataatcag cctctggttg aaggtggtgc ttctactatg    54720
gcgcatgcgc ctacccagtc tcaggaaccc cagcgcccaa cagcgcagga aagtctgaac    54780
caacaacaat ctcagccttc taatgcacag caatctgttc cagccaataa tggtggtgcc    54840
gatgcgaaac agacggcttc cattgatgag ttcgagcagt tcctgaagca agactaattt    54900
cgctaaagcc ccttcggggg ctttttagtt tttgacaaca tcctgcaaca atccgagtaa    54960
actactcttc tcagacgccg tcaggttatc attgcctaat atatccctct ggatgccgat    55020
agagatcctt tcgaaatcag ccaggctgat accagccaga ttgtttacaa gctgatcgag    55080
ttgcttataa gccagcaggg cttcacctgt gaagtttcct tctttgatct ttttatacag    55140
ctgtccggct tttgacgcag cggtttccca gtctccggaa gcaagagcat cagtaatacc    55200
caaaggaaga aaatcgctgg cgaggctgcg cgtttcatat tcagtctccg ataatacttt    55260
gttataagaa aaggaaatgt tgtactgatt aaattgatcg gcggcgcttt tatccaggtc    55320
tatagaactg aagttgatgg ggtgagcctc agtcacataa acgcgatgaa caacctgatc    55380
ttctgtatcc atttgttcta tacaaatatc ggtcacgaaa tcttcataat aacccatctt    55440
ggttgtgtat gggtcgaata tcagattctt ccatttgtcc atgaccgact tttcataata    55500
atcgttggcg aggaggaacg acaactccag atcaatgttc gtcttgttgt tcggcatttt    55560
aatgtggttg ccgttgttgg tcatgggagt agtgtcaatc cctgtaccag gtaaagatgc    55620
gaccatacac atcatttgca gggaacgaga tgtttggttt gtccctccaa agaatgcgtt    55680
tacaatacgg gcgctttgtt tgaacagatc cccaaatgat gaagatgaag gatacgcgtt    55740
cccatcattt gctagtgttg cattggaatc aaatatccca ggcggcaacg gaattgtaac    55800
acgaaatctg ttcttgcggg aaatacccg ttgaagcagt tgcgttagaa aattgcgata    55860
gtcttccacg atgaggactc catttaaata atatatctgt tgatatttat aaggagttga    55920
caaatggcta agaacgctat gggtgaagaa gacccgttgt tgcttcccgc cgagatggac    55980
gccccagaac tggtcaagcg ttacatccgc aaatatcgtc aacattttgg gccggaagcg    56040
aagcgtaata tccgtcgttc tcatgtgtgg tttatggagc gcgtgtcgaa agatgctaac    56100
ttatctccga atcacatgat gaaagcattc gctgaaaata acgtcctgt tcagggtgtg    56160 cgttatattg ttggtcgcat gtattatttc aaatatgatg cgctgactaa agatgaactc    56220
ccgtattggg atatgtatcc tctggtgttc ttcttcaatt ttgtgaaggg ggatggagtg    56280
```

```
aaattcggtg aacgtggtgt aacctatctt tatggcctaa acctccatta tttaccgcct    56340
aaactcagat tgttggtatt tgaagatctc attaaattga gaaatgaacg ggcatatcgt    56400
tctaaaacac gtttgagact tacctgggat gcgctaaagc ggtttgcgaa tcacccttttg   56460 tacaatcatt gtgtcaaatt ataccgcgca gatcaatttc gttcacaact ttatgaaatt    56520
gaaccgcaat attgggaggt cgttttgttt atgcgtactg ctcgattcca gaaacagagt    56580
cagatgtctg tttggaagga cgcacgtcgt aaacacaaaa atggttagtt ctaaaagccg    56640
ttctacgtga taattcgcga acggctttct ataaacatga ggttatgata tgtcacagct    56700
acatcgtatt tttggtattg aattcagttc taattgcgtt cgatatgatc gcacccataa    56760
agattcgggt ggtaaaaccg gatatgaact cggtagccag ttgggatatt ccaaggaaca    56820
attgtttaat cagcacaggc tgaatgaaac ggatcttctt aaggttatgg gtattgaact    56880
tgattccgaa gccagcttgg atctgggcga cgaaattcgt tttggcaaac cagaagcatt    56940
ggaattcatt gaagacttcg tttctggtta tacccaagcc gctacgaacc gccgcgctgc    57000
taatgatgca gtgggtaaat tctactttgc ggcgaaatat cttgccgaca acgtataca    57060 gatgaaagcg gaattcagta aagaaaatct gaaagcggtt ttcggcgaag aaggcgattt    57120
ccgtttaatg ccagaatctg gcactgattc agctcgtgat ttctttgaaa aaccatttgt    57180
ggtcaaaggc tgtaaaattc ttaccgacga agaccacgct ttcgcaatcc atactgaagt    57240
cgtttacaat gaagagaatt gccttgttat ttccagattg ttcaacagtc tgtcatatac    57300
agcgtattct ttgattgaac gttgtatgga agaagagcat cgtcaggtag tggtgaataa    57360
aattcgctta cacgttgagc agaattttaa cgggtttggt tgtgaatccg gcgaaatccc    57420
taatttctat ctgtagcaca agcaggggc tgtatgaaga atatgttcg cctgaacacg    57480 gtactggaat ctgtaatcga atatttcata atgcagcacc tgagagcaga aaatgaacac    57540
gtgagcgacg ctctgactta tgatcaccgg atagtggttc attccgtcga atagtggat     57600 gacgaaatgt tgattgccaa tgttgagcat gccctctggg atgaagtgtt ggatcagtat    57660
gttcaaccga agttcacaca gatcgagtta tctgccatgt ggccacctga acagttttc     57720 aatattgata tacaaagtta atattcacgt cagtccgcgc tattccagcg ttccgttgtc    57780
taacacagaa gtgttaacca acttttcaat aaaaagtggt ttacatcttc taaaaaggca    57840
gtatattaat gttccagacg cacagttgaa cattaaaaac tgccaaagaa ggttactaca    57900
caaaagggtt tttattatgt cctatattct tcatatcgag tccggcctga aatttgaaat    57960
tgatggtaaa accgctgctg atcttcaagc agaaatcaaa ggtgcagacc ttatcatcgg    58020
caacgtcacg ttgcgtcgca tgatggaagg cgtcctccag tcagccaacg gctttgaact    58080
cattgaaggt ctgagccagg aagagaaaga agagactctc gaagctcttg accgcgctga    58140
agccgaaaaa gttaaaccga ccgaagatgc gggggttaaa cagggcgacg gtgaatcaaa    58200
tccggtgatt gacgccgaag aaacggttga gcaacctgtc ggtgatcaaa attcccagac    58260
cgttgaagac ggttctcttg aagtcaacaa agacggctcc atttccctgg tagttgaagg    58320
cgaagaagtt cttgacgaag aagcgcaagc ccgtgctgaa gaagttcgcc gtcgtatgct    58380
gggcacaacc gttgctgaag caatcgccga cgttgaaaat ccgaaggatg atcaggcttt    58440
agcgaacgcg aaggcggttc tggccaagaa atcttctgaa atgcgtcctg cgtcttctac    58500
tgaagaacgc aagcgtcgtc ataacaaacg tgaagaaatg gttgacgctg ctcgtgcttc    58560
taactatggt ccaatcctgg cggcggttga agcagggggtt actcctggag tatatttgag   58620
```

```
ttatgtgaac cctgatatgc gctggttcca gttccctgtt acagaactgg cggatgaagc    58680
caatccgcat gcccgcacca atacgtatgt tgatctggca cctatcgttt ccggcggctg    58740
gggattcagc ctgtatgtga acggtaagtc attcaccaag cgtcagaaaa tcaaagaaac    58800
tgacgctgag tctctggtga aggcaatcaa cgaatggttg cctcaggcgt tggctgaagc    58860
gaaagatgct gcgtaattta actcagaagc attcaataga tgaaggggct gctataatag    58920
cagctccttt tgtttattgg agcacaccat gtcgtattcg ctcaaagggt tgttgaagcg    58980
ccctgttcat ctgtttgtaa accacccgc tgttgaaggg gaatatccgg cacgaggaga     59040
gttgtattac gttaaaggct ccaacggtag cggcaagtcc actgtccctt cctatctggc    59100
ggagaatgat cctcaggcat atgtcgtggc ccgcgatagc aagatcatgc tcacggtttg    59160
cccttcttat aacattatct gtatcggtaa atatgacaag tctaagtcta aggtgttga    59220 ttccctgaaa gacaccgagc agatgttgtt cgccttgtcc attgcggacc aaccagaata    59280
tctgaaatac gacgtgatat ttgaaggcat catcccttca actcttctca gttcatggat    59340
tccccgcctg acgcgcccac cacgagaatt ggtcgtcctc ttcatggata cccctcttga    59400
aacatgtatt gcccgtgtga atcacgcaa tggcggcgca gagttcaatg aaagcctggt     59460
ggtcgaaaag tgggagagag ttcatgacca ccgccaacgg cataaggct tgttccctac     59520 cgttcccgca ggtatgatga agtctcacgg tctaacagta gaccaagctg taatggcatt    59580
cctctgtcgt gattttggga gtattgattg tggaaattaa agcaataaac aacaacgaca    59640
tgctgaaaca ggctgtcttg gctatccgtg agcacgggat tgaatctgat ccaggtaacg    59700
cggagatcaa caccgacggc acccgcttcc tcgatggtgt gactattacc gtcagtgata    59760
ttcgcgaccg ctggctttcc gttgaaggtc gcaactcatc agcaatagca gccatcggcg    59820
aaaccttctg ggtgctgtcg gggcgcgatg atgttcgctt cctttctcgt gtgttacccc    59880
gcgccgctaa cttctccgat aatggccaca cgtggcgagc cgcctatgga ccacgcctgt    59940
atgcccatgg ccagctggat agcgtcatca accgcctgcg caagaatcct aacacgcgcc    60000
aggcatacct caccatctat gatccggctc tagactcaga ttttggtctg gcgaagttca    60060
gcctgagtgg tgaagcgaag accaaagaca tggtatgcaa cctggccctg ctattcgcta    60120
tcgttgaagg tcgcttgaac ctgacagtca tcaaccgatc gcaggatgtt ctctggggta    60180
tgagttcaat caacttcatt gagttctcta tccttcagga agtgattgct caggtgctgg    60240
atgttgacgt cggccagtac aagctcttct ctaacaatct tcattactac aacaatgaaa    60300
tgagccagaa gcagctcggt aagatcacga aggaaaccaa agtggaagcc gggttcatca    60360
actcgttgat ctacttcaag aacgtgacca accagaacca tatccgtgat ctattcactg    60420
gtgttcttca tcactgtgat attggtagcc cgtgggaaac tgtcgtcgcc catcttaaga    60480
aatacgacgc tgatcgcggc ctgataccac agatggcata ctgcttgtac tgcaaactga    60540
acgactacaa gatcaacatg gacatgatcc aagaccacgg gttgaacgca gcactgcaac    60600
attcacctgt tgaccgcaag atcattgacc ccaagttcct ggaaggtgtg gtatgatgta    60660
cccgaacctt gaattcttca cggggcgcaa gcgctccggt aaggacttct gtttggagtc    60720
cctgatcagt tttcatcata ttcagggtga tatggatatt cgtcgtctgt ctttctcgga    60780
tgaactacga cgtgtcgcta atttcatcta tccatggcta ccagcggagg tggaggatgc    60840
tgtgaaggac gttcccttcg tacaccctga taaccccaag ggcttatccc cgcgccaaat    60900
ctggcttcat ctgggcagcg atacgggctt gcgttatgta cagccagacc tgttcctgtc    60960
attctttaaa cgatatcaac ttcctttggt tgaacagaac cccaatgttc attatatcgt    61020
```

```
gagtgatttg cgtactcctc aggaatatga atgggcgctg agcactaaat gtcctatcac    61080
ccgcatttca aaggcggatc gtggtggtat catagaggat gacatagagg ctttcattga    61140
taagatggaa gttgattatg aatttgtcaa tccgtttgaa ggttggcaac cgttcgtcaa    61200
attttatagg gatcggaaat gatcacagca gagcatatta aaagtctgct cgaacttcaa    61260
aaggccacca acgtggccta ctttggggaa gagtggaaga atgtatggag tcataacgcc    61320
gtcgtcaact ccatatatcg tgagtgggca gagtttcttg atgaaacgac tgctgactgg    61380
aaggtttatg gaaacgacat cgggtttaac catgcgaacg cagtctatga actggtggac    61440
gtggttcact tcatgctgtg cttcgtcctg ttggaccgta ccaaaggcga gatcgaagaa    61500
gaattcgaaa tcctcagtgg tcgcgaattc accttatttg cttcgattgc tgtcggacat    61560
cgaggtgtga cgtatcgcct tgggcaattc atgaacgatc cttgcgtcga gactctcatg    61620
ttcttcctgt cggatgcttg cttttacatg gagattgaca ttgagaccta catgctggca    61680
cacaaacgca aaaatgatcg caatcggctg cgtgctgctg gtggcgcgaa ctacgataag    61740
tccgcagaaa cccctctgac cctggagttc taatgtttac agttgtcgta tcatattatg    61800
cggaacatgc cccgcacatg gcagagaact tcgctgagtt tattaaacca ggcggtcatg    61860
tcgttattgc gaccaatttc aagaaagagc cagatggtgc ggctactgta acacaacaca    61920
ttacaaccaa agagccggaa acactttta aacgcattga ggattttgct tttggcgggg    61980
aagaaattcc agagtcatta cagcatatct attttgaaga tgcgatatat tatattcatg    62040
ctataccaaa ggatgttacg accgaacaac taatgtatgt tttgaatatt gcgttaaatt    62100
tatcgtgcgt caacagggca cagcataatc gtttgcgcaa tatgtattta acagaacgcg    62160
ggggttccga aattaacgat gaaaaactcc cgtcaataat ggcgattcac gaagcaatca    62220
atatattgtc caagaaagtc ttgggcaccg atttattaat tacgatcaac aagcaagagg    62280
aaacgaaatg gccgattcat tgatggctcg catgctcaag acagcaaaga aactggaccc    62340
gaatgccgaa gtgctgtcaa agaccgatgc gctgaagcct gacattattt gcagtacggg    62400
tattcctatt ctgaatttgg cctggtccgg tcgtattgat ggtggtctga tatcaggcat    62460
caaacagttg gtgggggatt ctcgtacatt caaaaccatg tttgggctgg tggatgttaa    62520
ggcttacatg gataagtttc ctgatgcaat ttgtatcttc gcggattcag aaggcggtgc    62580
gaatgaaaac tactggacat ctatgggtat tgacatggac cgtgtcttgt atctgccgat    62640
tgaaaacgtt gaaagacga agatcaagct gacacagctt ctgaacgatg cacagaaagg    62700
tgacaagatc atcgtattca ttgactcaat cagccagttg ccgtctacca aagaagttga    62760
tgatgccatc gcgggcaaag acacacaaga tatgacccgc gctcgcgctc tcaatagttt    62820
ttggcgtgtt atcaccccgt tggtcactga aaagaaattc gttttggtat ggatcaactc    62880
gtactatgat gaaatcggga accaatacgc cgagccgaac atcaaaggcg gtaaacaggg    62940
gttcctgtct tctaaccaat tgtggttcat cacgcgtgct caagttaaag aagacaaaga    63000
ccttttggga tggcagttta cagtcaacat tatgaaaggc cgctttgtcc gtgaaaaagc    63060
caagttccct gtcactgtgt tgtatgaagg cggtattgac cgttggtccg gtatgttaga    63120
aattgcgcgc atgctggggt atgtggattt ggtgagtggt tcttggtatc aacgcactgc    63180
caaaggcggg tttgatccag aaaaagaaaa gaaatatcgt aaggcagagc tgggggatga    63240
cttctggtat ccgctgctgg aaaacccaga ctttgttgac gatgtgaaca acatgttcgg    63300
tatctctcag agttcggtta tgcctgcaga tatgctggag cgcctcgata atgtcatcaa    63360
```

```
aacaaccgag taatattgca gggggaggag actcccccgt taattacaaa atcatcgacc    63420
ctggttctga tcagttagca ataatcgaaa taacggaagg caaattccgt ggcgttcaat    63480
ttcgtatagg gaaagtgggt gtccatttag ataatggaga gcctcggtta tcctttacaa    63540
cagatatatt gaagaaacca tggcgtttgt tatttgttaa tttgaaagaa aatgacttgt    63600
tcactgtggt gtctggggat atcttagttg atctgataca gcaaaatgct caggattaca    63660
acaaaatttt ggtggggtag ttgccaatgt tactcgaatc tgtcgtgctt tcccaattaa    63720
tctataacga agaatatcaa agaaagatcc agccgtattt gaaagccgat tatttcgata    63780
acgaaggcga gaaaattata ttcggtctca ttgaccatta cacttgcgaa atataatgctc   63840
gtccttcggt tgaagcgttg tctattatgc tggaaaagac ttcgctcaac gaacacgtat    63900
ttgaacaagc tatttctgct cttgagaata tcaatgacaa cacattccat caggaatggc    63960
ttgtaaaaga aacagaaagt tgggcgcggc agaaagctgt tcataatgcg atcaaacacg    64020
ccgtcaacat ctatggtgat gagaaacgta agatgagat gaaacgcatt ccaactctcc     64080
tacaagaggc gttggcgata agttttgatt cttatcttgg ccatatctat tgggaaatgg    64140
ctgaacaaca atacgaccac atgaactcta atgaagcgaa gattcctttc gctgtagaga    64200
tattcaacaa agcgactcgt ggtggtgttg gtaagaaaac gctgaacatc gtgacgggtg    64260
caattaatgc gggtaagaca acaactctga ttgatttggc tgctggttac tccgagcaag    64320
ggttgaacgt attcgtattc accctagaag tggctgagaa cgtctggcgt caccgccttg    64380
atgcccgtat gatgcgcagg gacttcgagt ccttagagaa gctctcacga catgaatatg    64440
tcgctacgat acaaaagttg cgaactcgtc aagacggttc catgaagggt gatattgtta    64500
tcaaggaata tccttcaggc gctgggcata caggactgta tcgccgcgat attcttgatt    64560
acgcgacatc aacgggaatt acgccggacg tcattattat agactacttg ggtgaatcag    64620
cgtcttctcg tcttcctgct catttaatgc agaacaccaa cgtgtattat acttcggtgg    64680
cgcgtgaatt ccgtgcgctt ggatttgaat ttgattgccc tgtatggacg ggtatgcaat    64740
ttaaccgtga aaaacaatcg gcgactgatg gtgatattag cgacctggca gatgctatcg    64800
gtattccgaa ggttgcagac ttcatcatgg cgttctatgc tcctgatgaa ctggcggctg    64860
ttaagaaagc cagagcatca atcttgaaaa atcgttatgc caacaagcag aaactcaaat    64920
cattcttgtt tggtatggac caagataaac agatcttgtt cgacttggac tggaatgaag    64980
tcaaacgaga cctgactgat gaagaagccc gttatgttga gaatgttcat atcaaacatg    65040
acttaaacaa aacaggcgac tcgaatgatg tcaagaaagc cgagaccgtg aataattgga    65100
atttcggtta acttcaataa tggtgatcat agggtataat ctctatgatc tgaatattaa    65160
cccaggagca catcatgtcg gatgttgcat ttatagctga cctgattcgg gcggcacaac    65220
aggtgtgcca gtctggagaa accagtctca aactcactac agagcagact ctagaatttt    65280
ataagaatcg tcggcattgg ggtaagaatg tcaagataca ttgcgaacca ggtgaattgg    65340
ttcagcttga tcttccgtct tttccattgc cagtacagac caacactcag gaatattaca    65400
atgttgaagg cgttgatatt attcctaagt ttggttttca cagtatcgtt tatttcttcc    65460
tgcgccgttt gggaactagt atcggtccac tcggttctcg tcattaatga ggatatatta    65520
tgtcagttga acaaattggt ttttatcaac tcccttctga tccaaaactg cgtcaaaaga    65580
tgatgcagac tttagaaaat tgtcgtgccg cccagatccg tatcaagtct gaacagacct    65640
ttgttaccga agccctggct gaattggcaa aagaaacagg catcaaagcc gttgatctgc    65700
gcaaagtcgt taccgatcgc gctggtggaa cttataccaa gaccatcgag accagcgcca    65760
```

```
aataccaaga tctttatgag tcgctgtatc ctaacgccgc gcctgatcgc acggatgaat   65820
aatatcggtt aaagcccaac atttgttggg ctttacttca ataaaacttt acttcaataa   65880
aacttgcggc tatcatttaa cctacattga aaagtttcac tacatcatga gaggcaaaaa   65940
tgaaagccaa gaccttcagc atcccaattg ataacattgg tcgtgtcaag gaacgtcttg   66000
ccaaacttga aagaacggca aaccgcctga aactcgagtt ccctcttgtt gagttcagtg   66060
aaccatacaa aacacaacac cgctattcta tcactggcga aaaatttat cgttggtggc   66120 aagattgtac tctaactggt gaaggcatcg accgccccgt ttcttatggt gggtggagta   66180
tcattggaca attcaaccac cagtatccaa aagtcattct gaataaactg tcagatgaca   66240
tccaccaaaa tttcgttcaa agatttgaag ctgaaaacgt atcttggtgc gagcattgca   66300
acaaatctgt gcgtcgtcat aacacatatg tcgttcgtaa cgaacaatct ggcgcacaga   66360
tgctcgtggg tagcagctgt atgcatcatt atgtcccgca tcagaaatcc cttgatgcgg   66420
ttatgtctta ttacatgtct attcacgaaa tgtttacccc cgatgaagat gacccagaag   66480
ggatttatcg ggttaatgaa ccagattatg ttgacacaga aggatatttg cgtaaatgct   66540
ttcaggtttt gctgtccggc ctgagcatta aaagtgatga ttttggtcga gttcttggtc   66600
atatctctag cggtactcgt ccagagaaag gttctgacat tgatatattc tataacaagg   66660
ctgttaaagc ccgtgaagat gctcaatcag aaatgtacca tatgatgctt ttcatctcat   66720
cgttgtctga aaataacgat ttcaacgtcc ggctgaaacg tatgtgcgaa cctggttatc   66780
accttgttaa agactcaaca acagttcgtt ggggagcagc aaagtattat gattatatcc   66840 acacccccg ccaaacgcgc actgtatcaa attgggttgg tgaagttggt gaaatgttag   66900
aagcacaggt caaatttgaa gcaaggattt tcctgtattc atctgattat ggtgacacgt   66960
atctgtatac tttcaaaacc aaggaaggca ataccattac atggaagact tcctatatgg   67020
aaaccgaatt cctggaaggt gatatgatca ttcgtggtcg cgtcaaagaa ttgaccgaat   67080
tcaaaggtgt taaacaaact cagatcacaa gggcaaaact gaggaaatta tgattatttt   67140
tcaatttgtt ttgaaagcat ttgcattcgg tcttatcgca tgcggagtga tcacagctat   67200
gctgttaatc atagccctga tcatccccctt taagaggaaa cgctgatgga atgttcatgc   67260
ggagggcaag gcacaagtgc atacttgcca tttaacaccg tcaaggaagc cgaagacgct   67320
ggatatgccg tggacaaggc tccctgtgta attgccacca aggattgtcc gtgctgtaag   67380
aggcactctc agaacgtttg gtatgcccca gaagcaaagg gtaaaattaa tttattgaat   67440
atgatgagga agtaatatga ccacactcgt agaaacatta ttccccaggat gcacccttgg   67500 gcgcggcggt agcgaagcca acgggctggc aattgacgcc gaaccccaga actgcgttgt   67560
tatcgacaaa ttccatgaca atcactatcc tttgagccat cgccgtgatc attatctggt   67620
ttctgttggc gaaacattgg tctctcttcg tatttgtgaa gcaatgcctg gttatggtta   67680
cgatgcattt gcatatatcc atagcgtttc caatggggaa atggggaaag aatccctgac   67740
cgaacaattt aaaggatgga aagaatcttt cacttctgtc aaggaaagga gttagaataa   67800
ttctattgaa gtctctgggg ttataatagc atgacgaata accctggaga cacatgatgc   67860
ttcctctttt agaaataatt caaaatcttc gcgataccaa aggcaccaac gccaagaaag   67920
ctgtgctgac cgaggcgttc agaaccaatc cggaattggt tgatttcctt caatacgtct   67980
acgacccgat gcgttcttat taccgcactc aattcaatat aaacgcattc cctcgcatgc   68040
tctcgcgcgg cgttgttggt agctgggatc aggtttatga cgttcttgat atgatggccg   68100
```

```
aacgcaagat cggtgggatg aaggcagatc aagaacttgc gaaggccgcg accaacatcc   68160
atccggatta ccatccctg atacaaatta tactcgacag agacatcaaa gcgggaattg    68220
ccgagaaagg tataaacgca gcattcaacg cagcaggtgg tacagggcgt ctgattaata   68280
tccttccata tcaccgttat gataacatga cgattgactt gctgaagaag atggacttca   68340
agcgcggcgt cttcagccag ctgaagtcag atggcatgtt tgccaacatc atctgtcgtt   68400
atggaagaga cccagagatt cgttctcgtt ccggttctct tattgcgggt ggttccgttg   68460
ataacctatc attggttttc aaagacctga tctacgatgc ggggattggt gaaagcgtct   68520
tccatggtga actgctcgtc attgatctga aaacgaatac agtgttgcct cgggctatcg   68580
gcaatggtaa gctcaacagt gttatccaaa cgggtgaacc cctggaagat cgttacaagg   68640
tgatctatcg ggtatgggac gttgtgccgt atgataattg gttcaatgct cagcgtgtgg   68700
acaccccata tgagcgccgt tttgatatca tacaacagtt gttcgaaggg gatgacggac   68760
tggttcaggt tcaagaaacc cgtgttgttc attcatttga agaagctgtc gaacacttca   68820
aagacgcttt ggctcgtcgg gaagaaggca cgatttgtaa ggccgcagat atgccttggg   68880
aagatggaac atcatctgaa gggttaaagc taaaaatgga agtagaatgt gaccttgaaa   68940
tcgttggctt caacgaggcc gataagaaag gaagcacgc caagacattt ggatctctcc    69000
tctgcaagac ctctgatagc ctcttagttg ttggcgtatc ggggatctca gatgagttga   69060
gactacgaat gtgggaaaac caagaggact tcattggtaa gattgccgcc gtgctctcta   69120
atggcgtaca ggataaaacc gatgacgcca tgaagtctct attccttcca cgtctcgttg   69180
aagtacgcac agacaagaaa gtcgctaata cactggctga agtctatgct atccagaaag   69240
catatatcga aaatattttg gtgttgttgg aagcggcatg aaaattgggg ttcttcggaa   69300
ccccattcaa taaagacagt agcagtataa ttccaagaaa tcattaccag gtgttattat   69360
gaaacttatt gataagaaac caaggaaaga caatgattct cttcacctca taaacattat   69420
gagggaattg ggagtttctg aattacagat gatgaagatg atgaattgtt ctgacgttgt   69480
ctataattgg acaaacggtt atcgtcttat cccaaaatca ttccgtcgtt ttattttggc   69540
attggtgttt attcatcgcc aaggaaaaac agaagagttt caacgttcg ttaaatcaga    69600 ggagagatca cgtggttggt aaaaatccgc cgacatatgc caaaatcggg atcgctttcc   69660
ggaacgccat gcttttcatt aaagagaaag gcttggtggc ggagttcaat cagttctgtt   69720
ccgaacgccg cagattacag aaacagaaac agaaaagcag ggagaaacgc catgataact   69780
gagtgggaga aaatgcaata tgaaagggca ttcaacgttt attgcatcta tatggcgatc   69840
aaattgcatt tcaccacaaa agactttgat tatggcctgt atgggccgat gaacaattac   69900
aagtttgaaa cgttctattc taaacagggc gtggccaaac aatttgctaa acttgctcgt   69960
cggttcgaat cttcccaagg tgaagtggtg gaaaattata ttattgccaa ctttgttaaa   70020
tcaccaaaga cgtgggtgac aacattactt acaagacagg cccaagaaaa ttataatgaa   70080
tatcgccgcc tgtatgacaa cttctcatat aattttcttg aacatttga  gagatatatg    70140 atccctgaga taaagaaag aggcgtgaat tttatccaat atatcaaagg aaatggtaat     70200
gggcatccac ctttactgac agatattatt gttaaacgct atccaatttg gtttctcgtt   70260
ggattgaata aagtagtggg gttcatccat ttatatgata caatactcaa ggatgacatc   70320
tattggaact ctgagtcttt tttattaaag aaaaccaatt cagttgttcc tgatgaaaac   70380
acagaataca caaaaggaaa actccgtgag ctaatccttg cccacggaat ttgattacca   70440
atcccagaga atgcgccctg tatcagtacg gttggacggc tccagttgtg aactgttgaa   70500
```

```
gttgttcgtc gtactgactt tcttcgagtt gtccacattt tgttgtacag gcattaccac   70560
actggctggc gggttagcat aggcggattt aacttcttcg atgttattgg ctgctcttcc   70620
ttgaaccgga taagccccgc ccagagtacc tcccccgatc ccagcatatg catctttcaa   70680
ttgagaagtg cgatctgtta cgttcacagc atccgaagaa accccagaag gcattggagt   70740
cagcgtgctg atatctgcat taggttgtgc tggcgattga ctgttcggtg gtacagaggc   70800
attctcagga gccttatcgt cttggcttat cagcatagac tgtcttgctt ccaccatctt   70860
attcctggct gcttcaccac ccaacgcatc ggggataatg ctgacaaact tatctacgat   70920
atcaaacatc gcattggtga tagcattcaa catgttgaag aaaggtttct tcacattttc   70980
agcaaatcct ttcttcatgt cttcaacgac tttgtttgca gccgccatgc cgtcatctat   71040
caggccagtt attccacccg ttacccaatc aaccaatttt atcaattggc cttgcaagtt   71100
atctgcaagt ttaccaggta tttcggtcag tgatgtactc ttcccgatac ccgcaaacaa   71160
atcgttggtg acccaatcaa caatcgagtt caaccaacgc acgggcgctt cggtcatttt   71220
cagcacttgt tcacggaacg cctttccaaa cccagcattg ttccatccga atatttcagc   71280
aacccaatcg gcgagatccc cgaaactacc gaccagctct gttatccctg cctgaacccg   71340
atcaacgatc gatacttgcg ctttaccaag gatttcttta gcattaaaga acccttacc    71400 gaattcaaat acagatgtta tcagagccaa aggtccgact cgaagcatct tggttgctgc   71460
tttcagaggc gcaagcaacc cgccgatccc agcaccaaac cccatgaata atttaatgaa   71520
gccaccaaca agtttttaatg gggacatcag gagttttaac gcgcccagtc caaggagtgc   71580
ccccagcgcc gcgcctaacc cagaagattg accatcttgt ttaggctcag acggagggat   71640
agaaccagcc tctgggttgt tcttgttttc cttaccttct tcgccacgac ggaatttctc   71700
ttcttctcta tattttgat cactttcata gatacgtgtc agagtatcat taagatcttc    71760
gttcatgtat cccaatttgt catcaatgct gtcgaggcgg gtaacagttt cgttactggc   71820
atctttattg aaatccagcg tgtccttatg tgtttgaagc attatgtcag tcaggtttac   71880
gatctcccct ccgaccaacg ccagcttatc ctttaatcca tcaaggcgtt caagactatc   71940
ttcgttggcc gcacccaatt gatctgatat catgtcaaga tattcaactg acatgtcgtc   72000
aaccggacca ttcgccgctt caccaaattt ttcgatcttg gtggcgatac gcatcagttc   72060
ttcattgcca tcctttgtta gactgacggt gtctttcatc caagtgctgt aatcccttgt   72120
gaaaatagga ctgacgcgga caaacccacc aacaatatca ttcaccgatg ggaatttaat   72180
tggcgggact ttctgctcct gattagacgc ctggcgtgtc ttcagagatt gcagttgttt   72240
gttgacatcg gcgagctgtt tattcgtctc ggattgggcg cgcaattgct tgcgctccat   72300
catttctttt ttgattttat ccaaaacctt gacgatgtct tgctgccctg gtgtcggttg   72360
attgttatct gccatttgtc acctctcaga ccttctgggc ttgtcctttc tctattggcg   72420
tcggagttgg tgtagaagcc acagtttgac cagtctgagg cggtaagacc ttctggatca   72480
tactatcttt ggcaatctcg gcgacgcatt gataatcatt tgtcaggcgt gaaatcttat   72540
ggcgtatctt tgtgacgata taatggcctg atgataactt acttaactcg gcaatgtttt   72600
cattagattt agggcggttc gacaaatctt caatataata aacctgccca acattcagac   72660
ggttatcccc cacgaccagc aaacgcataa ccgttgacgc gaggctgaat tctataacgc   72720
gtcgtgcgta atctatttgt tcggcaccat ccggttgcgc ttcaatgtac ctaacgttct   72780
cgcggtcgaa ttgatcagag aacaagggaa aaggatcaag gtgagcagtg ctgtcgaacc   72840
```

```
attctgaata aatgcgttgg gtcgctgtcg tggattttgt actaaagtca tacacgcgct   72900
cgttcactgc caagatatcc cgataattcg ccatgtactg atcacgcgcc agtttctttt   72960
cagccttgat gatagtccgc atgaaacgtt ctgagttgaa attgttatcc tgcatcaacg   73020
gcgcatcttg agggtctcgg aagaatttct tttcaataga agcctcttgc ttctcttcag   73080
cagtcataga ctggttgccc tggttgaaca atgttgtcat gcttttgaag tgataacccg   73140
taaagtcttc atagaaaacg aatggcatga ataattcgtc atatgcacgg ctggccatat   73200
aatctatgga gcggagtaca ggccaaagag gggtggcgaa cctttcttgt atcccatatg   73260
aaggatctat gtcttcaaat tggtgcgtg aattcagttg ctcaaagatc ttagctgcca    73320
tctcagaata agaaccgctt aatccaagag atttacgcaa catgctatct cgatacgcgt   73380
ctgttgtcac caagtgtaac cagaatgcct ttttcgaaga agagttcgat tcatcagcaa   73440
ctctccctac ccgactgact cgcaatgaaa gcgtagtgta gtcggaagcc gcaggtgatt   73500
tgaacgatac cactacttcc tcacctccga ggattggcat tgtatccaat atatcccagc   73560
cttctttgat cagaatatta gctgtcagcg acggtgaagc attcccttcc agaccaagat   73620
cctgatatac gttgaattct tgaaacaacg atgaaaggtc ataaggcttg ggagtaccgc   73680
cttcaggcgt gtgcggtaat atcgccatat atttcaaatc aaatgttgtg gacggagtta   73740
aaattccgtc ctgggattct ttatttttcga tcatttggtc agctcctgtt ccagctgatt   73800
aacaaaggaa gaaacataat ctgggtctag aacctgaata ttccgtttgg cttcgttttt   73860
gtttatagca tcatcatgat atgtaatacc tgtcagacca tagttggcga taatcgtgga   73920
atcatccata gaaccaaggc catatgctaa acgtattgct ctaggatctg tttcatgacc   73980
gaattcgtca acatagtatt tcacatccca cattccgtca aggccgtatc gagccgtcag   74040
ttcttcaatg atacggcgct ctggttttgg ccagtcctct gtgatgtcca tgataccatt   74100
gataagacat gggatccaaa acagctcgaa ggaaccgtag acgcgttcgg caaaagacct   74160
tggggtttcc ccatcgaaaa cagtatacgg caggagaagc ccttctatgt ccctaatttt   74220
cttaacaacc ataacccgtc gtgttaagtt ctgcaacagg acttggtcat cctctttgac   74280
accaattaat tgatgccaca cgagtggaaa tttctcaaaa tatttcatgg catcttctcc   74340
ttagaagctg tcgccttcgg tatcaaagcg gcctttgtgc aacggttcta gttctataaa   74400
cgtcatgtcg atttgtgtcg acacgatgct gtcatctttg tgtacagcat atgaagagtc   74460
aggcgtctcg ttgacaaaca tatttgatag gacgcaagtc gatatccgat gcaaccattt   74520
gttgcgttct ccctggacca tgaacgtgat atcaaacgtg gatgggtgaa gatagaatgc   74580
gctggaattc ttgttgtatt tgtattctgg atacatgtgc atcttgaata aacggataat   74640
ctcccgcacc attttcgcct cttttttgcga tcttggagtg aatttgaatg tgaacgggat   74700
ttctcggttg cgcaccccctt ggaaaatcat ctccacatac gggttggtca tcgtacctgt   74760
aaacaattct aatgtatcat gagcattaat tgtcggcaag aaaggaattg cttccgaagc   74820
agattggatg gcctttgtcg ccgcaaatct ccccatttct ttcccaacat tcaaagcatc   74880
cccaagtttg aattgactca tatcttgggc ggcgcgtgat aaaaattggg cacccatacc   74940
tgctaatccc aactcggagc cgttccagcc aacgccatag ttggttgtaa tggattcggg   75000
catacacaac acaattgact cgttagagcg gacatgacgc gcccaagcat atttgctaat   75060
agacccgat ttagaaccat aaaccacagg agtcttaccc aatggatttt gtatcggatt    75120
ttcgacggtt tgggttgtgg tgtctccata tgaagaacca gatattcggt tgatgttgaa   75180
tagaacataa tggccgaggg ttttaccccc tgttatgtct aatggataga ccaattgctt   75240
```

```
ctgagacttg gccaagcctt ttgtgttcag aactttgatc ttatcgatgg tcgtcttgaa    75300
attcgccatg gtctgaagcc ctttaattag aatagagtga tgacactatt taggactaga    75360
atatggctat gtatctcgta taccaaatta ccaatctgat aaacaataaa atatatgttg    75420
gggttcataa aggaactcca gatgatggtt atatgggttc tggccgagtt ataacaagag    75480
cgatattgaa atatggtgtt gagaattttc gcaaagatat attgaaagtt tgtaaaacat    75540
cagaagaaat gtatgaagaa gaattcagga tagtgaatca agaatttata gatagagatg    75600
acacatataa tttaacatgc ggtgggcgtg gttcatttac gcacataaat tcggatccat    75660
taatcagggc caacgcttcg gagaaggctc tcaaaaccct aagtttaaaa tcaaaagacg    75720
aattacaaag aatttacaaa tctaggggat ttcctggaga agaaattttt tggtttggta    75780
aaaacaggtc cggtgaaaat aactcaagat ttggctatgt aatggaacaa gaaacaaagg    75840
acaaaataag aaattccaac aagaaaagag tggaatccgg cctcgtggat tattctaatt    75900
gcaaaggacc aatcacaaaa gaagggaaga acgcaatatc ccaagcgaac tccagagaat    75960
tcaaatttgt taatccagaa ggaaatttgg tcacagttat caacctttcc aaattctgta    76020
aagaaaatga attgagcgaa ggatctatga gacatgtcca taacggccga acatacaaac    76080
ataaaggttg gaggaaagca taatggcatc gtatttacaa ggaaaattta ttcccaacaa    76140
tcctcaaaaa tatgtcggag acgtaaaaga tattgtgttt cgatcctctt tagaattggt    76200
tgcattcaaa ttctgtgaca tgaatcctgc tatcgtgaag tggggttcgg aaacttgtgt    76260
aatcccttac atatctccgg ttgatggccg cgcccatcgt tatttcatgg atttgaaggt    76320
ttggactcgt cggcaggatt ccgatgaatt acaaattact cttattgaaa taaaacccaa    76380
agaccagatt aaagaacctc gcaaaactaa aacgatgaag gaatcaacat tcaataattc    76440
aatgcgcact tggttggtaa atcaggcaaa gtggacagca actaaagaac attgtgcaaa    76500
ggtaggttgg aaattcatta tctggacaga agaacatttg gtgccaggtg aagacccaga    76560
agttaaaaaa caatttgctc ttcgttctaa gaaaaagcgc gaagtcgaaa tggaagatcg    76620
acgccgcgct caaaggatta atgcgttgaa agagcaaatg aagaaggaaa ctgctaataa    76680
acaaccaacg caatcggaag atgatggttt gttattaccc tgatttcctt ggatgtccag    76740
gggcaaagca agtttgtttg tccctgcata tcatccatcc atcagcacgg gcttgtctag    76800
cacagtctcc ccaagattca ccagcataag acttcatccc acatctgggg tgatgttctt    76860
gccaagccca attacaagat ttgcattcaa cacactcaca atacaaatcg acggtgtatc    76920
ctgcagtaat catttagtca cccagatgat cataaatttt ttgacggaat tcgttccctt    76980
tagcacaacc tgtagccaac aggcgagtac cgcccgtacc aataacactg atggtcgaaa    77040
acttcaggat acgcctgta atagactggt ccaccttaat ggtttctact ttaccaagac    77100
ggagttcatc agcatcacga cgaataaatc cccgtttgac aataacacgc ttgttggtga    77160
ctgcgaattc agttgtcaat acatttaaaa ttgttggtat cagaaataac aagctgaatc    77220
caaatgttgg gataatcgtt aaaataacca gaacataaat ccaaaaaccg ctccaccaag    77280
tcgggcgggt gaaagcgatg acatgttcat tttcgccgag catgcggtct acataacgca    77340
ttttaattcc ttactttgtc tgggttggat aagatttgtt cgtatccgac ttcgccttga    77400
tcgtcgaaaa catgctgaag aatcgccata tcgtctacca tccgataaac ttcaattcca    77460
gcgttcatca attttttgat tccatccatg atacgtatg gctcttgata atatacttta    77520
tcgatcttgc cgttgtcgat gatcttctga gtgcaatcag ggcatgggct atgtgtcaca    77580
```

```
aacataacca accctgtgaa atcatctgca ttttcgggga tacgcattag agcatttcc    77640 tccgcatgaa tgacacacgg gtttgtaaca atttgcccgt gttgttccat ctcacaaaca    77700
ttcggcatgc caggaggcgt tccgttccat ccgatagcca caggctgatc agtttcaggg    77760
tttacgataa cacaaccgac ttgcagacgc cgagcataac tggttacacc atatgctgca    77820
gctgatcgca tatgggcgaa catcattcgt ggtttgatag ccattatttt accagagcct    77880
tttcaagtaa aaagatcatg tcatcctggt cggcgcggcc aaagatctga ccgagggaca    77940
ccatggaatg aacctctttg acaatcaggt ctttgcctgt tacaccgctg ttgtccaatt    78000
cgagaattgt agacatgcgc tcaaccatat gaggtggatg attgatataa cgttgaagat    78060
acttttcacg caacgcaatt ttttcgataa gatctgacat ttctgcattc tcttctgaat    78120
acagacgttc tttagatttc agttcttcga ggcgttcgta catttctttt aatgaaatca    78180
tgtttgtctc tcccaataaa ttaaggggaa gtataccttc cccttcttc aataacctaa     78240 aatattattc agtacatgct ttaccgaggt ctgtaagcct atagaatgtt acttcagact    78300
tcggccaatg cttatactct tcagagttgt catgaaccat tgtaaacgca ggttctatca    78360
gacctttaga caacaaggat tgacctgaac gcgtatccca tggatcaccc tttacagaac    78420
gaaacccgcc agatatcggt ggcgcatgaa aagtccaaac cgttttccct ttatcgttcg    78480
tccaagattt gggattgaaa taccaatgac aaaggcgtct ggcttcacct ttttcaaaat    78540
tcaacattcc taaaaggacg cagagttgat gtcctgtgat tcttggcttt ttcataatat    78600
atctctcttc ttcaacatgc gttccacctc tggccagttc acgcaggggc gattggaaac    78660
ttcatcccat accagagggc agccaagagc ggcgtcgtcg atgtaaacct gggcatatgc    78720
ctttggagac tccgtccaag tcttctgtga tgggtttgta ttaactccat acagagggat    78780
gccacggaca tggaaccagg ttttcgcttg ctccaattcc gcaccagaac gcatcgtgaa    78840
caaaatcagc tgatgcccctt tggcaacgag cctcttcagg caggcatcag caccgatgtc    78900
ccgcccgacc tttgggtatt cgtgggtcac acaagtcccg tcaaaatcca ctgcaatgat    78960
cataagatcc ccaagtcagt aaggtaacga taaaacaaga ttatagacag aaatccaatt    79020
aacacccaag acgacaggat gggcttgcaa tttagcgtag tctttccatt gggtatgttg    79080
ggacttccag taataacaac cgaatccgtt ttagctctca gcgtcatgac agaacccatg    79140
aggatgattg ggcgcacata atgcccttca tgattgcgct tcacgataca tggtgaagaa    79200
aatcgcagga acggatcacc gcttttataa ccaaataact cgaccttttg tatttcttcg    79260
ggtactttct gaccaggaaa gaatattttc atagcacaat tcctaaattt gtgtataaca    79320
actcagccag ggttacagga cgcttgaatt gttcccaact gcagttcagg tattcgcgct    79380
cttcgcgaat attttcgtga agatgaccat ggatattata cgcccaacgg tctaattgat    79440
aaggaacatg tgttgtcaac acacggccaa caggcgtgtc acgttcatac atagcgccga    79500
aggagctaat ccagccgtcc agatacagag acaacaacat cttaaagctg tcatggttgc    79560
cttgtgccac cctgatgata aagttcggac gccagtcatc gggaacgggg cggcgtttga    79620
actcatcaat gtttcgcttg gcaccctctc gcatcaggcg aatgaaccct tcagccccga    79680
tgaagcatat atcaccagcc agttcaagaa cgtcccgaga cttcaacccc tgaaagatac    79740
tgtcaatgac cgcagcgtca tgggcttcct gtgtatcaaa tccacgcggt ttaaagacct    79800
tcttatgccc aagatgagtg tcaccaaggt gctttacaat tcccgccatt atggtttcct    79860
cagccattct aaaatcggca ctttcacaaa ccctttatgc caacgatgcg gtttgtgacc    79920
tctattatat tcgagcaaac acgtgtctgg tgggacactg aagtggatgc cttcgatgtc    79980
```

```
gtagtaatgt ccgtcaatca gagtatacac atgaccttcg atctggctgt aatggatctc   80040
tgcttgagga tacacatgct tcagaaccag agcaacctga tagcactttc cgttcttccc   80100
aacatactca acatccacct gttgtgggaa gacgtctttg ataagattta tcaatctcgt   80160
gatgtcattt acaacaactg aacgtttcat ctctatgata actcatggcg atgtcgaaca   80220
cacgcaggac aatcacaatt cttttcaaa attggcaatt cacaccatgt cattaagtca    80280
tgtattgggg acatgtgatg atagaaccaa gatttcttga gactaatcaa tggatataaa   80340
atttcaatag atctttcccc gtctctggtc atcatgttgt atccttcaat aactttatta   80400
aaggcgggta tccagtgtat tgcgtcatcg ccgttaacat atgccaagat atacgtggaa   80460
ggcaagccac tgccttaaa ttgcgtgttt aataaccata tcggggcttg tgctaaacaa    80520
gcgcgaaaac caccgttcgg gacgttgatg ctactgatag gttcttgatg atgtgtccaa   80580
cgatacatga gaagtggggc attttatta atccagttgt atattttatt cctcgcccaa    80640
ttttcgcgtt tagatttaaa tttattattt tcgaggtggc aatacacagt atgaactgaa   80700
tatcctttcg atagcaacca atcaacatg tatgtgctat ccaccccacc agaccagaac    80760
aacgtcactt cttgattatt ctgcggcaat ggagcatccc cttgaagaac acggtataca   80820
aaatcacaat cagatattga gacaacaatt tccattaaaa tattcctctt aaagaatcat   80880
ttatcctgcg caattcgttt tccactttta tcttcatatt tttatcgtcg ttacgaaaa    80940 tcatttatc taaatcttcg ccattaatct ttgtataaaa ataaatgtca tgctcaaaga    81000
aaatcgtttt tccaacagaa cgcatggcaa agaacgttgc aatagttctt ggtaaaggtt   81060
tgaatttaat ggcattgaaa cgcaaagcct gatagagagg ttttaatgtt cctaagcgaa   81120
tacaatgctg gataatttct tgctctttca tttgttgtgc gccataaaga tatgatggta   81180
caatgataat acattataca aatagaaaag ccccttcgg ggcttatttg tcttcagatt    81240
cgtataaacg ccaattgccg atgctaaacc actcccccac attatttgaa tatctggttg   81300
ttcggactcc tccgacttca tacgcccatt tgaagaattt ccatttggac gataaagaag   81360
gacattcgct tccggatttc aaagaacacg ctgtgagcca acgcgtaata ctgagagcct   81420
gaaaaatcgg atggataaat gaagaataca atatccaaag cgttatggca acaaaaacaa   81480
tggtcgtgat cacccgaca atttgaaaga acatttaaga acctccaaaa tattgaacac    81540
agactatgaa gaaaactatg attgtaaaca accatgaaac aaggaaagat tcatccttcc   81600
accttcagcc ccatcaggtc ttccatggtt ttctgaatgc gtagccagtc aagcgccgca   81660
tcataacgag ggtcatgata gatcatacct tccagttccc acgccttgat accagcatat   81720
cgatcctgct gcccaatacc cttcagccag cttacgatgt caaatgtgtg gtgatagtcc   81780
caaggttcgt tggaatcttg cttacacgtc acctcaatga tgtgctgagc cttgcgtagg   81840
tcaaacagat tcctatcaca ccagtcaacc gatcgcgggt cgatcccaag gcgatggcat   81900
cccttgcgaa tttcatcggc caatttgaaa atagaaatat ccttgtcggt cggatataga   81960
ctgatagctc gggcggcgtc gcacgggttg cgtttacctg tacccagcca ccattccaca   82020
gtgccctggt ctttcacacg gccaagttca atctgttctt tgacatccag tttgataaat   82080
gtcgtgcgct ctacaacaag ctgctgaaga gtataacgct tggtcaggtc ggcgatagtc   82140
tgtgcccaag acaacatgac agcatcatcc caacgaccga gagtttcgct atcagcgacg   82200
gccaagaaat tagattttata catcagtttc ccctgctttc tctaaaagga gtttcaaagg   82260
atatgtccca caagcggtgg catactcgac tttgaaatat gaattatcgt tcatggcgaa   82320
```

```
attgcgatgt gggaaatatt ccccgtcatc caacccgcct aatccccgc cgacgcgata    82380
ttgttttaac tcgacttcgc cgccataacg gagttgggca tataggccga taggagcgcg    82440
aacgtaatgc tccagccata cccaatttcc atcgtgtaaa cgtgtaggga taaatgcaaa    82500
acgcaccttg ggatgaagaa cggctttggc gagcatctct tctgttattt cacgcttcat    82560
ccaatacctt cctcttcgat gatatcttct tcactagcga cgacagagat tccgtagtct    82620
accatctggg aaagttcttg taaatcttgt tcaaacccgt caccctgtcg gatataaaag    82680
acgggtacga cacgacgcct ggtatcttcg aagatagtct ccgcgatttt attaatctga    82740
ctcaccacgt gaaacagttt taatccaccg atgccacagc cgatggcggg taaaccaaca    82800
tagactgttt cgtcagtttt tgcctcaatg atatcgtgaa cttgttcaaa cataatctga    82860
actgaactga taatggaagg catgcgtgcg ttaggaccag ggtagaactg agtatacaaa    82920
ttgaatcccc agacaccagt gtcatgatca aacgcatagg acatgttccc caaacgttgt    82980
tccggaccac gttcatctaa ttggtcggct cggtaaattt ctgggaaatc taatcgaaca    83040
tggttggcga tacctgcgcc catcacagac caacaatttg ctccatgagc gaaagcattg    83100
atgagattaa aactcgtagc ggctttcagt aaatcgccgt ttgtgataac atatgtggtc    83160
atgcgtaacg tctccattgt ataatttcgt tgttgacaca gctaacctgg atgatacaca    83220
tattctggcg atggtcagtg agtgtcataa taaaactgtc tgtctgtgcc ataacacaat    83280
tgacagatat tcctcgcatt atcaaacgaa cacagatttc ttgatataat cgtttcatgt    83340
atcctgaaac tgaagcggac tcatacacgc gttcaaattc atataactcg ttcatttatt    83400
cagaccatca atagcgtgtt cagaaatata ttcaacgaat tggttatcag ctgccatctt    83460
taaaagttca ataattccg ttccaacggt actcccaaac atcccttcca atacaccctg    83520
aacatcttca tctatttctt cgatgacgag tccatacgat ttcaggcggc gtgaaatagc    83580
acggaactgg gcaatatcac caatttcatt tgccatgtta tttgtctcat tatggggtta    83640
ggcggcaatt ataccgccaa tttattcaat agaggtcttc ggaaaagagt tctttgaaag    83700
gagtgttctt caaacggacc tgattagttt gtccggcttc acgagcgacc acagcagcct    83760
cttcacggga catccattgc ccatagttat caataaaccc ttgttcacga gtgtgggtgg    83820
tttcgataat acctgcttcc ttcaatcgtt tgagttgcgt gttcatcaat ttgtcgtgat    83880
gtcgggcgct tacaacgatc acatcaccat atttgttggc agcagccaca acacgccgat    83940
caaacttggt tgggtcaggt atatcacgag tatacaaggc gatgtgagtg tcgtccacgt    84000
cccctttcac ctcagaatat aactgacacc cattaggaga tccagtaggt aaagaacgaa    84060
aatatccaag taatttcata atctaatcta tccatatttc aggttcgggg atatcaacca    84120
tctccaccgt ttgattcttt aattcgtgga aacagtcacc aaggaattgt aatttaccat    84180
cagtcaagaa caaatgacaa cgactcgccg gatcagaatg attcaccaac agactaggag    84240
tgaaagtcgg tgattcgaga tcgtgattcc attgccatat tgggccaggc gtttgccctg    84300
aaatgcgata aggatgaagc atattacatc caggacaatg aaaatatatg gaaccaccca    84360
ttgataataa ttttggagtc aataattttg acatatcacg cctccacttc ttcatcagga    84420
ttgtatgggc gtaattctcc aattaactta gggaagaggg caaacccgaa cagattaaaa    84480
gaacgcatgg tcccaaccat accaacatca tccaattcgg taacgtcaga aagggcacac    84540
aacggtatcc acacgtcttc ttgtccttcg taatttacga aggcaacttc ctctttaata    84600
aaacgagggc ataagatatc gaacaaccaa tagaagaaag tcagcaatga gagactgcgg    84660
aaatatacaa acatggtgaa ccccttgctt gtttggaggg aattcaccct ccggatttat    84720
```

```
aggcccaatg cctttcaag atcatctaaa tcttcagtat aaagatcgat gtcttgctta    84780
ttatttaatt cttctcgttg aacttctaaa ttctttatct ggttcaacaa acgttcacgt    84840
gcgtctaacg taattgatga taaagacatc ttgaataaat catcgagatc gccatcaaaa    84900
tcaggatagt ctgtctggaa taacgctttc agttccgtga ggctccggcg catatctgta    84960
acgacagccc acccaatgaa tatggcacga ttgttcaaac ggtgtatttt gtcggtcaat    85020
tccttgataa gatactgacg tctatcttca tagcgactca ggcgataatt gaaaaatgga    85080
agcaacatgt cttccaacc atcataacgg tgaataacac catcttcatc ccaagctgtc    85140
cacacgggct tattagctga gtagagacgg aacatctgtt caacctgttc gtcattcaac    85200
ttagacaatt caccccgctt gaatacaaca gtgatatccc aaccatcttc ggtcgtatcg    85260
ttggcgtact cagtgaggac acccgccttg tacaggggca acagcacttt ggtctcatag    85320
gttttagaga accaaccaat aggaacctcg gtgatgttca aagtggttgc attaacgcgg    85380
gtgaacaaac cacggctgta tgctcttcct tcctcagtat agcccgtttc tcctttgaaa    85440
ccattccagt acggttttaa gtctttcggg tcttcgccac ggagaagcgc tctcagggca    85500
ctgagcacgg acttaacgga atggcatggg gtgtcggtgg cataaccgga gccgatacca    85560
ttgataccat tcacgagaaa catgggcagg atgggtaaaa agaatttcgg ctctagtttc    85620
tcttccccaa gataattgta ttccaatatc ccatcgtcct cctttcggaa gattttacgg    85680
ataacttcag acactgccac tgaaatataa cgagcggaag acgcttcgcg ccccatgatt    85740
gaaccaaact gtccgtcgcg gtcaaagtat gggatgttat tcgtacctgg aaccccctga    85800
gccatgttca caatagtgcc gctcatgttc tcgccaccag atttgtagtt ggtgcgggcg    85860
gcggcgaaca tgccaaggcg gtcaacgatc tcctccttgt tgtactcaag agcagcaaag    85920
aggatcttgc gctggctggg cttgaggctg tcgatcagtt gagggatttg acggatgctg    85980
ttgaccacag agaactcctt gtggtcacca tttatgaaat ccgtcacggt aatagtcgtc    86040
atttatcgta tccccctaaa ttaaatacgt ccacttggta atcgaccaac caagatacca    86100
gtttaatcgc ttgttccgat tcatctgatt catcaagagt gtaatatggt ttacccgtcc    86160
ctttaagcgg gtcatacacc accaatttac catctcgagt gtccaacaat atctgatgta    86220
atatgccagg ggaagtcagg gaaggggcga ccaggacata aacataatcg tgataaatcg    86280
ttatattttg attagcccca cgcccagcta taaatggcac accattgaga tgcagtgcgt    86340
caccaatagt catctcaaat gattcgaatg aatcatggaa ttcgtcaata acattctgta    86400
cagggcggtc gagaatcatg gccaaacacg cagacataca agtgttgcct gtcggttgtt    86460
tttggtgtac taatggattc aaaaccatct tattcccctt ccgtttcaaa taggcaaacg    86520
tcgctaaacc aggttttgcg gtagtcggcg gcctcatcac cgaagccatt cttcagtgac    86580
tgttgatagc catcgtccag cgtgaccgtc gtagtatacg catccaggtt gtttagaata    86640
cgcttgaagt cttcagtgct gttaccgcca agacctttca gatatttatt cttcgtgatc    86700
ttcttggcgt caggtgtctt caggaactcc tcatactcgg tgttgttcat gaactcatgc    86760
atcaccttac cacaccacac gcgcatgtat ggagtacgaa ggagcttcag cctaccctga    86820
cgaacgtatt caggccagaa cgtacaatac agagttatta caacccacg gatatgaatg    86880 ccgtcgtcat ccgcgtctgt tgccacgacg gtctgtggat agcgactgat atcaagcggc    86940
tggcctggca cagcaccgcc gtgaatggtg cataaattct tgaattcttc gttcgccatc    87000 accttttgagc gcggggcgtt caggcagttg atgaacttac cacgaagcgg gaacaaacca    87060
```

```
attttcttgg tatcacgagc gttcaggata gggttggatg cgctatcacc ttctgtcagt   87120
agcagcgaac acccactgcg gtcgcctctg gcggtcgccg gataatactt ctcaatctca   87180
cgataatccc gtttgctgat atccttcttc gccttttcaa attcggcatc ttcttgttca   87240
ttgcgtaatg aagccagttc tttactcagc cctgctgtca cgaactcaag cgccttgcga   87300
atcagtttat cgctgggctt gtaggacgta ccaaactggc tcacaggagt cgtcatgcgc   87360
tccttggtct ggctgtcaaa gcgagggttg ttgatgtcgg cggcgatgaa caatgacatg   87420
tggttcttga tcatcgctgg cttcagttcg gtcttgaact tcttaaccag ctgagggcgt   87480
atagccgcca cgatctggtc agcaacataa tcaacgtgag gtccaccgat gtgcgtggcg   87540
attgagttca cgtatgatgc atgcatgaac gcaccagatg agggagtgat agcaacagac   87600
caatcatccg tttcatcaac agccgagcca gcgtagaagt aatcaacgaa atgaccaaat   87660
cgatcaatgc ggatttgctt gccgttgaga acaaccttca ggcgcgggtt gcatgccgcc   87720
acttcgaatg cacgacggta aatcatgagc aggttgttct ggtcaagccc cttaacaccc   87780
aggcgcgcat aatcagggat ccaggcaata gtggtgccga actctttcgg tgtattgccg   87840
atgaccggat tggacttctt gctcatgttg tcttcaaaca gctgagtata agacttcttg   87900
ccgtcactgg tagcaacgcg gaaccacttt gagaacacgt tgacgagcga agccccttca   87960
ccgttctggc cgccggactt ctggttgttg tactcctcgt cctcatcgtt gaagttgctg   88020
cccgcataga gcgagccaaa caacatctca gggagccact cattggtgac gccatgcttg   88080
accacaggga taccccgtt gtcagaaacg atgatttgac cgttcatagg ggagaccgtg   88140
acggtgattt ccgtcaagcc tttaccctca ggggtcttgc tgtggtcaac acagttggtg   88200
atgatttcat caaactgttt gatcagcgca ggggagtact caaagttgtc acggaagatg   88260
actttgtctt tggttgggtc atacacccac accgtcccca cagacgaacg gatactgccc   88320
agatgacgct ctgggcgaag taggatatgc tctatgtgag tgagcttttt gtatttgcgt   88380
tcaatatcaa ttttgttgga catcggccta tcccgtcaat ggtaaacaca caagattatg   88440
tatggggttg gcttatagac caaatttagt gcgccatttt tccactttgt gttctatggc   88500
atgttccact ttaacgatcg tgttgatatg gttttgatta tatccacacg ccaatttggc   88560
agtattgcgt atcagatttg aaaccaggtc caccatatta tcttctgaac gttgaggttg   88620
gttcagtaaa cgagtgatgc ggcctttgta atgattaacc atcgcaagat atttgtctat   88680
agtttcaaca ccactgcaga accaataatc ctccaacgta tgttggctga gatcagttgt   88740
gtgattggcc gtagccaaag caaacaccat ggagtcaaag atttcttctt tggtcataga   88800
cccatgttgt tgaacttgtt gataatccac aacatataat agatccagag ccgagatgat   88860
aacgtccgcc acttcaccgt tcaggggttc ggatgcagcg attccataaa gcacatctga   88920
tagttcacaa gactcttcca cgagtttgca atatacaaac acaggagaac gattaggatc   88980
gcgctggctg agttcatatg atgtgttgaa gatagttttt agaaaattca tttcaaatat   89040
ccttctagac ggaagcggtt aatatgctgt atgataaaat ccatagagtt ttgaaaactg   89100
tatttcccct gatgctcata tgcatgaata aggggaagac ggctgtgggc caattggaat   89160
ctcaacttgg atggcattgt cagcaatttt tgactcgtcg ctgcgataat gtctcgttta   89220
aatttgggat catcagggga caatacaacg atgcgtgact tggccagggt ttgtccaaat   89280
tgcttggcgt cgttcccgta aagactacgc aagtcgtcgt ggcgatattt tagccaatac   89340
cagtagcctt ctattgagtt gaaattacca tcaacagtat ccatgggatg gtatgcaaaa   89400
tgggaaagga atctgcctag ttctgtgcga cttcgactgt atatgttgta atgggtctta   89460
```

```
ccttcactat ccggcgtcat acgttctttt ggaacattga gtaatgggag catgatatag    89520
ggtctcaaat caaaattgct gtgtgtgtgt gttaaatcag atcttttgt acgctttcaa     89580 agcactaata accgagacgc cgccaaatag aactaacaat atgaatcgtt ccatcctgaa    89640
atcaggaagg gaaagcagtc ccacaaggct gtctaaagca atcatgaacg ttactccagt   89700
cagcatgccc aacttaaagg agttggaacc tcttttgcaa cgtagcataa atcacctccg   89760
attcaaatgg ggagttctct ccccacacag atatctagcc cagaaacact actaaagtca   89820
aatttgtgag actggtccga gcatcctgca acatttcacg ggcagcggct aaacgtttta   89880
catcatgtag agtgtcagag aacacgatta tgttagcctt atcgatcctg gtccccatga   89940
aatgggtgat tgtcgtcgtg ctctctttct tgtcgacatc agggataagt aattcttcgc   90000
ccgtctgagg gttgcgggaa ggatagaaga atgcatcacg ttcacgagaa gtatggaaga   90060
cgccaaacac atatgcatcg ttttcgacct gaaactttt agaaagtagt ttcttcagag     90120
cggctgtatg tccggtctgg cggagcattc tgtagtagag catgttgccg gagcaaatag   90180
ggtctatcac tcccctaatt tgacgttcct tttgtatctc atacgcatct gccacaagct   90240
gctggatcat atcgacatgg gcattcatgg agatttctat tttacgtttg atcatagatt   90300
gcatttggta tatcctcagt taggttccgc tcatggggaa cgggtccatt atacacccaa    90360
tgctggaaat gaaaagagg ccgaagcctc tttaatcgtc gtattggcct gtcctgaaat     90420
tccattttcg cgccttggat aaatccaaat ctttgaaaat gctgccaaag atcttttaa    90480 aatcagactc ttcttcaaga tcttttggtt ttttgacagg ctccttaacc ataccgcctt    90540
cgggtttccc cacatcggcg gtcgtggttg ccggagcaga agagtcttca aggaaatcct   90600
ggaagctctt cataaattac accacagcca tttcacaacg agtagacgtg acagaatggc  90660
catctgcatc agaaacaaca caccaatatt cgccttcatt tgcggcttca actgctgtga   90720
taaccaggtt agcagtggcg gcggtggcat tagtgccagc atcgataact gaccccgcac   90780
ccccaggagt atcagagaaa tgccacacat aagtgtatgg agttgtaccg cccgcagcaa   90840
caacactaaa ggttccgtct tgtccagaag tcacgtcttt ggtggcaggt aaatcagtcg    90900
acagcgatag agcgcctgca actgtaataa ccgtagaatc tgtgtgattc ccttcaaccg   90960
tgacaccata aaccgttaca gttcctgaag ccagcaattt gaatttacca ccaccgacat    91020
gtacagcttt cgtaatatca ccagaatacc aattaacgcc ttgatatgtg gcattggcag   91080
gggataccgt cgctagcaat tcaacaaatt gtccgacctc tccgctggct gtagctggag    91140
taatcacaag tccggtggtt aaaatggcat tcggatcgtg gatttcataa gatacttgaa   91200
agccgatagg cttggtggga tccactttgg tgacaccgtc cgcttgtaaa ttgctcttgg   91260
tgagcagagc gtcaagacct ttacattcgg tcaggatctc atcaggatct ggttgaggc    91320 tggtcttttg ccaaccctt gcaacacccg tcacgacatg attgcgttcg gtttcgggtt    91380
tgttgcggac aacttccggt gcgactaata ctgtgattgt tggcatggtt tcctccactc   91440
atccaaatcg ttgttcagag ccatcatcag ctcattatct ggttcgtatg aaccggaaca   91500
taaatcatct cgccaaactc ctaacgtcaa cagcgctgct ttaagacgag gatgttggtt   91560
cttatccgtt ttcaacacca acattcggca cacggcttcg gtttcaaagg tattgaaaag   91620
aataatcaat tggttgataa gtacgcgagg acttttccct ggcacaaatc ttttcaatga   91680
ttgattaatt agcgaaattc gctgaatgtc taccatcaaa tcatctcttg agacaccagg   91740
ggtgatataa tgtcttagag cgtactccat caaattgctt tcgtcaacga tagccatatt   91800
```

```
gaattataat cagcagttat acactgggat tatttaatct gcagtttttc agtcaattgc    91860
gagattattt cattacggtc agtcgcgtcg atacccaggg gttccgcaag tgtcttaaga    91920
tcattgatat caagcaaaag aagaacttca actgtaatat cggttgatac cacagtacct    91980
ggtttcatag gttaccgaa tttatctaac ccataacggc gcaaagttcc ggcaagtccg      92040
gtgagttcct ctagaagctc cttagagccg tctttatatt cacacaccca accgtagtca    92100
ccagcgtaga caataccgcc gtcgccgccc tgaggcacgt tatccaccac gcgttgcaga    92160
taactgggaa gtttattttc ttcctgtgca gtgatttctt gaatggtttg agtgtttca     92220
attttctttt gtgtcttcgc catgatcagt tctcctatag actgtaatat atttaccaca    92280
acaattgcag caataaacat gcatggaata tccgtcgtcg ttaaagtcac agccgccaca    92340
acgacaaaat aatttcacga actggtcgcc tatgacttct ctcggaggaa aattcctgaa    92400
cgagtattcc ttgagttctc catcaaattg gaatgaatca acaaggaatt ttgttttccg    92460
gcgtaatgaa ccaaatgctt gttgttcata cacgaagtaa acatctctag tttccatatt    92520
cacctcaaag aaaaggaggc cgaagcctcc cttttatatc catttacact tacttgtata    92580
gaccttcaac atcaatggat ttatgttggc ggttgtattc cgtggtgtaa tcgtctaata    92640
ccagatattc acagcagcgg attttactgg agccataatc atcagtgata gacacgatat    92700
ctttcgggtt cagtttgcaa cggacaacgc gttgtcccag gctaccaaaa cattgtttca    92760
gataagccag agaacaaacg tgaagaccgt aagagcacga atctttgttg ttatcgttca    92820
cgaatgagcg agccatccga acaatggtgc caggagcatt actaactttt cctgtgcgct    92880
tgtccatgta gttaccgcga acggatttat acaggatgat atcaccgtct tcatgaattt    92940
cgatatccga atatgccatg aattcataga ttcgaccgga ctgaaccagc gcggcgctcg    93000
ggttttggaa cattttgtcc agaaaacgac ccaagcgttc taagttcgga taatcgcctt    93060
ttaatgccag tgccaaaatg cgtttggcga cggaagttcc cgtgatgtca tagccacccc    93120
agcgaacacg attgtctgaa aggtcaacca tgcctgtggt gaatttgctg atggcttcac    93180
gcggtttcat cagagtgtac gctgtttga cgtcacgatt tttaatcgct tcaacaatac     93240
gatcatacgc ctgatggctt gtggttatcg tttccggttt gccatccata acgataacga    93300
tgctttccgg taaaatcatg atctggtgct cattcaagaa cactgacaga tctttttctt    93360
taaatgagtt ttgagtttgt ttgtcgccag actcttcctc aacagccgtt gtcttaaccg    93420
agaaaacaac agacgacaac gccagtcgaa gtgtacgccc cagaattgcg tcaaagtatc    93480
ccacacgccg acgggcatca agggaaccgc gcatcgggta tgtttcgccg tcatgttgta    93540
cactgattac cacgccgtca ttgactttgg taacgccatc aaccagtgct gtcgccaatt    93600
cggccaacgg agaaatgttt tcttcattga agcggcttga ccgagtttct aacggtttca    93660
gttcttcgct tctgaaaagt ttggcctgaa tagcagcaga gctatcgtaa cgcatacaga    93720
taaacactgt ttggttttcc aggaaacggc aacatacca ttcttcgcct tcagaatcga     93780
cagacaccga accttccaga acttcatagg tgtcggggat tttcccttct tcagtcaatt    93840
ctttaattgg cgaaatcacg accacgttat tagattcttt gatgatacga accatcaggg    93900
cgcgggcaat tgtttggca ctgacgccat aaactgatgc cagagaagaa ttgctttcac     93960
ctttgctgct cttggtttgt atttcttgaa tctgttcagt ggtcagagac ttaatcgaag    94020
ctggatccac tcccagttct ttatccgaca cgcgttgtat cattgagcgc ggtacgccca    94080
attcactggc tattgaactt tgacttctgt tctcattcaa cagcttgaga atacgttttt    94140
ctatagcatt catcttgtag ttctcactgt ggggtaatgg ggctattatg ccccgagaat    94200
```

```
acgttttgaa atagccttca caaatctagt ggcatcttca atcgcgttgt gtgccgaagg    94260
ctgatatgtt gacatcatga attttcaccaa acgatgacat tcaactcggt atcggttttt    94320
ggccttttgc ttttgagata tagtgctagt gacctttatc tcatcaaatc cttcagcagt    94380 taattttttca ttcaataaat caacaacttg agttaactgg ttacaggcgc ggaaaaatct    94440
cgtagttgag aaaggcattt ctatatgata atgtaattcc tcaacagcct tgcggaaata    94500
accgtacccc gatccagacg gatttcgttt ggccagcata cgaacaatct tccattcttc    94560
ttcagtgatt tgttgtttcg cataaccgat gattgctttt gccctgtgtt gatgatgggc    94620
atagccatcc gtaactttttc catgggaatc aatcaacagc ttggcaccat aatcaatgcg    94680
atgagacatg atgtttatgc ccttgcgaag tttcaggagt ttcttagatt caagcgcctg    94740
aaattcatct ttataatgct caagcaacat atcaaacact gcgtcaatgg ggatgaatac    94800
ttcaggaaat ttcttcatca tcggaacaga tttacgacgc gcaagaacga ttgttggatg    94860 tgctcccagaa aaatcaaaca ggttttcgtt tccattctcg ccgaacttcg ttctttccat    94920
cgcttcacgc aaatgtccag ccgtggattg tcgtaaggta ttaccatgaa ttttatggat    94980
accttctcgg ccagatactt cgatatatac gatcttttg cccgaatcaa taatatctga    95040
aacggttttt ccatctaatt cataaacgct gtcgaagtta aatgaattgt aatggaaact    95100
aaacatccca ggatcttttt caacggtcgg gcgaacatat tccatttcat gcatgaaata    95160
gacttcatcc ggattgaata aatcgccaaa gacctcgatc agtttatcgg caaagaccag    95220
gtagtccggc gttgttttctt gtacaccgat ccatgattca aaataagact tcaattcctc    95280
atggttggta aatgattctt tatgtgccgc cagctgattc cgattactga ataattttc    95340 attcggtttg acgacgataa cgacattgaa gttattgcgt gctgtttgta tcttcaggtt    95400
tcgagcacga ttcgagttat caataataac agcaattttt gatttagatt tcaaccaatt    95460
tccgacagag ttcacataaa tgctgtcgtg tactacaccg ttgtcgtgta cttcaatttc    95520
gtaaggacta ccaatagacc ggaaaggtgc atccaaagag taatcgcgca cgacgtccgg    95580
cgctccgata taacggaacg tgcctttgta gaaacggtta tctgcaggaa attctcgctc    95640
cactaattta cggaaaccgc taccgaacat atcagtcagc tgagtctttt tcatatacaa    95700
cataagagga cccattgact ccgcttggcg aagttcatac atcttcgctt gcatgatatt    95760
ttcggccaca tgcttgaaca cgcggttcag gctttcacga gtgaattcgt cgtatgacaa    95820
gtcttcgcgt gacggcggta cattcagttc tccaagttcg aagaaggtat aggaactcgg    95880
gaatttttcc agcacggtgc atatttcaga gtccaattgg tcgagatcta tcgggtaaga    95940
aaccccgccc atgacagcat agtggatgtt gtcggaatct gacttcggtt ggatatatgt    96000
gttgcctaca cggttttcga agttgatgtc agaccaacgg aaagaataac tggcgttttc    96060
aaccttcggt cgcattgaag gtcgcatcac tcgacccaaa cggaccaact cttgttcaaa    96120
ggcggtaaaa cgctgattct ttacaggaac tttaacagtc aggccgttga actcatcagt    96180
gtcttccggt ttaggatcac gggtatctaa atccttggta atgagatcta cagttgggat    96240
tctgtccgca ttcagataca tcaggaagcg atacagtttc ccttcatagc gactttctac    96300
tgtaaatgaa tcagataccg caaatgggga tttagaacct agcccaaacg cccctatttg    96360
cccgtcgtcg tcctcttttg tactatggaa gagtgttgta tacaaaccag gaccacgaat    96420
gatctcgcca tcctcagcgc ggaataccag taccccatta taataaccag gtgtaccaat    96480
aacagcagtg ctatcaggga tttcgtcttc cttcacgacg atattacctt caaccagcac    96540
```

```
ttcatcttca cgcgctgtaa taggctcgcc gatgatcatt tctaatggaa gaccaacccc   96600
ataatcttta atttccagcc agggttccat aacatccggt aaatgtacaa caacaggagt   96660
tcccttgggg gcaagatgtt tgctgtatcg ttgaggcata ggagtgagag gagcataatg   96720
cgatggcatc cagcgttgtt ggcgatcacg catattatgt gagtctatac cattacacaa   96780
cgtctcacgc aaagacgccg cctctttata tttgtagaga cttgaaaata atgtttcaaa   96840
taatttatcc gtcatcttga cattgaatgt ctgtccgacg atggtagaag aagagcgcac   96900
gaaatgctcg gacttgcgca ttttcatagt atagaattcc tgttcagatc aaagaagaac   96960
acattattgg gtaaggttat gatactggcg ggtggttcaa tagaaaagcc tccaatcgga   97020
ggctttaatc aggattaact tccctgaacg tttacaacgg tggcgttgaa attgaatatc   97080
gggtgggtgg cacctggctc taacgtctct tccagataac ccacaatatt gcgtgtcaca   97140
gatttcggct ctgcgcggga aggcttcgtt gcgccgaggt caataatgct cgaagtgact   97200
tgttcaacct gagtgtgatt gacaacaaaa tgataacgac taccgaaggc cgcaacttca   97260
acttctgtta tttctaaacc actcaattca gagctgttca actgcttcac attcaattga   97320
gagcggaggt gctctacaat attgctgtaa acatattgtg gtgtgatcag ctgttcaata   97380
gaactcatga catatcctca tttctttggg ggtttattgt tacttaaacg gatcacctct   97440
gctcgaagga agaggatttc atcggccatc attttacctt cttgaaacat aacatgacat   97500
cgtgatgatc tgggttcacc ttccgataat gcgtaaaggc gatattcggg gatgacatca   97560
tttacggcgt ttcttttttgt tctttccatg ggtcttggcc tttttaggac gactgacgga   97620
aggacgagca tgcccaggtt ccccagggggt acacccttgt gcataacgat gatcatccca   97680
gagacgacca ttatgcgtca tatcttcagc catggcggac aaagcaaggg ttgctacagc   97740
cgcagcagat aatggtttag acatttgttt ctccttttgc tgcatacgac agagctttta   97800
cgatcataac agccaaaccg ataggatcgt atgcattgtc gaattcttgt tctatgttct   97860
gacgaatttc atcagaagat tgtacttcag agcagttctt actctgtctg cgttgctctt   97920
gctcgactag atctttgaac agaaggtctt tgaaagaata ctcatcgaag ttttcaagat   97980
accgttggat gcttggttgt tttacatcca tcgtttgacg caaattgcta atagttgaac   98040
ttgcctgttc gcggtgtttg ttcataacag caaagttaac gggcttgccc caagcattca   98100
tcactggatt agagcatact tggccaaaga gatcttggaa ggcatcatcc atgtggatca   98160
acgcagtggc caattcctca taagtcggtt tttgagtagt cattttcgtt tactccgatt   98220
tttatatttc ttagcctgac gtttatgttg ggcggctcca tataggcgcg gcggcttttg   98280
ataacgttgt gacgcaatta tgtctctgtc atcggcttca caatacgaaa tatctgcctt   98340
ccgtaactga gccaccgctt gagataccaa ggttttgcgt tcactttcta ccagatcatc   98400
acaaattatc atgcgttcac ctggttcaca acgacgttta ggaatatcgt ctacactgat   98460
acattctact tcaacgcctt tcaacttttc ttgaaggata aaggcccatag cacgagcgcc   98520
caccctcct ccaataattg caatcttct tggcttgtca gacataatac attccataaa    98580
aaggaggata gagcaataat accctatccc cctttattga agaacgatta gtctttggat   98640
tctactttat caccgcgcag atcctggacg ggttttgccat ccggcgacat gatgtagatg   98700
gtgttaattg tctcaaaacca ggatagttca tcaactcctt cagtgtatgg agttaccgga   98760
actgaagttt tgatatgatc accatcgtta tttggggtgc catcagactt cagcactggc   98820
accaggaagg cgaaacgacc atttggataa atcaccccgc ctttaaacat ccggatcttc   98880
ttgcgagggt tgttggcctc gccaaggcac acgaccagat gatggatcat ctccggacgg   98940
```

```
gtaagcaacg tgtcgtcacg gatgataccc tgtttaatag cggagatcac cacttcgtcc    99000
aacagcgcct gctgctggtc cagcgtcagt gattcagtaa gtttcagagc cattattcgt    99060
accccaaaca tttgtttaag aaagtcagga catcgtccat ggtcttgacc tcaatttcaa    99120
tgccgagttg ttccgccaac ttgttggtgt tctcgacgat ctctttgtct cgcgctgaca    99180
tgatgtcagc ctttgaagtt gatcggtttc tgaacccag cgtcaaacgc ggcctgggtg     99240
cgggtatcgc tcaccacctg gcaggtcttg tcaagatcga tgcgcgggta gccaaacaca    99300
ccagcaatca acgaaccagg gaactgagcc agcttggttt cgtacatcgc gcagatgtca    99360
agcttcttgg tctgactgat acggaactca tcgcggcctg agctgatgac aacctggatc    99420
tctttgtaca ggctggaatc gaactgaatg ttctgttcct ggatccactg catcacagcc    99480
ttggaaccat cagcgccata acgcccttcg aatgtacctt tgatcacttc cttcaggccg    99540
tctttgtaca tgtcaggaat ctgcgccgtc tcctgaactt gagcgtgta gttgctcagg     99600 tagttctcgg agtctttgtt gaacttcttg acctgctgct cagtgcggtt gaagtcgttg    99660
aaataactga cgaaactacc aacaccgatt acaacaaaag ccagaatcgc caaaccgatg    99720
atccaaccaa ttgaaatacc tttacgctgc gacatcttta cttcctcttg ttaaaacaaa    99780
cgtttgtaag tgcgaccatt gtactgcata tggcctaata tgaaaattgc ggtaaacgga    99840
acacaaccta ataaaacgac gataatcact tcccatgtct tgaggtcacg ccatttcaga    99900
tactccattt ccttcatttc aacgcggtta tagcctttgc ttatattgac tgcaacttct    99960
tggaatactg atatccccat gggtttgcca gtcaatgaaa gaccgtttcg ggaatgaagt   100020
tccatgttat tcatcccatc agcaaatgac gtggatttac cccaattgat tttcatatcc   100080
ttcgatatgt cagtaaccac aatgacatcg ttctttttac caccagacca tgcatatagc   100140
agcccctgaa atattccac aggctggcca gaagtcacta cccacacgat attgacctga    100200
cgtgatgccc ccaatgtttt caaagtgttg ttcagataat cattccaata atcaacggga   100260
atatccatcc ctgacatatt caaaacacgg gttactcggt aataatcata caccctcgga   100320
tatgacggga tatgatcttt gaacttctca gcgaattgct ggtcagattt agagaataat   100380
gaatctttgt tgcccagcac ataattcata tatgaatgtt cacgtgccgc aggttccccg   100440 atttttaactt gtgcccaacg cggaggctct gtagtaccct gacgatcaat acggtcaatg   100500
ctcagatcac cgacggttgt taatacgtcc caatcaacgt cataagagtg ctcatagcac   100560
gtgctgcaat gacgcgtttg tgtacaagat cggttatttc ctgaaccaga gcaagaagtt   100620
gtgtaatagc acatacattc ataagaatgg ctacaaccca ccttatttcg ttgcttgtca   100680
gtaacgtacc cattcaaaat ttcaacatct cccgaactac ccagggaaaa tgcagcgtat   100740
gctcccgact ggataaggca agacaatacg ataacaatgg ccgtggcgat caaagtctcc   100800
tttggctcat gagtcttgcg gtgatatatc acaaacaaga tggccaaaat tacaggaacc   100860
acaaacagaa ggtaaatcat aacacaccat ccacagttg ttccttcgtc ataccaagaa    100920
gttgattttt atgagaactg tgcgccccgt tcaatttgag caattcccag cgttcttcat   100980
gatactgtgg agttattgca tcgtcaaaag aaacatggtg gcgatgcata attgttgcaa   101040
cggtgtgaag aacgattgct gttgctcttt ttaaagcacg tgtatccgtg atgtggtctt   101100
cgtattcgat tcccatcaaa tcgagttctt ttcggatata tgctatagac aaatcacctt   101160
cagaatgcaa tttaacgata gtcgcttct taggatgtaa cacgccgtct gtttctttca    101220
tgaacagatc gtacaaatat tgtttgtatt cggggcgctt catctcgtaa tccctccggc   101280
```

```
acagataata ttcagttcac cgcgacggaa accgccttgc ccaccgttca atttagtcgg 101340
aagcgtatct tgaactttt gtgcgaaccc ttccgacact accagatgac ccttttcttg 101400
tttcggggta gattcaaaat aatcgccaaa tgtcgcttcc atatcgagca cagacatgtc 101460
ttcaattcgt tgcattgcca tgatatagga cctcagtata atttcgtata aacttgttta 101520
acgccaatat cggcaggagc tgtgctctgc tgcatattat agaatgccaa atctgcttgt 101580
tctttgtttt caaaatcaac tacaactgtg tgtactgata ttgcttcacc ctgtccataa 101640
gcataacaac ggctggtgac caatatttg tattgaggtg tcataaatca atccttgcaa 101700
aagaaagggg aacgggctaa taataaccca ttcccctta ttgaagaacg caatcgcagt 101760
cagattactt tttcttcagc tcttccagct tggcttcaat ttggtccaga atctctttac 101820
ctttctggac gatggcttca ccgtcttgcg cgtgtttacg aaaaaccaga gcgccagcta 101880
cgaagccgac aacaacgcca ggaagcgcat acaccaacag atcttgtaac atgatttatt 101940
tcctcacttt tataagcaag gatatttata tcatcgtttc aacaaagaca tgaggtttac 102000
actggtcgac ttcggattgt cctctatatt ccggacgggc attttcagat tagtgtaaac 102060
ctcagatggt tcccaacgcg taccctgctg caggtgccat atatgtagag gaacacccgt 102120
ttcaaagaac acaggcatct tccacttctg gacgccagga acgtgccctg caggagcttt 102180
ttcgcacaac agggtatctg gtagccagag ggaacgggct tcccataatg ccttacagga 102240
gtactcaggc cagatgcgtt ccatgtagtc gatctcatcc caagtacgct cggcatccca 102300
cccgatgtaa cgggtattct tcagacggaa gaatttctta agccaacaag caccggaggt 102360
ctcaaagttc agacgattga tgaacgtgat gtggccgaac tcttcaacgc attcctgaaa 102420
cgctttctca aggtcgtttt cgagtatatc acattcttcg tctgtaatag acaaccgtt 102480 gatctttttc ttcccgtgct tggtcaccca atcatcacgg ttggataaga acgccgcgcc 102540
gttacgattg gattcgctac catcacggtc acgcaacatg aaaccaggga cgtctatatc 102600
ccatatgtta ccgaagacca tgttcaggc ttccaggaag ttccatgcgc tcaggcgacc 102660
gaagtatttc catgacatcg ccgtattcca cagttcagtg aactggtctt ccttggtagt 102720
gcattccaac atccaacgaa aagaatccat ttgggtttta ccacccaacc aatcgatata 102780
ggactgaacg cacggaatca tcttcgactt acgataacga caatctgtat cgaagcgcat 102840
acgatcaaag ttcaggttat accaatcaga aaatcgctga aactcttcg gagattgtgg 102900 gggtacagga aattcactgt aaattgtcca tggtccaatc ccattatagc aacaaccca 102960 caaaaaggcc atccaaatct tgcgctcgat cttctcgagc tgtgtgatgc cttctgtaac 103020
ctctatggca taatccatca gacggacttg ctggttatgc tcttcagtgt aggatagcgc 103080
ctccacccat gccttgagca ggtacatgcg atttttctggc ttacgataat ctactgccag 103140
atcaatcggg tatttccatt tttcaggggc tttataccc tgcggcattt tagaaatgtg 103200
tatcatccga ttttactccc gagttcaaca cggaacgcca gatagaagaa agtggcgatc 103260
gatactggac agatcaccaa gaatgggcgc tgttgcaccc cttctgtgac catgacgccg 103320
accagcgaaa ccgtaaagat aacgaacatc agcatcatga agataaatc aacatgcttg 103380 attttcatct ttcacttcct ctacaggaga acaacttca ggctcagctt cgggagccag 103440
ctgaatttct tcggggctta ctacgggctg tcccagagac cagataggca ggaaacgacg 103500
atcattcgtc accaaccaaa tttgcttggc ggttttcgtc ttttcggaaa taaaatgctg 103560
ggcattgacc tgggtacgag ccaaacccac ctgacgccaa gaaccgaaat ccttagaaga 103620
aggattggta ttcagttgaa attgtgggac gatttattc tgttccggat agtaacggac 103680
```

```
agcgttaatc atcttcgcat caccacggta atcaatagca acagcgacaa cgttgcgtgg    103740
aatgaggatt ttcattttaa ttccttttga aactctgaat tatgttatag acgaaaggcg    103800
ttaataagat agcaccccc aaataatata acgcgtaaac gttcaatatt tcggttgaat     103860
ccaactcaac gatgcccaaa tatttcatga caccgacaag cacagctgtg atacacatca    103920
ccaatccgac gaacacaaaa tatttagaca tctgtttcat ttctaaccct tactcaacag    103980
gccgagaagg gatacagagg actttgttac ctctcccttg gcgctcgcct tggttttaga    104040
tttggtcgcc ttctcaggga ctcgatgcgc tagaggatca tccccaccga cttcacgcgt    104100
cattgggtca gtttcacaga atccgtaaaa atctttgatg tccagaccca tggcgtgaaa    104160
ctcaccacgc atttgatgat gaatagcgtt accaatcacc cacaaaggtg catcaaacgg    104220
catcatggct aattcgctat catttcctgt tttgaattct tgagtgtttg tagacgattg    104280
gcgatacaac acgtcttgac cgctgtaatc attgaccacc acttcccaac ccagcgccag    104340
catttcggcc ttcgacttct caaactcctt ggagtaagat tcgttgcgtg accagccgga    104400
atctcccgcc tctttaccag aacgcccacg gatacgagcg tcgtactggt agcggtcagg    104460
gtatgcaaag tacagcagtg ccagtgattc aatcggatag ttcttgaaca tccattcagg    104520
acgccattta tccgacagca tgaggggttc accctcgcac accaaagtgt aaccctgagc    104580
cagccaacct ttgaccagat cacgggcgat atcacccgag cctgtggcgg cgtggatggc    104640
gtccatggaa gtccaggaag ccaggccgga tttgttagac acagtatact ggccaacgaa    104700
gattaacttc agttcttcga acttcaggcc gaatgggcgc gtcttgtcac caatggtgta    104760
ggtgagttca gtaggggtta gggtagtgcg cagccattcg atgaactgaa caacacgggt    104820
gcctttaccc gtgccagagg ttcctttcac tacaattatt ttagccatta tgcatcttcc    104880
tcaatacgcc agctcacacc acccaaccag ggagaccaga aaacagcaac ctgtgggcga    104940
tcgttttcta caaacttcac tttatactgg tcatcaaagt tatagaaaat ttcgtcgtca    105000
tcaggtgcca taccgttttc gatcagaact cgttttaatt ccaacgctgc gccaacggaa    105060
gttggtggat tctgattacg gatgaagttg tttacatgga taatgatacc atccatatca    105120
ctgtcaccgg aacgcttgtc agggctttct acaactttat tttgttcttg cacgatgtgc    105180
tcctatcgga catattgata atgagaaacc aggcgattca ccacttcatc gaggttacga    105240
tttaagaagt caaagtggtt ttggccttct acatgcttaa tataaagcat atcctcgcaa    105300
ttcgaaagat ccagtttttc ataattgccc tgagggacga agatgacgaa gatgttattc    105360
agggcacacg gctcaacata cttcggattg tcgtcgatca ggacatcgcc agcaagcaga    105420 tgctttttcat ccgtgctcac gaacccatta atcaacgatt caaagtgatg gtatgtgaac    105480
tgacgcttgc tgcgttcgtg ttccggttcg cattttgtaa ctgccaccat ttccacttgc    105540
tcaaacttct gaaggagaga ggcctttaaa ttcgtaagga attcaacagc ccctggcagt    105600
ggtgacattc tggaatacag atcaggcata cgccaccaat ccatcggatc acgtcctgtt    105660
ggcgaatcca tccactgacc agcaacgaat acacggcgcg ttaaccaggc cggatgcgcg    105720
cgttcacgca tgaggatcgc cagatcacca gcgtgtgaca tatagcactc tttggtgatt    105780
ggttgaaatt cagatgggta gtcgtgacat cccatatttt ccgcagcggc tttagaatta    105840
gagatattga accattcaac ccacggcgaa agggaatcaa ccagagtcaa atccacatcc    105900
accagaacgc gatataaccc gccaatttta gaacatgcgt catacagacc aacgtgatta    105960
ttcatcagat ttctccactt gatcataacc agttgcggtg cattgttctt cggtgcaatc    106020
```

```
ggcatacaga accacagaag attccttcac gtaagtggtg cagtgatagg tttcatcttc   106080
ctggatggaa tcatcataat tgcaaacagt ttgcaacgga ccaggagtgg tgttgtccaa   106140
agctgcatgt gccttgatgg tgtcttccat cttattcacc gcttgctgat tggtgaacgt   106200
cggcgcatcg aggtcaacgg tagacgcaac gtccagaagg gtagagcatg cagtggtaga   106260
gaaagccaga gcacacacca gaagaatctt attgagtttc ataacaatac ctgttgtcaa   106320
agggataaca gggggaatta tatccccctt tgttttattg aatcaacctt tcttgcccat   106380
catggacaac agattaactc gacgtttgtg agaccaacca accacgtcta gaatagactg   106440
tatcggctct atgaaggtct tttcaaacgt agtgtggtaa tctacccact tatccagccc   106500
caactccgga gggaggaagt cagggaaggc tatgcggtcg ttccccacag ggttcccagg   106560
tttcaggtta atgattttaa ccttatcgcc agattctatc ggcgggagac cgaggtcttc   106620
atgcttgtct atcagcttgt tgtacataat acaagccttg gcagcaaagt gtgtgccact   106680
gatataattc ccgttcgcgt ctaaccactt ctcaatatca ctaacgccag aggcttgagc   106740
aatatcatcc acgttaatt ccatatattc cttcttataa cccgcgatca attcctgaac    106800
ttcagcctcc gtcccagca gaactttctc atagcattta accagacgtt cacgacacca    106860
ttccggcgtt gtagatttac gcgcttccag acctttgaat ttgatctttg cttctcata    106920
cttgatgcct tcgctatcgt atactgccat gcaatacatc ttcttggctc gccatacagc    106980
agacgatgcg atgacctcac gttcccagac catgcgctgc tcaaacccgt tcatggtatt    107040
acacaacaac tgcgcccatt cactggtttt tggctggtaa ttctctttga tccattggtc    107100
aatgttatca acgagtttgt gatggtcctt ttcttcaggc acaattgct tgaccaggcg     107160
ttcaatgcaa atgtagttgg agtcagtatc acccgcgata acaaaatcct gaccagtagt    107220
gccgcaaagt ttgttcagat aatcatcggt gtggcgtttg ttccatttgt tgatcagctg    107280
gccggaagtg gtgattgctt cagcgatgtt gatgttgaag tattcttta accagacgtt     107340
agaaattgcg ccatatcctg cgttcatcaa gattttcaga ccttgttgta acgtatcttg    107400
ggcaactccc aaatcttccc acttatgcat gacttcagtc aggtgatcaa gatcgatgtg    107460
cttgtgttct tcataccatt caggatcgta gaaacgagac ttcatggcgg attcaaggtg    107520
gaaatcacct ttagacatct ccttacacca accagcccat tgctcatatt tcaggcctgt    107580
tgctttctcc cctttacggt cagcgtatat gcctcgcata atttcggaaa ggaaggacat    107640
cttctcatta ctgaagaact gaacgttcgg ggtaaacgaa acgttatatc ggcgtagtgt    107700
ttcaaaatgg aattcgccca gcgcgaccaa ttcatcaaca acttgtatgc gttcatcaat    107760
agcacgctgc aacttgtcgt gaagattttt gagatgacga cgtttattca tcggcgttgt    107820
catatcattc atcgctttgg tcaattcctc acacatggcc tcaataatat cacggcgggt    107880
gtgcttatca gaaacgatag tctctggacc aaggttgtat tgttgtataa tgtgagggta    107940
cagggagttt aagtcctcag agaagaccca gaaatatatc cctggtgtaa cctccatgac    108000
atacgcgcct tcaaaatctg ttggcccgtc atagacgcgc tgtatttag ggacaatccc     108060
cttttcataa agacgataat agcacattgc cagccacggt gctacagtgc cgagaccgtc    108120
ttcatagtta gatttggtgc gatacgccaa tacaaacatc agctgtatca aacgcagttt    108180
ttgttctaag cgccacacga gtttgacgtc tttgatacca tatcgcgtat gcttgcaata    108240
atcattgaaa taaaggtcat acaacgattt gctttcacta taatccaact tcttctcgcc    108300
gagttcacaa taagcgatcc agtccagtga gtatttttcg cgggtggtgt aagtgtgctt    108360
cttgtacact tgcatgtagt ccatcattgg acaacccaca aactgataag acgtgacgtc    108420
```

```
cccttttacgg tctttgatga aacgtttctt cagtttaccc caagggctga gacgttcggc   108480
ttgtgtttca ccaagaacct gcgtaattcg ttcaaccaaa tagggctat cgaacgtttc    108540 aatgttccac cccgtccaac cgtcaaattg acgttccgac cagtaatcca agaaggcgcg   108600
aagcagatct tgttccgtcg tatattcttt atattcgacc tcaagaccgc cgacttcttc   108660
atcattggga tcatatttga atttatggcg atccttggaa cacggcatac cccagacata   108720
gaatttgttg gtattcatat cttggagctg aatcagcgta atagggaacg ctgcattcat   108780
gttctgggtg atcttaccat tactgtcgat gattgggaat tgatcagtaa cattgttgga   108840
aataaaggaa ccagggaaat gctcccgaac gaagtcatgg ttggccagga cttgcttatg   108900
gaagcggcga acccgcgcct cgctgccttt aaacgtgtgg gattcaatgg ttgcgtgtgg   108960
gaatggacct ttagtcattt ctccgtcacg ccaaccagcc gagaacactt cgatatccac   109020
gttggcgatg tggatatttg aataatcagg tgtgatcatc ccaggaaaac tatgggcgat   109080
gaattgatat gcataatccg tttgtccata caccgcagcg ccttcgacct ccttgtactc   109140
ctcaagatag ttgtcagcgt cgcgcattga tgcaaacttt ttagacacca acggttcgtt   109200
gaggaggcca atcttttcaa ctttggaata atcagctgtg ggtaaataca aggtgggttc   109260
gaatttctta cgcaacattc ggcgattgcc gttgtcgtct gcgatacgaa tcagaaggtc   109320
gttaccctgt cgggcaacgt tcgtatagaa aacagtcatt gtttgtctcc ggttaaccgt   109380
gccgtcagca cgtccccgta atttaaccga ggaacgttca atgaccaagg agtttaaaat   109440
ggcaatcccc tttgtgagca tgattccagg ggcgctaaag caactctgga atcttgggac   109500
tgatttggtg caatataagc gggaaattgt tcaggctaaa cacgatgtta aactggaggc   109560
aataaagtct tcttcagaat gggaactttc taagattacc gaagtcggcg gttcttggaa   109620
agatgaattc tggacaatcg ttttggctgt tcccgctatc cttgttatga tcgctccggt   109680
tgtggaactt ctaatgttcc ccaccgagta tcataaaggg gatttcatca aagcagtaat   109740
tgatggtatg caagcccttg aaacagcacc tgattggtat actgcttcgc tattgacagc   109800
aattagtgca tcattcggta tcaagggggta caaccattac aaaagcaata gccggaaggc   109860
gcaagctgtg gatgctctca aacagttttgg ggtcaaagtg gttaacaaag atcccactgt   109920
tgttactcag tcgggttctc ccgatcttga gtctgctccc ccagctgggt ctactgcgac   109980
ctctggtgcg tggcctgatc tgaagaaata agttcaaggg gaggaaactc cccttttcttt   110040 tggtgtttag ggaatgaaag tggtaaacaa gagattgctc gttacccaag gcggggcgac   110100
gatagtacgc ggaaggatat atgaacaaac acagcttggt gatcataaga ctcgtctgac   110160
ggttaaagca cccgacggtg gttggccaac aaaggtgatt gtcccagacg gcctcataga   110220
acgagggacg cgcgacgtata aaggagcaga gttcaaaatt tattaaaata tttattgaat   110280
aaagtttact tcttcaataa ctggcgtata cttctaattg tagtacgaac aaacaacaat   110340
ctgaagagaa ggaaatacat catggcaatc gaaattatcg ctcaatcaaa atcaggcaaa   110400
acagttctgt tcggaaccga agaaggtcgt gcaatcacca ccctgggtac ggttgacggc   110460
agcaatccag taaaaggcgg tcgctttctg gttgaatacg gttctcgtgt tgtaatgata   110520
agcaaaatcg atggtcgtga aatcactgct cctcgccaag agttctttga ttcacgttcc   110580
gctgccatgc agttcttttt cttccagaaa cgtcatgaac tgttcgttga agcgaaagac   110640
gcaggtctgg acgacgcgac ggctgaactg attgccgaag gtaaaatgac tcttgaggct   110700
gctctcggag acatggattg cgaagccgaa gcacattata ttgaatattc cgcatatcag   110760
```

```
aacgaatgtg aagatgatcc ggaagatgac ggcttcgacc ctgacctcca cggcggtgaa    110820
gacgataaca ccccttccct agaagttctg atggctggcg gccaggccgc ttgggaatgg    110880
cagaacgaga agaacgcctg gctggattcc cgtatctaat tgattgaagc cccttcgggg    110940
gcttactttg aactgaagga ctatatcatg agcaacccaa aaactcctgt ccgtattgcc    111000
gtcgagcctc tactggttga tgctgagaat gctgctgagc agtacgcgaa caaagtcatc    111060
aagaacataa tggacgatct ggcatccaac ggctgggacg tcgagaagtg tgctccgtgg    111120
ccatcttcgg ttggtgtcaa gtttggtgat ccagattacc aacgaatgaa atctaaacac    111180
gcgctctacc gttctttgac ccaggcagtg aatccttctt acatacctgg gaagccggat    111240
attgtcaaag ctgatcttga tcgccatgct ctgtttgtca agaagcacg tcgaaacgct     111300 gcgatgcaat atgagtcttt catttgtaaa ctggaaaaca aaattggtag tcatagtgcg    111360
gctgtactga acggttccca tgtatggggt tattcaatcc taaccgtgac cacaccagag    111420
gggattcagc gctggaagac tcagacgatt atcaatatgt ccaagttggg caaactcttt    111480
aaccaatatc caaccaggaa ggtgaaggag taaaattaga caacaaagg ggcattaagc     111540 cccttgttt atttcccatc ccaaaagtcg tcttcatcgt ctacttcatc aaacgcagaa     111600
tccaattctt cgtcagagta ctctggaagg cgaccattct gtttcagata ttcaatctcg    111660
tcatcttcca attgaagatc tgttgctata acagcgctc cagtctcttc atcatgttca     111720
atgctataag acgtatattc agaaccttga actgtaatga tgatagatgt cggatcttct    111780
ggatccacgt gggcttcaaa cgggataccg tcaatcggag cgtcttctaa gaatgttgca    111840
agggctacgg cagcgcggac aacatccgta ccctgtaccg atgcataaat ttcttctgcg    111900
cccgtttccc cgcgctcaaa gaattcaatc gttgtcccgt cttgaacccc agtccagata    111960
ggcatatcgg ctggtgtatc agcttcaaat aattttgaaa ttggcatgtt cgtttcctct    112020
atggataaac cttatgggat atttaggctt ctctgtttgc cagccctggt ttgaatacca    112080
ccatttcttc tacgttattg gcgctcatag aggctatgga atcgaatcct ttattgataa    112140
gttccttcac attatcgtga atcttaccag gttctattcc caactcatgc attttgtttt    112200
cccaaacaga aacgttatta gaatctatta ccagagtctt cttggcttta acacgaaatg    112260
ccatgacaac aggttcacca gattggcgat agcgaacggc attttccgcg tagatctgcg    112320 cttttttctgg atcccctgtc aggtaaaatc cagcacccat cgtaccgag tcagtctggc     112380 caaatttttc aaaatcaaag acgtcgaatt caacattcga cccatgatat aaaacaatat    112440
ccgtaaaatc gggcaatgtt gattcacgat agaattctag gaaggttttc atagatacc c   112500 cacacttact gtatggggta tttaggaggg atcaatcagg ggtaaactcg ttcacaggaa    112560
cttgttccgg catagacaat tcggggcatg ctgccttcat tgactcaata tatggcttgc    112620
tacccacaat ccagaacaga gtattttcgt tgagcagttc tggcttatgc tgttggatcc    112680
aggtcatgac cttgccttca tagcgtggat gcagctcaat atcgcccac tgataatcca     112740 tcaggtcatt atagcgaacc caattcgttg tgtgtaaatc ccaatggtgt actgcaaagc    112800
gtgggagcgt tatctccggc tctcccttct cgcggatacc catcaggagg ccagccagcg    112860
aaacgctctt agaggcatgc tgaagatcct tcttgccgta cacataatct gggttgtcgt    112920
gatagcaacg agtgaaatcc gttatgtgtg gaagattagc ttgttttcca ataacacgca    112980
aacggctttc aataaagtcc agacggttgg gaccaatccc gatcagatat acattttcta   113040
gattcggttt cgggtgcata gccagccctg tcaaaatgct ggtacaagaa ttacatgaac    113100
ccgcaggaat gatcagatct gtgatatggt ccggaatgtt agcaacctgc tcgccgccca    113160
```

```
gcatatggaa tcctgcaatt cgctccggag aatgcaacgt atgatccaaa gtgatcccat    113220
attctagata atatgctttt ggattctgct gctcaatcaa tttcttgcag cgcggttgga    113280
tagtgctgtt gtaacccgaa ccgacgaagt tgaattcgct gccgaaccat gcactcatct    113340
taaccatatc gtggttcata caggtggttg gtttggtcgc gcccaggact gtagttgtct    113400
tgccgccaaa atgccgagag actgccgtcg ccataggga ctgcggacta ccaacaacag    113460
tgccatggat aaggtcgggg gagcctccga ccttgaggtg ctcaaccatc agccagatgg    113520
cctgacgcaa tttactacca ttgatcccct gcttaccatt catataacaa dacagcggcg    113580
cgaagtaatc ttcacgtttg aaccagacct gctgattggt ttcggggttg caacgagtt    113640 cgcacggggt gtgtttgtag aggtagtctt cccagtgaat gatatttcta tcaagtgaga    113700
gagcattgaa gattgtttta cgccctgcca taagggcgtc aggggtatat ggggcaaaga    113760
tgataccttc tttcgccatc tcttctttta gagtagtggc caagagttct tccacttctt    113820
caccgtgtaa aatttcttgt tcggatgtag gcttcattct atttctcctg tagacattgg    113880
cttatcatag cgtatctaca ggagtataga aaggagaat ctgagattac ttggtcagaa    113940
aatccatcag gcggcggaaa aacgatttgc gttctactgg tttcttagat tcagggaccg    114000
gaatagaact atcatattta acaaccggag caccctgatc gttcagaaca cgactggctg    114060
gtggagtcgg tggagtcggc ttcaaagatt tgatcgcctg attcagatcg gaattgtcca    114120
caacactcgc ttcttcagcc acagaaacac acggcttgat taaaacagat ttcttggact    114180
gctcatactg atgagcgata tctagatatt tcttgcgctc agcgtagaaa tctacgttct    114240
taactttacg gcggcgagca gtagaactct cttcaccata aaagtcatat ccattttga    114300 acatccaatt cactgcttgc tcaaatgaat tgaataccat atacaggccg cgccgcccgt    114360
tgaccatatc gtcttcgctg gaataaccga tgaacaccgc ttggccttc ttgttcagat    114420 caaatggggt gcagacgccc gtatcatcta gggaacgcgg tgcgaggtgc ccgtctctgt    114480
aaatgtaagc cggatacaag aactcattca gagtgcgctt gttgccttta tatgtgtaca    114540
gacgagcaaa tggaggcaga tcacaaacaa catcattgta atcccaaatt gttacattgc    114600
gcatggtgtt tcctcaaatc aatgaagggg tttataaacg gttaaatttt aaacccctta    114660
ttgtcattga acaaatcaaa tactggtcat atagagtggg acaacctgct cagcgatgaa    114720
gatggcttcc gtaatggtaa aatcatttcc ataagatctg gcaataattt gactaccgtt    114780
tgttgctaaa ttaccgtcct tgtccacact gaagaatgta ggaaatgaca agatatcttg    114840
tcccgttaac gcagcgtctc gacttttcgt taattggttc cccgcagacc caacaaaatt    114900
cagttctaat gttcggttat tggtggatcc ttgccatgcg cctatcaaat ttattttcag    114960
cgttacagtt gagtcattat taaaaacttt gaatttatta gttgctaaat caagaatgg    115020 tgtcatcgcc gtagaaccag cgacaggagt tttatcaaca aacaacgaca ataaatctac    115080
gccagttgca ccagtaggaa tattgagaga caatccggaa aatctgactt ctgttttgat    115140
gcgatgggtc tgaagcatat tccccaaata gggagatgtc aaaatggcca tactccctcc    115200
ttaagaaacg ataaccgtcg catcagaatt aattgcctta acccatccca ccgtcggcgg    115260
ggttaaaacg accatatttc cttgatatat gatatgcgcg ttgttacccg ttggagtgct    115320
ggggctatca cacagataca cagaaccgtg agtcacttga agagttttca aagatgtgcc    115380
gtctgagact tgcgtccatg tacttgcgtt tggtgtgatc ttagcagttg ccataataga    115440
cctcctttac aagtcagatc tatttattac agacaaaaag aaacccgatc atcctgatcg    115500
```

```
ggctatgtta aaccatcgtg gggatggaaa gactactcac agcaatttct gataatgggc   115560
gttgggagag tgcgtcggga atcgaacccg aaatcgtcag gacgctgaaa gctatttgca   115620
tttcacttgc atatcctgcg actttcttaa cttccttaac cccagattgt tatgaagtcg   115680
gcatgcacac cttcttcatc ttcaggaagt cacactcata atttgatttg cgatgatgaa   115740
cccatttcat ctggggttgg gtgagtggga gttgaaccca caacgcttgg ctcgctttcc   115800
ctaccattca ggccacccaa ttccaggagg tagagcacct ttgccgtcgg tgcccatatg   115860
ccagtcttcc gccctggcct ccactcgcgt ctgggatttc cgcgatgatc gcaaatttgg   115920
tgtgagtgga tggatttgaa ccaccgcgct gttacgggga gatttacagt ctcctgcatt   115980
cgaccgctct gccacactca catttagtct accgccgcgt gctgggccac gcttgaggac   116040
atcggccatc cttcctcagc taatccacgc ggcggtagat ttggatcaga gtgtacggtg   116100
tagcattccg caggggtgca cctactgtag cccttccact ctgaaattgg tgggtgttac   116160
ttccgtcggg ttcagattcc gttcggctat tggacttcgc ttcaagagct tgtcgttcgc   116220
gtacttcgtg cttacttgct ttcgttcaca cccattgttt gtcgtcgggt gggggattca   116280
aaccccaatc tttagtttgc gtttcttcaa agctatcata tgttcacttt gaataataaa   116340
ctcccctgga catcataaca ggatctctat ttcatcctgc aagacccgac ataatatggc   116400
gacgatgaca ggacttgaac ctgcgacata tggattaaca gtccaccgtt ctaccgactg   116460
aactacatcg tcaaattttg tgaagaccaa acgccggatc gtaacggtcg tatgtcttcg   116520
ggtggctgtc gttcttgatg cttaccatgc gcagatcata agactgattc tgcaggacat   116580
acaccaacca cagctgtttt ataaattcca tcataaagat acctcaccaa attttattga   116640
acaactggtt tatttagtgg tgaccctggc tggacttgaa ccagcgacca atcgattatg   116700
agtcgactgc tctaaccact gagctacggg gccaaaattg gcggggtctg aggcttttca   116760
cctcacctgc tggattggcc tccagctgtt ctctctgggg actcgctgtc cggacagcta   116820
tcccttaaac tatcgcccca tattcaattg caccagagca taattaccgc tatacgacca   116880
ccctctcggg caggttggtt ctgacccaac gtctctctga tgcgttttat tgtgtgccca   116940
atcaaggact gtcaacctttt tatcccgttt gtgcatgatc agttcatgca tgcctcttgt   117000
gcgcctcacg gcaacgcgct tctgtaggtc atcgacttgc actgtagtct caccacaggc   117060
gtttattttt ccagggcttt ccacttacaa gtcttaacca gatcgggata cgggcttgta   117120
agatcggatt ggacacaact ttgatggctc taggactaaa gatcccgcgt cacccataga   117180
cttggtttat aaaatctaga gccatcaaag ttgcaaccaa tgtcgcaact cgcacttcag   117240
cgtcttcgtc tcgcttcagc acttgtcctc tacgttcgga ccaaacgagg ctggccgaca   117300
gaaacataac accactcatc actagagcga ggatgtggtt gatagccacg atgttacgtc   117360
tctgtcgtag agtgatcaca cttgtcagga tgatcactgt tttgcgaact tgaaaatact   117420
gcgcctgtct cgggtttccc cttagttcgg cctctcattg ttcgtctggt cagggagcta   117480
cccttgatga ccagcttatt ttgagatctt cgccagcacc cactagtgtc tagaatatgt   117540
aggtgtcgag gtctgcaagg cattgcccta tttcatacaa cgctctctca agtgcgcaaa   117600
tcgaagttct ctgggcttaa caggttcgac ccaacatgtt gtatatcgcc taacttgctc   117660
atgggacgga cacatctgtg tacagacctt gagggttaaa agatataccc agagaacttc   117720
gatttgcgta gcccttccact tgccaaagat cagggctaat aacaagactt cgctcacatc   117780
tttgaggaca ctgcgcggga ctcgaacccg ccatgaacat ctggcgccaa atgcttccac   117840
ctgtcaatgt cctcaaagat gtggagccgt tttagggagt cgaacccaaa tgattggcca   117900
```

```
gcgctgacct cacatcccat ctgacttagg caacccacct ctgctactca ggagcttatc    117960 cccctttggac agtcagatat aacggctttg ggattggagg aaggactcga accttctcat   118020
gtacgctcct gatttctcag aagtagcctg ctcccatcga cctattaagt acacgctccg    118080
ctcattgttc ggcgggagct tattaatcac accctcccac ctattgttag tgcgccgaat    118140
tttgttatga ggaatcggaa gacctcactg acttataggc tattacgccg ccatcagaac    118200
ttcggaatca ttagcagtta tttgcttggt cagtttctaa aaacccgcaa agtcacgcac    118260
aacgaaaacg aaaacctgtt tgagtcctaa acctacctgt cttggtctca catcgatatg    118320
agtggccagg actcaaacag cttgccgttc agtgagttaa ctatactttg taacccgtta    118380
ttgataaaac ctttttatttt gttggcgagg gtgcggaatc gaaccacact tctgagcgct   118440
accccgtgtc accaatgcac cacctcacca tcgatttgcc ggaacttacg catccggcct    118500
cgtcctgtcg gtgttcttct gaatccggga agatcagcag gaactatgaa tcaagttaat    118560
tcaaccaaca ggaatcctct tgttgcccct tgacgcaaca ttatgaaccc tctatgaaga    118620
ctcataatgt tgtcggcgtg atggagatta gcgcccccga cctcccctta tatgttggtg    118680
tcgacttgcc aacagggtgc tctctgattc tgagctaatc acgctacaac agggagtttc    118740
gttctccgac ggtcaagtgc gtccactgac accagcgagg tggctattac gcctctattc    118800
acacaagccc ctgagactag gggttaactg gttttgggct gcaaacccga ctcccactgt    118860
gttatttccc tcatgtttaa tactttaccg cagcccagct aatttgaaaa gtcctctccc    118920
ctttgagcta cactgcccac agcagtgcgg acgaaccttc actcaaaacc ggatgcgccg    118980
aagtgggcaa ctgtttaccg gactgatcgg gtagacccag gagagagcag gtaatcccga    119040
tcaggaggat gaggagtaac atcatgtaaa acatagtgtt ccctcccttc catgcaacta    119100
actttactac aattatttat tgaataaagc gttattttaa cacttctaac ttcacaacac    119160
gacgcagaag gtaaacatat tcgccagcag cttcatgcgt catataatgg gtagaaggtg    119220
tggaatgatt gttctgggtt tcttttaatc caacacgttc tgcccaacca ttaatagagt    119280
tcccatagaa accgataatc gcgccaaaat aaatgcgctg gctttctggc tctaaaacat    119340
agttgacagt gaagcaaata tcagaacgaa tagactccag tttcatacca acacgacctt    119400
cggagaattc gttacgaaca tataaatgac ggaaacgatc gcgccgcgct tgtgatgatt    119460
cttccaattc ttgtcggagt gaagaagtta cgtcaatatt aaatgaaaat gttggattct    119520
gtaaatcgga acgggccaac tctaacgcag attcaacaac gcgacggaaa ttgatacttt    119580
tacctgtcag gcgtttcact tcatctgtga ttgttccaaa agggatttc gtggcgcgtt     119640 cccccttcgta ttttgccaat aaaggaataa tgtgtttcat gattgctgtg ttaatgtgca   119700
ttccggagcc tcaccgaatt gattaaatgt ctccattatt atattggaga tacgtttatt    119760
gaatataaac acaggaatgg ccaataaaat aatgacagtg attattaata ggtaaaaact    119820 actttttctac aacatcaaga aactgtatct taacgcggtg cccttcgagt tgtgagtgtt   119880
aacgaacaac gagaagcagc ctccatggct gcggaatggg actgcctgtc aaggcggtgt    119940
tacgagcgag ggctttagcc ccctcgcgag tatattcgaa taaattaacg cgcgagagcg    120000
ttttgattcc ctttggctaa atatcttcaa caccatattc aaactcaggt gatggagatt    120060
atcatggcca cgcaaacagt tccttcactc gacgtcagag catttgaata cattattaaa    120120
cagcgaatga aagctgatcc caccctttaaa gattatgact ttgaaggttc tggtcttagt    120180
gcgattattc gtttgttggc atctgacgcg aacgccatag cctttatgca aaacatgctt    120240
```

```
aatggtgaag gccatttgaa gacagcaaat caacgttcaa acgtcggttt atctgctgca  120300
tttctttcct acacgcctga caactatcgg gcagcataca tgtatgtcaa catcaaagtt  120360
acgccttatg acgccagcac agcccccaat gagatcatca tggatcggcg cgtaatgttc  120420
gttgggcaa  aagacggcag ttcctacaac tttactgttg agaaaccagt gtcagcaacg  120480
ttgactgcag acggttatta catgttcaac aatgtaaagt tggtacaggg gaattggttg  120540
tacaagacat atgatgttga aggaagcgcg atttcaacat atacgattcc ttctgggaat  120600
gtcgatatca atcatatggt cgtgcaagta caagaatcag agtcttccga cgtttcgacg  120660
acatatcaac gttacaacag tccatttgat ctgagccaat atgcttacct gtatttcgta  120720
gaattgggta ttgacggtct gtatgtgttt gaattcggtg atggttatct gtctcgccga  120780
gtagaagacg gaaacgttat tttcctccag tatttagaaa cttctggtgc agaaggtaac  120840
gacatcacca gcttgtcttc cgcgtcttcg ataggcgggt ttaaccaggt tgacgtggaa  120900
ttggtttctg aacgcagcgc gggcggcggg gatccagaat ctattgaaga catcaaacgt  120960
ctggctcctt tagcttatca ggccgatggc gctgccgtta cggaaacgga ttatggtgtg  121020
ttgacagaaa ggctgttctc taacgttgcc cgtgccaaat cttatggtgg tgacacgctt  121080
tctccaccgg attccggcta cgtttatatt gctgtgatac catctgttgg tgagactctt  121140
tcagacgcgg agaaggctga tatcgttgct tctttggaca aatataatgt ggggtctatc  121200
actcccaaag tggtggactc agacataaca tatatccaag ttgcgacaac aatattttgg  121260
gatccgactt cgacagttta tgttgaagaa cagatgaaag tcgtggttgg caacagtatt  121320
gtcaaatggg gcgaaaacaa tctcggcggg tttgatcagt tgttcgacaa agagatattg  121380
caggaagcaa ttacgaaaat ggaacgttcc attaactcaa atatcacgtc tgtcggttat  121440
aaacgtcatt tcaaacctga ttatggtgtg ttggatagct ttactttcag ttatggcaga  121500
agcattaaac ctggttctgt aaaaataaca gggtttaaac cacttccggc cgaagttgat  121560
ttcacttatt acatgcgtga tgaaaatgga aatttgaaca tgtataaggt gaataacaat  121620
gacacaacca aagaattttt ggttcagaaa acaggcgttg tggattacac caacggtgtc  121680
gtcgaccttc agcagattac ggtttcaaat tataatcctg aagggataac gattgtcgtg  121740
ctaccagatg gactgaatca aaatatacag gcttcacaga accaagtatt caaaattggt  121800
gatgtggttg ttacgccaga ggtgcgctat gtccaaagat cttaataatg gacacaatgg  121860
ggttaagtat gaaaccccat tgttctatca gaacgatttt cctctgttca tagagttcat  121920
ggacacgttc tttaattggc tgtatcggca gcagggcttc actcaagaag aaattttggc  121980
atatctggca gacacttcga gttggatgaa ccctgaaagt gaagattctc ctgttaaaca  122040
actcatagat ttgaaggccg acaaaacgcc aggctctgaa gccaaagatt atctgtcaga  122100
taaattttg gtcagaacat tgagaacat gatggcactt gatgctgaga cgttgttgga  122160
tgctgatgga agaccattat tttctattga agataagaat aagcagatag acgactggta  122220
taatgatttt gggtttcaac gaactgtcga taaatcattt caagaatttg gacatttat   122280
cccagtcggt tcggattcgt tgttgacggc cacgggcgat acgttctctg tctatattga  122340
aggaactaac cgaagaactc tggatcatcc gcgttggctt aaattgttga agcacatcta  122400
taaaatacgt ggaacaaaga aagcgattga attgttcttt tggatatatt tcggttgtcc  122460
agtcagcgtc tattttacga aagaagacat aggcggtctg gacggaaatt ttgaatgtga  122520
cggcacgaca gggatgcgtg atgattacta ttatgatgaa tacacttatg ttataggagt  122580
cccaggcgac gtatctgatt ttgaaggtgt gtttgaacgc gtcttccgtc agcatttcca  122640
```

```
tcctgctgga tttactgtat tcctagaaag cacaaggagc taaaaatggc cgatttcctg   122700
agtcaatata caggtcagca gatagatcag atattaggtt ctgttgatga caaagtaagt   122760
aaaaacgacg tcattgatga ttttgaagtc agtgacccat tgtttccgcc ttctgctcgc   122820
ctgacttatg agttgaaaag gtctgtggat acgattaatg acaccctgac caacaaagtt   122880
ataagaacgg atagtggtga acagacaatc aacggtaaga agacatttaa tgcgctgttg   122940
gtgaccaatg ggggcataca agtccccgct gggaaatctg tttcaatcgc ggacgaacca   123000
accaactcaa cagacggtgt caacctgagt atgttgagga acatggtgt cagtgaagac   123060 actaccccgc ctggttctgg tttggctggg gagttgttga catccggata ttacaaattc   123120
aatttggatt tcaccagatt gtctgcgtat accggaccaa cgttgccgac ttcagttcct   123180
gtgcagacag attctggagc gcgttattgg acaatgactg cattttttga tgcgttgttt   123240
gcagacaacc gatttaatgg atatgtgaca acgacagcgt atgacgcaga tatgctgagt   123300
ctagagtctc agattaataa catcaacacg tcgttgaacg ggaaagtcaa cacctcgact   123360
tacaacacta agatggcgtc gttggatttg agtatctcca atatcaacac gtctctgggt   123420
aataaagtcg aggtcagcac gtacaacacg aagatgacat ctctggataa cagcatcagt   123480 tctcttttcca gtgataaagt tagtgtatca acgtataatg ccaagatgac ctctatcgac   123540
aacagtttgg ggaacgccgt ttatcgtacc aaaacgaatt tgtcgtcata cacgtttcg   123600 gcttcgggaa cgacggctct tccagatttt gatttggtga acctttgtca atactggta   123660 actgcgcaat gggggacagg taacgttgtt gacacatatc gagtaaccat aactcgtgac   123720
ggaacgatca aatcagagtt gttggttcag aaaagtacga gcggtacagt gacgttcaca   123780
ggggctgtgg tgggtggtaa attgagaatt ccgttgtta atgcaaatac aacaaccgct   123840
tgttctgtcg attattctat tacagcttct ttctaaaact aaataccct agatgacatg   123900 aatacattta ggggtattac aaatggccaa caaaccaaca cagcctcttt tccctttggg   123960
tttagaaact tctgagtctt cgaacataaa aggcttcaac aactccggca ctattgagca   124020 ttccctggt gccgtaatga cattcccctga agatactgaa gttgcaggtc ttccatcttc   124080
tgtgcgttac aatcccgata gcgatgaatt tgaaggttat tacgaaaacg gtggttggtt   124140
gtctttgggg ggcggcggaa tacgctggga aacgctccct cacgctccct ctagcaattt   124200
gttagaaggt cgcggctatc tcattaataa caccacaggg gcatctacag tggttctccc   124260
ttcccctacg cgtgttgggg attccgttac tattgtgat gcctatggga aattcgcgac   124320
gtatccattg accgtatctc cagcgggaaa taacctgtat ggttccactg aagacatggc   124380
tataacaact gataacgtat cagcaacgtt cacttggtct ggacctgaac aaggttgggt   124440
tatcacatcc ggcgtcggcc ttggccaagg ccgtgtctac agtcgtgaaa tctttacaca   124500
aattttggcg tctgaaacaa gtgctgtcac tctcaatact ccaccaacaa tcgtggacgt   124560
gtacgctgac ggaaaacgtc ttgcggaatc caaatattca ctagatggga atgtgatcac   124620
tttcagtcct tctttgccag ccagcacaga acttcaggtg attgaatata ctccattca   124680 attgggtaat ggcggtggtt ctggttcttc tacgattacc tgggtctata atgggggttc   124740
agcggttggc ggtgaaaccg aaatcacgtt agacatcgtt gtcgatgatg ttccagccat   124800
tgatataaac ggaagtcgcc agtataaaaa tctggggttc acattcgatt cattaaccag   124860
taaaatcact cttgcgcaag aactggatgc agaggatgaa gttgttgtaa ttatcaatgg   124920
aacgccaaac atctataatc aaattgatta tactttgcgg gaagtggctc gtgtaaccaa   124980
```

```
tgttaaagat acagaggtca tttattttag tgttggtgct gtgttaagtg ggtataaagt    125040
tatctatgat aaagtaacac agagatcata ttttattcca gagctaccga ctggaaccac    125100
ggcagtcagc cttagttctt cggctgtact tgtgcattca gctggtagtg ttgatctggg    125160
cgcattagct gtatctcgcg aagagtatgt taccttgtct gggacatttg attctggtgc    125220
tgtcatcaat actaaaaatg aattactcac ccatacgaac ggtaagtatc gctgggatgg    125280
ttcacttcct aaaactgtcg atgctggatc aacacctgaa acatctggtg gagttggtat    125340
tggtgaatgg gtaagtgttg gtgatgcttc tttaagatct gatttgaatt cgacaaatgg    125400
agctggaatt gtaaaaactg gaaatgggaa tactgtacaa gaaacatttg attttataaa    125460
aaatgttcaa caaacaaatc tacatccttt tgttccttca ggcaatttcg gttctggact    125520
tccttttgat tcttcgttac aggtattcaa gtataatgat gaatattact catcaaagg     125580 acctattgtc ccaggttcga cagttccggc aaccccatcc gttgactcaa actgaaaaaa    125640
agaacctatt tctgattaca tagaaaatta cggtggtggt gtgcatgtag ctgatcagac    125700
acctgcaatt atggcggcta tatctgctgg tgttcgccgt atcatatttc ctaaaggtga    125760
acttagaatg tctcagtgtg atatcccaga gtacacacaa ggcctcacgt tgaagggca     125820 aggtgccaat caggcgtaca ctggaacaac agtgatcaaa ccgttaaatg ataatcaaaa    125880
ttgtttattt aattctggcg taaaccagca cggacaggat tctataaaat ttaaaaacat    125940
tcaatttgac ggagaatggc gttgcaatca tgcaatattg catgagtctg gagctggttg    126000
gtactatgaa aaactgacag gtaaaaattt caatacatgg gttatctacg atgatcaggg    126060
tttgactgta atgcgtgacg tttataccga agcaaccagt tcagatctga cgaaaagagc    126120
tacaggtggg tgtatccgta tatactcaga ttctgtaatg gacaccgtaa actgttatgg    126180
tggaagtgtt ccgctattgc tcgctgctgg tggaaaccga attacgaata tctgggcaaa    126240
tggtgggtat gatgttggcg caataatgtt gatgccaaaa aatgacagta ctaaccatat    126300
caataccgct atgagcaata tctatatcgg agaaagcaca aatacatctg caactgcaat    126360
tccagttctt cacatacaag gtaactcaat tcgtcgcgta tctggtgttc agatttcaaa    126420
tgcacatttt gtgcatgctg acttgactct caatacaaac atggtgatga tacgaaccga    126480
taaagttgat ggttttgtga tgtcatcttt tgatgttctt ggacgaggcg agtacagttc    126540
tgcaagcagt cgcacatata atttcttaaa tgcgacagat tctaccggaa tggctttttc    126600
tgccggaagt gtaagaggta ttaataataa cccaatagtt ttatcatcag gtctaggtt     126660 agctattgat gccgttgaat tcgatgggtg gagtacgaac tctgattcag gtatagaaa     126720 taaagctgct atacgttcat ctggtgctgg aacaaggtgc tgcattggta gctcatgtac    126780
tttcaatgct tcgcaagcgg atgcttacgc tgtgtatgca ggggatgaat ttgcagttga    126840
tatttctatt cttaatctta actatcctag tagcaatata ataattcctg caaatacaaa    126900
ttacagttac atgtataagc gaccaggcgg aaaattaacc ttagtcaaca cattgacaat    126960
ttgataacaa gaacccatga ttcataaatt ttattagttc agactaaata ccccatattg    127020
gtcatccttt atgggtatt  atcatgattt ctcaattcaa tcaaccacgc ggctccactt    127080
ctatagaagt taacaaacaa tctatcgctc gaaatttcgg tgtcaaagaa gacgaagtca    127140
tttatttcac tgctggtatt gatctcagtg gatttaaagt aatttatgat gagtctaccc    127200
aacgggctta ttctcttcct tcaggtattg tttcaggaac gactgcgata gtctgaacg     127260 aacaagccat ccttactcat tcttctggct ctgttgacct tggggaatta gcagtaagtc    127320
gcgaagaata tgtgactttta cctggttctt ttaatttcgg ccataccatt aatgtgaaaa    127380
```

```
atgaacttct tgttcacgat gataaaaaat atcgatggga tggttcactt cctaaaactg   127440
tcgatgctgg ctcaacacct gaaacatctg gtggcgttgg tttaggtgca tggttgagtg   127500
ttggtgacgc agcatttaga caggaagcca acaaaaaatt caaatattca gtaaagttat   127560
ctgattattc tacattacag gatgcagcga cagcagccgt agatggattg cttattgata   127620
tcaattacaa cttcacagat ggtgagtctg tagattttgg tggtaagact ttaaccatta   127680
actgtaaggc taagtttatt ggagatgggg ctttaatctt taataatatg gggccaggct   127740
cggtaattaa tcaaccattc atggagagca agactactcc atgggtcatt ttcccgtggg   127800
atgctgatgg taaatggatt acagatgctg cccttgttgc tgcaacgctg aagcaatcaa   127860
agattgaagg ctatcaacct ggggtaaatg actgggttaa attccctgga ttagaggcat   127920
tactcccaca gaacgttaaa gaccaacata ttacagccac tctagatatt cgcagtgcca   127980
gccgagtaga aataagaaat gctggtggtc ttatggctgc ttacctttttc cgtagttgtc   128040 atcactgcaa ggtaattgat tcagatagca tcattggtgg taaagatgga atcattacct   128100
ttgagaacct tagtggtgat tggggattag gtaattatgt tattggtgga cgtgttcatt   128160
atggttctgg tagtggtgtt cagttcctga gaaataatgg tggtgaatcc cacaatggtg   128220
gagttattgg tgttacatca tggcgagctg gtgagtctgg tttcaagact tatcagggtt   128280
ccgttggtgg tggtactgca cgtaactata atctacagtt cagggattct gttgcattgt   128340
ctcctgtttg gatggttttt gacttgggtt ctgacccagg tatggcacca gaaccggata   128400
gacctgggga tttacctgta tctgaatatc cattccacca actgcctaat aaccatttgg   128460
ttgataatat tcttgttatg aactcacttg gtgttggttt aggtatggat ggtcgtggtg   128520
ggtatgtttc taacgttacc gtacaggatt gtgctggtgc aggtatgctt gcacatactt   128580
acaaccgtgt attttctaac attacagtta ttgattgtaa ctaccttaat tttgattctg   128640
accaaattat cattataggt gattgtattg ttaatgggat taaggctgct gggattaaac   128700
cacaaccatc aaatggcctg gttatcagtg caccaaactc cacaataagt gggttggtcg   128760
gtaatgttcc tccagataaa attcttgttg gtaacttact tgacccagta ttaggtcagt   128820
ctagagtcat cgggttcaat agtgatactg ctgagttggc tctacgtatt aacaagctgt   128880
cagctactct ggatagtggt gctttacgtt cccatctgaa cggttctgct ggttctggtt   128940
cagcatggac tgagttaact gcactctctg gttcaacccc taatgctgta tctctcaagg   129000
ttaaccgagg agattataag acaactgagc tacctatttc tggtacagta ttaccggatg   129060
aaggtgtgtt ggatattaat acaatgtcct tgtacttaga tgcgggtgca ctgtgggctt   129120
tgatacgact ccctgatgga agtaaaacac gtatgaagtt atctgtgtaa taagtaactt   129180
atgccccgct ttggcggggt tcttattata cctttgttca taaattttat tagttcagac   129240 taaataccccc atattggcaa atcctttatg gggtattttc aaatgactag aaatgtagaa   129300
gaattattcg gcggcgtaat cacagctccc caccagattc ctttcacgta taatcaaat   129360 gtcggtggag aaactttcct ttccttgccg ttctatcctg tcactggcgt agtcacaatc   129420
aacggtggta tgcaagttcc gttagacaac tttgaaatcg aaggaaatac gttgaatctc   129480
gggcgcgcat tgtccaaagg cgatgttgtg tattgcttat tcgataaaat tctttcgcca   129540
gaagatacag ccaaaggtat ccgcatatac aaatttcaag ccgtaggagg tgaaaccgag   129600
ttcactcctg atttcacatc ttatggagtc caatctcttt atatcggtgg cgagtacaaa   129660
acacccgaaa ttgaatattc ctataacagc atgacaggga aagtatcttt gcaaactgca   129720
```

```
ctgactgcag gcgtttgggt agtcgctgaa atgtctgtta gacaaccgaa tatcagtccg   129780
gcatttgatc gaagtattca agaaatcgcc cgttctgcta atgtaaaaga ctctgaagtc   129840
atcgttagta cggacaccat atctttgttg gatgggaaga agttgttta tgatatagcg    129900
acgcaaacca gttatggttt accaaccata cctgatggtt ctgtcatttc ttctgtatct   129960
gctgggaaat tgaattacaa cccaggtgat gtgcaggttg atttgttgcc tttagaagat   130020
tcatttatta atgtgataaa cactctgggg cgcaatgatg gtgccaagta tattggaaaa   130080
tgccattctg ttgctgatct caggaatact gaacccacta tggatggaca acgcattatt   130140
cttaagcaac acactgcggg tactcttctt ggtggagggg tattccgtgc gttaattgat   130200
ggtacaggaa agactgataa taacggtact gtgatcaaaa ctgttggcgg cgcagcatgg   130260
ttacgtgtta atgctgatag agttaaccca ttcatgtttg gtgctttggg tggttctaat   130320
gatgatacta ttccagtaca atcttgtgtg gatagtggta aggccacaca attaactgat   130380
gcacattacg ttagcaatat ccagttaaaa tataatacgt cgtctattta tgggtctgga   130440
ttacattact caaggttgca tcagttgcct tctgctactg gaattgtat taccataaaa    130500
gatacatgct ccccttattgt attagacgcc tttggggtat atggcacagg tgcacaacaa   130560
ggcacgtcat ttactgcggg cacaacaggt atctatgtag aaactccttc aggtctctca   130620
gccgattatc cgttccacac taccgcagac ccaagacgcg acttgtgtat ttctaaagtc   130680
catatagcag gttttgatga atatgggtta aatattgata gtggtaactt tagtgttact   130740
acagattctc ttttagtcaa ccacatcaat caggtgggtg tccgttgtgc tactactgat   130800
tggacttgga caaatatcca ggttaatacc tgcggtaaac aatgtctggt tcttgatggt   130860
tgtggtaatg gtcgtattat tggcggtaaa ttcatttggg ctaactggca accttatggt   130920
acagtaggac agttcccagg cattactatt aataacagcc agaatatggt tattaatggt   130980
attgaggtac aagattgtgg tgggaatggc attgagatta gcgattcata ttcaatttcc   131040
atgaacggat tgaacaccaa tcgtaacggc atcaatgcta acaacacttt ctacaacatc   131100
gtatttaaca aaagtgatgc agttatcaac ggattcgtag gactcaatta tgccgcgaat   131160
agtggttcag gtgctaactc tagtgcaggc aatttttcagt tcctgtctaa tgattgtagt   131220
gtcaccatta atggtgtggt tgagactggt tatatgggca ttaacttttat tggtgataac  131280
aatattatca accccaccaa ttccgacctg agcattaacg gattggttaa ttattccaag   131340
actggtttgc aaaccatgaa cgagacccct acatttgatg gtgttagcac tacacctgtt   131400
tatgtaagtg tcccatcttc tgtagggcaa gtaaatggtc tgagactatc acaagccaac   131460
aaagataaat tactgtactc aagaacagca ggtccagaag gtattaccat ggctgctgtt   131520
atagtaccta ctatatctgg agctgaagta ttaacttca tggccattgg ttcagggttt   131580
agtgatacat ccaacagtct tcatcttcaa ttagttatag acgcttctgg aaaacaaaca   131640
attgctttgc tattgggggg cgatggtaca acccaaattt tatctgggga tttacctaac   131700
gaccttaaac tacaaagtgg tgtgccatat catatagcta ttggtgctaa acctggatat   131760
ttctggtgga gtattcttaa tattcagacg ggtaagagaa tcagacggtc attccgaggc   131820
gcttatttag ccgtaccatt taattctata ttcggattaa cttcctcatt aacattcttc   131880
tcggatagca atgctggtgg ggatgcttgt tctggggtgg gcgctaaagt gtatgttggt   131940
atgttctctt ctgagaacga ttatgtagct tcacgatact acaacctgat taatcctgta   132000
gaccctacta agtaattag ttaccgtata ttggattctt ctatttaaaa aatataccc    132060
tcttcggagg ggtctttact agaaaaacaa tgaggtactt atgaacgaaa tgtttagtca   132120
```

```
aggtggtaaa ggttcaactg gaatcttaac caataaacaa gcagtagcca gacactttgg   132180
agttaaacaa tctgaggttg tttatttctc agttggtgta gatttaggtg ggtataaagt   132240
tatctatgac aaggaaacgc aaagagctta ttccttacct gttggtattg cttctggtac   132300
tactgccgtc agtcttagta ctgctgctgt acttgtacat tcagcaggtt ctgtagactt   132360
aggtgcatta gctgtatctc gtgaagaata tgttaccttg gctgggacat ttgattctgg   132420
ctctacgctt aacgttaaaa atgaattact tacttataca gatggtaagt atcgctggga   132480
tggggcatta cctaaaactg tcgatgctgg ttctgcccca gcttcaagcg gtggagaagg   132540
tcctggtgga tggattagtg ttggtgatgc ttctcttcga tcttatttag caacgaactc   132600
aggttctggc gctgttggct atagcttcaa aggtcttgtg aatgcatccc atagaaaagt   132660
aaacgagaaa ttggatgagt atgctagcct ttgggatttc cactgtgact caagtggtaa   132720
cgtcatccaa cctgggttat ccacagatag caggcagtat attcagaacg cggttgacgc   132780
tatttctgat gctggcggtg gcacattagt tattcccgtt ggttatacat ggtatctaaa   132840
cagcacagac cctgcatctg ggcacagcgg tattattcag ctcaagagta atgtcaatat   132900
ccagattgaa ggaaccataa agataggtcc tgcattagct tcttcatcat ttcagatatt   132960
cgtagggttc gataatggaa gcccggctgc atcaggcaac ctgaataact gtcatatcta   133020
cactaatggc aatggtacaa tagactttgg tggatacgat tttgataaca cttctcaatt   133080
aaggaacggt attgcctttg gtaagagcta taactgttcc gtgtctcgta ttatcttcca   133140
aaatggtgat attacatggg ccgtaactac aggctggaat gggtacggta gtgattgtgt   133200
ggtgcggaag tgccgtttca ttaacctcat ccagagcaat aacaacgcag accacagtac   133260
tgtttacatc aactgccct acagtggtgt tgagggttgt acattccgtg cctcatctac   133320
tcgtgcacag atgattgctt gcactgtaga actacaccag catgatactt ggtacaggga   133380
ttctttcatc gaagggtatg tacgtgggtg ctacattgcc ctgcatggtg tagaggcggc   133440
tggggctggt acttatatct acaatgctgt tgtatcaggc gttactggtg acatctcagg   133500
tcaggctatt atattagcag caggacctga ctccgtgaca actacacaca tcaatggtgt   133560
ttctgtggag aattgcagaa ttactgctgg caaccaagct ggaatgtgta gctttattga   133620
cttcttccag gatagtaact ctgactcaag ccagtacctt attaaccacg ttacggttaa   133680
ggggtgtagt tttattgtag accgtaatcg tgcactcagt gcagcaataa caattaacgg   133740
cagcatacag ggtattacgt tccaagataa cttctttgac gttaaacaag ccatggtgtc   133800
tgaattgcct tcaggaaaaa cagtgcagtt agtacggttt aactgggatg aaagtaatat   133860
cattggtgat gataacactg gtacgcgtaa tgccctcaat ctgttcgaga ctcggcgtgt   133920
ctccagtatg accaaatgca atatatcttt gcgtatgcgt cagccaagcc cagagttatt   133980
tagccttatg tattttagac caaatgaaac cactttcagt gactgtacat tgaggtact   134040
gccatacaac tggtcgtgca catcaggaaa ccctatagtt tttgaaacta cagataccc   134100
accatctgga atgcgtgttc gttttcctaa gtcaatttca tttacgttgc ctgctggttc   134160
gaacgcccaa cgtgctacag ggggttctgg ttattcttgg gtggctagag cagatgctct   134220
tgataggcgt agcatttctg ggcaatttga cgctccggca tcttactccg gatcagtga   134280
tggtaaattg attggaatag ggtggcagtt agacggagta cagcataact acgaccataa   134340
tgtgtatttg caaacttta cataatagat taattaacaa aaaccccgct tcggcggggt   134400
ttttatttct atcctgtttg ttggctgtat actaaatatc tctataaaat ggcactctat   134460
```

```
ggagcatcaa aatgcaatct acaaatttaa accgtcgccc gtattgggat gactggaatc   134520
ctgggaaacg ttttcacgg attcttttc gtccgatgcc tatcaaggtt cagactcgcg    134580
aactgaacca gatgcagact attcttcagg atcaaattga aaaactgggc aaccatttgt   134640
tcaaagatgg ttctatggtt atccctggtg gtctgacgat taccaatgcc gcagtctctt   134700
tgaaattcac tttggctggt ggtactgaat tcactgatct ggaaggtatt tctgaactct   134760
acgttttggg gaaggacaat aatgccaaag cgcgtgtgtt gtctcttgaa cgtgatctgt   134820
ctgctcctga tacgatgctg gctatccttg agatgactga agcgggtaat gctgacggat   134880
tccatgttaa cgataatctg tatttccaga cttacgacgt gaatgataat ttcattcgta   134940
ttggttatgg tatcgcagct gcagtgactg gttctatcgt cgctcgtatg acaaaaggcg   135000
tttacttcat tcgtgggatg ttcctagacg ttgatgacgc aactcttatc gttgataaaa   135060
cttctaacat cacttcccac cgcatcggat ttaaagtcac cgaaactatt gtcaccgaaa   135120
cagaagatga atcccttat tcaaatgctc agggaacgat taactctaaa gccccaggcg    135180
ctcatcgtct tcgaatagat ctggtcttat ctcgatttga ttatgatgct gtggttaagg   135240
actttgttga actggccaaa gttcgtgaag gtaaaatcca gtctatggtg actcagtcca   135300
cctataatat tctggaagac acgttagccc aacggactta tgaaaccaat ggcgattaca   135360
acgtttcaac ccaccagatc gatattcgtg aacacctgaa agtcaataac aatggcgggg   135420
tattcaatgc cgctgatggc ggtgacgaga gcaaatttgt ttctgtgatg aaaccaggca   135480
tatcctatgt tcgcggtcga cgtatcgaaa acgtcgggga agagttggtg atcgttgata   135540
aggcgcggga taccgatgtc ctgaacaaca ccctgttgc ggtggccaca ggcaattatc     135600
tggtcactaa gaattctaaa ggtgtgccag tgatatcccg caccgttcga tacaaattac   135660
tgaatgcttc aggcgttacc caggctacag cactttgtat atcagctgaa cgtaattcaa   135720
cagaatttcg tctgtatatg cgcgacctgg tcgttactgg cgatgcatcc actatcacca   135780
aagtgtctta cgaagaaagc ggtatcacca tgttctctgc tgaactggaa tccaatcagt   135840
ttaaccagag ttctatgata gatctgatct tctctcttcc ggtattcggt gtcaagactt   135900
tagcaccaac tggctccgtg gatatcaact acactgttct cagaacgtat aaagtgacgt   135960
tggacaacag cggcgcgggt tctatttctg ctccattggg atatagtttt tccccagaat   136020
tttcgttata ctctgcagcg aaatcagatg gttcggaagc gcagttcgat atctctggtt   136080
ctttgtcttt gactggttct ccggtcggtt cggcgctgca gatttctctg ggcagtggta   136140
atgctaacca gtcaatcaat ttgctggcgc tgatgattcg taccacggcc acaatcaaaa   136200
cgaagaccat cactgaaaca actgaaacag tgacgttcac ctcgcagact agccgcccctt  136260 tggcgaatca cgatggttgg aaattggtgt cggtcaaaaa cgatactggc gcagacgtga   136320
cctccagctt cgtcctagat ggcggacagc gtgatgcagg gtattacaag tctaacttgt   136380
tatccagcgc tggagcaatc tcagggacgt atacagtggt gtatcaatac ttcgcccaca   136440
gttccggtga tttcttctct gctgattcgt atacttcgat ggattataaa gatatcccga   136500
attatacatc ttctacatca ggcgcggtgt acggcctggc agatagtttg gatttccgtc   136560
cgaaaatcac caacggaact tctgacacag atatggttcg tccaaacact gcagttattc   136620
tggacacaga atattatctg ccgcgtattg acgcgattta tctggcagac aacggcgtgt   136680
tcggagtggc tcgtggcatc agttcgaaca atctggcttc tccagcaatc ccagcgaacg   136740
ccatgcgttt gtatgaattg ttgatcccgc cgtatacacc gaatattgat gatattcaaa   136800
ttcgaactat tgataatcgt cgttatacga tgcgcgatat cggtaaactg gaaacccgta   136860
```

```
tttccaatgt tgaatactat acctctctgt cacagctgga atcttcagcg atgacacagc    136920
aagtgttcga ccccatcacg ggtaatcccc gtttcaaaaa tggtattgcg gctgatccgt    136980
tcaaagactt ccggttgatt gatgacttgt ctgaagattg gatgggttct atcgataccg    137040
aaaacggacg tctgcgcccg tttgtacaac aaaacgttgt tgacatgact cctgttggct    137100
ggaacaaagt gatggatggg atggtggttt gcaattacac gcctgaaatc tcagtgaacc    137160
aagaatatgc gacgacgacg atcaacgtta acccgtatgc agtattcaat tgggaaggtt    137220
tcttgaagat taacccgacc acagactact ggttcgaaaa ctattatgtt gcgccgcgta    137280
ttatcaatga aacgatcaac acccgtggta ctgtacaaga aggttcagtg tacggaacat    137340
ggcgtactgt ttctgtttct gatcgtgttt gggaaccgca tggcgctggt ggtgtgtggt    137400
ggggatatcg ttaccgcacg actgtttctg cccgtgatgt caccacatat acatacacgt    137460
acaaaacaac cacgaccatg actggtgaac agattgtgga gacgcaagtt atcccataca    137520
tgcgcgagat cgatatttct ttcgacgcat ctgggctgcg acctttcact cgtatgtatg    137580
cgttttctc tggtcgtgac gttaatctgt attgcaaacc gaatggtggt aatttcggag    137640
acccaatcac cactgatgcc aatggtgctg ttaaaggtgt attccgcgtt ccacagaacg    137700
atacaatcaa gttcaacaca ggcgacaacg tgttccgctt aacggatagc cctgttgaca    137760
gtaaatctgc ggatgataca ctgaccaatg cagaaattgt tcataaatct ttcggtaaga    137820
aacaaggtat tcaaaagacc tttgtcaaca ctcgtgtcct gggttacact gctagtactc    137880
gcaccgaaac ttctacttct gaagtggttg ttgatcaatg gcgtgatccg attgcccaat    137940
cgtttatggt ggcgactaag aatggcggcg agtatatcga aggcgtggaa gtattcttct    138000
ctaccaagtc acgtgatgtt ccgatcactc tggaaattcg cgagatggag aatggcttac    138060
cttctcatac agtcattact cgtaaaaactt tgaacccgtc tgaagtaacg atctctacag    138120
actcttccgg cggtacgaag ttcaccttg attatccggt gtatctgcaa gcatcgactg    138180
agtttgctat cgttttgttg gcgaatactc aggattacaa cgcgtatatc gcggaaatgg    138240
gcaagaaaaa ccttctgtcc aacgaatata tcgccaaaca accgtatacg ggggtgttct    138300
tcacttcttc aaacggttca acttggtctc cgaaccaaat ggccgatatg aaattccgca    138360
tatatcgttg caacttttgcg gctggtcaga acgttgtaac atttgatccg aagctcgggc    138420
caaaacaacg tccgttggga ttgaacactc tgaactgcgt aagcgggtct tctgttgtga    138480
ctgtgtttgc acctggtcat ggtttggttg ctgggaacaa tgtcacgctt tctgaattga    138540
caggcggttg tggctttact cctgaacaac ttaacaaaac gtttactgtg acagatgcga    138600
gctatacttc attcaagatt gacgtcggta cggcagcaga cagcaatgga caaatcggtg    138660
gagataatgc ttctttcttg ggcaattatc tggttgatat gttctatgcc agcgttacca    138720
attcggctct ggaaggttca attctgaaat tggaataccg ttatcgcgat gccacttcaa    138780
attctatgtc tgattgggct gagtttgaaa ctgacactga cgtggcattg ccgactgaag    138840
gtatctatcg tcaggtcggg gatttccaaa tccgagccac catgacgcgt agtgaaaaca    138900
acgtgtacac tgctccaatg attgatggtg atgacctaag tgtgatcttc aactcttatg    138960
gcgtagatcc ttttgaagac gttttcaaat atgtcacaaa ggacattggt ttcgataacc    139020
catgttcgac tgtgaaactg ttcttcgggg cgatgctgcc ttctcaatcc tccatgaagg    139080
tgcaggtgaa acttctaaga gcagggcaag agatggatag tgtggcttgg gaagacgtca    139140
ccccaacttc gcctctggtt aacgacggtt ccacattctt tgaatatgag tatgacaaga    139200
```

```
ctgtggcgag caataacccg tttgttggcc tgaaagtccg agcgcttgta cggggggaacc    139260
gcgttgctcc tccatcattc aaagacttcc gtcttattgc tctggcataa ataatgttga    139320
aaggtgggcg taaagcccac caaaccaata gaggataaag atatgcgtgg aatgaaagta    139380
caggggcacg catccatgtt gagaagcagt tcttgccctg gcgcgattat ttgcaccgat    139440
cacgccgctg gtatggctgc attgcaagcc cgtcaacgca atgaaacccg tgaagccacc    139500
attgttgaac aatcaaacca gatatctaat ctggaggcaa caatcaaaat gatgccgaa     139560
aagttgggga ttgaaatccc cgaaggaggt cagaatggcg acgcaagctg aaagaacggg    139620
gcttgacatc cgtggtatct taaccgctgt cgtggcttct gcattggtct cggcagcatc    139680
gttcctttgg ttcatgggcg ggatggaaac gcgcgtgaat gtattggaac gagattccaa    139740
caagatggat caagttcttc agaaagtgaa tgacatgagt gaacgtatgg cgatcatgaa    139800
tactgacctc gcatatgtca aacaaaacat ggctgagtta aaactcaata gcagcagtct    139860
ttcagatgat gttcgcacac tgcggattac tgtatctgat ttgcagcaaa aggggaataa    139920
caatggccgt caataagatt cgagacaaaa aatcttttat gaattatgtc ttgcgtaaat    139980
tgggcgctcc tgtgatccaa attaaccttg acagttcaca agtcgaagat gcagtcgatg    140040
atgctctgca gaaattttgg gaatatcatc gtgatggtag ccaagatgcg ttcttcctgt    140100
accaagttaa acaagaagat atcgacaagg gatatataga attccccgat gatattgacg    140160
atgtgattga agttatccct ggacctccta ttgagtcaat cggaaactgg gcaactcctc    140220
aatggcaaat ggctcaagca atgcttgtcc ccaaagcagc gctggtttct attcgtctca    140280
ttgattatgt ttccatgcaa caacgtctgt cggatatcac aagcgtctta aatgttcgcc    140340
gtaattttgt gtacaagaag ttccagcgac gcctttaccc gcagtttgct gccattgttg    140400
atgaaaccct ggcttttcgt tgttatcaaa atatcgaccc cgaatcggaa gaaaacgctg    140460
aagcatggaa tgatatgtgg ttgaaagcgt atgcgactgc attggtcaag cgccgttggg    140520
cagaggtgct taagaaggca agaggcatcc gtctccctgg tggtatcgaa ctggatggtg    140580
atagtatgtt cagtgaggcc gagaccgaga tagagcggct ggaggaagaa ttgcgtactg    140640
gtcagcaata ccctatcgat tttatgatgg gataagagaa ggcgggttat cccgcctttc    140700
ttttttataac ttgatgtcgc gtccggaagg atctgaattt gctagaatat aaccatcaac    140760
cacgttcttt tcgtcccacc attcaataaa atcattaccc ttttcgcctt tgataagacc    140820
cacaatgtta tatgaaccat cggcgatttt agcatctaca cagataattc tcacacgcct    140880
tccgtcacga gtttctttaa tatcttcaac cttcatttat caattcctca aaagaattaa    140940
tgattgacta aataccttca aaattgaggg taaagtcatg gctacttcaa aatatttctg    141000
ataaaatcta cgactgatcc atcgtataca aaccattcgg tagcaccgtc aaaatcctta    141060
taccccgcgc tcttacacat tctatgggca attctttcca acctggaaac aaataatccg    141120
tcggttgaat taaatatttc tagaacgttg aagtaaaacg gggtggtgct tctcaaacaa    141180
tttatacgtt tcttaggcga gttggttatt cccactttca tacaaccttc gtcgttgact    141240
agaatatata agaaaccttc cttagaataa ttgtaacccg attctgcgca atacggacac    141300
caacttcggc tgttgactaa attaccgtac ctggattccc acctgtgcgt ttcagaacat    141360
tccatgacac aaattgtcac gttgtctttg tacttcccgc caatgaaatt tatgaattta    141420
ccaccgttgc ttacggcgta ctccgatatc ctgatttag cttcttcatt tgagatcttc     141480
ttgtttccac gacacgaagg acaccaactt cctttattta tcaaattcgc ataagttgct    141540
gagttccatt catgaccaaa ttcgcaagac aaaatgcact tagtttggtt ggtgacaaat    141600
```

```
ttaccaccga caaatccgtg aaatattcca cctctagaag aagcatatga tttgattctt   141660
ttagaagcaa ttccttctgt caggacgatc atattgattc accttaaaaa caaattcaac   141720
taaatatatt taaatcttga ggaaaatatt atggctactt ctcgatactt caattacact   141780
gcacaccaag gtactcaaaa attaattgat gacttggtgg tcgagatgat acaattgcgt   141840
gggattgacg tcaagtatat cccacgttct attgttgaaa atacccaat tttaaacgag   141900 gctgaacaca aattcgacca agcgtttgac atcgaagtgt acatgcagga ttatcaaggc   141960
ttcaacacac agatgtggga aaagttcggc ggtatccaat tacaagatga agtgaccttc   142020
actattgctc gtcgtcgttt ttcagaagtt attggtaatg gtccaggcct tgaacaaatg   142080
cctcaagaag gtgatttgat atatctgcct atggctaaca aaatatttaa agtgaataac   142140
ccgaacaacg atgaagaatt catgcaattt gggaaatggt acacatattc cctaccatgt   142200
acgttgttcc aatacggtaa cgaagatttc gatacaggtg tatctgaaat agacgatatc   142260
gataaacgat tgcaggatct ggaaggagac ggtgtgtaca aagacgccag cctgcaaacg   142320
gataaccaat ttgcggacga aatagagaaa gatctttcgc ccaataaaat gaagatagac   142380
ttcggggaat aatcatggcc agaccatttg aaaaatattt ctatcatgaa tcattgttga   142440
aatacataca tgtgttcaac gctatcatgt cagatttaaa agtcaaaacc gaacgtggct   142500
tgatggaaat cccgctgcat atggccattg gccgccgtaa tgacctcaac aggaacgtgc   142560
cagccaatat gctgccattt gcaacaatgt cctttggtca gttcgaaatc aataaacagg   142620
tgacgaagtc ataccacaac caaatatcga ccgctacggc acggtccaaa caacgcattc   142680
cgatcattat agattttgaa tacaatatca gaactaaaaa attggtcgaa atgttgcaag   142740
tattagaaca aatttattct gtgttcactc cttctattga ttgtcagata aaagacaacg   142800
atacgctatc tcaagatcag aacgtgaaga taatgttggt aaatcacacg atttctgaca   142860
actgggaagg agacgcaaca gaatcaccac acatagattg ttcattcaat tttcaattac   142920
atggtcacat ctatggagaa gattattggg ttgatgatga ttcgggcggt ggggatccaa   142980
acgtcatcaa agagataatt attgaaatgt ctaatgattt gaacatgcca tggtcggaac   143040
ttcctgaatg gttccgagtt gataaagacg gcatacatca tccggaggat tgatcatgag   143100
caatatgtca gaaaggttac tcgccacact tgatgcggtg actgcccgag acgaagttgg   143160
gaaggaggca atggaggctg tcgcccctcg tccaggtatt gacttcgatg aaaatacagg   143220
tgaatggttt ggtgaacgtc cggaagggta tcagccgatt cctgaaccgc cttcattgga   143280
ggatattgct tccaaggaat ccaaagtacc tgagtttgcg gacactgatg ctacaacgga   143340
ttacaaacgg atacgcgaca caacatatgc catgcaagaa gccacaatgt tcatgatggg   143400
acaagccgct aaattggctg catccacaga agctccgcga gcattttctg ttttccgtga   143460
attgggtgaa ctcatgcgcg gtctgaataa agacctgatg gaaaaccaga aaaccatcaa   143520
ggcggtgaca ggtgataaag aaccacctgt tgatgacacg acagtggatg ttacaacttc   143580
accagacgga acaacaacag tatcggttgg gaaaaaggcg cgatcttctc gcgatttatt   143640
gaagacgatt gaagatgccc gtcgtcgcgc tgaagaaaga gcacaagcaa aggccgcaca   143700
acaaccagaa gatgaaatca ttgatggtga acagttgat gtgaaggaag aagacgatgg   143760
cgtatcagaa gcgtgatata gaatatgccc caattaaaac ggggttcaaa atagacgatg   143820
tgaaattgcg tatggaccaa acgttcatgc gcaaaccttc tgtgcgtgct ccccgagtcg   143880
agttaatgct gacagatgaa caagaagacg aattcgttga atgttctatg gatgcacact   143940
```

```
acttcgccgc caactattac aagataacca cgatcgataa aggctttatc cttttcgata    144000
tgcatgatta tcagaagcag ttgttccacg actttcagga ctatcgattc aatgcggtcg    144060
tccaggctcg tcagtccgga aaatgtgtaa aaggcgacac gcttgtcaca gtttacgata    144120
ctctcagcca agaggagttg ctcctgacta taggggagct tcacagtcgc ttcgaggacg    144180
tcaaccacgc tgtgccgctg aataccattg gcaaccatga caagttcgtg gacagccgct    144240
tcggcaaacg ttactttgta caatccgata gtggctgggt tccggttatc gcagcgcata    144300
agacgaagaa atatgcggaa ttcgttattg tcaccgttac cggaaggcga attaacgtgg    144360
ccgatgaaca tatgttcttc actccggaca tgaaggagat atttgccaaa gacctgaatg    144420
ctgggtcata catcatgacg acagaaggtc cagaagaaat ccgtgagatt tggcagactg    144480
gtgaatatca ccatatgtac gatctgcagg tcaaatctag tgatcaacgt tattacacga    144540
atggctttct cagtcataac acgaccgtgg tggcggcgtt tcttctttgg tacgcgatgt    144600
tccattctga taaggaaatc gcagtactgg caaacaaaga gaaacaagcg atagaaattc    144660
ttgaccgtat cagaaaggca taccaagacc ttccattctt ccttcagcag ggttgtgaga    144720
agtttggttc taccctgata gagtttgaga atggttctaa gatatacgct tatgccacgt    144780
cttcggactc catccgtggt cgttctgtat cgctcttgta cgttgacgaa gtcgcgttta    144840
tcgaaaacga cttgaatttt tgggaatcaa cttcccagc cattgcatct gccgatacat    144900
cacgctgtat tttgacaagt actccgaaag gccagcgagg gttgttctat gatattgtca    144960
ccaaagcaga tccgcgccat ccacaataca acgacttcca cctaactgaa gtcccatggt    145020
ataaggttcc ggcatatacc aaagatccag attgggaaac caaacaacgt gcccgtctgg    145080
gggatgctcg tttcgatcaa gaatttggca ttaagttccg tggttccgtg ggttcattga    145140
ttccggccaa atgcttagat aaaatgacgt ccaagttgta tcgggaacct aatgaattca    145200
ccaagattta taaggaatac gacccacaac gtctctactt tgggattgcg gacactggga    145260
agggggtgga aggagattat tccgtcttaa caattctgga tataactgaa tatccgcatg    145320
ttatagcagc caagtacagg aataacacga tacctcctat gatgtatgca tacacgatag    145380
ctgatatgtg caccgaatac ggggaatgcc ctgtccttgt tgaaacaaac aacgacgtcg    145440
gcggtcaggt tattacaatt ctttatcaag agatagaata tccagaaatc atattcacat    145500
caacagataa caaagggacg gggaaacgga ttggtggacg taaaccggaa cctggtatca    145560
ataccaacag aaaagtccga tctatcggtt gtgctaacct gaaagcgctc attgagaaag    145620
aaatgttggt gatagaagac caggacacga tagatgaact cagtcacttt gtgttcaaag    145680
gcgctcggta tgaagccgat gacggttgtc acgatgactg tgtcatgccg ttggtcttat    145740
attcatgggc ggtaaaacaa gaatggttca gtgatttgac atctacaagt atttctcagg    145800
acatgagaaa ccgaatgtct tcaactgaat ctcagcaggt attcccatt ggtggtttag    145860
tcgttggaga caccccatcc gaaactgagc atttgcctgg tttcggggt attcaagttt    145920
tcaacgaaat gtcagggatg accatggatg agtggtttaa gaattgatca ctaaatatct    145980
ttcaaattga gcgaaactct accgagaagg aatgatatta tggcaactca agcttcagc    146040
gttgcgccgt ccgttcagtg gactgagcgt gatgccacgc ttcagacgtc cccgtccgtt    146100
gttgttcagg gcgcgaccgt cggcaaattt caatggggtg aagttgaact tccagtgctg    146160
gtgactggtg gtgagacagg tttggtgaag aaattcttca acccaacga cagtactgcg    146220
accgattttc tcgtaatcgc ggacttttg tcttacagct ctatggcatg ggtgacccgt    146280
gttgttggtc ctctggccaa gaactctgtt accaaaggtc agacagcgat tgcgatcaaa    146340
```

```
aacaaactgg attttgaaac agcaagtcct tcggcgtcca tcacttggac tggtcgttat  146400
ccaggttccc tgggtaatga tattgctatc aatgtttgtg atgctgctgg attctcaact  146460
tgggaattcc gtaataactt tgcatacgca cctcagtctg gtgaattcca tgtagttgtc  146520
gtagacaaag ttggtcgcat taccgactct gctggcgcgg tcggtcaggt tgaccgtatc  146580
tccgtttctg gtacggctac tgctgctggc accatcagtg tggcaggtga agatatcgca  146640
tatctggata ctgatactcc agccactttg caaccaaaa tcggtacagc gctaacttcc  146700
ctgacaagtg tttattcttc tgttgtcgtg aagtccaaca ctgtcatcgt gacccataaa  146760
gctatcggtc tcaggccgt tacagctatc gttcctgatg ataaaggact gactgcaaca  146820
gccgtaatca ctactgttgg cgcttctggt tccatcattg aaaaatacga actgatgcag  146880
aacacccagg gttctaaaaa atccgatggc gcgaatgcgt acttcaaaga cgtgatcaac  146940
gatacttcaa attgggtgta taccttcgcg ggcgaactgg ttgcaggtgt cgttgaatta  147000
gaaggcggcg tagacgatta taacatcaac cgcgtggcag ctatccaagt cttgaacaat  147060
gctgaagcat atgatgcgaa gccagtattt gcgtactgtg aagaactgat tgagcaacaa  147120
gcattgatcg acttatctac tgagcgaaaa gataccgtat cttcgtatc cccgctccgt  147180 gatacggttg ttggcaaccg tggtcgtgaa atggatgatg tcgttgcttg gcgtgaaagc  147240
cttgttcgcg actcttctta tttcttcatg gatgataact gggcatacgt gtacgacaag  147300
tacaacgaca aaatgcgttg gattccggct tgtggtggca ccgcaggtgt ttgggcgcga  147360
agcattgaaa tcgcgggtat ctacaaatct cctgcgttcc acaaccgtgg caaatacaac  147420
aactacaatc gaatggcgtg gtctgcgtct tccgatgaac gtgccgtgtt gtaccgcaac  147480
cagattaaca gcattgtgac cttctccaat gaaggtatcg tgttgtatgg tgacaaaact  147540
ggcctgactc gtccgtctgc tttcgatcgt atcaatgttc gcggtctgtt tattatggca  147600
gaacagaaca tcgctgcaat cgccaaatat taccttggtg agaacaatga tgcgttcact  147660
cgcagtctgt tcagcaacgc tgttcgtcct tatattcgcc agctggcaaa tatgggtgcg  147720
atttacgatg gtaaagtcaa gtgtgatgaa gataacaaca ctgctgatgt tatcgcagca  147780
aatcagcttg tagcgggcat ttggttgaag cctgagtaca gcattaactg gatttatttg  147840
gattttgctg cagttagacc agacatggag ttctcggaaa tcgaatcggg cggtggcatc  147900
gttgctgcat cctaagacaa caaccccgct tcggcggggt ttttatttcc tgctgatatg  147960
ccatcctgta gtgtttgttc tcttcagtga agatttcctg taaggtttag ggatgggatt  148020
ctgcatcctt ccagctaatg ccatgttgaa agattctata cacaaacatt gttcttgaca  148080
aaatttgttt agattcttga tttcatattt ttcaccatct ggtgaaagaa gtgtaaacca  148140
tcttccgaga gatcgtttta ttttctcttg gtattcagga ttcatgcgca ctttgttcat  148200
agcggcacgg agattttctt tacattttgg attttcgtac gctttcttca aacattgtga  148260
atgtatatgg cgtttgtttt tgtcccaagc cttggtttga gattcagaca ttttcgtttt  148320
tgtttcttcg gaaagtttaa tgcctgtcat tgaatgaaca aacaaaacat tccaaccagc  148380
atctttaact ggtttcatcc cgatgaattc tctggtttct atatcatatg ctgctgccat  148440
acccgatatg tctatttgac caccatgact gatgttcagt ccaccttcag agatatgagt  148500
cttatgtaat tttatgagtt caatttcttt agaatttagt tcatcgactt ggcattccag  148560
caatatctct tggtcagtaa ttccatattt tcggatataa ttgtagagga tagtttttatt  148620 tcctcttctg gcctcaccca gatgctcctt tattcggtgt tcaaccccat ttcttgtttg  148680
```

```
tccaatatac ttctttccac caacgattaa catgtaaatg tgaccgatca tacaacacct   148740
ccaagaacat gatacccga  aattgttcaa cactaaataa aatagaggtg aatttgaaat   148800
gatatacgca tacaaaattg aaacgataac taatggaaag gtctacatcg gtgtgaccaa   148860
tcacccacaa cgaagatatg atcagcattt tgcgaatgct tttcatcatg gagtccaaag   148920
tgaattgtat gatgccatgc gtaagtatgg aacatctgga tttactttcg ttgtaattgc   148980
tcagaccgat gaagtccata aatgggaatt agagaagcaa ctcatcgctc aatataattc   149040
ttatgagatg ggttacaaca tgaataaagg cggtaatgat ggaagtcata tgctgggtaa   149100
aactgcagca aaattgacat ctacaggtga acacattggt cttgtttctc tcatagatcc   149160
ccgttgggaa ttgtgtgaaa tcgaacccgt tttaagcaat gttgaccacg gatttgattt   149220
ttcttccatg aagattaaaa gattgacgac taattagaat tgtgtactct tatttggaga   149280
tataaaaatg gcgacagtca atgagtttcg cgcagccatg tcacgagggg gcggcgtaca   149340
acgccaacac cgctggcgtg tgactgtaaa cttttccttct tttgttgctg gttccgacac   149400
aattcgcgac gtgtccttgc tagctgtaac taccaacacc ccgacaggtc agctgggtga   149460
aattctggtg ccctggggtg gtcgtgaact tccattccca ggcgaccgtc gtttcgaagc   149520
actgcctgta acattcatta acgttgtgaa caacgcgccg tacaacgcat ttgaagtgtg   149580
gcagcaattc atcaatggta gtgaaaacaa ccgcgccagc gcgaatccag atgattattt   149640
ccgtgatatc atcatggatc ttctggatgc gaatgacaat gtcaccaaga catggacttt   149700
gcagggcggc tggcctcaaa acctcggcca attggaactc gatatgtctg ctatggactc   149760
ttatacacag ttcaccgtcg atctgcgtta tttccaagcc gtgtcagaca aatctttata   149820
atgtcctcag tgctgggga  atcatattcc ccctcactaa ttacaagaaa atgttgagga   149880
cttagatcat ggctggatac ggcagagggt tcttcggttt gtttggcggc ggcggttttgg   149940 tgaacgctaa agtcgacacc gataagttag cccaaaaaca agatgaacgg ttgctaacca   150000
aagcgacagt tgttgctctg gacgacgctc aagacggttc tataatcctt cagggtggtg   150060
cgaacaccta caactatgtt ggcgttgaaa gtgaacttct cagcgttaaa actgttgtag   150120
aagaatatca gtccatggcc cagcagcctg aaattcgcaa agcggtggac attattgtca   150180
acgatgttgt cacatgtgag gaagatgaaa ctccagtgac agtaaatctt gacaaagttg   150240
aagggatatc tgatactgtt aaagaatcta tcaccgaatg cttcaaagaa gttatgcact   150300
tgatggactt tgacaatacg gcataccaga agatccggaa atggtatgtt gacggtagac   150360
aagcatatca tgtcatcgtt gaccccacga ataaaaaagg cgggatcaag aaattggtca   150420
tgttggattc ccgttgtatt cgccctgtgt acatcgtaga aaaggtgatg cgagaaggtg   150480
gtatcgaagc catcgaatct gtaacgctga aatattatta caacccgaat tacaaccgga   150540
accaattcac tggtcagtca gggacttctc aaaacttcca gccttcacaa caagaactcg   150600
tattcgatga cgaaagtatt gtttacatcg atagtggtga agagccattg gccaacggta   150660
ttgttccagg gcttttaaac cctgctatcc gtccgttgaa taacctggtc acaactgaag   150720
atgcgactgt aatttatgcc atcactcgcg ccccgaaaa  acgcgcattc tatcttgacg   150780
tcggtactct tggtaagaaa tctgctgaag aatacatgac catgatgatg ggcaaattca   150840
aaaaccgtaa cgcatatgac cgcaccactg gtaaaatcac aggcaacgcc catcttatgg   150900
gtattgcaga agattattgg ttgccgcgcc gcgaaggtca gaatgctaca gagatcgcga   150960
ctgttggtgg tgggaatcaa ttgggcgaaa tggatcacgt gaactatttc cgtgaaaaac   151020
tctatgatgc tctaatgatc cctaagagcc gcctccaaga ggaaggatct attaacattg   151080
```

```
ggggttctaa ccttgcggag attacacagg aagagctgcg tttcagcaag ttctgtgctg 151140
ggttgcgtcg ccgttactcc catttcttta tggagttttt acgtcgtcaa ttaattttga 151200
aaggcgtaac ggatgaaaag gattggaatg agaagatcaa accatttatc aagtttgaat 151260
tcacttccga cagttatatc cgtgagcaac aagaaaacgc aatcctaaat gatcgcctgg 151320
cttctctgaa cactgttgag ccttttgttg gttctatatt ctccatcgat tatgtcatgc 151380
ggaatgttct gcgtatgtca gacgaagaag ttaaagaaca acaggctaag atcgcggaag 151440
agaagaagaa aggtctctat ccgaaggttc aagcagatga aactggcaat tatagtggtt 151500
cagatgttag tccgttgaag tttaaacctg agactatccc attctccggt tcaacagacg 151560
atagtattta aagttcaact aaatatagaa aattaattcg gagatcaaaa tcatgagcgc 151620
aattgatatc gttcgtgcag taattgatgg cgacacagat actgctgttg cagaatgcaa 151680
catggaactt gatgcacgta gtcaagaact attgaaccaa ggtacagcat atgttttgga 151740
ttctatcgcg gctgatatga attcaaataa cgacggtcag taaggagacg catgatggaa 151800
atcacagaga tcgccacgtt cgctgatttc ctggcctctc gtatggacga gcagcgagtc 151860
atcgataaag tgaacgctcg tggtaaacgc cgccgccgac tgaaatgtgc ccctgggttc 151920
aaattgtcgg ctgatggttc acgttgtgaa gttatggacg ccagcgaacg tcgtgttcgc 151980
aagatcggca accgcaaagc cctccgctct aaaaagcgta tgggaatggg ctatcaacgt 152040
aaaatcgagc gccgcaagaa aaaggctatg aagttccgca aaatgatggg actgagtaag 152100
aacaagtaag gagtttatga tgaaactgtt gcgtgagatc acagcgatag ggaaggatct 152160
tcaaatcggt gaggccacaa cctcaactgg tgggaaggcc atgttcatcg aaggtccgtt 152220
tgtgatgtgt aaccaagtca accgtaacgg gcgtaactat gatctgcaga aagtgggtat 152280
tcctgctgtc gaagcatacg acaaagagta tatccaagat cgtcgcgcaa tcggtgaagt 152340
cacacatcct gactatcctt tccctaattt agtggaagct gcactcaaaa ccgaatccct 152400
tcgttgggaa ggcactaatg ccatcggacg ggcgcgaatt ttaaacacac cgaaaggcca 152460
aatcattcgt gcactggccg aagcagactt caatctggcc gtgtctactc gtggcctggg 152520
tgagactaag tcggtaaacg gttatgatga cgttcagcct ggctttatgc ttaccgccgt 152580
tgatgcagtt gaccgtcctt ctggacaagt ttgttatgtt aaggctgtga gtgaatctgt 152640
tgaatggcag ctggacgagg cttctggtat ttggatgcct cgtgatgtta agggaaagt 152700
tgtagaccag ttggtgaaag ccaatatcca ggttgaagac gatttcctgc gccgccttga 152760
tgcagcattg aatcatctgg gctgaaattc agctcactaa atactgaaaa atcgttcaga 152820
aggaaactat catgaaacct gaattgcaaa acctgtttga aggcgttaac ggcatcagcc 152880
cagatttcct ggataaagta tccaatctgc tggaatctaa agttgaagcg gctcgtctga 152940
aagctatcca agaaaccgaa gcagctggca acgccgagcg cctgaatctg gtcgaatccc 153000
accagaaaga aatcgccgac ctgaaagaaa atttcattct gcaattggct gggaaagttg 153060
actcattcct caatgcggta gttgaagaat gggctaacaa aaatgcccca gctattgacg 153120
ctcagatcaa aactgaagct gctgaacgct tcctcactgg tttctccaac gttctgaaag 153180
aagcaggtgt gaatttcgct actgacccag acggtcagat cgctgctctt accagtcgcc 153240
ttgctgaagc agaacaacgc gccaacatgg ctaataccga attgaaccaa ctcaaagaaa 153300
gcgaaactaa acgccagcgc actgacgtga ttgatcgcat ctgtgaaggt atggttgaca 153360
ccaagaaaga cactgtcgtc aacctgctgg aaggtattga attccagacc gaatctgaat 153420
```

```
tcgaatcacg tgttcgcacc ttccgcaatc tggtagaagg caaagatgac ttctctgaca   153480
aagtcggcaa agacaatgaa aagggtaagc caaatggcga caaagatgaa aaggacatca   153540
aagaaggcaa aaaccgaaa aaagaaggcg atgacaaaga cgacgatgat gacgatgaca   153600
aagacgaagt tggtaaagaa gtcaacgaat ccgtccgtcg ccagatcagc gccttgctga   153660
acggctaatt ttagcagcca cagccctcga aaggggggctt gattttgaac tactaagtaa   153720
tttcaactta actgaatatc aatgtaagga acgagcatca tgactaagaa acttgtaacc   153780
gaagaaatgc gcaaacagtg gctgccagtt ctccaaaaag aatctgaagc catccaacct   153840
ctgtctgccg aaaacgtaac catccgtctg atgcaaaacc aggccgagtg gaacgctaaa   153900
aacctgggcg aatccgacgc tcctggttct gtaaacagca ctgtcggtaa atggcagcca   153960
gtcctgatcg acatggcaaa acgtctggcg ccgatcaaca tcgcaatgga cttcttcgga   154020
gttcagccgc tgtctggtcc tgacggtcag atctttgcgc tgcgtgctcg ccaaggtatt   154080
ggtgacggtt ccaccaccgc acaggcgcgt aaagaactgt tcatgaacga agccgattct   154140
ggctactctg gtgatggcac tgtacaggct ggtgacccgt caggcttcag tcaggctgag   154200
atcgaaggtt ctggctctgc tgtgaccact atcggtaaag gtatgccgtc atccgacgcg   154260
gaactgctgg gtactaccac caatccgtgg gcgcgtgttg tatcaccgt tcagaaagcg   154320 accgttactg ccaagtctcg tggtctgtat gctgattaca gccatgaact gcgtcaggat   154380
atgatggcaa ttcacggcga agacgtggat aatatcctgt ctgacgtgat ggtaactgaa   154440
attcaggcgg aaatgaaccg tgaattcatc cgtaccatga acttcagtgc tgttcgcttc   154500
aaaaaattcg gcaccaacgg tgttgttgat atcgcgcagg acatctctgg tcgttgggcg   154560
ctggaaaaat ggaagttcct gactttcatg ctggaagttg aagcgaacgg tatcggtgtt   154620
gacacccgtc gtggtaaagg caaccgtgtt ctgtgttctc cgaacgtggc atccgctctg   154680
gcgatgtctg gcatgctgga ctatgctccg gttctgcagg aaaacaccaa gctggctgtt   154740
gatccgaccg gccagacctt cgcgggtgtt ctgtccaacg gtatgcgcgt ctatgttgac   154800
ccgtatgctg tagcagaata tatcacccctg gcgtacaaag gcgcgaccgc gctggatgct   154860
ggtatcttct tcgcgccgta tgtgccgctg gaaatgtacc gcacccaggg tgaaaccacc   154920
ttcgctccgc gtatggcgtt caaaacccgt tacggcatct gtgctaaccc gttcgttcag   154980
attccggcta accaagaccc gcaggtttac gtgactgctg acggtattgc tcaagacagc   155040
aacccgtatt tcaggaaagg tctgataaag tcgctgtttt aatagctaaa acaaagactt   155100
acgctataat caaaccccgc catatgcggg gtttttcttt ctaagatatg gggttatatt   155160
actcagaaag gagatcatta tgaccccgta tgtgtacaga ataaaatcta acaaggaca   155220 tttctattac ggatgtcgtt attccaaaga ttgccatccc gatgatttgt gggcaacata   155280
tttcacttct tcctccctgg ttaaatcttt aatagaagaa aatgggttag aattctttga   155340
caccaagatt gttatggtat gtgaaactcc agaagatgct ctgcgcgtag aaggattatt   155400
aatatcaaag actcataagt ttcctggctg tttgaatcaa ttcctttgtc gtaaagatgg   155460
gacgcctgtc cacctgggta catatggcac tccttctgaa aaggtacgac agaaaatttc   155520
ttcgtcaaac aaaggtaaaa agaggacaaa ggagacaaga gaaagaatta agttaggaa   155580 aacaggaacc acttggtctg aagcacaaag ggatggtgtc aaggctttcc aacaaacaga   155640
agcgtaccaa caattaagaa acaaaatcaa tacaaccaat aagaatagaa caaaactcc   155700 cgaagagttg gcttccattt cagcttccct gagaggacgt aagaagcccg ctggatttgg   155760
ggaaaaggta tcagccacca ataaagtaag aaactcttct ctgagcattt ggcaaacgaa   155820
```

```
tagagccaaa ccattacaac acgtttgggc tatggccgac caattctatc aattatggaa 155880
gaatgaaggt tgggggcatg aacgattttg taaccggatg aacgacggga ataatattcg 155940
agtgttctat aacatgtaca aaatgttcaa atacgaaaat tgggttccta tggaagaccc 156000
tgaatgggta aaagatttca tgtagttttt ctttatctac cctcagtgct atcatgatat 156060
tgtctatcac tgagagatct atattatgtc aaaagaaaaa tacatattca tcagccccgc 156120
tacgaaagag ttcttcatct ctgacgtgaa agatcgtgtt gagaagttcc gctacatgcg 156180
cagctatggt ctggcatccg gtgatattga ttatcagtca ctggacaatg atcgccaaga 156240
tctgatcgac gacggttggc gtttagttcc gtcccctcag tacattcata tcacgttgta 156300
ctatatgaag gacagcggga agttctattc cgaaggtgaa ctcgtactca atcgaggaga 156360
agcagaagcc gaacctgcca aaacctggat gttggcgatg gatcagatcc gtgaattgct 156420
ggactccggt aatctgcctg gcctgatcaa gggttcaaaa ttcgacgtgt tcgttactgg 156480
ccagggtcat cctggtggat acccacatct gttccgtatt aactgaggtc aattatgagc 156540
aatttaccac tgcttcaagt cggtgacgta ttcattctca cagaagaaat gaccattgaa 156600
actcaggtgc ctaagcattt cttgtattct aattgcaagg gagattggca aacgactct 156660 ggttatatca cccctgaggg attcttcggt tacatgcaag ggcattatgt cgttaccaaa 156720
acagccctac aaggcggtag cactggtcat gatccatacc ctgacggcca tcatgtttgg 156780
gcacagcata ccgaaaatga acgcatcaga atctgtttct atcagacagg tagtttcagg 156840
aatatgcacc ggaatgttcc agtagtcgga aaggctaagg cgcaaacatg gacttgggag 156900
aaattatgaa aatcaaaaag ataggtgcaa gcccattgac gggaacaatc ttccagggta 156960
ctttgaacac caagaccagt atgtgggtcg gtgagaagac tgatgtgacc gaggactgtg 157020
tagcggccac ggccgaacac ttgcgccaca ttaaaaagaa atactgctgg ccgacaaccg 157080
acggcaagtt cttagtgttg tctgctcagg tgtatgacac cctccctgac gaattcaaat 157140
agttaaaaga attcaataaa cggggtttac ttcttcaata aaccccgtat acttcattcc 157200
ataagcagca caacactgac tctgaaatga aggaactaca ccatgaccac agcaaaagtt 157260
accatctacg ctttcgacgc tttctctaaa ttcgacgcat tcgtctcctc cgcatttggt 157320
atcaaagaag ttgaagcaga gaaaactttc tgtggtggac tcggcaagtt tgccaacctg 157380
agtttatccc tgacagagtt catgaaatct cttgaaggtc actttgacgc cgaaaccatt 157440
cgcacttcct tactcaagaa agacggcacc cctcgcaaac tgtctggcaa gactagaatt 157500
tacgatgctg acggctttac tgtgtctgtg cattttactg aagaacctgt gtacgaactt 157560
ttcagcgggt ctgaagacct cactcactat gtggtcagga aaggcgattc ccgccctgtg 157620
ttcgaatctg gcgacatcct cgccgctatc aaagaacttg cgcgtctgaa tagcctctaa 157680
cagacgtttg ttctaaacct ttgaacgggg tatggttaat ccataccta tcccatacaa 157740 atagaggact ttatcatgac tacaagaatc ccaccgcagt cgattgaaat ctcgaaggtc 157800
gtcaatatcg aacctcgtcg cggaacccgt aaaccccgca cggggcgtca tttgacaacc 157860
aagctggatc ttctgaaaca gaagtttagc gaccacagtg tgtttacccg tatccgcaac 157920
gcattaaagg aagggcgaac cgagttggag ctatatcgcc caaacggttc gactcgtgcg 157980
tatcagacca ccgacggttt gctggaactg atccgcctct cgggaatgag catagaacct 158040
cgttcatcag ggactccctt gtgcagcctg tacgtcatca gcaatcttgg ggcactgtga 158100
gttctatgaa gaaatatgtc gtgctcatca caggttcccg ctc                    158143
```

<210> SEQ ID NO 2
<211> LENGTH: 76622
<212> TYPE: DNA
<213> ORGANISM: Unknown
<220> FEATURE:
<223> OTHER INFORMATION: E.coli bacteriophage EP335

<400> SEQUENCE: 2

| | | | | | |
|---|---|---|---|---|---|
| atgaaatgta | aacatgatta | ctatcttctt | cgtaaagctt | acggggatga | aagaatacac | 60 |
| gggctatacc | tatcaacatg | gaaatgtaag | gattgtggta | agctacggtt | tagtgaatgg | 120 |
| atagacagac | cgggatgata | gtgccttaac | gtgacatggc | ctttacatga | ggtccccttt | 180 |
| atatcagcgt | acacggggttg | tcaatgatga | ctacgccttt | acggggtggc | cttaatatga | 240 |
| gcgccccttt | atgtcttccc | ttattcagag | gagaattaat | atggatttta | tcttagactt | 300 |
| tttatcagag | gtgattcctc | ggtttcgcac | tgaaagatgt | gcattcacat | ttgaagatat | 360 |
| gggtgacggg | gagttaatcc | tcacctgtat | tggtcgcttg | gtagacctag | atgatgacga | 420 |
| agacttcgat | gccacaatgg | acgtaagcgc | cttgggttgg | ctttacatga | gagctttcct | 480 |
| gtcattcaaa | acaaacacat | ttactgatta | tagaaaagag | gacactgata | atgaataaca | 540 |
| caacaatcat | cgcagcacag | gctatggact | taaacaacta | caactctgct | ctgtgtggct | 600 |
| caggcactgc | aactaaactg | gttaacggag | aagttgttac | ggtgaatggt | ctttactctc | 660 |
| cggatattta | tagtggctct | atcctcaagc | cagaacacaa | gaatccttct | acactggaag | 720 |
| ttattcagta | tgaatctacc | aagcacaaca | acttgccgga | acatgcacga | cagatgatcg | 780 |
| aatggattga | agaagcagaa | tatgaaatgc | tgtacaacta | tatgaactca | aaagatgagt | 840 |
| ggactcgatt | ggtaagtgtt | aatgaagatg | gtacagaaaa | gattacgtgg | attcataaag | 900 |
| acgaagtggt | taacgacgtg | gtagaagatt | acgaaaaatt | tttggtcgga | gggttggctg | 960 |
| aagttgagaa | ggggtatgca | gttcctgtag | aatatgaagg | tgaacttgtt | gctctgaaga | 1020 |
| agatgtttaa | cctaagcatc | gattgctaat | ttggtgtgcc | tctcgtagtg | ggaggctttt | 1080 |
| tgttatagtg | gtaatgtaag | aaggagagaa | acatgtttgg | tgaaaaagga | gaactcacgc | 1140 |
| ctctacaggt | agctgaggtt | acaggaagat | tacccggagt | aacggaagaa | cttgaatcca | 1200 |
| agggtatgaa | cccaagcaat | gggaagtttc | aaaaaggaaa | taagtttggt | agaccaaaag | 1260 |
| gtagtagagg | taaacttact | cagcttatgt | tagaccgagt | agcttctagt | catttgtctc | 1320 |
| ctgatgaagt | gttaattcaa | atttacgaag | accctaatat | tccgcctgat | cttagattca | 1380 |
| aggctgcatc | aaaagtcgca | gatctagttt | atcctaaggc | agcttctgtt | gaaattaaga | 1440 |
| tggaggatga | gaatgcaatt | aatgaggaaa | cgttgaatgc | acaaatcaag | gacttcttga | 1500 |
| ccggagcttt | aggtattgat | gttatgcctc | cagaagactc | tgaggacgct | gaaaaggagg | 1560 |
| aggaagcgga | cgagagtaaa | taaggaaac | ggggagctgt | cgaagattct | tttacagtgt | 1620 |
| acctcagtat | agaggggagg | gttcttttcg | cgagggatct | ctcccttttt | ttaatttttg | 1680 |
| gaggaagtat | gtcattagat | aaagaaatat | atgaagctct | cactggagat | aaactaacag | 1740 |
| tagaggaaaa | gaagcgtctg | ttaggaatat | taaagagcg | agatacatgg | agaaagtata | 1800 |
| ataagattct | agctttcaaa | gcatacgact | ttcagaagaa | gttttatgag | gcaggactga | 1860 |
| agcatcgctt | taggttcctg | tgtgctgcta | accgtgttgg | taaatcttac | agcgaggcat | 1920 |
| acgagtttgc | ttgtcatgtc | acaggtcgct | acccaacttg | gtggactgga | tataaattta | 1980 |
| aaagacctat | ccttgcatgg | gcagtcggga | ttacagggga | ttccacaaga | aaggttttgc | 2040 |
| aaaaggaatt | gtttggcaca | cctattggaa | aagatacaga | tcttattggt | acaggtgtga | 2100 |

```
ttcctcgtga tgctattgtc atagacacaa tagaacgaga tggtaacaag cttcagatcg    2160
tacaaatcaa acatcaaaac gaaaggggag agtttgacgg cctgagcaca ttagaattcc    2220
gttcaaccca acagggtgaa catacattga tgggtgctac agttgattat atttggctgg    2280
acgaagaaga tccttatgaa agtatggcaa tcttctctca gtgtgtaaca cgtacactca    2340
caactaaagg tttagtaacg attacagcta caccagagaa cggtttaaca gagctggtgg    2400
ataagtttat gaaaggtgaa ggtgatgcag atacaggttc tctgtatttc cagaatgctt    2460
cttggtggga tgcacatgtt gacttaggtg gtcacatctc agacaaggat ataaaagaca    2520
tgaccgaagg tattcctgct tggcagctag agatgcgctc caaggtatg cctctgttgg     2580 gttcaggttt gatttatgat gtatctgatg actcagttaa gtgtgaacca ttcgatatcc    2640
ctgatacatg gaaacgtgtg tgtgcggttg atatcggtat tgatcaccct actgctgctg    2700
tttggtcggc ttacgatgct aacactgata ctatttacat ctatgactgc tatagagaag    2760
gtggttacac tccagcttac catgctccgg ctattaatgg tcgaggacag tggattccgg    2820
tggtgttacc tcacgatgct gacaatcttg agaaaggtag tggttcttca gtggcccaat    2880
tctataggaa tgcaggggtt aacgtacaat ctgagacctt ctacaacaag attggaatgg    2940
atggtaaaaa gaacttcttt gtagagccgg gaattacaga tattcgtgaa cgtatgatgt    3000
caggtcgatt caagatcttt aatactgctt cctgtgctaa actctttgaa gaaaaagcac    3060
gataccaccg taaggtcggt aggattgtta agaacatga cgacttgatg gatgcgatgc     3120
gctattctgc ttgctccgta acacatagag gtcgtagtaa acacgatgct agctacggaa    3180
gttcgtcgct ttatcaagaa aatattaaca gatggaattc gagttactaa ttgtgcaggg    3240
gcgctagatt cgtaagttaa ctaggcgtgt acaaatcgaa ggggaggcta aggtctccct    3300
ttagtaattc cttcccagct atcaaccgag ggagagatta gatggctaag aagaatttta    3360
gtgaagatgt attggatgaa ctgcgcgttg accttcaacg tcgattcaac tacgctcaag    3420
gctacgtaga tatcgctgta aaaggctatg ctcgtgaggc ttgggaatat ttttatggga    3480
accttcctgc tccagttaca gctggcagtt ctagttgggt cgatcgtaca gtatgggaat    3540
cagtaaacgg tacactccaa gatatcatca acgtattctg ttcaggtgat gaagcagtga    3600
catttgtagc ggacaaccaa gcagatagtg atgcagctga cgtagcaact aagctcgtta    3660
accaaatcct gttgcgtgat aatccgggat acaatgttat ttcctcagcg gcacaagagt    3720
gtcttgtcac tcgtaactct tttatcaaat actattggga tgaacaaacc tccactcaga    3780
cagaagaggc agagggcgta cctccagaag cacttgctgc atatgtgcag ggattagagg    3840
ctggcggtct tgaagagtta gaagtcttta ccactgataa tgatgacggt acagtggacg    3900
tcaaggttaa ctacaaacaa acagtaaaac gtgtgaaggt tgagtatgtt ccttccgaac    3960
aaatctttgt agatgaacat gcaaccagtt ttgctgatgc acaatatttc tgtcatcgtg    4020
tacgtcgctc taaagaagat ctcgtagcta tgggtttccc taaagatgag attgaagctt    4080
ttaacgattg gactgatacg atggacacta cccaatcaac cgttgcttgg tcacgtaccg    4140
actggcgtca ggatatagac tcagatatcg gtgtagacac tgatgatatc gcttctatgg    4200
tttgggttta tgaacactac atccgtactg gtgtactgga taagaataaa gaatcaaaac    4260
tctatcaggt tatccaagca ggtgagcata ttctcagttg tgaagaagta accagtattc    4320
cgttcgtaac tttctgcccg tacccaattc cgggttcatt ctatggtcag tctgtctatg    4380
acattacgaa agatattcaa gatttacgta ccgcactagt tcgtggttat attgataacg    4440
```

```
taaacaatgc taactatggt cgttataaag cgattgtagg ggcgtatgac cgtcgttctt   4500
tgctagacaa ccgtccgggt ggcgttgttg aaatggagcg tcaggatgcg attgatttgt   4560
tcccatacca caatctacct cagggtatcg agggtctgtt gggaatgtct gaagaattga   4620
aagaaactcg tacaggtgtc actaagctcg gaatgggtat taaccctgat gtgtttaaga   4680
atgacaacgc ctatgctact gtaggcttga tgatgaatgc agctcagaac cgtctccgta   4740
tggtgtgtcg taacattgca cacaatggca tggttgagtt aatgcgtgga atctacaacc   4800
ttatcagaga aaatggtgaa actccttttac aggttcaaac acctcgtgga atggttcagg   4860
tagatccgaa acagttacca cctcgtcata atttacaagt tgttgtagct atctctccta   4920
atgagaaagc agaacgtgca cagaaactga ttagtctgaa acagctgatt tctgctgacc   4980
gacagttagc acctctcttt actctggagc aagatcgtta catgactgca cagatctttg   5040
agttgatggg aattaaggat actcataaat acttaatgcc tcttgaacag tatcagccac   5100
cgcagccatc tccaatggaa attctccagc tggaaatgac taaagctcag gttgagaacg   5160
tacaggcttc ttctcagaag atgattgctg atgcattcga ccagcgtgaa cgtactacat   5220
tcgaacagca gaaagctgcc gatgagttca gtctgaagca ggaagagttg cagttcaagc   5280
aagaaaatgc agcagatgta atgaccttag agaatcgtaa ggaagacaat agtgctactc   5340
tggaacaagc taaacacaaa ctgtctcttc ttcagcagca ggttcgtcag tatgaatccg   5400
tactgaaaga actacagatg gttatggacc atcaggttga ccaagagaag attgttgctc   5460
aagcacaggt tcaggataag actttggaac tccaaaagaa agagtcaaat gtaactaaga   5520
aagaccaaca gaagactcta aaagattcta ggattcctaa cagacgtctt ggtagtaaaa   5580
aataaggaca ctgaatgaat acacaacatc aattcaataa agagcatgcc gccagtttgg   5640
cggctctcaa tcttcaggc agtcttgacg cagcattaga ggcattgaaa gagaaactca   5700
tgaaagagat cgtatcaacc gagcctcatg agaacaagaa acgcgaagat tgttatcaaa   5760
agtataaaat ggtgggtagc ttaaaagagg tcataaaagc tgctatcaat agtgcaggag   5820
atgtttcata atgccacaag ataattatat tgacccgaac gattttaaat ctttcctcca   5880
actggatgac ctgaaaggtt ccttcaaaga agaacttggt cgattagaat ctgaacaaga   5940
gccagaagtg gacattgacg aagacttccc tgaatctcag gctgatgact tcgacattga   6000
caccgacctt tcggcaaag gcgatacgct agcgttcgaa gatgaagatg gatgggaaga   6060
tgaagaagga acggaagacg aagcagatga gactgatgat gttgtcgagg atgacgaatc   6120
agatgagtcc agtgatgctg aacacgaaga aacagctgac gaggacgtag actacgaaga   6180
cggcgacgtc tatgatgttg actacgaaac cgttatcact cttccggacg tcgtgaaat   6240 gacaatcgaa gaattgtcta acggctactt aactggttca gcaatgaccg aacgagaaga   6300
aactctccaa cgtcatgttg aagcttttga agaacgtgtt acaggtttga cggatgtatt   6360
agatttggcg tctctggaag cagaccgtgt gattgaagat tacaacggct ttgattggga   6420
caagctcgca caagaagatc ctcaggctta tgtagaaaac aaacgtttct tagaaaaata   6480
tgtagctcgt cgtcagcagc tggaagcagc tcaggctaag gctaaacagg aagcgcaagc   6540
taaagaagaa gctgtattcc gctctaagag tgctgaatgt gttgctattc tgaagcgtga   6600
gattcctaat tgggatgaga atctgtatca gggactgatg caatatgcaa ttgatctcgg   6660
tgctacagag gaagaagtat tgcgggagaa tcgtccgtct atcttcttgg ctttacataa   6720
agcataccaa tttgataaag gtaagcaaca ggtaatggct aagattaagc gtccgggtgc   6780
tccacgaaaa gtcgtgaagt ctgatgcttc taaagctcgt acttccggta agccagacaa   6840
```

-continued

```
cgctaaggtt gccaaggcat ttgcagaggg tcgtattcgt catgaagatg catttaagta    6900
tctcgtagat taatcgacaa atttattttt taatagtata ggagctaaca taacatggca    6960
aatccaactt tatttgtatc ttacgaccag aacggtaaaa aactttcctt cgctaactgg    7020
atttctgttc tgtccccgca agacactccg tttgtgtcta tgactggtaa agagtctatt    7080
aatcagacta ttttcagctg gcagaccgac gcactggcag cagttgatgc atctaacgca    7140
cacatcgaag gctctcgtgc tgatgatggc gaaatgcagc cgactgtaat taaatcgaac    7200
gttactcaga tcctgcgtaa agttgttcgt gtatccgata ccgctaacac caccgctaac    7260
tacggtcgtg tcgtgaact gatgtatcag ctggagaaga aaggtaaaga gatcaagcgt    7320
gacctcgaaa aaatccttct gtccggtcag gctcgtaccg acgtgctggc tgaccagtac    7380
ctgactaact ctgcaactga tcctgatctg gttggtaaga atgacaccaa tgcagctcgt    7440
aagactggtg ctttccagtt cctgtgtgct cacggtggtc tgactggtgc ttctggttct    7500
caggttgttg ataaaactaa gaacggtcct gctgacccgg atactggtgc agtaactgtt    7560
aaagttgcac agaatgcttc taacccgacc actaacgttg gttttgatga agctgatatc    7620
tttgatatga ctctgcaact gtacactgct ggttctgaag ctgatattat catgatcaac    7680
cctgctcatg ctaagatctt tgctgctctt caggaaaact ctgttggttc tcgtcagcgt    7740
atctttgaga acaccaagca gttcatctat gaagttaaca gcattactga cccgctgggc    7800
cagagctaca aaatcatcgt taaccgttgg atgcctactg atgcagtata cttcttccgt    7860
agtgctgact ggactcagat ggtcctgcgt gctccgaagc gtactgaact ggctaaagat    7920
ggttcttacg agaagtggat gattgaaatg gaagttggtc tgcgtcaccg caaccctat    7980
gcttccggcg ttctgttcac tgctgcggga aaggtagtgg cggcgtaaca gtagataccg    8040
taactgttag tccttcgtcg gttgcaagcc ttccgacggg ggctactcag cagtttacag    8100
ctacagcaga aatgagtgac agctccacaa gcacaaccgg atttaattgg tccgttgagg    8160
gcggtgggc tatttctgtt tctgggctat atactgcacc gagtgcgtcg caagaaaccc    8220
cagcaactat tacggctact aaaggtggta aggcaggtac tgctacagtt cagtctgttt    8280
ttgaacctgc tactattgaa gccaaagcca acatcactgg taaagtaggt ggaagcacta    8340
cagcctttac tacaatgttt acagcaacta attcttcggc agaagattat tctttttgttg    8400
tatctccaac atcagcagga actgtcagtg ccgcaggagt tttaacttta agtaatgatg    8460
caactggcac agttactgtt aaagcaactc ataaaactca gtcaggtgtt gaagccactg    8520
taaccttac gggtgttgtt gctaaagctg ctattactgg aaaaacagtc acaggtaaag    8580
ttggtggtga tgtgattcct ttcacggaca tgttcactag taacaaacca gcatcagaat    8640
tcaactacg gttgactccg actggtgatg taggtgaaat tgcactact acaggtgcac    8700
tgactctctt agatgaccct acagacgaac ttattagtgt taaagctact cataaaactc    8760
aaacttctgt aacagcaacc actacaatca cagctactcc gaaacttacg ggccttgttg    8820
cttctactgt ttctaatact gtggtcgtag gtgctacaga taaccctctt gctacagact    8880
ctatcacaat cactgactcc gctcaaccgg gtgtagttcg ttttgatggt gtacctcagg    8940
gttcagtagt tggtgctcta tcttatgaca cagaaggtac tgatgtaggt ttgatggaag    9000
ttgatttaac aggtcaggtg ttgacaatca ctttatcagc tccgattacc agtgaagata    9060
ctaaaatctc aatcagaact aacccagcct ccacaatatt ccgtacttat gttgtcaagt    9120
ctggtgcata aacctaagct gccttcgggc ggcttttctt gttttaagac ctatacatga    9180
```

```
ccaagtgtaa tgtatattct tgtctacat  acaactagga ggacaatcta tggcgatgcc   9240
agacgttcag tacccaatta atacctacgg atggcttaag aaggctgtgt ccctctgggc   9300
tgaccgtgat gaccctgaat tgttaatca  gattccgaac tttattaact tgcagaaaa    9360
ggaaatctat cgtaatttac gtattcctcc tctggaaaaa gaagtctatt tagatattaa   9420
agatggtgtg gcttttatcc caccagatta cttagaagct cagtggatga tgagatctaa   9480
agatggttta atcttccgtg taacctctct tgaagaagtt gattggctta agcgtaataa   9540
ctcagtcaac cccactaatt ggaatcaagg agaagttgtc tttgctcgtt tgggtagtcg   9600
gtttatcttc tatcctgcaa ttgaagcaga tactccagtt taccctgatg atggcagccc   9660
tgagattcca gcagagaatg cggtcattct tagctattat gctgacccac cagagttctg   9720
ggaagattca gacacaagcg ctattcttac tatagcccca gagcttctac tgtattttgc   9780
tttacgtcat gcttccttgt tgttcagga  tgacaatgca gttcagaagt ggtctgcttt   9840
aggtaaagcc attcttgatg aagttgttga gcagagtaag aaagcagaat actcaggttc   9900
acctttagtt attcctaaca cgattagccg tctacatagc tctcgtgaag tatatgggat   9960
tcgtcgtttt agataaggag agaatatgat cgtttataat aaccaagcac cttcggctgt   10020
taacaacgtt ggtcagtttg gtgcaacaga aggctctatc ggagcctata acaagctgc    10080
tgaatacgca gctgactcta agtattgggc acttttagct gagtctaaat ttggtacagt   10140
tgatgacttg attgctcagg ttgaaattct gtacaaacaa ggtgttctat aaaagaaga    10200
tattgaagac ttaaaacaag acttcattgc acaagatgct cgtttgatga atctcattgc   10260
tcaaactaac gcaccgtag  ctgatgcaaa taatgcagtt gctctgatta atcagaagct   10320
tgtagaagtt caacgccagc tggatattct gttgggcatg acagtcaccg ttacaaccct   10380
ccccccaggt tctgaggcca ctggttcatt taacagccag accggtgaaa tcaaacttgg   10440
tattcctgaa ggtgagaaag gtgcagatgg ttctgttact gacctatcta ctgcccctac   10500
cggtacacca gagctggggg atattggttt ctatgtagac aaagatgata cactgttca    10560
taaaacctct cttgaagcta ttgcaaacct gatcccatct gttcgctctg tttctattaa   10620
cggcggccct gcgcttgatg gtgaagttgc tcttacaatc aacaaagaga cagtaggtct   10680
tgggaacgtt ttgaacgtgg ctcaatatag tcgccaagag attaacgata gtttgataa    10740
aacaactaaa acataccaat cgaaagctga agctgatgca gatgctcaat tcgacaagt    10800
gggagagaag gttttggtgt gggattcaac taaatatgaa ttttatactg ttgcagctaa   10860
taagacactc actccagtta aaacggaagg ccgtatcctg actgttaact ctcgtgctcc   10920
tgattcaaca ggtaatattg atatcacaat tccaacagga aacccatctt tgtatttagg   10980
tgagatggtg atgttccctt atgacccagc taaaactgtt tcatatccgg gagttcttcc   11040
tgcggacggt cgtcttgttc cgaaagcaaa cgcagcagac cttggaccct ctttagtcag   11100
tggtcaattg cctgtagttt ctgaaacaga gtggcaagct ggtgctcgtc aatatttctc   11160
ttgggggtaaa cttgctgatg gtattaatga tgcagattca accaacttca tcaacatccg   11220
tcttcctgat tggacaggtg gtgaggctat tcgctcccct gactctgata agatactaa    11280
ctacaaaggt cgtgttttgt ctcaggttcc ttatattgtt acggttaacg gtaaagctcc   11340
tgatgacact aatgggaatg tagttctaac agcagctaat gttggggcag cgtcttcagg   11400
tgctaactct gatatcacgt ctctcaatgg actgactact cctctctctg ttgcccaagg   11460
cggtacaggt gttactgaca taggatcttt gcgtagagcg gcgttggttc aggggggttct   11520
gtgtaatgat caggctggcc ctcaatctta taacagctat agatctccta acgggagta    11580
```

```
tgctttcaaa gtggataact cggggcttgt tgcttctatt aatgcaggga cggaagaagt   11640
tgtacctttt gctatagaat caggtggtac gggagcaacc acattaaatg atgctcgaat   11700
tagtttaaat ttggagagat ttttacagcc tagcaatgaa accatagtta tggctcctag   11760
taaatcttca tatttaacaa tttcagacac ctcttggggg gcttatagtt cttctgactc   11820
atcatggaga gctttaggga taggacaagg tggtacagga gcgacctctg aggctgctgc   11880
tcgtgtcaat ctgaaggtgg ataagcttgt tcaaagttca acagacacaa aacttctgga   11940
tggttcagga gaacacacct tctttattac agatgcagat tgggggtatt tcaataactc   12000
cgattcttct cgaatagctt tgccggtaat aagtggtggt acaggaggga agactccagc   12060
cgaaggttct gaaaaactag gagctatgca ctatcagtat ggtcaatcga cttttttatgg  12120 tagcgaagat ttgccaacag gtattggctt ctacagtcaa gacgtttccc cgttccccgg   12180
gggtaatgga gcaccctact cctatgcaga gattatgacc atctctgaag gaggtcgtgg   12240
tgggaattgg tctcagattg gtttctctac catcaccaag caagctcctc ggtatcgtca   12300
aagaactaat gacccagctt tgatcactaa ctggagagac ttcttggtca gagacttaaa   12360
cacaactgtg gatgttaacg gttttgttaa aatagcatcc cctattgtca agcttaaacc   12420
agacggctcc tctgaagtta atgatcaagc acaaggcgta atcacagaaa gattagatgt   12480
tggtgtttat aagatctctg gagttctagg ttttaactcc gacccttctt ggggtggtaa   12540
tgggggtgga ttctctattc ctcaaaactc taatggactt cctttactgt gggtggatta   12600
tgaagtggat gagattggtg atataaccct taagacttac cacagagttc acagtggggt   12660
tccttctttt gctagtaatg aaaaagaagg ggttgttgat ggagaacctg ttgacattcc   12720
agagggccgt tgggtagatc ttcgtgtaga gatgccaacc gagtaaataa tatatgctcc   12780
cttcggggag ctttaaggag attttaatgt ctagagaatt aatgcccaaa tctggcataa   12840
tgatgcctca tgttgttatt aaccgagatg ctgcggtggt gggtgtctca actgttgatg   12900
gtgttgctgg tgcggttaat ctgactgata aatatttaca gaaaacagat gcagcttcta   12960
cttatttaac tagagccgaa ggtgctacta aaacttttgt aacagatgca attggaccta   13020
tcatgtctgg tgcactgttt aaagatgacc ctgttgttgc aaatgatgta gctttccgtt   13080
caggtggagc taatggtgta gaatctgtgg atatgattaa agtcactcca gagaatacta   13140
tcaaacttgg tagttatgca tcttctgttc agggagtaga gattcactca gctggtcgtc   13200
ttcaggttgt tgatcagaat gacagtggtg tagaaactaa atacccctgtt tattctaaac   13260 ggtatcgtcc tgagattgaa gatttacctt ttgctgcaat tgggtcttat gttaaggatt   13320
ctaaaggtcg tactattggt gttactcgta ctggtatcaa ctctgatatc aaacagctta   13380
cacagaaagt cacatttact cagcctgtaa ctgtagcaga tggtgttggg gactacgatg   13440
ctgtaacaat gaggcagctg cgtaatagtg gtggtggctc tggtggtcct accatgagtg   13500
gtatttctaa ctttggtatt ggtgattttc acctacgtga cagtcgtgct ttcatccccg   13560
cttttgaggt agtctctgac gggcagcttt tgaatcgcgc tgactaccct gatttatggg   13620
cttatgctca actcttaact ccaatcagtg acgctgcttg gttggcggat gcacagcaga   13680
gaggtaaata ctctactggt gatggtacaa ccactttcag ggttccggat agaaacggcg   13740
tacaagcagg atctcttaaa gaactgtttg cccgtggtga cggtggtaat tcttctaata   13800
acggtatgat gtatgatgca gctcttccta atatcgtggg ctataccgca catactctgc   13860
taacagcgtc tagctctcaa ggacaggtgg caactgatgg agctttcact tcaaccacat   13920
```

```
caacccaagg tgtatggcct gttagtgggg gggtggtct ttatactaac attcgttttg    13980
atgctaatca atctgatcct acctatggta gatatggaat tacatcaaac gtaatacctc    14040
gtaactttat aggtgtttgg actattcgtg cgcatggtgg ttttactgct gctaatactt    14100
cttggtctgt tattgatagt gactcgacag agcctgcatc cggaacagtt gttaggggcg    14160
gtagtgtcaa atctgaatac aagattggta caagcccaaa atatcaagca tatcttcagg    14220
catatgggaa aattggtggg ttagcaattg accgaggtgc agttctatca aacgggtac     14280 aggagtggtt ctttaatcaa gatgggactt tgtatttccc agacgcagag acgcaaattg    14340
gtacattaag gtctgatggc gcgttacata ttagcgcata cgtcaggcca aaggatgtcg    14400
ttgtaaatcc attaaactct gttggggttg cagcttcaga aagaaacgcc gtcagaatga    14460
tcaactacgc aaatgtacca gaaggggggtt atattaactc agttggtggc gactggtatg    14520
atgggaattg gatgctcggc ggagtcagaa gtggcacaac agcattggac cgtgcgcaac    14580
ttaacatttt gaatggcatt ggcagcagcg cctcgtatat attggctct gatggtatag     14640 caagatgtca agaatggaga agtacatctg atgaacggat taaaagcaat attgagcgta    14700
tcagtgatcc actctccaag atgaaaaaca tcaaggggggt tacgtgggtt ctggaaacca    14760
acggctcggt agggtacgga ttcatcgcac aggacgtaga gaaggatttt cctgaagctg    14820
tatcagaaat aaaggcttca ccagtcactc tgcgagacgg gtctgtgttg gacaatgtaa    14880
agtcagttaa caccccggga gttgctgctg cgttgcacca tgaagctatt cttgaactta    14940
tgaagcaggt tgaagatctt aagaaagagg tgtcagagct taagtctagt aagtaatcta    15000 gtagccccctt cgggggcttt agtagtaagt atgttcaaga agtaatgaaa ctactatatc    15060
acaaaaggaa tacacatagg agatacgaag atgaaaatga tgaaacaaat cagttatggg    15120
ttagcttgtg ttgctaccgg ttttgctgtg tcagtggctg ttcctgttaa cgcagtgcat    15180
cctctggtaa cacaccctgc accaattgag aagttaagtg catcttgtaa gcagcgtaca    15240
attcagaata atcttgtggt tatttgtcca gactctgatt ctagtgctct gagaaacatg    15300
cttcagtaat ttagggctaa ctgggaaggg aggtgaaaaa atggataatg tcgcattgcc    15360
accgatacag ctgagcttaa gcccagacgg gatggaattc atcatgaagc atgaaggtat    15420
gagaactcgt gcttaccaag attccgcagg tatctggacg atatgtgttg ggctacgcg    15480 cgatatgaat gggtatccag ttagacaggg attaacgtat tctatagagg attgtctagc    15540
tctgctagat agagacacac aagactctgt tcgtgccact cagaaaaata ttagggttcc    15600
tttgttaacc cacgagtttg atgctctcac ctctttcaac ttcaacgttg gtggtggggc    15660
tttatcaact tctaaactta ggaaagttat taacggagat gtaaagggtg atgtttattc    15720
tgagttcctc cgttgggata aaattacagt taaaggtaag aagattagca gtccgggatt    15780
gaagaatcgt agaactgctg aagctgacct ttacactgaa ggtaaatact aaaaggagtt    15840
gtcatggcag tagaaactaa tgctaacaca attaatgacc tcaaccccct gtaccctcgt    15900
gacagggatt atctttacga aggggcggct cagattcgcc tcgttaaaca agtattgcag    15960
aacacttttc caaacgtaac agaaccagtt caattggact cagactctct caatattctg    16020
gctagcaaag ttacttttac tggtgactct atggatgttg gtgggttgat gatcaagaat    16080
gcaactccgg gtacaggtga tagagatgtt gtcactaaag gccagatgga agctttcatg    16140
cagaactgga tggctaacaa agtattcagg attggttctt actatatcac tgaagaagat    16200
attaaccccg gtgatagttc ttctcttggt tttggctctt gggctaaagt gactggtgtt    16260
attatgggtt ctggtgtagt aaaccctgac ggttctgttc ctaatgctca gcgtgttgaa    16320
```

```
ttccaagcag gtggtacagg tggtcgtgtg tttaacacta tccgtgctga taacctacct    16380
cttgtaacta tcaatggctc aagcttctct gtatctagta acactcacgg tcacaacatg    16440
gtgtttggtc gtggtgacgc aagtggtcat aacagctccc ctaactggta tagtccgggt    16500
ggtggttata gtcagagaac tgaaaatgat acacactctc acacaatctc tggttctgta    16560
tcttttggtc gtgatgatgt ttctcgtcag ccaattaata ctttaccacc tttccgatct    16620
gcacacatct ggagacgtat tagctaagga ggaattatgg cgttataccc tataaaatca    16680
cttggggctg tcggtgttat cgctgatcag gcaccaactg atttagcacc taacgctttc    16740
accaacgcta tgaacgctcg gtttgttgag cagagagttt ttaagacggg gggcaatgcc    16800
cctctttctt acgtggaaga agacaaagat ctgactccac tctcttttgt ctccatgcct    16860
ttcgattatt atagcgcagg aaatagcttc cttgtagtag gtacagataa gaagttatat    16920
aaactgacag atgaaagctt aactgatatc agtcgtaaag ttgctacggt aactaagaaa    16980
gcttctgcta tcataaagat ttatccagtg gtctcaagga ttgttcctaa agagagtact    17040
atcacaatga actttaacca gacaaaagag ttagaagttc aggttttttcc agaggatgct    17100 aataatgcta atctgacttg ggaagtaagt aaccccttctt atgccagtat tgcagtaaat    17160
cctacagatt ctaaaaaagc caccctcact acattatcta cagaaggaac actgtccatt    17220
actgtttcca ttgaagatga atctgtgaca gctcaaatct ccgttaacat tgttgatggg    17280
gatacgggta tcttcttgag tcaagacaca atcacaattc gaagaggtgg tacaacaact    17340
cttactgcta tctcaggtaa gactcctatc acttggatta gtagcaatgg tggtgctttg    17400
tctgtgacac ccaatgccaa tacactaact gctgttctca atgccatggg agaaggaact    17460
tttactgtta cagctgataa tggctctaag tctgctacct gtacagttaa tgtgataacct    17520 cagattgatt ctatttctct gagtcagaca gatgttcaga tggatagagg gactcagtat    17580
gttctaactg caacagtcaa ccctgctgat gctcctaata aagcaatcac ttggacttct    17640
tccaatccta atattgctac agtatcaggg acaagcacag aggctacaat tactggactt    17700
ctggctgggt ttacagagat tacagcagta acagaggaag gtagtcgttc agctgttttgt    17760 actgttcgtg tcaacctagc aggtagaatg ctaaatacca gaagcctagc gatggctgct    17820
agtgcacctc tagtggaaga gttcaaagag gaagaagaac cagttgtgca gaatgaagaa    17880
gttgtttact tcatgtctga ctctatggga attgataccct ctggcatggc tgaaggcaat    17940
aacttctttg actactctaa cgtatttgat atggaaggtt ttgctcgtgc tgcggagaac    18000
tcaagagctg ctcctctgac aaatgtgaca ctagatattg ttgaagcttc tctagatgta    18060
ggtgaagaaa ttgtcataac tgctacagca gctccagaag gggattactc ctatcagtgg    18120
gttgttgaca agagtggtta tgtttctact acctcaacaa ctggaagatc tttgaaactt    18180
acagctgttc gtaaaggcga gattaaagtt acatgtacgg cgagtcagat gactcaaaga    18240
gactacgatg cttttgatga ttaccccttgg tatcatgcag taatctctaa ctgtgcagta    18300
gcgacaactc actatgaaac tcctcaggtt aaagaattcg aatctgaata ctttacagac    18360
cttccgggct ggggtgaaca aacaattgtt gatggtgatg ggaacccttc tgttcgtaag    18420
tttaactgga agtgcgaaag ggttagagct tttaacaaca gattgtttgc tctgaatatg    18480
agggaatcta atgcctctgg tgttaccact cactatcctt tacgtcttcg ctggtctaac    18540
tttgcgaacg agaacaaggc tcctactttg tgggatgatt atgcttacga tcgactgaca    18600
acttctgatc tttcagcgaa cattgttggg cagactgaag ctcttgagaa tggttatgca    18660
```

```
gggtatattg atctggctga ctctaacggt agtttgattg atgttctccc tttgaaagat    18720
tacttatttg tttacaccga gtttgaaacc tacatcggtt ctcctactaa caacacatac    18780
cagcctctga tgtttaagaa gctgtttaac gattcaggta ttcttgctcc tgagtgtgtg    18840
gttgaagtag agggtggtca ctttgttgta acacagaacg atgtgattct tcataacggt    18900
gcatctaaga atctattgc atctaaccgt gtcaagaaca tgcttattaa tgaagtgtgt    18960
ttggtaaacc ctctagctac tagagttcac ttgcaccaag ataagaaaga agtttgggtc    19020
atgtatgttg ggccgggaga gccgaaagaa agttttgctt gtacgaaggc tgcggtctgg    19080
aattacgagt ttgatacttg gtcttttccgt actatcccgt atgctcaatg tattggtctt    19140
gttgatcctc ctgttctcga aagaggtcca gtgtggactg acttccaaac tatcacttgg    19200
gacgaccctg ctattgataa actggtgtgg agaaaggatg caactaactt ccgtcagaga    19260
attactatcg taggctcttt cttaagggt ttctatcaag tagatgttgg tgctttggat    19320
tatttctatg acagagcgaa tgacaaaata atagagcgcc ctctggaaat gaggttagag    19380
agaacaggga ttgattttga taacgtcact aacgaatgga atcaaaaaca catcaaccgg    19440
ttcagacctc agactacagg ttctggtacg tatatctttg aagctggagg tagtcaattc    19500
tctaacgagt atggtcacaa ccacacaact aagagttata cgattggagt tgataggcac    19560
gtagctgtga gactgaacca tccataccta ttctataatg ttatagataa tgatgttaac    19620
agtaacgcag ccataaatgg gctgacaata gagtttaatg ttggcggtcg aagataacaa    19680 ctaagggct tcggccccctt ttcttgtttt taaactttgg aggtacttat gggtgctgga    19740
ggttttcgta agaatactgg acgtaacaac accacacttc cctacaacgt tgggtttctc    19800
aacagggtag aggatacaga aacgtataac actgctgtct atgatgaatt acagaaagtc    19860
agtacagcga ctaaccaaat gttccaagca atcgacgaga ttcatgatga gattgatgtt    19920
cgtatcaaag ctcttaacgc aatgaatctc cagttcgatg agcttgagaa tcgaattact    19980
acagagattg aaacagctat tgcagacatt caaactcaaa tgggcaatct atctacggat    20040
gatatttggg ataactcaac gaatcctcct actaaattga acggtacggt agctggtatt    20100
aaaactagca ttgaaggtaa tgatttaaag attcaaactg ttcaaggcat tgtgaatgag    20160
caaggacaag agattgcttt agttcaaaca gaacttacaa ctcaaggtca gaagattgtg    20220
gatgttgatg aagggttac aactgtacag aactctcttt ctcaatatat gaagcttacc    20280
gaatatgaag ctacttgggg tgtgaactca gtgttaacg gtcggtatgc aggagttaag    20340
ttaactaaca acggaacgaa cagtgctttc caagtaactg ctcagaagtt tattgtcggt    20400
gatggtagct ctggtaacac cccctttcgtc tttgagaatg gtagggctag aatggagttc    20460
gctgatataa agaatgtcaa catcacaact gccatgattg ctaatgctcg tatccagttt    20520
gctcagattg ataatgtatg gattcaagat ggtcagattg ctaacctaac agctaacaag    20580
attactgctg gtagtatgtc cggctctaac tggagactta cagtaggtgg ggattttgta    20640
atgggcggaa caggtggggc acagctttgg atgaatggaa acagaattga tttctatgat    20700
gggagtggtg ctttgagaat tagaataggg agttggtgat atggcatatg gaatttgggc    20760
acaacctgta gggccgggc cagctgcccc tgctcctctc tttatagata gcgggagtac    20820
tttccctcag ataaagaata ccataagtgg tagtttcaac tttaacggcg gtgggagatc    20880
tttccctatt agtgggtggg atggttcagg tcagattgtt attgtcccaa caggatctct    20940
ttgttggcaa tgggaagtcc cacctaacct agtaccagat gtttattgtg taaacaatat    21000
ctacgtagag aacaccacat catttcgtgt caaccttaac cagaaccccg gaagcaaccc    21060
```

```
tcttttcgat tgtggtttta acgtttacca aatctggccc agagctgata ggaactacgg    21120
tataacctttt tctaacacag cggattactt ctctatctct gatgctggag ttgttggtca   21180
gtgtgtttgg gcttggcaag gaacaataaa caatgctttta caaattccag atatcggtgg  21240
attctacatg cctaacgctg tggttttttgc taactggtct gatggtggtt taggtctatc  21300
ttacacttct ggtgacaggg ttatacgtgt ttatcaaaac cgtccatata ttaatggaaa   21360
cactaacgaa ggtggttctg tctttgctag ggttgctgtg ttttgtaatg gtgctggagt   21420
tcctgagcac aatggtggtt tgaatattta ctcaccggga actgcacagt gtgtattctc   21480
gacaaatagg acaccttttta ccatcgacaa ttttataggc tctggtgggg gtaacactgg  21540
aatggcttac cctatgatac ctctttcctc tggtattggg gctataaagg gtcaaggaag   21600
tggttggaga tatcagcaga tgagatctca tacaatgtcc ggttctagtg taggaacggg   21660
ttatgggaga tatcttttcc agtgggatca gaattatgat ttagggtctg atactgtggt   21720
caatttatct atacctgtaa ttaatgcagc taaagtttttt gctggttttat aacaaggaga  21780
gattatggat aggattttag gagtttcaga actagaccca ctggttcaac aagctgctaa   21840
gaagtatggt attcctgctg ctcttgttca tgcggtcatt cagagggaat ctagtggtaa   21900
gccctctgcc gcttcaggaa cagggccagt agggctaatg cagattagta aaagtttggc   21960
taaagattat ggttacaaac tagaagaccg tctagaccca gctaagaata ttgacatggg   22020
tgctagatat atcaaggaca acttaaaagc atttaatggt gatgtaagaa aggcaatggt   22080
aggttattca gaagggactg gtggtgctaa gcaaatgttt gctggtaaga aagggttcac   22140
ccctcaagca ctagactcca tgaacaacaa acacttcctc cctttcttca accctaatga   22200
tgcagcaaga cagacagcaa accctgtagg agctttacag gaggctcaag ttgtagatca   22260
atacaatcca tcaacactaa ctcgtgaggg tgctgcaaac gctcctacac aggctgaggt   22320
gatggctagt aagacaggcg ctcttggtgg gaaacctgcc gagttctacg ctgaagaagt   22380
acaaggtcaa gatcaacaaa gacctcagaa ctttgggaat gctgcacttg ctgctgctgc   22440
aatgttggct ggtaaagttc ctaactcaca gactgttcaa agagcacatg cacctactgg   22500
agcttcctct aattacagtt ctcaaactca agcggtgctc agacgtttag caagcatcgg   22560
tacagacatt tacaggtaag gaggttctat gtctctcttc ggttcttcgg ctaaatctaa   22620
agttacagta tcgccttctt ctcaagtgga tgctctgtta cgtcagattg tttccaacgc   22680
tcaaggaatg aataaaggtc aatttgttgg tcgtgaaatg gcaggattca atcagaatca   22740
aagtgctgct ctctcaggtt tggctaactc tgatgtacag aaacaattgg ctgctctttta  22800
tacgcctcgt actcagcaag gcttagacca gatgaatact ctggcccagc gatatcagag   22860
tatgcaaac ggtggtggtg ttactggtca agctgttaat gattatagca atcccctgaa   22920
taactcggct cttgcacaag ccacaggtaa agcagcttct aatgtatctc ttggcaatgg   22980
ctctgattct ggttcactcc gtcgtgctag tgctcaaggt gctgctctgg ctagtgcaaa   23040
cactaacctc tctcgtagta tagatggtaa gaacatgggg attaataacc tccagaacaa   23100
tgaagctttc caacgtggta tcctaggtgc tcagacaggt ctggctggtc agaatcttaa   23160
cttgggtgca caaggtgttc aggctactca gcaagccatt cagaatcagc tcttggctgg   23220
taatctgcaa cagcagcaag atcagactca ggctaacctt aattgggaga atgctattgg   23280
taatcaacag ttcggttgga atcaactcaa caaccagctt aatgtactta actcagtaag   23340
tcctatggct gggtacacaa tcaagaatgc acaacccggt gttagtcaag gcagcaact   23400
```

```
gcttggtgca ggtatgactg gactaggtat tgcaggtcgc ttaggtgctt tcactcctaa   23460
tgctcagact cagaatgctt ggaactctta caacgcttct ggtggacaat ccggtatggc   23520
tggtcctatg attggtgggt ctaacctttc taatcaacag agtcaaaaca actggctatc   23580
taccgcaggt aataatattt taggtggtgt tcttggagca ttcggggcta actaaggaga   23640
aaactttatg gctttattcg gtggtggggg tggttctact acctccaaaa tgacaagacc   23700
tgactatatt cagagttaca ttgatcaatt agttaatcaa gtaaacaaca caagttcagg   23760
cgattatgtt tatcgagaga atgtagggtt taataataac cagaaccaag ctcttaacga   23820
tcttgctcaa tctggtgccc taggtgctct ctcttctcaa tatatggatg cagctggtca   23880
agggttaggt tatatggata atgcctacca aggctttaat aacctctccg gacaggggcc   23940
tatctcagca gaacagattg gtgctcttgc tggtgaactc tacgacgatt ctgctgtaca   24000
agcagctatt actgctaaca cgaacaaac tcaacagagt ctggcacgta atgctcttcc   24060
tcaactggct cagcaaatatg ctggtcaaca aggttctggt gctcgtatgg ctaaatcttt   24120
tgctcagggt gatgctctga atcagatgca gaatacagca accaacatta ctaacagtgc   24180
ttatgactct gctttaggac aagctcagaa catcctctct ggaaacagac agaaccaagc   24240
agctgctctt agtggactct ctaacattgg tggtaacttg gcaggccttg gtcagcaagg   24300
tgctcagttg tcacaacagc aattaactaa tcaatggggt gctggtttgc agcaacagca   24360
acagcaacaa gccggtttgg ataatgctta tcagaatgct cagaacgcag ctaattgggg   24420
atggcaagat attaataatc aactaggtgc agcaggcgtc cttaatggtg ctctcggaac   24480
gactacaact actaaaacaa ctggtggcgg cggtggtttc cttggtgggg cagcaagtgg   24540
tgcagcagct ggttcagcgt ttggaccttg gggtgcatta gctggtggtg ttattggtgg   24600
cttatcctct acctaactag gagattaatt atgcaacaaa cttcatatgc gtacctccgt   24660
agtcgagacc cacgcaatca gatttatggt gtaagtcagg gaggggcaca agcctctcct   24720
tatgttcctc gtcctgctta cccacaagca gatatgtctg tttataccag tcctaatatg   24780
gctcctgctg gattagctgg attggtttct caggctaatg aagatcaaga agcaatgctt   24840
ggtccaaaca aacaagttgt tcagggtgct aatatccaac ctgatattcc taacgaaact   24900
cctgtagcag cctctcagtc agcttctccg tttgctaacg atgaaagcat ggttgctgct   24960 ggccttttctc cagaaactgc ttctcaagag ttctcagacc ctctaccggt aagtgttcct   25020
cctaaaccgt tggaacctac tgatacagag tttactcaag accaagttaa acaggcacaa   25080
caggttatgt caacccttc ttccggctta cctgaagctg aaggtatggc aggtgcttct   25140
cgtagcgctg atcaagaacg tgttaacaag gatttaatgg aagtggctaa ggctaagaac   25200
ccgatggaag agtggggtaa gttacagaaa caacctttct atcagaactc tagcttctat   25260
acaggtttga tgggtgtagg tctttctatt atgtcaggta agtctcctat tgaagctttc   25320
cagattggtt ctggtatggc tgcacaggat gagactaaga accaacttga agctaaccgc   25380
gaatctctta ttgaacaggg ttactctcca gactcagttg ctgctgcaat tgctactggt   25440
gacccttctg ctctgaagat gcgtcagatt agtcctcaag agaaacttgc tttgtctgct   25500
atcgaagatg agagagctaa ccgtgaatgg gacagacgcc aacaggttag tgagcagtct   25560
atgagtcgta ggatggatgc aactcgccaa gctgctgaac aacgtgcaca agaacagttt   25620
gctcgtcaga aagagttgat tgggtatcgt gatcaagtga agctgatcg tgctgaacaa   25680 gctgctaaga gttttaattt taacccgaaa gaagttcgtc ttgctcagaa cacagctgaa   25740
ggtacagttg ctaagcagtg ggcagagaaa ggtggtctgt ttaaccagtc ccataaagac   25800
```

```
ttggacttgg cagatcaggc agttaaagat aaagactacc agacagctcg ttctgcttac   25860
atgcaggcta tcatgaactc cgcaagggct gaaatcggtg ctactcgttc tctgactgaa   25920
gaagacttac gtcactttgc agaagacccc tcaatctttg ttaaggttgg taatacttgg   25980
tctctgaaag gtgggtatcg tcctactgat gctgctcttg cttatgctcg taagcaggca   26040
accgttggtg ctacttcagc aatgaagggt gttaaggatg ctaagaaagc aaccattgaa   26100
gcttacgttg ttctggtat ggataagaaa cgtgctactg cacttgttaa ccgtgcgata    26160
ccttctggtg gtttctatga cccgttaggt acttttgaat cacaggctga ggaagaggtt   26220
ggtggtgctc ctactaatcc acgcctgaat ggtgctcttt cagcttctga agatactagc   26280
tggttcactc aataagacct aagtcctgcc ttctataatg tatataggg gtaggacatt    26340
tttatttata aggagacgtt atggctaaca ttaaatcttg gaagaagca tcgaaaagcc    26400
ccaagtatat gaacgcaact cctgagcaac aagctcagtt gagagagcaa tacaaagcgg   26460
caggtggtac aatccctgaa gataagccag tacaaccaca acaagaagag cgtggcttag   26520
ttggtgagtt cgctcagggc gtatctaatg ctatcgaatc tggtggagct aatattgcag   26580
ctagtaccgc tcgtggttta ggtggtctgg ttgaaatggg tgagaacgtt ctcggttccc   26640
aaacaagtta tggtaaaaga attcaagata acgcaaaaca agtattagaa aagcgtatgg   26700
ctggtatcga ggatggcttt ggtaagactg ctgggcagta tgctgagtg gctgctgata    26760
ttggtttgac ggttgctaac ccagctttgg ctgctggtgt tattgcggga cgtgaagcag   26820
gtcgagctta tgcagaccag accccagaag agggagaaga caagtcagtg ttagatgctg   26880
ctcttgttgg tggtgctaac tttgcagctc agaagattct tccgggtttt acaggaacag   26940
ctgaatctac tttaggtcgt attggtcaga gtgctgcttc taacgccgtg gctggcgcta   27000
agggtggtgc tctcgtaggt gctgctgaag ctcagaataa gtatggtgat gacactacac   27060
ttgccaatgt actagaaggt gcaattgatg aaggtgttgc tggtgctgct tatggtggag   27120
ctatcggtgg tgttcatggt gcaattagtc gccctagtcc tcaagtgttt gataagactc   27180
ctgagaatgt taagactgat atctccgctg aagatgaagc aattcgtagt gcgaagaatg   27240
ctgatgaact ccgtgaagct tactctcaag ccgatactgc taacacagct tccgctctta   27300
acctgctaga ccagaacgat ttccgtatta cagatgctgt ggctatggat tctcctgctg   27360
cccaacgtat ccttaatact gaccagactc gtgctgagaa agctgcttcc tctcttacag   27420
agcgttctaa tattccgggt cttaatcctc ttgtttctcc aagtaaggtc aagggtaaag   27480
cttttgcgga taacgaacat aaccagaagc aagccgtagc aatgaaagat gcaatggctg   27540
actacactaa agacaacacc aaggctctta atgatgttct tgataaccta gaccgagagt   27600
tgaacgacct tcgtgttcgt ggtgactta ctggtagtgc tattgacatt aagaatcaga    27660
ctcgtaacga tcgtgatttc attgatgctt acaagaactt ctatactgaa gcaaacagat   27720
tcaaagctcg tgatggcgaa gactttaata acttgtaga gaaagctact gaactacaga    27780
aacttgctga caatgtttct ccagagatga gcaagctat tggcggtttg aagaaactca    27840
aaggtatgcc tgaaggtttc aaccctatcc aagatgcctt tactctgaac aacacagcta   27900
aactaatgag taatcaagac cgtggttgga cgacactgac agatgatggt ttccgtgaag   27960
cctcttctcc aagctttgtt atgaacaccc taggtgctgc taagtatgct ctgaaccgct   28020
tctcttcaga gagggctaga tctcaacgtg ctcgacagca ggactcaaac agtgaagcaa   28080
ttcgctcttt ggctcgtggt gatttagagg ttgctcgtgc tcgaagagca gcagcaaaag   28140
```

```
cacgcgaaga aatggaagcc gaaccggttg ttgatgacgt ccaatttaag acgcaagctg   28200
atgaccaaaa tcaggctggt tctgaacctt cttctccagc tactgtgacg gaagatttct   28260
ctccttctcc agctccttta actgctcgtg atttggttgc tcaaagacgt gccatccgac   28320
aggcggaaca acgccgtgca gaggaagaag cgcaagctgc tcagaatgct ccagttgaac   28380
cagaagctcc agcagaaact ttacctacgc gtaaccctct tgaggaacgt agagtgcaag   28440
aagctgagat ggaacaacag cgtgcagcag aagaggctgc taaagctcct gagacgcccg   28500
tagaagagtc tacagctaaa gctgagccat tacctgctcg tgctcctaaa gctcctaagg   28560
aagctgctcc tgaggttaaa ccggctactg gtgtagaacg tcttgctgct atgtcaacag   28620
ctgctcgtca ggctactaaa aaccgtgctg aacgttttgc tcgttctctg tatactgctg   28680
gtgctaaagc taaagctact gcggaaaact tcttggctta caagggggac ccgaaagagt   28740
taatgcgtcg tatccgtcag gaagaccaag cgaacaatgc tgctcgtcat gaagagatgg   28800
ctcgcaacca attaacttct cagcaaggta ttgcagctgc taagtctaac cgagttcgtt   28860
ctgcattctc cgattgggtt aaagaacgtg gactaccttc tgaaatcgcc tctaaagccc   28920
tgcgtgctga gaacgtggat tggatggta acgtgtcaag tctagactct ctgaagcgta   28980
gagctgagcg tatgtatcag aaagaacgtg atgatgagtt tgatagaatg tatcgtgaag   29040
ctctggaaga aaacaaagct ttcgataaga acgatgcacc taagctgaaa gaccagaagg   29100
ctgagttcca gtcagagatt gattctctgc ttgagagcga acctcttcgt cctgctcaga   29160
aagatgcaat gcgtaagatg atgagtgatt ttgttgatgg gaagtttaaa gcggctgaga   29220
aagctggaag ggaagaagct ttagaggttg gtcaaatgaa ggatttgtgg gatgggttta   29280
ttaataccta caatcgtgaa gttggcatgt tcaataaagc taacaagaac tctcagtatg   29340
aagcagcagc taaacatcta caggctcgtg aagaacgtct tacctcttta cgtaacagag   29400
cagaagctcg tgctcaagcg aaagctacag cagaagctga acgtcagtca ctcgaagcga   29460
ttgctggtca gaagactgag atagagaaga tgtttgatga gttacctaaa cctgtccgcg   29520
aggctcagga aagtcgtact ctgaaacagc ttgcagctca ccatgataag aactcccctg   29580
ttcctccaga acgtttccgt agtattatcg aacgtatcca taacgcagag tcagactacc   29640
ttgatcgtaa gcgtcgtctc actgatgcag aggaagatgc tcgtgaagct aagtggaaca   29700
agatgtatga acaagcagag gagatgaacc gtaagttcga tatagatgct cgtgtatccc   29760
gtgataagag cctcaaagaa gctcaggagc gacagaatga tctcatggca gtacaacgcc   29820
aacgtgatga cattcatagc cgtctggtgc gttctatcga agataagggc atccctaaag   29880
ctgatgctga agcatttgct ggttcttata tggataaccg ttatgctctt cttgaaaaac   29940
ctatgacccc taccgaacac cagaatgctc gtgcacgtat tgagtccgat gtagagaagt   30000
ttgctaagaa gtatgaaagc ttgtctccta ttgagaaaga cgtggttaag attactggtg   30060
atgtggaagg taaactggat gggttggatg ctgagactgt gaaggcagtt gaggaagcta   30120
ggaaggttga ctctgatatt aagaaacttc aggacgaaga gttggaaatg gagaaaatcc   30180
gttcagcttt acctgatgat gaaaagtctc aggcaaattc cgacattctg gaaagcatca   30240
aaaagcaaga gatgagtttt gcagggaagg ttgagaaggc attcttggaa ggcaaggact   30300
tgaaggaact ggctagtgtt gcagaggttc tggataggggt tcatggtgct gacaaggctg   30360
ggaacaaccg tagatttgtt cgtgctctac agactgctgc tgacaacaag aagaagtatg   30420
gggataatcc ggtagcttgg tttagtgctg atgattactc tgctattgct aaacttggtg   30480
ctgcatcagc gggcggtaac aaatcgagag cgttggagaa gatctttggt tctacagcag   30540
```

```
atcaagctaa ggctaagctt ttggggagag atgatgtagc gaagatgaga cgtgtgattg    30600
aagcgaatcc tgaagtcaag attccttctt acaagactac tactcgtcaa gagtatttac    30660
agttcttgga gaagtataat gatgagggag tgttgaaagt caaacgtggt tctctgtctg    30720
acaaattaga aaggaataag cgtcaagcta aactccgtgt tagagttcgc tcgaaagagt    30780
aaacaagaaa agccccaacc gaaaggaagg ggctttattt ttatctaaat tttagaaacc    30840
atcaaattcg tcatacatcc caattttctt cattcataca acctcctaga ttaagtcgta    30900
atattgaata atatctttca gagcaaagtc acgaatctga tctttctctg tatcataggc    30960
tgtcataatc cagcaaggat tcccgtcatt gtgataaacg gaaacaccaa ctgaagttcg    31020
gataggaata acggcgcggt ctgcaacctc acctctccaa ttacgatagc gaaagcgaag    31080
aatttgtttc gtagagactg gagcatcagt tgtttccttt tttaaattgt tttctagcat    31140
tattttcttc ttgagtttta gtcttgtgac aaggttcttt acaaagcact tggaatccgt    31200
gtttctcaac aagtgctctc tgaataattt catcccaagt agcttcatgg tcaataggga    31260
ccagaggttc tatatggtca atagccattt ctttaacagg gtgatcgttg ccacacatag    31320
cacattgata gtgcattgcc agcttccctg tcttggggtt tatcttgcgt tctgtttgag    31380
catctttaag agcatcgaac ataggcttcc acttcctagt cagagaacga atccctgact    31440
tgatgaagga attgtatcga gcttctgtcc aagtgccact acagcgagtc ttctcaacct    31500
tcgccataac ctacatccat atcatcctcc tgccagactc gtttgttaac acggtgacta    31560
accttgtcag ctttagggat acgaccagta cgttgatcaa acagttggtg tttaatcttc    31620
tgatctttac gagtttcacg gttaggtgaa gtttcatcat aagtacggta gttgaattta    31680
ttacccatta tcaatatcct tattccaaat tttatcaagc catgaccact cgaagaggtc    31740
ttctggtgtt tgacctacga ataggagacg agcattctca agcatcttct cttcccattc    31800
tgtatcaaac ttcttataat attccattcg cactatatga taaagagtcc acttatcact    31860
tacaccttgt aaaaggttga tagcggcttt ctttccaacc ccttgacgac ggagttgtaa    31920
cttacctccc cacataactt cctcacgttc gccacaaccg ggaatgttat ctgttccatc    31980
accaatgagc atttgataaa agaagttttg ccaagcaacc tcatctgata catagtgagg    32040
aggaacctct ttctgccttt ctccacatgc ccaccgataa tgccaaccgg gagttatcag    32100
taaatctttg tctcgtgtac agatgatggt gttcttgtca gttcgctgcc tttctgctaa    32160
tgcgtcatca gcctctcttc cgtaaacatc tatatactca taattgtttt taatgtaatc    32220
accaacgttc tgccagtgga aaggtctttc tcccggaggt cggttggctt tgtatccttg    32280
ctgctttgct acatcaaaac ggaagttacc gccttcactg aaatagaaga ctgtctttcg    32340
acagccagcg cgagcaatga ttgtatcaag tttgttttga agtcgttcaa ttagaaatcc    32400
ataatctact ggtgtacgtc ctgtatctag gaaaggatgc tcctgagtca gagcacccac    32460
ttcgtatcgg agaacatcag catccactaa agctacttca ggatacttaa cgtcttccat    32520
attactcccc taaaagttta cgaacttctt tcttgaatgt ttcatactct tcagggtatt    32580
caaacccaca ctctagcatt gcgtagtgaa caaccttaag caagtcttga accttgttct    32640
tatctttgtg acgataagca tacttaatca tgttgcattg ctggaaattg agctgagggt    32700
tatttgcata gaacatactt aatcatgttg cattgctgga aattgagctg agggttattt    32760
gcatagaact caataggttg aattttctta gagtcagggt cgtagtgagc accaccaacc    32820
ataacatcta gtgctggact tcttttgctg gtttgttcag ttgtattctt aaaactgacc    32880
```

```
acaggaacag aagagtaaac tatatactct tccectactg gtggttttac tcttagtcca    32940
cgcatggcat attcaatctt tatgtcagcg gaacctgaag cgacctcttc aatagatttt    33000
cgatagctgt caataactgc tcttagcata gagattgttt tggtcatatc ttttactttc    33060
tcattcagta caacaatctc tgattctttg aaatcgaaca aattcatttc cactctccaa    33120
tgatttccat atcaaattta tctcctttct tcgtaaggag tattgccggt ttatctttac    33180
ttttcatgta ctcaaacata tgcagagagc ctcttgactc tccatcccag aagactatcg    33240
ctgagtcagc atactctccc atgtctacgt ttcgaaggat accagctttc tttcctaagg    33300
ttgtccaaga agggataaac cttttaatac caaggccgtt atgcttagca ataacctctc    33360
catgagagtc tggccctttt gctcccectg atacaacttc agtgaagagc ttaggtatct    33420
ctttcgggag taaatcccac atctgaataa aagaaggcca gtcaatagac cggcttcctg    33480
ctataatcac tttcatatta agacccttgg aattcttcct tgtcgaagtg cttctctacc    33540
acatactcat acagatcttt atactctgca taacgccgat agaaagtccc gtgtgagatg    33600
cctagctctt tctgaataga atcatgaggg atacctaaga agagcattga gaacatgctt    33660
gcgagcttct gtgtgtccat tgtatcactc aaatcttgga agaagtagaa gatacgagat    33720
tccatgaaag ggtccccaac tgaatcatgc ttattaactg catattccag aggaccttct    33780
gagtaaatgt cagggttgtt aaacatatct gcttctggaa tagcatagat acgtcgatca    33840
ccaactgtct gtcgattaga acggatagac cagatgatat tcttcacacg ataggtcatg    33900
tgctcaatct ctacttcacc ttccagtaga agctcttctt gcttggaata gataaaacgc    33960
caaacattaa gcaacacctc ttgagctaca tcctctgctt catgatagtc acgaatgtca    34020
tacataaaga atttgtgaac cactttccag ttcaccttat agaactcatc gaaggttggg    34080
aagtatttga ttggaatacc gtgaatacga tatcgagtag gtgttgtttt cttagccaca    34140
agttatcctt aactttgttg gttttaaatt tatacgctga tcaagtaaat agctgtttct    34200
gggtttggtg tgtgttgttg tggtgttccg gggatacgaa tccactcatc gttttctggt    34260
tcgtaataca accaagcatc tgtgaatttg aaagttcttc caaacacttt attatcatgt    34320
tcccaaatta cgtgaacatt cctagtatca ggtaatactg tttgcgctct aatcattgga    34380
tacctctttc ttttagagcc tctattaacc cgttgtggtt agcagcacac tctgtatatt    34440
ggtcttgata ccactctagt gtcgttgata gtgcaacacc ttgtgggcct tctagcatcg    34500
gtaaatctac cctacactca gcttttaggt ttgctggtaa gggcattaat tgcctgctgt    34560
tgtcgctcat tgaacagctt gacgtactta tcactagcgc aaacattata aaaaactggc    34620
ttagtctttt catagtgcat ctctttgtaa actgtctcag tgttcttctt ccaatctgat    34680
agaccgttga gaactctcat agcaacctca tcagctgctt tgtttctctc tatctctaat    34740
tcttgctgat gtttctcttt gtccagatta ttactatctg tttgatattc gttaaacttc    34800
ataccaccaa agaacacaag agctgaaaag acgatgaacc ctaagttatc acttaacgtg    34860
ttttgcatat tatctccaac gaaaaaagcc acccgaaggt ggctaaacta ttacaaggag    34920
agatacttag aatggagatt cgtcttcttc aaaagtagac tcaggctcac gatcgatagt    34980
agggatagaa gcaaccggct cttttctgctc gttctcagaa gccttagtga cttcacgacc    35040
agcgagagga atgttcttag cgtcattagc ttgggtaagc aggttacgct ggaatgggaa    35100
gattacctga taagcagcta cgttatcatc tgtttcagca tacggttcga agaagaccag    35160
aggactgcga gcagcagcaa cagcttcacg atacttggta ggaatcggag taatctgttt    35220
gatagagttc ttaacttcac cagctttgtt ggtgtaagag ttgattagaa cgtttacagg    35280
```

```
ctgacctaac agcatttctt taaaccaagc caaatcacct ttcagtgctt ggatgctagg    35340
gtcaaccatc ttaattaggt tgagaatacc agagttctta gctcgtgggt ttacatcgaa    35400
gctcttaaac tgacatgcag ggcgcgggtc aagagcattg ccttcagagt ccttaccggt    35460
tgcatcaaca ccaatcagct caaacgccaa gtccatacgg aaagctgggt tcttaggagt    35520
aactgcttta gtcttagggt caacccaagg gtcacgattg tgaacaccaa gaccaacaac    35580
acgaacgata cgagcttcgt actcaccatc agggattacg tcgtagttgg atttacggga    35640
aacggacata gttgggatag aagacatatt ttaatttcct tatttaattt aagattgttg    35700
ctcactttga gcggttatgt atagtataca ttacacctat accgataagg gtgctatata    35760
gtataagcag tagtggtagt agatattgac tactagtaat gtatatattg tatagatgat    35820
aattctattg caggcttgta tattgggcaa ttctcagaat cccttgcaag taccgaaggg    35880
caggagacac ctgcgagata aaatagaga attaaggaat ccttgattta ggttgtaggg    35940
actcctaggg actttgattc tctatttaaa agaaatatta attacttact acctaaatag    36000
ttaactaact tacttaaaac cttttcaata agaattgcta aaaggataat tcctaagaaa    36060
gctaataaga gaaaggcata agttaccatt ccatcattcc ttttaatcta gattcttcta    36120
ctattcgctg atagagtaag ttagactcag cttgatcttt taacatttta ctgtattgat    36180
ctctgagact atctttataa acaacaggtg gtttaaatag tgatgatact tgttctcttt    36240
cttctttcat caaaagtctt cctaatctct tgcagagata cagcttttaaa gttgatttgt    36300 tccatcgagg tacagaagta tctccaatca tcaatcacat gattgtgagt atgagcatag    36360
atgttgaact tccctctcat ttcatcagcg tgaatgggaa tgtgagtcac ccaaaactct    36420
ttgtacttga agtcacctga tacagttctg aacactttca taatctgtgg taacaaatcc    36480
agtctgtcat gattccctaa gacaagatgc ttctcgcctt taatctcata gatgatatcc    36540
agtgcatatg gttcaaacac ccaatcacca gtgaagaaag tcttatctcg tttagtcaca    36600
tggtcaaacg ctgaaagaac tgctttatcg tgctcttcaa tactaccaaa ctgtttacga    36660
aacttgcaga tattacgatg acctaagtga ccatctcctg cgaaatatac ttcagccata    36720
aagacctctt agattgtgca accatcacac acgaaatccc cactcaggga ttcttgtaat    36780
aaacgacttt gttcatcaga gactaactga ttaacaactt tctgtaactc taacagttga    36840
tcaaaatcta tatatcccccc ttcctcaaga acgttagttt caatccccca taaaggtgat    36900
ggcatgtttc tgcttgcatt aaaaatcatc gtatgtttcc ttatgtccaa gatttagctt    36960
ttacttcaac gtaggtttta acttcacctt tcagaacctc ttgagaagcg atagcgcttt    37020
cttcagagtg gtgtacaaca gtaattactt tcttcccaat cttataagta tgaacccaaa    37080
tcatttaact tcctcaatat caactagttc aaaacttcct atttcttcaa gctggataat    37140
ctctttaacc ttctcaacag ctttaatagg gttttcttct tctacaactt tacaccctga    37200
cacttcgaga ctgcctgttc cacgaaggta tagatttaac ttatagatca cttttgtaata    37260 tttcatcgta ttcccaattt cttttcataat atccagagtt gtagtttagg gcgcatttct    37320
cagcctcttc tatgtcatct gtgtttagga tattaaccca accaccaact tcatcaaaac    37380
cctcttcttc ttcattaaac catacgctgt atttcttcat cttgataaga ctcttcccca    37440
atccttgatg taacagcgac catcaaccca cttggtctct gatttaaact cttgagagat    37500
tcttgtttca cagtcttctt tactgtaatc accaagcatc tccatcacac aaataaacag    37560
agctatacca atggcccaca gaattaattt cttcatcgaa tcaccaaagg ctcatcagaa    37620
```

```
tacacaggag ctgctatttc tacaggaggt gctgctctga ggtcattaag tcttacacct    37680
tttagcattc catctagatg gtccatttta ggaattccaa cagggaagtc gtcaatccaa    37740
atatctacaa agaaaccaag ctgacgacac acatcatcct tctgtacgcc gttacaaaag    37800
ataataggaa tctgcaagca ctctgcatca atcttaatgt cgtggttgtc gtacccatta    37860
ggctctgcaa agcgataagt tacgaatcgt acatcataac ccttcgactg cattaatgct    37920
accacagaac gccacaactc tttatcagag gtgtaggtat catcgtaatc taaaccaatg    37980
ttcatatcta atccttagac aagaaaagcc gcccgaaggc agcttttag tttatgcttc    38040 ttgttcttct ggctcttcag cattcagctg ttccagccga tcattctcaa tactcagatc    38100
gataactaca ccagtaagct ctactacagc ctgacgcagt gcatctttac ccatcgagtt    38160
aacttgggtc aggaagaatg ctttaccttc ttcggtggat agggtttctt taagttcaat    38220
aggggtcatt tattatctct cataaattcg ggttactgta ccacccgcag cttctacttg    38280
agctacgaat gaatcacgct cttcgtctgt ataaaccagc tcattcagga acgtcccttc    38340
agagtcttgg tacaggatgt tccacttagg caggggctta cgaatcaagt ccatcattct    38400
ttatcctccc gttctttcca cagttgggct agttctaaat aatactcagc ttcttcagtg    38460
cgtccttgtt ctttacagac actgtactga cggaagcacc aatctgaagg ttgctcttcc    38520
acttccttgt ctccttgaga agtaatcaat aagactactt catttgtttt tccaattcac    38580
tctgccattt gaggaatctc tagatgcttt atagagaaac ttttatttgg gaaagtcttt    38640
attagccaag ctgcttcttg gatagctttg ttttctttct cgtaaataca aagcctagca    38700
tccaaggaaa caattctccc ggtttcactg acgactaccc atgttttata tgtgtaagta    38760
ggtgtcattt atttctccaa cactgagata ctgtaccaat tgtgtaaggt ttttctaacc    38820
caagcaatgc gtttagggtt tttgtgatga gagcctgtgt aacgttctct gtggtatgtg    38880
tcacaaccga aagggtatac cgggtcctca aacccttcgt gttcaaacat atacgtcagg    38940
tcattaaagt ctatatgttt tgtgaagaag taatagcttt tataacaacg gtagttgaaa    39000
cacaaaccgt gctcaggact gaaccatttt gggtattcgt ctgtctgaga gatgttataa    39060
tactggagga ggaaatcctc catcccccctt tctttggcaa tacatcttag tgttcggtac    39120
ataatgttac tctgcttcat tgtgaattct cagtgtgtgt gattccagtt taatccaatc    39180
tgacaatcag atgccagagg gcattccatc ttgagatact caccagcttt cttaacacaa    39240
agctctgtaa gttcttttag ttttttgtgca tcattacggt gaacagagaa ctgcccttca    39300
tcgtgcatgt caataacctt cgcacaacga acactatcac gctcaatcca cttgttaagg    39360
aaaagcatgg catacttcat aacaatcgca ccagcactct gtaagagtgt attcagtgct    39420
ttatgaacca taaccttacc tgttgcgtca cgtctcattg taatacgacg accatcaaca    39480
cccaagatat aaccttgagc tgctttctct gtcatacgct caataagaat tgcaatacaa    39540
ggattctctg ccaagaaacg tgttctcatt actgaacctt cttcagagcc tccaccaaca    39600
atagaaccaa gcttagcatc acctgctccg tagttgaacg catagataaa cgtcttagcg    39660
ttgtcacgag taggaagacc agcaagtctc tggttgtggg agtggatatc accttctaat    39720
agaatgtcac gatacataac agcagaagct aaaccacgtt cagctaatgc tttcttacca    39780
gcgttacctt ctgcaattgc ttcagcaagc atgtctctac actctttaat gaggtagtga    39840
gcaagcatac gaagttctaa tccagaacca tcataaccta ggaagagttc tctaccagct    39900
ggtacataat acttatacag ccctactggt ttgtctttct ttccgggttt tccacgttcg    39960
tagataacgt ttgtattttt tcgtaagtaa cacccatcag ggatattgtt ggtaatgatg    40020
```

```
aaaggatagt tatgactatc atctgtggag tagttagatt gaaataaact cctacactcg    40080
tgaccaaaca gaccgcgaga aggaatatta acaacaatgc gatgtttaaa acgaaatgtc    40140
ggagtagcgc agctattagc ttccgctgag agtttaccat ctggacgttc cttatcaatc    40200
agtccattaa tcaagcctag tctgtgagcc gctacaacac gtctcttaag cagacttccc    40260
actttaccta gatcaccctc aagaccttct tcaagagtct cttcgaggtt tgtaggagct    40320
gtgggccact tgttcgaagt agctaatgct ctcttaattt catcaaaggt tacaggtttc    40380
ttcctgttag ggtttaaacc taaaccaaag acataagcct tcatgtagtt gacagttttg    40440
tgacgaaagt gcttatccaa gaacttcttg atatcagcat caaccatctg agctgtctgt    40500
cgctctttct cattgccacg catccaagag ttgtaccatt cttgatacgt tccacactta    40560
cgcatggctc gcttaatctc aaatgtgttc caaggcttct tagatgtatt aaattctgga    40620
ggaagaaaac cttcatccat cagtgcttct ttaactcgtg catcctttga tgggtcaaag    40680
tcaacatact caacacaagt aaaagctcca ccaatatctt ctctctttaa ccccactctg    40740
tcgcaatata attgaggcca cttctgaaga gcaccagtct tcttaaaggg tttcatgtaa    40800
gtagaaccat caaccctcat cttaggtaac agaggaatca gctctctgtc gatgttaacg    40860
ataatctctc tgagaaggtg aacataccac cgtgcattcc tccgattaaa gttgacacca    40920
ctcttcgctt gctttgaaat tatatcagcg acagtcatct ccgttaagaa cggaagtaca    40980
tcagggttct ccatcaccct ctccttttat tatcggtata gtaaatctgt aaacgcttgg    41040
ttgtctgcta ttacgtccaa agcctcatcc gtgctaggaa cttcagtttc ttccacttgg    41100
tacgcaacct cacgtacacg gaaagctctt gcaggaaccc taaagccagc atgtctctcc    41160
ataacatctt tctgaacctg tgcaagcttc atacccacaa cttcttcata aagctctgga    41220
tgtttattac taataactac atactgacga tgtacggact tcgactctct gaccttagct    41280
aataactcat taaacaagtc taactcttct tcagagagcg catctacaac gtcttcccac    41340
ttctctacac agaagcggtg ggcatgtctg ataggaagtg acatcattta ccccttagga    41400
aaaggaagaa gattctctac tgcaacacga taaaccttt ctacgttttt gtttttatag    41460
gagatgaact tgccatcagc accacgaagg attacattag tgcgagcagt cttcgggttc    41520
tgggaaatct gaccagcaat gatagatgca ttaagtgcgt tctcagcgta gttagtaaac    41580
ttccacttaa caagtttatt ggcaattgaa tcgataatgg ttacagtttt tacgatagac    41640
ataatttctt acctaagaag tttaatttgg tttatataaa agaaaaggcc acccaaacgg    41700
gtagcctctg attaactaga gcttaaagct cctttgcgac cgccagctga ttttccagcg    41760
cgatctccac ttttgccgcc agctgaacga tttccgctga ctgtctcaac acgtaaattg    41820
cttgacgcat tagagcctcc tgatttaatg gctcgtttgt gtccgacatc tttacctttg    41880
agtgcagatt ttccaacgcg tttttcaacg atgcgacgtg cacggtggcg ctgagcatct    41940
ccgctcttac ttccaattcc cgtttcacct cttgcgatgg ctgtacgtct ttcttgtgca    42000
taatctcttt tagccttatc agtcatttac aactccttaa tatatcagtg tacactaagg    42060
agtatacatt atgagagggt agctttagtt gccatccttc tccatagctt taacgattgc    42120
tttacagaaa ccagaacgaa caatatcatc cgagtcacca tcaacaatat cagcgaactc    42180
atacagatcg tgctcgtcaa tgaactcggt agcccaagta agaccactct ctcgaccttt    42240
catatcgtgc tggttagtgt cacccatgca gaacagctgg gatgtttcac ccaagcgagt    42300
cataatagag aatgcttcat ctttggttgt attctggaac tcatccacaa taacaatggc    42360
```

```
atcattgaaa gagcgaccac ggagatattc cagaggtacg aactcaatat taccgttacc    42420
aagctggcat tcatagaaac ctttaccata ccgctgagtg attacatcaa caataggcat    42480
taggtacggt tcgaacttat cacgaagccc accggaagt agtccaagag agttacccat     42540
gccaacagaa ggtcggctaa tgataatctt ttgaatctta ccgctcttca gtgcatcaat    42600
gacagtagag gtgatgacga acgtcttacc acagcccgca ggagcgtctg tgaacaccac    42660
ttgtttagtc ttgatagcat tgagcagctc agattgaaac tgattctgag gaccactgg    42720 cttcgctaaa acaacctctt catattcacg cttacccttc ttggtgacta aggcttcacg    42780
acgtaaatct ttacgagact ctctacggga ctgtctacgg ctcatttgcg ctctcctagc    42840
tcttcgtaat taaatacaga ggttcgacaa tctttacatg ttgttgtata gacccgaaca    42900
ttaatgaact tcttgttctt ccctttggtg ggtgagcctt tagcaagctc actaataacc    42960
ttagaactca ggtttaggtt tgtgccctcg catttagagc acttcactca ggctcaccaa    43020
cagtaacttc ccatacaact tgagagatga tattgttgat ctgtttgatt tgctcgtgag    43080
tcagttgcat gcctttcatt ttccgagagg cattacttcg tgctcttcgc tgacggtaga    43140
agttattctt cttaacagag tgtaagctac tcatttcaca agctccactt cttcaatgct    43200
gtacccttca taatcccact catctcccca taaactctcc ttaccttcga gaagtgattc    43260 ataactcgc tcacggtgtt tatctggaat aggaagactt tctaaatcct tgcgttcagg     43320
gggtgataga aaaactttga cagcatagga gtaatcagaa ctcccttcca tctctcctgc    43380
aagttttgtt aagacgaaac atttagatgc agtcatttca caaccttaaa cttaaatgtt    43440
gttgggtggt agtagtgtaa cctgtttatt gtatgcttag tctcatgata caggatacaa    43500
gagtggcaca ttgaatggtg caaacaggtt actggattac gtttgaaatt ggcaataagc    43560
ttccgcttgt tacagaagct acatgttttg tgtaagtcca ttaactctcc agagttttcc    43620
ttagagctga ccaagaaatt gggtagagtt tagccatctc ttcatctaat gactgagcaa    43680
acagtcgaac ttcatactga gcatgggatg atagtcgttg acgacacaat tcaaaccagc    43740
catacaaact accagtccat acccactcag taatcatccc ctgaggaaga acaaagcgag    43800
cttgctctgg tgcaacaaat tcaattaatt tgtcataggc tgccagtgaa gcctcatacg    43860
cattattgat tagcattaat gcttcggctc gttctccgtt gacaagctgt gtccctgaac    43920
ctgcatggag gtccgaaggt ctcgcaaaaa tctctttagg gatgaagact tcaactgctc    43980
catctttata ccgccgggac atttcgttcc acgagaatcc aacctgatgt ttttgtagtt    44040
gacgagctat tgcaattgga gctttacatc gaaaagatac ttgagggtgt ctgaacggag    44100
tacagtgttt ctctctggca agaaagttga ttaatcgagt atcacgatca ttcaaatcac    44160
cctctcgcac aacaccgaaa gaaactcttg cagcattaac aactgtttta tcactaccca    44220
tagcttcaat caatgttgcc ttcaattgtt cattcatact tcaacttctc cttgttataa    44280
gcaatctctg cttcctctgg agtgtggaaa gttcccaaat gtttagtctt tccgccaact    44340
ccgatgatag ctctgaattt tgtaccactc gccgtctctc tgatatagac acccattggg    44400
agctttccag ctttccggc tctgttatat tgtttcctgt tatgacagtt tgtagatggg      44460
tcaacatctc ttaggttttt aagagagtca tccagtttaa tctggttgat atgatcaatc    44520
tcaaactcag gcatctttcc ataagagaaa accaagcta acgacaagc tctgtaagat      44580 tttccttcgt aataaatata cctgtaacct agtgtagaga tacacccagc aatattccca    44640
gccacccgtc tacctttggt attcttccac cgaaagattc cagttcagg gtcataagac     44700 aggtcttctt ttatcttgtc agttaatatc aaaagctgtt accaagaaag atttcaggtt    44760
```

```
tgcttcagtc tgcataccag ataagctata atgtgcaccg ctgttacggt taggtacgat   44820
gaaagcagga atacttcgta caccgtattc gatagctcga tcacgaccat tgccttcgag   44880
gatgttaacc tcttcaactt ctaggttaag ctcttcagct aatttgttga gggtaggggc   44940
cattgctttg caaggagcac actgattact ataaaactta ataactttat tcattcactc   45000
ttcccattta caaacagctc aagatgtcgc ttggtagtgg ggactacgat atagtccttg   45060
tagccatgag acttagcaag ctcttctgct atcttttgg tagcacctaa tgctactaca   45120
catcggcaca cgatgattgt gtgcgctttg tattcatctt tgttcataaa aaccttaagc   45180
agtgatcagg tggaggataa acgggatgac tacagagatg ataacccaag caacagatgc   45240
gatttgaatt tcagctttct tgtcaggagt ttcttcaata agtttcttgc taccataata   45300
aacacctccg ccaatgagaa gtgcccaaat actccaaatg attgctgata acatattcaa   45360
ttccttataa ataagttcgc cctacctcgg attaggagac agggcggagg ttttagtatg   45420
agacgtcact agagtgtgac atgttacttt taacgaagta gcaatacttg cctaaccctt   45480
cgttgatttc ttggagcatg ctctggtcaa ctggatactc gctcaaacat ccatcgaact   45540
catccatttt gtcaatcatg cacattaaag acatgcacat atcagagagc ataccatcca   45600
tatctaggtc tgcatttcct tcagagaacc aagagtgtga taggtagtta gaagcagttg   45660
catccacctt aatacagtgg aaacgcatac gttcagctat ccgatcacct gtctcacgag   45720
cataatcttc aagctcatca aacattccat gaacaccctg aaatcctgca ccagatacgt   45780
tccagtgata attcttagct ttgatatgca agagttctaa attagcttga ataccgcata   45840
gaatgtgttc taggctgttt ccactaatca tcccttgcat acgctctaaa cgggagatag   45900
aagagtctgt ttcacgtaat acatcacgga aagaagtctc ttttgttaga gttggtaggt   45960
cgaaaacatt gtgattaggc attaggattc tctccatcaa gttctactga gttcgcaaca   46020
ttgcgtgtaa tgttatccat tacctgttgg gtgataacga tgcagttctg tgggtcaacc   46080
gacttagaac gtcccatctc agggtcatac actttaacgc gctttgctgt agaaccagtt   46140
acctgtaaca ccttgagaag ataaccctga ttcccgatag accatgcaac aacatcacga   46200
ttcttgatga atcgaccaag catatcacga tgatagaact gctgcataac ctttgattta   46260
ttaatctctt cggctggcgg agccactta ctcaaatcta acatttcact ctctcctgtt   46320
caatacaata ttcttatact gtatatacat ttgagagtga tcatatctac taccaactag   46380
tagaaaactg ctttggatat aaaagagcca gtattagggt cctcatgcca tcgatgcata   46440 gtgactttg agataaacctt gcaagctttc aagttttct tggtgagacg agcttcttct   46500
ctggtgttga ataacttgat ggtatcttta cccacacgct cttctactct ccacactatt   46560
cgtatagccc atctttttt cattagtaat gtacctttcc gctgatataa atacggcctg   46620
aggtatactc atagcccttg aggattttga cagaggaaac actattcatc ccactgagag   46680
atttcttaag attacgtgaa ccctctcgtg ttttctgata ggtcatggtt gtattaccat   46740
tatcccactc tatcttaact atccaaattc ttttcataag acctgctctc tttaccatta   46800
gtagtacacc ttgctattgg cgaaaaaagc accttcgcta ttcacaatag cttttcctaa   46860
tgtaaccttg ttaagtctaa aagtagactt gtattgattt ttgaccctac gtgcgtgatc   46920
tcgagtctta acaaaatcta cagctaccaa gtctccagtc atgttatcat gtacacgaac   46980
aatccacttt ttcatttaca cacccttaga agcaacaaca ccttcgctac cattgtagcg   47040
acctttaact gcataggaat gctcaccagc atgtgaatgc tcaaacatca ccatctgacc   47100
```

```
gacacgcata ccagcacgaa cccgtaagct gtggtgcttg gttacgttat ggaactcaaa    47160
tgtcagcttg ctattgttaa acccagcgtc tgcccaacca gcgtgcaagt ggttcaagcc    47220
acaacgagcc attgaagatc gtagaacaaa caagctggag atgttatctg ggaggttgaa    47280
ctcttccatt gagtgagcca agaagaattg tcccggagtg atgataatgc catcttcagg    47340
gatttttact tctttccact tgaggttttc tttcgcatca atgtcaacaa tcccatcagc    47400
ctgttcttca ataaggatag tatcaccaac acggatatcc acactagcag cgttaacata    47460
cttatgctcc gcatccagaa aaccgttgtc gataacgtcg tgtaattcca tgcttcctaa    47520
taaactcatt cttattcctt atgttaatct gcgatactgt cgctttcgtc catccagact    47580
ggactgttaa cctgtcctag acgacgagct gatgtttcgt taatagagtt aaccctgct    47640 gtgcgagggt ttgtgtacca cggtcgagct atggtgccct ctcgaatcac ttggttcgtt    47700
tcgacatgcc atctgtttga taccgtgttg gctccgaagt taccaccgc cccaccacta    47760 acaggtacag cttgagctgg ttggtttact cggttagttc ctgccccaaa ggctgctgca    47820
aattcagaca cacgtgcatc aaatgaagaa cgaacacgct gagtaggtga tatatcattt    47880
cgtgtatcta ctgcacgagg catagcccaa gtatcatctg ttgagatatc aggggtaggc    47940
tcttgctcta gaggttgaag attagctgtc cattgactat tcagtatacg atagaaatct    48000
gcaccataac cacttcggat aacatcctct ctgacaccaa agaagcgact gatatcccca    48060
ccgattcggg ctagtttgtc attgtatgca ggtatgatta ttccaccctc tgtcactaaa    48120
tcagagacac gacttgttgt aagtggtgaa gtgatccaac aataataatc agtaatgtga    48180
ccatcgtatc cgaagaatgc aatctctgca tcaggccatt tcttgtggac atatgccact    48240
tcacggttag aacaaacagg gattgcacct gtttcagtca ttgcatagaa gccgtcagaa    48300
gagaaccaaa gtgaatctag tgctaagaat ccacgcacaa cgctcgggaa agtagcagcc    48360
agcgccccaa gtgaggtagg ttcattgaac attaactgaa tctttgcacc ctgataatta    48420
atctctagga tatctacaaa attcaaagaa gacccagggg catattgatt attacttcgt    48480
ccaatatcct gctcaatgag aagagatctt gtttcaacac catgagcctc tgcccactct    48540
ttgaaatctt caaggaacaa gcgagcctta gctcgccaca tcgaccgatc aattacagac    48600
tgtctcggca atccaccctc tgtagtgatg agaaagatat caatgtcgtg aggttcacgc    48660
gtctgaaaga ttgcatccct aacagcacca cctgcaatga tagggtacac accatcaggg    48720
attaaacggt ttgcaatcaa ctcgttaatt aacgtaagac cagacacaag ctgcggacta    48780
tcatcaatcc gtcgacgaat tagtgcatta gggatattat acatttacat tttccaatat    48840
aaagatgggg ggtcatttgg gtcaaagttt gcaatatgac aaagatattt ataaacctta    48900
accgttaagt ttacgtcctg ttcacaataa gtaaacatgt cctctgtaaa ggcatcccat    48960
gcttcttcct gttcaccgta atcgccctta agctcttcta agaactcacc ccattgcttt    49020
aagccatgac ctcttgggcc atgtctaggg tcgcctttcg gatactcagg actgtcacca    49080
atacggtcag gtttaagata ccgactcaga cataaagtgt ctaggacgtt gaatttgtat    49140
ttgattaatt tcggatatac tttcttcaga gctggaaggt cgaagtcaat aatattatga    49200
cctacaacaa tatcagcctc tgtaagtttc ttgataccct cttcaatctg gtgaggacga    49260
aatccccacc gttcaccagt tgctatatcg aagataaaga tacaccatac gtttgtgata    49320
ttgtcgtaca gtgcatcact ctcaatatca aatgcgtaga cttctcttta cacgggcttt    49380
tctctccatc ttgagcaaga agtgatgctg catcctctcc atttgtcagc gagaatggat    49440
tttcttcatc aatttcatga tcttcacgct caagcaaccg tcccgtctct cctacatact    49500
```

```
tcgtatagca cacccctgtt tgtccatagt tacgctcttt gaggagtcgt ataatggata   49560
ggttcttagc cagaccatct gcttgtttgt cacgttcaaa accgatgata cattgacacc   49620
aacgcataag agaacgagaa ccagtaaact gtacctctcg aacctgacca ccttcttcat   49680
gaggtgcacc acctgccgga gcattaagat gagatagcac gaatgctgtg aagtttaatt   49740
cttgacacat accagcaagc tctgaagcaa tcttactgat ttcagtgtta atctctgaag   49800
gtgttaaatg ggataccaga gcggtaatgt tatcaaggat gataaactta cactggtttt   49860
caacaaccca gaaacggata cactgtttaa tgtcggccca ttcattctga ccaaagttat   49920
catagaggaa gaatttatct gcatatcgaa gagcttcgtt acgcaatgta tcttcatcat   49980
actcaacatc aggtctgtgg aaaggaatag atgctgactt acctgcaata ttcttaacgg   50040
acattccgac cttctcttcc aagaagaatc caccaccatt aaaaccatgc tcaagacaaa   50100
gccaagcaac cagttcatgt gcaatcaatg ttttaccaga gcctacacct ccaccaattg   50160
ctaccatctc tccccaacga ataccgtagg tcatctcatt aagagtcttc cacggatatg   50220
ggatacccca ctctgctttc ttcagagcat catctaagca atcaaaaaca gttacagcac   50280
cagctgggga ttcccgcttc gctgaatatt taagaatgtt aaacaactcc tgaccacgac   50340
cagagaggag catatcattc gcatctttaa gctctttctc aacaccgttg tactggaaag   50400
aacctttagg aatacgagca aacttcacat gggggaacag agcacgccct ttggtaagag   50460
caatctcacc agcatcatcg ttgtccatac agagaacaac ctcttcaaaa ccattcaaga   50520
actcacggtt gcgagataaa acggaagaga ttgaccctgc accgaagggt aaagagacgc   50580
acgctggttt aatatttgtt gcatttgtaa aagctgtaag aacatggaaa ccagacatgc   50640
aagacaaagg gtcttcaaag atgaagagct tcttattgta cacatctcca cgtttagcct   50700
gtgccatacc aaacaaatca gcttctttca cactaccgat gtaataaaac ttttactat   50760 caagtagttt aacctcataa ccaacaatgt ttccatcacg ttcacgaggg aagaagtaac   50820
tgtctggtgt ctgaccatca gtttgactga gaccgatacg acattcaaaa cgctctgata   50880
cagctttagg gattaatcga cgagtgagtt ctccttgagg taactccaag caatcatcca   50940
agacttctcg aagttcttca ggggacagct cttttctttc gtttggtgta ggtgtcgtgc   51000
ctttctcaaa gacttcgtaa ttaccacacc ggttacaact accccactct tcaccggatt   51060
cctcattacg gaagagaatc atgtgattgt gggtttatc acgaccatga gagatgcact   51120
ctttacagcc tgtatctccc aaaatgatct ttgacatgct ctatcctcct tggattctcc   51180
ttgagcaaac taccttactt ataaaaactt cgaatcatgt cccagatttc ttcctgctgg   51240
accctaaaga aagctaaacg tgtcgatgta cgttcaataa attcttcact atgctttct   51300 ctatctagca tactgacaag cttttcatat ttattgatct tccatcgcat ttttaaatag   51360
tctgattcca gtgtccttaa cctctgacac tcaatcaaac ccattagtta tcctctgaca   51420
gataaagaga ccagtcacca gattcaacca gctcatcctg ctcttcatcg atgtgataaa   51480
tccaagcagt gatagtttca ccactatcca ttacaacttc gataggagta cgcttataga   51540
aagtgtgtgg gttgtcatta ccgcgatgcc cttccagcat atcataagca ccctcaacac   51600
catccatatc cgtcttaaat acttcaacac gaacaggttt accgttgctg ttgtgttcca   51660
gagaaacact tgggaagtat gaaccaccgt agcggtacaa gttgtagttt tctttagtga   51720
agccttcacc aattgattca gcacctgcac gagcattcac tcggaagttg gcctgaccag   51780
tgcgaagaga accgtaagtt gctacataaa ttacttctga catttttaaat acctttccaa   51840
```

```
tcgttcatga ttttttcaat ataagcacac tgttgatcag tggcacctgt tacaaatatt   51900 tcacaccta  actgttcaca gaaaggattg agtattaaga tttgagattt accatatgag   51960
tgatgctctc tgtaaataac acaaccagca tcccaaactg aatctaatgc cttacttaac   52020
cttttgtgtt tcatacagtc tccagttaat ccgaactagc ctcctctttc gaagaagcta   52080
gagcagattg ctatgctgtg aagtttttga ttacaccgca ataacatct  gtttcaaacg   52140 tacccaccag aacatcgtct cggtagaaat taatcgcttt accatctcgg ttaaagtgat   52200
ctgcttcaat gagcatagat tgtacctgac catctggggt ggaggttcga aagatgacgt   52260
tatactgact cataaagaag ttactcccct atcttcttga gcgatagaga tgatacgact   52320
cacacactgc attgagtact catcaccacg ctttaggaac gttacgatag cagagaattg   52380
attaccaatc atccgctcat ttgtaatacc gaactctttg cagagttctt tcagtttgct   52440
acgagaacca ataatcagag gttctttttc ttcagtcatt ccacgactaa tcaaatcttc   52500
aatagacaac ataattccat tccttggggg tttaattaaa agtttactgc ttcaccatca   52560
acggtagtta ctgatgcaag acgacgaaca cggccaatct gttcacgact gattggagta   52620
ttccaaccag agcgatagaa gttgcgacca cagaagaaca caacaacatt agaagcaatc   52680
cgtccgtagt tacgatcagg gtgattgatg ttagcaagat aataaccacg ggtcaagttt   52740
gcattttcgt tgatatgccg agcatttggt gcagttgttt cagcttgcat catttcagga   52800
acatcttcta cgataggctc aaccgtaggt tcataccag  ctaaagcaaa gttctcatca   52860
gcagcctctt ctgcatcatc ttccagctcc acagtttcct gaataactgg cagagggtat   52920
gctacacgat actcagggtt ttgaccacgg agagattcaa catactgcaa gaagttgtgc   52980
tggtaagttt ccagagttgt accagtcagg cccggagcgg tattaacttc taacacccac   53040
gcttcctcac ctttactgat aagatcaaca gcaccaaagt taagaccgag tgcttgtact   53100
gctttgtgcg cttgaattag aacctgatca ggtggtgaat cattaaaaga gttggaataa   53160
acccaaccag tgtggtgatt acgaacatct tcacgatagt cagggttatc acgatacca   53220 ttacgacgaa tcttcttctg gacgtaagta ataacacctt caaaaacatg cacacgccat   53280
tcacgacgtg gaccagtgat tgcttttgta tacagaggag cctcagcaac accctcacga   53340
ggaagacgaa cagtgatgcc ttcaccagag tgaccattaa gtacaccacg ttcgtaaaca   53400
atactgtttt ggttccagtt aagtgcttca tctcggttag tggtatactc aacagtcttg   53460
acttccgcaa gacgcatggc attgaaagct gcaaccttgt tagccgcacg attcaatgct   53520
gctacgttgt tcagaaccgt tgcaccttcg aagaaggatt cttgataacg acggtttcca   53580
tagttgataa tcacgtcacc agaacgagca cggaatcggc tggttccatc agacagaaga   53640
gccattgcgt tggcattgat tcggttgtca cggagatgtt gattcaagct ggataccaga   53700
gcattaacag aatcagaagg gccataaggg agaacacgga tacgagtagt cattttaga   53760 tacctttaag tttaagaatt tcgttgcgag tacgttggat acgttcttca agagtatgat   53820
aatcaaagat gcacatctct tctgcttcat cagaaggtgc atccattaaa cccatagcaa   53880
tcggatacac ctttcgctgt tccgttgtca tgtcctgtag ccggagtcgt tgatactcca   53940
gcagggtaat tttcggcttg ttagtttcct tgcttgacat gaggctcaac cttgatacct   54000
ttcagtttca catagtcagc cagcacgttg ttaataactg ttgggaaagg aatctcaaca   54060
ggtgcattaa ctaacccacc aataccctct tgcatccact tctggattgc acgaaggtta   54120
tcacatcctg tgcttgtcat tggaatacgg cgagtggtta caacgttatc caacatcatc   54180
ttacgaattt ccataataca cctcttaatt atgacctta  cagtgcactg aatcgcacac   54240
```

```
cacttgattg gtattgttta gtgtgcagag ttctgcatca cgccacgaa tcttttaaa      54300
acagactgca caaaacccaa gagtagacca gagggctttt gtgaaggttg ctgatcggtt    54360
tccatcgaag gacgcaactg ttctggtaat tgagactttt gactcacgaa aggtttccgc    54420
tgctggagcg ggttcctcct ttggggtagt cactgcaata gcataaacac cacccaacg     54480
cttctcaatg taagcaccga acacatcttc cagagtgatt tcactcttac gtttggttga    54540
ggattccatg acaatcatgt tgtccagaat cttttgatca acacgaagag ctacttcagg    54600
acgtcgagca cttgttgtat caacatactt ggtccaaaca taaccctctt tcagagtgac    54660
ttgagttgct tgcttctttg ctttattagc acagatttta caaacatcgt caccacgaag    54720
tttactgaac tcttcatcaa attcaaagtc agacttcact tcgccgcaca ctgaacaaac    54780
gccgatagga atctcatcct cttcaacgtc ttccacttgc ttctggatag aatcaaaaca    54840
agctttatgc caatatgctt ggtatgcgaa gatcgcactt ggtgcttctt tccagtcaat    54900
gtgcttatca catccaccac aatcaccgtg ggaatgggct tcccagaact tacgagtgat    54960
agtcacccca ttcttgctga caaaactatc ctctgcatca aaagggatat catcatcgaa    55020
atcagctgta gtgctttccg gctccttttt cgacaagtca aagaagtgac cagagatcaa    55080
caccaaacga atcatgctat taacttcaga gatacagcca accgtaccac ggtaaaccat    55140
atgcttgttc ttaagagcag cttcgtaatc agtttgcagg atgttatgaa catcaccctc    55200
aatatactct tgagctttgt catcataaat ataaccaacc atcttaccgc gatcggtatc    55260
tttataacaa acaaactcgt gaggaataat atcaacctgc atatcacgac ggacatcaac    55320
acctttgtca gaggcgatct tgttttgttt caagattgct tcacgacgac gtacatcacc    55380
tgcggttacg ccgggctttc tttgctcgtc gctgttcccg tttacgtaac ttttttgtcac   55440
gcttgagtga ttgttgctgt agctgttcga gtaataactt ccccaacgcg ttgctaccgt    55500
aaaaaccggg agttcatgta cgacctcctc taccaaagtc atcttgttgt cagaaacatc    55560
aaagatgtac tctgtaccga ctttacactc aaagtgctca tcaattcggt tcttgtggct    55620
cttagaacgc tgaagaatcc acattagcat cgcttcttct gaagcaccaa accatgaagt    55680
tcccagacgg gccagatgga aaggacgttc atcgttacga atgatgtgaa gacggttatc    55740
acttgcatca tgccagatta gagtgaatgc accatccaac ttctgaatag tctctgctgc    55800
accaatcttg ttaatagagt ggcagatgtt ctcactatca acctcaaaag ccttactgtc    55860
aggcagaagg tcttgatcaa ctaaggttcc gttatgaacc agagtaatat ttccgtgaga    55920
gaatgggtga gcgttacgtg agttaatagc gcctttcgta gcatgtcggc tgtgaccaac    55980
aatccatgaa ggaggcactg tgtaattagt aaggccagtt gtcagctcgg tgtactcttt    56040
ctgtaacatg aaagcatagg aaggcagtgc ttctttgtaa gagacacag atctttcgct     56100
tttacgctga ccgaaaatac cagttgagtg ttgaccacga aatacaccag cataaagaag    56160
ctggttgtaa atatctaagt cataacttga gaggcttcca cctgctaata cgataccaca    56220
aattttctaa tccacctgaa gggtaaaccc tttcatctaa ttaaccttta gttgtgcccc    56280
tttcgaggca cccattgtta cagcagtcgt tctaactgaa tttccaagtg atctggaata    56340
tattcagtga cgttgttatc ggagacgcca gattcacgca tcatgttgag catgctacga    56400
atctgtcctt ctgttgcttc acgagtttca ctaatctctg tttcatacag agccatgatc    56460
tcgttatgaa catcttgagc attaccacgg acatatccga ggaagccata gaagtcagac    56520
atatcacgaa gggatacaac taccgaccca ctattatcaa gagtttgtaa acgaatacgc    56580
```

-continued

```
ccaacctgac ggacagaacg attacgacag aacaggatat cacgagccag acgataacca   56640
ctatcaagat cttcgtgtct tggggtgtag tctagaggta ggtgagggag catagggtca   56700
aaacgaaccc tgttaagcat ctcaacaaac tcttcattgt ccatctctgc attttcaact   56760
gctaatttct taagaaccaa gaagcggttt accagattta acagctgacc tttcttccac   56820
ttaggctctg agatacggaa ctcaacagaa ccgaactgag ccagaggaag taggttaagt   56880
gatgtgtact tatcccaacg atcaacaatg tgtcggaaga agttctcacc ttcgtagtta   56940
aatgcttcag aagcattcat tacttgagcc tgcactaccg caaaagcagg acagaaatta   57000
ctacggtaac ggtgataacc agagcactta aacatcaatg cttcatagaa agtccaccca   57060
aggataactt tcttaacgat attgctatca gcatctcgca tatccatatg aacgtgagtg   57120
gaacagcgcc aagtcccttc tgcttcggac tccatcactg cctcactcag attgttgata   57180
gcgtcaaaca gttctacacc attgtaaggg cgagaacaga ccatttcaca tccgttgcga   57240
agcgagccat cctctgtaca ttcccacata tctgcttcga tatgatcgtc accttcaagc   57300
tccagctcaa taccaatacc gcattggaat gcgatactcg gatgtgcttc actcagacga   57360
ttactacggt atccaaaagc ttgcgctaca gttgtcataa cgactccact aactccacag   57420
tgtattggtt aaaatcactt tgaatatgct tgaacacatc aagcagttgt acggtctgac   57480
gaccacggct gtcatgtcca gcaccgagaa gcacgcgacc aacgtgtgct cctttataat   57540
aaacaagacc atcggaaggg ttgatgaaga taaagcgagt caacaaacct tcaaaagatg   57600
gattaaacag gttataaacc atctcaccgg agatgttacg accaagagaa gttacgccac   57660
ggagtttgtt acccatcaac cccttagctc gctgacgaac tggattgata tgggtccaac   57720
ttaccatgtt acgaccatgt tgaagataac caacatcagg ggattccaga atcaggttag   57780
ggttgaacac tccaatctga actgttgtac ggttaaaccc tgagtctgtt ttaacccaac   57840
gctctgcttc gaacatcaaa gccatctctg cttcgtgaga gaagtcatca cgagagaact   57900
cgccttgttg gaatacgttc ataacaaaca atgggatgtt taagttccca cgtctttcag   57960
caatccatgt cccacaatag taatgagaga agtcagttac taagctcacg ataacccctt   58020
acgctacctg taaacgtttc aagaacacat ctgcttcacg aacatcgttg gtgttgatga   58080
tctggtgcag cttttcaatc ggaaggcgag agtggaggcc catcaagaac tccatgtcgc   58140
tgttttgtac aaccttgtca acttgatcat acacaaattg acgatcttct ttcttgccaa   58200
tccagaagtt tgacagagag cgatactcaa tgccataagg tttgtaacgg attgcggatg   58260
ctttaccgta tagctcttta cgacgagcat caccgtccat cagaacagca ggcaatgaca   58320
ggaagtaatc acacagaacg cccagcatca tctgaacctt cttattcaca tccagagagc   58380
cagtgacacc gatatgcaca tgaccgcctg ctgtacgcaa gcccttgttc tctgaagttg   58440
gggaagcatt cttttgacca gtgaatgcgt tgaagtctgg agtacaacca aacacgaaag   58500
cggacggatg gaatgattcc aattcttctt tagagaagat atgagaactt acacccagag   58560
ccgcttccat gtcctgtttc ttcagaactt cgttggtaag atcaatacca cgctgaacgt   58620
tgtcattaaa cgcttcaaaa ccttgttgtg ggttgatatc aaattcagca agaacgttgt   58680
cttcttggag acgaacatcc ttagccagat cgattttatt ttctttagaa cagcccagct   58740
ttccagcaac agaggtgatg atgccagaag aagtacgaac aaacatttca gggtcagtgc   58800
cgattaaaaa gatgcgctta gtcattgtag tattccacca attctttaaa gagggatgtg   58860
attgtttctt tgttgctctc tgtactagag tcacaacgac tttcaatacg ttctaagaaa   58920
ccatttacac tgatgttaga aatctttcca tcaagagatg aacgtttcca accagtgctc   58980
```

```
atagaccaaa ctctcaaaaa ggtactcatt gaagagtaca tctctgcgtt ttggtttcga    59040
cgacgagcaa tacgacgaag ggctgcacgg tcatggtttc ggatataccc tgatgtgtta    59100
tcaccttctc caactttgtt ttgcaaccaa acatcggttg aaaactcatc tgtattgcaa    59160
atgatcggaa gaaatgcaaa tgctggtaag tcgtgcggta agtagataga tgttgattca    59220
tcagtggaat cattaactct atcaaagtta agctccccaa agaaatcctt acttacccca    59280
gcaagagcta gagctaatcc aacacgacga cggaatagcc attcttctct atcatcaact    59340
ccctctgaaa gaaaatccat agattcatac tcgcaatcga gataactacg gaaagtcatt    59400
agtcctgtaa aaactttatc tgctgcgtgt tcacgaagat caacctctac actattagca    59460
gaagtgattg tgaacatatc tttgtacata gaacaggagt ttagtacatc agcagtatcc    59520
aacaaatgag actcaatctc atccatgttg cagtgaggcc agtagttaat cttacccatg    59580
tgtgctgtga agttatctaa gctggttcga ttactcaggc cattaatatc acgagtgctg    59640
aagttgtgca tagagttgtg gataccgaaa cagactcggc tcgtaaaact ctgctcaccc    59700
accatatcac taacttctac aggagctaat gttgtggaaa ttgccattgt ctttaacctt    59760
taatttccta agaaaagttt cgtgagaatt gaatcccact ccgtactagg cagtacatca    59820
aaactgctat tatttgacag attcgactgt tgaaagtggc gaatcattgt gtaagtatta    59880
acacggtcat tgccaaatcg agtatacaac aactcatttc gagtcttgtc tgatagggaa    59940
atagctttgg caaaagctac aatcagcata ggctctttga gggcacgatc ttgaagggct    60000
tccggttgaa gaataggtaa gaacattgag ttgtttacat acagctcatg ctcttcgtgt    60060
ccgggaacgt cataccaaac actcgaatag tcttcatcac ggaaatgtcc ttcaccagcc    60120
atatatgacg gttgacgcca cgcagtctgg cgaggttctg ccatattagc tccgatgccc    60180
actgtgtaca gtgttacagg gaacaggcag ttatcgtatt cattaccagt aaaggcaact    60240
cgtacttcgc caaacagatt ctcttttgcg ttaatcaatc gagaataggc aagagcttgt    60300
aacggagacc aatcgtccat aaagagctta tcaaggaaag tccacacatt tgcttgctca    60360
tcttcttgat aaaacagacg attaaccata agatagaaca ggcaacgatc agcaggcact    60420
ggttcagata catcttctgt taccacaccc ataaaacctt tttcatgcca aacaagacat    60480
gaaggacgat ctttatccat gaaagcttca agtgcttcca taactgactt gacagttaca    60540
tcaggtcgtt cacgatattc agcccaaagc tcaactgcgt tcttaggctt ttcatcccct    60600
acatcagcgt gatagaaagc atattggaag gagatgatgt tgttgctccc atcctttcca    60660
cgcataggga tatgggttcc agagttccag ataatacgaa tatcttccat tgacattaaa    60720
ctgcttagga gttcatcgct gccagagctt tgcatcaagc tatagctgct atcccaaaca    60780
tggacatact gcgtccagcc ttcattggct tcgtaggtaa tggggtcgta ataatcacta    60840
tcttcgtcac aatcatcacc accgtggtag ttgctgtgct gaagaaagcc atagcaagga    60900
ggccagactg ttactacatt gtcctgctta tcctgcaatg ttactggaaa catttttgaaa   60960 cctcttattg ttgtttgatc aactcaacgg acttacggat gtaaagaata tcacggaagt    61020
tacggtagtt gttcatgaat tgatgcttct ggaactccgc ttcaagcaga gattctttgg    61080
cactttcata actcttacgg gcaagataca caacccgctc tggtaatacg tttgcacgac    61140
ggatgatata cttgtgagct ttcatattgc tctgctcacg agatatctta cttttcgcta    61200
ccgtaatgcc atttgcaagc caaacaagct cttgctcaag ctcttcgttg acattccac     61260 cgaggtttga tgcaaccttg ttcagagttt caatgttaac gttgcccttg atgggacgtg    61320
```

| | |
|---|---|
| tattcatacc tactcctgtt gtttacactc accaataacc cactgataag aagtggattg | 61380 |
| acctgaaaag aaacactgaa taaatccaga cgttctctgc gttaccagtg ctagtgcaca | 61440 |
| tatcactacc gctgctgcta gcagtttcat atctaattta gacatatttc ctctctttga | 61500 |
| atttaaaaaa ggactctccg aaaagagcca agctttaaat acaaaaagat attacccaat | 61560 |
| atctgtggat aacctgctct taaaatatct atccgacgga tgttcgagga ttgttcctct | 61620 |
| ccctagcatc ggccccatac gggaaatata ttaagattag gttagttgag tcagaatgac | 61680 |
| tcacatagcc ctccgaaggg aaggctataa atgtcactct atttatcccc accaaaggcg | 61740 |
| aggtaggcat ctctgatttc agtaacctgt gaatcaggtt tgaatgcaga caaatgtcct | 61800 |
| gtgttcaggt taactgcgtt ggcagggatg atgcaaccct ctactttagt atcagggatt | 61860 |
| ttcatgtagt aacttgaaaa gtgctctgct gagaaaactt ctccaacagt gatatcacta | 61920 |
| atcttcgcta gaacatcctt agctggttgc cctattttca ttactcacct tcttagcac | 61980 |
| ggtctttggc agttttacca gtgcggatac gatgggaaac gttaaccaga gtgccaccct | 62040 |
| caataatggt aacgctcttg ttcttggcaa tgtcaaacac agacttctct gtgccaccca | 62100 |
| agcgaatctg cttaggctcg ctgaaggttt gagtggactt ggattggatg ttgaacggct | 62160 |
| gacggattgc atcgattgcg cttactttac tcataggggga atagctccta aaaatcatga | 62220 |
| ctgcgcagag ggaattccct acgcaaaaac gacgctaaaa gaagcgtcac agtagttgaa | 62280 |
| aagaggtaca gaaacagggg ttatttagct acctttttct gaccgtttac gaaccagata | 62340 |
| attgaaccgt caggctgtcg ttgaccgaag cctttcatgg ttagcatgtc ttccgaaaac | 62400 |
| tctttaaaag taatcactta cttaccctta cattggagtt aatataatct ctgctttggc | 62460 |
| atacttaaca ccgacttcaa gattgtcagc aacaggacga ggtttgcctg tacccaaatt | 62520 |
| aactgctctg cgatatcctc cggatacagt catcatcaaa tagatggtgc tgctgtcatc | 62580 |
| ttctttaaa gtgaagatat cagcggttga cagatctttta acaaagagtt cttttcttc | 62640 |
| ttcgtgacga accttgatat gtattgtgct cataccctact cctgaaccac ggacatacga | 62700 |
| atcatttcta ccggagtgtc acccttcata acacccagca cgccagtcag aaggttaact | 62760 |
| gtagtaatcc agtctttttc tacagagatt ttgctggata cattggcaac acgcatatga | 62820 |
| tactgaggtg atgctgaacc tcgctgaatt acgaaagggt ttccggggat gatagtatcc | 62880 |
| agtggataag tgttatcttt aaccttgggg ataattttca ttagcaacca ctcactaaaa | 62940 |
| gttcagctga tacagggaca acatggcacg tagaatctgg tgctgttacc aatccatcac | 63000 |
| acagacgaag ggctaaggta cgtccacttt ttacggacac attaggagta ttgtgaacaa | 63060 |
| agcctttaac atagagggtg tcgctgtctg ggtgcttgaa caccgctcca ttttctaagg | 63120 |
| actcgagtcg gacacgatct gttctgttgg taattttcac attaaccctt aacaaccctta | 63180 |
| gcttcaacat tgacaggata aaccttcatg ccatcaacag gggcactcag ttcgccattt | 63240 |
| tccagtttaa cacacacaat acgaccgaga ggtggctcaa tccaagacgt cttatctgtt | 63300 |
| gtacatacca tgtgaatagg tccacatgac tcttttctga aggtgtctcc gcttttaac | 63360 |
| tcggacagct ttacagtttt agtaggacta acatcattaa ctttcatatt atttaccctg | 63420 |
| aataataagt ttagactcga acatctcaac agtattggat tgagggactg gatagaaaat | 63480 |
| ttctttggag ttctgaacac ccattgcaga gtggtctcct attttcatcc agaacttagg | 63540 |
| ggctatgctg tcaccagtaa aacggaaaac atctccattc tctaagtcag agaaggtctt | 63600 |
| ggagggttct ttgcttttttg gtacttgctc aaagttcatc ttgattccta tttaagttta | 63660 |
| aggctgatat taaggtgcat acacgccctg ttctgtacag cggcataact tctaccgagc | 63720 |

```
atgtctgcca ttctctgaat aggcatgaat ccagcattac gaataacaaa ctgatcttct   63780
tcttccgtcc acttgacacg tagagtagct ctggaaattt tgaatttagt acaagctgtg   63840
ttaacagcat tctctgtaac attcataatc aaagctatct cagggataga gtattctttg   63900
atcaaccgtc taagattctc gatttgcatc ggagtccata tggttcttct ggctttcatc   63960
tcaccaccca tgtctacttt taactaggat gccatcaatt attagatagt gggaatggtt   64020
aatcatatcc gaagacaaat ctccgtgaga gctattccat ttaaggaagt tcatattttc   64080
ccaatcggtg tagtgcttct tggcctcttc ctctacctga ctaagagtta cccttctgaa   64140
aggataagga ctgtacttga taagcatttc acattttgtc atacatcctc caattaaaca   64200
tttatgtaag acttgcttag ataaagattc aataaaatag ggggagggga cgaatcctcc   64260
catatcctat taattaattt tgcatgtaag atctaacaat cggctgcctt tgtaggataa   64320
gcgttatgct tttccagcac taaactcccg cccccttagt gggctgggtt attaaagggt   64380
aacgcccttg taggctagtt acgtgaatgt tagtttgata ggagatctga agtcctatct   64440
caaaggactc tcgtaagaat ccttcacgat attacttatt cattttttcgt cggctatctc   64500 tccaagccaa ccaagtgtag gttttcaact cttcaaaatc ttctggagag aatagatatt   64560
ctttgaaggt gtcaccaaac cactctaaaa actctttagt cataaatacc cctactcctt   64620
tttagggaga atgaaacccc acagccctgc ccacaagcaa agggatataa acatcacagc   64680
aacaatgggc catagaaaaa ccataattgc tatctttgat aggtttggtt cgttacccca   64740
tcctctgaac tcgacactac cttttacgtc aaggattttt atcagggctg aagataaacac   64800 cataccttatc agataaacga ttaacacact aacaagactc atcgcaaggt tggtctccac   64860
atgttttaca aatcactggc gaataactac aggcaggata tactgacaca ccatcccacg   64920
tctcacatcc acagtcaggg cattcaccgt tggattccat gtcatcatcg tcacacactt   64980
caccgccacc ataacagctc atgtgaactc cttagtaaac taaacctaca acctttgcat   65040
caggctgagg tactacttgt gcattagggc gataaccatc tactgaacca ttccaaatat   65100
tgatgcaggt tatatacccg tcatttacag tatctgtttt aatccagaaa tgttatcgt   65160 gcccaaaaac atccccgtta gagagggagg acagttcaac agttttaagg cactgtttag   65220
aattcagttt catgataacc tctgattaat aagtgacacc agttaatgta gcttcaggca   65280 tatgaccac tttaactcct gctgcgaacc catccatatc accgttgtgc aggttgactg   65340
ctttatagta accggacaag aaactagagg tctttaccca aaagccatta ttccatttga   65400
atacagaccc acctttgaga gtggaaatct caactgtagt ctcactgttt gttgcatcaa   65460
taatcataat cagtgttcca atgttcgtag ttaatatgac ttctaggacg accatacata   65520
atgaagtggg tcttattaat ccttttcttc aaggtataat aaagatcgct atcgaaatta   65580 ccaatctta cttgccatct aagagagcgg gcatccattc gaagcattga tatcatctga   65640
ttatgactct gactactcat tgcttccaga agcttcttcg tattccaata atgagttgtc   65700
atattaccac tccttaccag atgttgttac agaaccactg caccactgtg cattcgacag   65760
tgttttagtt tcttcatcaa cagatgcacc attaaggcaa gagattccat tatagcgcat   65820
atcaatctca ccactaggaa ccttgttccc tgaatgccag cgagatacgc acacaccttc   65880
aacagacact gcacaccatc catcaggacg gctctgtaca cagcctgtaa ggaccacaca   65940
agcgatgaag atacagatta aggatattac accaccccaa ctcataggca cctcctaatt   66000
aaagtggtgg actatctgga atcgaaccag aagctcacta agaaagcaat tcccactgtt   66060
```

```
ataaaagcac ttgcctcaac agggatacac taactttggt gccgtaccca tactagccct    66120
aaatgtggtg cgccctacag gattcgaacc tgtaaccaat agcttagaag gctactgctc    66180
tatccgttga gctaagagcg cagaattatt taaatcatgt cacgcttggt aacatgacca    66240
cacactttac actgcataac atagcgaaga cctttgtgct ttgtctcacc gtaatcgtca    66300
gtaatcctca gtgtatattt ttcaaggatt acccaatcat gcagatgcac aagacgttta    66360
aaccatttga acatagtcag gaaccttaaa cagaaaagga tatagcttca tttagagaac    66420
gaaaccgtcc aacatactga cctgcggcag aagttacaac aaaccactga cctacaaaag    66480
agattccagc aatccgtcgg ttgtcatcat cagctactct ccagtagtct ttatgaattt    66540
gttttacttt cacatcaacc tcaagcacat gcagggagtg taacgatctc aggtttacct    66600
tcgaactctt caaacaaacc caagaacgtc gggctatacg taccagtaca aacaaactca    66660
tcaaagagtt cattgtacga aggcttaatc ttccaagccc acacatagcc catcttatca    66720
atcgcaatgt gacgagtgtt cagaggaaca gccatcatca catcacctac tgcaataact    66780
ttggttatcg gtgcagcttg gaagttttc atacttacc tttgattcgc acgttgttga    66840
tgtaacagga aggacaagga cgaacaactt ccccgccttc tttgattatc ttaatctcac    66900
tacgagtgat attcacacga gcaccacaac aaggagaatt aacgtaagag taaccagatt    66960
gggtatgttt gatgatttgc ttgttcatat tacacctctt tcggagattt cagcaacaaa    67020
ccagacttgt ggagtgtgtt gataaacttc atacgacttg actacggata agcagtattc    67080
taagaaacct ttcacaagaa ttgttgtttt ctctacaggg atttctgaaa tgtcaacacc    67140
aaagatttcc ataacaacct cacccttttg gatgatgcga acattcatat cagtacctct    67200
tgttagttta agtaagagtt ggcccttaat taaaacaaca aaggccaccc gaaggtagcc    67260
ttatttgatc agttttgctt taagccgagc agtctgttct gtaagaactc atcctctgca    67320
ttgtacagga aagcgaacaa caactcttta gccatatctc gtgagcagtt aaggcactta    67380
gagatttgag tcagttggag atttcgatca tcgtgttcaa ctacagcaat gcgaatgatc    67440
tctcgcatac cgaacacatg agttgactta gccgccataa gaccaatcac cttgacgttt    67500
acggatgtta ccagtcagac gcagcatggc agactcaatc ttcagagcac catttgctac    67560
tgcatccata cgctcaggac ggttcatacg cttggttgac ttcttcataa cgttctctct    67620
ttgttagtgg aggcattatt gccagttgat ataagggata gccctagtca ggaggctaat    67680
tctgaccgcg tactcattgc cgaccttctc tgcctaagag ttcaggttct agagctatct    67740
cttattccaa ctggtgaaga cctcctaccc ctaggagatc tcccaaatcc caaaccaata    67800
cgtaccccta cgtagtggaa agtctaccga aattgaacag gttttagtct aacaccggat    67860
gttcgagcaa gctctcccta gcggtgcggc atatgcctga ttgatatatt taatgaggaa    67920
caccctcaca tagccctctg ataaacacaa gggctataag tcggtgttac ttttgggata    67980
aacacagatc aggacgtggc ataacagtgg ttgatagacc gaagacttca acagaaccgc    68040
tgttcagatc ggcggcctta cacaaaccat caggagtttt atcttctaac atcagccaga    68100
aacgtctatc gtaagagaaa acatcaccac ctttaacatc ttctgcattt gcatatttag    68160
gataatccac tactttaatt tccatctact taccttatt agtaactact gcatcaggaa    68220
taaggactac aggaatatct gaagcgagct tcatgacctg attgatgttt aaattgatca    68280
ccacacaacc cgcactaggc ttaacttcgg ctacgtgtgg agtgaagagt tgaacaacca    68340
tgtaataact tataccggtg ttttttaactt ggaacacatc gcctagtttc agatcactca    68400
acttaagttc tggattcttc cactcaagat caatcttcat cttttaacctc tatattggtt    68460
```

```
atgtggagat cattgcgcac ttggcagatt tcatttctac tgatagcgac aagcacccct   68520
gatactacac taacacagtt tacgtgatag tcagttgttg aacctgttct gataaaaagt   68580
ttatctcgga aagaaaataa aacccctggc ttcatattgc ccaaacggag tatcgtacca   68640
tcagatttaa tattaacctt cactgttgat ctcctgttgc ttggcaatag ctactcgcaa   68700
gtcttcatta gcacgagcaa ggcgtttaac ttcatgatca aggctgataa ggcgcttatt   68760
tctatcttca acctgttcaa ccagatcaaa aagctcaact ctcaccttt ctgtatacat    68820 ctcctctact ttaaccagac tgttatagcg acgttcccag ctggctgctt tattgcgtag   68880
cataataaaa cctaacacag caacagttaa cagcaataca agtaagaatt tatatacttc   68940
aatactcatc ttattcacct ttaaagtaag ttattataag aaatattatt tagaattatt   69000
attttctaaa cataatttct ataatctttt tcagaggtct atatacagtc attcccta     69060 gttccaaatt gcttccactt ttcagcgact attttctaag tggttggttt ataagggaat   69120
ttagtttgtc aattctggca cctatgatta ttcatgagca tcattattga acactaaatc   69180
accacaatac atcggattgg tataccactt tggcaccccc tcgctcttac tctgaaagta   69240
ggttccacta tacagaggaa cataattctt cttgagagca cgtctagcaa gctgttcgct   69300
ttcccttatg gcttgtttag tcataggatt atcatcacga atcaacttta cataacgctt   69360
aaaaggtttc tcctttctaa gtaatacagg aatccactca aactggttct tttgtcttat   69420
cacctgttca gcggtcagtt ttcgttgtga cattctgttt attacggtat ccgcaactag   69480
tgctttacat gcggttggct gattccctgc ctcataataa atagtcaatg tcaaaagtag   69540
ctgggccgtt gttatcagaa cttactaccc cctattctat gggtacaaaa aagccccagc   69600
cgtagccggg gcaaacctga aagcaataca tgactattgc agtaaatgca ctcgtaaatg   69660
cgcttacggc aacgacaaaa gccgctcaaa ggcggctatg tggaagcttc aaatggggag   69720
agggcacgac gctacagaaa gagcgtcata gtactaaaaa gagaggctat tggagaggtt   69780
acttattgcc ttccttaatg ccttgtttc ttgtttaacc aattcgtttt cttcttgcaa    69840
ggatgctacc agatggacca gaacatcaac tactgcatca ccttgccgca tctctctgac   69900
tttatttaga atctctgaat aaatcatttt accctcgcct ctttgatggg gtcaatgtat   69960
ttttcaactc cccatttgtg tttactatct gcgtagaaaa catcaggtgc acactggctt   70020
gtcttaggaa aggcttgcgg gtcttttgtg ctacctttaa acttctgctt accgcgagtg   70080
cgaccgttac aaaagatttc taacttcttc tcgtcttctg ttttagcgcc cccgctctgt   70140
aacaaagaac gcttatgatc agctaacagc aaggcatcag cacgatgggt acgatggcct   70200
acacgcttag gcacactaga aggaatatga gattcagctt cagcctttgc agcacgacgt   70260
tttaaactac gcttgctgac gtgattggtt gcttttggtt tctcttttc cagttcagag    70320 atagagaaac agcgcccgcc cttcatgctg attttagatt tagccattat cttattcctt   70380
tcagtgataa gttatatcgg gcaagcccat caaggtgaca ggcttgaaca aacaactcaa   70440
tcaagtaaac taaatgattt ccaactacgc aacaaaactg ttccgtcatc catcgctacg   70500
cttaactgta gtagcttctt attaatacta cttaccgtta aaatccgtcc agttgtagct   70560 ttaccttat tactataaag atacactaca cgacgactca ataaacgaga tggcgctttc    70620
ttaaattcag atatattagt tatcatgatg cttgatacct tgaatatgt tcgatacggg    70680 tggattgagc aaaagacgct ttaacagcca tttcttaac ttcttcttta cgctgattag    70740
cgtgtacagt atcccaatgt ttatggtcac gacgtcgctg taatatctta ctacatttgc   70800
```

```
gatggtttcc actgcttcga tgtttctcac aaataggaca cttaccaaaa ttactactaa    70860
agatcatttt ctcaatccca gcttgcgtaa tacacggcct aacattgttt cttgtgttat    70920
ggtgtagcta attgcttcac gttctagcat ctcaattttc attggcgacg gataccattc    70980
accggtaagc atacatttgc actcgacacc atatttttta gataggcggt aatgttgacc    71040
gttgcgaagg tttctataaa ccgtggtatg tgtagttaac ataatcgtca cctttgatta    71100
gattctttga ttagcacact gaatcaatgc actgataaaa gaaaggcgc tacccgttaa    71160 gatagcgcct tatgttgttt atattgtggt gttatgctgc attttgacgt gctgccataa    71220
tctcagccgc tttccgcaag atctcttctt gctcagccgc cgccgcttgt tctgtacgga    71280
ttgcaaccgt tgaagagata cgaccgcgca gattatctaa cttctcctgc attttttgtga   71340 tggttgattc catttcatcg gcataagaat ccagtgattc caattccttg cttgatgcgt    71400
tcatcaagta gtcatcagag atcgctacgg ttgaagccgt tactttctta atcagtgaat    71460
cgaaggactt cttaaccttg cccacttctt cactaagggc aatagtgtta tcactggtag    71520
cgccgttacg ttcatcagcc aataatttgg cttcaatacg gattgcattt aagcgttcta    71580
ccagattgta aatatcctga ttaaaatctt ctttaacttt cgccgggatt tgcaggtgtg    71640
ccgctacgtt atcgttacaa cctttgaaga agttaggatt atctacttcg atttcatcac    71700
ctttggcgaa ttttttcgaaa gagttagacc aacgagcgcg gttttgttcc attttcgcct    71760
taatttgcgc ttctttcgca tcttctttcg ctttcgcttc accttccaga ttaatccact    71820
ttttacgacc atttgccgca tcagtgttat atttgatagg agttaagaaa gtaattgcag    71880
tggcgatcac atccatatcg cggaaacgtt cggttaacag gaagtcaacc gccgcctgca    71940
atacgtccaa cttcttaccg ttgctacgga agtgctgcaa atgtcctaac aggaagttag    72000
aaacatcttg tttgatcgcc gcgttgttgc tacgaatgtt gttagccagt gcattaaaac    72060
cagattcgtt aaccagatta aagatttag ccatgatatt cacctttcaa ttgtaagggc     72120
gctattgccc cgctctctat gagctttttt aagtcactat tgactatcg ataaccactc     72180 attttttaagt agttattgat aagtaaggga gtcttatcag gaattaaccct tgctccctta    72240 ttatctgcga tgtttcatcc ggtatcttta attagtcgct ataaactaag ccgacctgat    72300
agcgatgatc aatcatcaca ataaggcagt gtgcccgact ctaattagtt actttattgt     72360
aaccgtcggt aatatcgttt actctgtttt cgctcccgcc tatccttttg taccgactct    72420
taatcgctaa ccatcgccca ctacgggagg ttattacgag aaagtcatca gccgtctaat    72480
acattgacgt tttatatctt tcagcaggtt tactacataa actgactatg tacgccatca    72540
atagtgacct caaatcattc acttcgtaaa cgttcacact aaaccttatt gttaaatagc    72600
aatttgctac tctttaacca ctccccgccg ctcgcaattg agcttgtatt cgtcggaatt    72660 gcctacctg attaacttct ttcaccgtag cgccttgtta gcgatgaccg ccgctaccct      72720
taaccgtggg cgattagctt aagtctttgc gtgcactcga tgaatctgct tatcagtggt    72780
gacgtttcca gtaagggatt gtaagattgt ttactctgat aacttagaga atcttacacc    72840
gttttatctg gtatgctatc cgatggttat tatcatctag catattcaac cgatatagga    72900
gaatgtttaa attgttaaag agcggtaaat ctatcagtgt gctttctcac actatgcaac    72960
tgttagccgt tgttacgctg ttcacttcgc ggtgatttgc ttagtgagtg ctcattatga    73020
atcatgttgt tttagctgtc aaccgctttt taatcttttt cgtcgttccc tttattggga    73080
ggagatatca atcagctata tttgattgaa gattaagcgg taatgcttaa cttatgattc    73140
atatttttaa agagcggtta ctacactttc agcttaacac atcgtgttag cttgtcaacc    73200
```

```
tctttttat   catcttcttt   taattccgtt   cccttatctc   gcgtgaatct   ttgcgaaagg   73260
gcaagacgat   aagtctgatt   tgtcttttag   gaatctagtg   cgctttcaag   catcgaccat   73320
ttgaaagtat   cgaacaaatg   aggcttattt   tgttgctcat   cgtccgcctg   tttcacgtat   73380
gaatcaggaa   tcaattctag   cggtcaacta   agcgccttat   agtaatgacg   ttaccgccac   73440
ctgtaagaca   aatcatattt   ttaaagagcg   tagcacttcg   ttgtgcgtct   taccatcggt   73500
attcctaccg   ctcccccgtt   gaagccttt    accgtgatgc   taatcaccta   tcagggagtc   73560
ttgttgcttg   ttgcttactg   cttactacgg   gattcatatt   aatatacagg   aaaattatgt   73620
caatacccct   ttttcaaatt   attttacatc   tcattgattt   ataaaggttt   ttattttact   73680
tcactctgga   actagcaacg   atttataggc   tggcagtgtt   ataaagtaac   ataaaaagta   73740
tcataatcgt   gacgtaatag   accacgcgcg   ggataacata   cgcaaaacag   gctgaaagc   73800 agtttctaac   gtcctgtaag   ccattctaac   gagctaaaag   ggggcaaggc   atacaatcac   73860
cctataaatg   aaaaaagcct   catagagagg   cttataggaa   ggatttaaag   tattagatag   73920
attatgacca   taggcatgac   tacggcacaa   tacaggagaa   agattaatcc   tatggattta   73980
cacattgacc   gttaccggat   gccacttcat   tcatagactc   atcgaacaag   gttagggatg   74040
agcgtaacag   gtgatcaatc   atgatttgct   tgccagtggt   ttcatttacc   agttgaatag   74100
ttttatcgaa   tgataatacc   tgatcgaaat   caccaacgtg   taaaataata   accttcggtg   74160
attgtttacc   agtatcataa   ttttctatga   gataggtaca   ttgcaagcct   tcgatagtct   74220
taggtgtgaa   tgttgcagcc   ttaacactac   ccatagacga   taggagaaca   cccagcagga   74280
gaacaaccag   aaagaagcct   acgaacactt   ttaccacaaa   tttgataata   cccatgatga   74340
taatcaccta   tagttagaga   atgtaagaat   aaagcatatc   agcgacgaat   aacgccactg   74400
tagcaacgaa   caagcaacgc   caaaaataat   catgaatcat   cgttgccatc   ctcgccaaaa   74460
aaggatatac   tgatttgttc   cacttcttcc   agcgacaaca   aaatcccacg   ttgggctaaa   74520
tacttcccaa   cagtcagata   gtcctgcact   aaacagacaa   caggaaagcg   gatagtctgt   74580
atctcacctt   tagaaagaaa   agacaaataa   ccaacgtcac   ttgactcatc   aaaggataaa   74640
gtaacgccac   cgtaattatg   cgtatcaatt   aacgcgatag   tttcatttcc   cataatgttt   74700
ccaatcctca   ttattgtttta   gcactgatac   aatcagccag   attaaaatga   atggtgtaca   74760
tcgcattatt   ttcgctattg   taaaccgtgg   tagcgagcat   tgattcattc   atcgggccat   74820
agctgaccag   attagtgaca   gctttcgcat   ggctgtaacg   ttgtacagta   ccaaatgtga   74880
ctagttcggg   atcattatca   gtacgcttta   ataacagatc   ttcattgccc   tgattatcta   74940
gtgttttggt   actaacgacc   agaccatcac   gggaaacatt   actaaattta   accttaaaa    75000 cgacctgatt   ggtgtcacta   tccgcaccat   tacagactag   ccattgctta   ggtgcaacct   75060
taacgaatag   attagcggca   tcactagcaa   caggagcagg   actagcaata   gcgttatcag   75120
agatagcacc   aacgacagca   ctgacaccga   tagctgcaac   cagtgcataa   cttgcaaggt   75180
tgacagactt   cataatctta   cctgcaatag   aaggcttgct   atctttcttc   ttcatgttct   75240
ggatagcttc   aaccatagca   gacaagcggg   ataataatgc   gttaacatca   cggcaagatt   75300
caggccaatc   gttttgagtc   caactatcta   agttagcctg   aatgtaacag   ttaatagcgt   75360
cctgcatatc   ggtaaaacca   ttctctttga   atgactcact   atcttcacac   tgtaaagcgt   75420
tcgcagcaga   atcgatgata   agacaagcca   gaataataga   gttttttaaag   ctggtacggg   75480 cttgctggtt   atccatccat   tgagtaggca   caccaacgga   aagacctaac   ggggaaagtt   75540
```

```
tttcatttgc ttgattcaga tgtttgattg ctaactttga cattttcgct aatcctttcg    75600
gttgatgtga actacaaact acactcgcaa ctatatatta aaggaaaaaa ctgtcaacta    75660
tttattttct aactttctta taactcactg aatcataaag gaatttaatt tactaaactt    75720
tctcattcag ggcatagctt actactctta ttgttacttt ataacataac gccagaccaa    75780
cggggagaac gtgccgcata aacagatcta cggggcaacg gtacaacgca accagcacgg    75840
gggagtataa acgggtaaca tataatgtat gttgttacat gatgctattg ttagcggctt    75900
gcggaagtaa tataccaatc aaatatttcg ctactgacgt agctcatatg cttcactcat    75960
caaactatca cgcactgcgt gcaacgctga aaagaaaag attaaaagaa taacataaag    76020
aaacaattaa aagaataata ataacatcaa ttattaaatc caatctaatt aatacataca    76080
tcattaatcc actcataatc atcacactaa tcattattta cattcaaact atggggcgat    76140
gtgattgtta ctatccggta ttattagtca tgaaatggtg tgccctgtac agtgctggcc    76200
tctcataccc tcccaattaa tgaatgaaat aaacggggca aaagtaatgg gtactatatt    76260
acacggggta atgattgcac gggataggac acgggggag gttaggcatt caggcacgtt    76320
cacggggaag taaggaagtg agggaatagc cataaaataa atgaggactc ccccttttg    76380 ggaaacgcgc gcgaggcggc taggcacact cggtcaaatc agaattttaa actgttatat    76440
ataaggttga atatgaatct cgatactaaa gagtttatta aaattgcaat agaagataac    76500
ttaaagaaga ttggtgatat ttctttatca gatagagaac gggtggaatc agctcagatg    76560
ctagtgttac taaccaaagc tttacgggag gtggaatgaa tctagttaaa gtgtttagac    76620
gg                                                                  76622
```

<210> SEQ ID NO 3
<211> LENGTH: 754
<212> TYPE: PRT
<213> ORGANISM: Unknown
<220> FEATURE:
<223> OTHER INFORMATION: E.coli bacteriophage EP75 ORF 167

<400> SEQUENCE: 3

```
Met Asn Glu Met Phe Ser Gln Gly Gly Lys Gly Ser Thr Gly Ile Leu
1               5                   10                  15

Thr Asn Lys Gln Ala Val Ala Arg His Phe Gly Val Lys Gln Ser Glu
            20                  25                  30

Val Val Tyr Phe Ser Val Gly Val Asp Leu Gly Gly Tyr Lys Val Ile
        35                  40                  45

Tyr Asp Lys Glu Thr Gln Arg Ala Tyr Ser Leu Pro Val Gly Ile Ala
    50                  55                  60

Ser Gly Thr Thr Ala Val Ser Leu Ser Thr Ala Ala Val Leu Val His
65                  70                  75                  80

Ser Ala Gly Ser Val Asp Leu Gly Ala Leu Ala Val Ser Arg Glu Glu
                85                  90                  95

Tyr Val Thr Leu Ala Gly Thr Phe Asp Ser Gly Ser Thr Leu Asn Val
            100                 105                 110

Lys Asn Glu Leu Leu Thr Tyr Thr Asp Gly Lys Tyr Arg Trp Asp Gly
        115                 120                 125

Ala Leu Pro Lys Thr Val Asp Ala Gly Ser Ala Pro Ser Ser Gly
    130                 135                 140

Gly Glu Gly Pro Gly Gly Trp Ile Ser Val Gly Asp Ala Ser Leu Arg
145                 150                 155                 160

Ser Tyr Leu Ala Thr Asn Ser Gly Ser Gly Ala Val Gly Tyr Ser Phe
```

```
                165                 170                 175
Lys Gly Leu Val Asn Ala Ser His Arg Lys Val Asn Glu Lys Leu Asp
            180                 185                 190
Glu Tyr Ala Ser Leu Trp Asp Phe His Cys Asp Ser Ser Gly Asn Val
            195                 200                 205
Ile Gln Pro Gly Leu Ser Thr Asp Ser Arg Gln Tyr Ile Gln Asn Ala
    210                 215                 220
Val Asp Ala Ile Ser Asp Ala Gly Gly Thr Leu Val Ile Pro Val
225                 230                 235                 240
Gly Tyr Thr Trp Tyr Leu Asn Ser Thr Asp Pro Ala Ser Gly His Ser
                245                 250                 255
Gly Ile Ile Gln Leu Lys Ser Asn Val Asn Ile Gln Ile Glu Gly Thr
                260                 265                 270
Ile Lys Ile Gly Pro Ala Leu Ala Ser Ser Phe Gln Ile Phe Val
        275                 280                 285
Gly Phe Asp Asn Gly Ser Pro Ala Ala Ser Gly Asn Leu Asn Asn Cys
    290                 295                 300
His Ile Tyr Thr Asn Gly Asn Gly Thr Ile Asp Phe Gly Gly Tyr Asp
305                 310                 315                 320
Phe Asp Asn Thr Ser Gln Leu Arg Asn Gly Ile Ala Phe Gly Lys Ser
                325                 330                 335
Tyr Asn Cys Ser Val Ser Arg Ile Ile Phe Gln Asn Gly Asp Ile Thr
            340                 345                 350
Trp Ala Val Thr Thr Gly Trp Asn Gly Tyr Gly Ser Asp Cys Val Val
                355                 360                 365
Arg Lys Cys Arg Phe Ile Asn Leu Ile Gln Ser Asn Asn Ala Asp
        370                 375                 380
His Ser Thr Val Tyr Ile Asn Cys Pro Tyr Ser Gly Val Glu Gly Cys
385                 390                 395                 400
Thr Phe Arg Ala Ser Ser Thr Arg Ala Gln Met Ile Ala Cys Thr Val
                405                 410                 415
Glu Leu His Gln His Asp Thr Trp Tyr Arg Asp Ser Phe Ile Glu Gly
            420                 425                 430
Tyr Val Arg Gly Cys Tyr Ile Ala Leu His Gly Val Glu Ala Ala Gly
        435                 440                 445
Ala Gly Thr Tyr Ile Tyr Asn Ala Val Val Ser Gly Val Thr Gly Asp
    450                 455                 460
Ile Ser Gly Gln Ala Ile Ile Leu Ala Ala Gly Pro Asp Ser Val Thr
465                 470                 475                 480
Thr Thr His Ile Asn Gly Val Ser Val Glu Asn Cys Arg Ile Thr Ala
                485                 490                 495
Gly Asn Gln Ala Gly Met Cys Ser Phe Ile Asp Phe Gln Asp Ser
            500                 505                 510
Asn Ser Asp Ser Ser Gln Tyr Leu Ile Asn His Val Thr Val Lys Gly
        515                 520                 525
Cys Ser Phe Ile Val Asp Arg Asn Arg Ala Leu Ser Ala Ala Ile Thr
    530                 535                 540
Ile Asn Gly Ser Ile Gln Gly Ile Thr Phe Gln Asp Asn Phe Asp
545                 550                 555                 560
Val Lys Gln Ala Met Val Ser Glu Leu Pro Ser Gly Lys Thr Val Gln
                565                 570                 575
Leu Val Arg Phe Asn Trp Asp Glu Ser Asn Ile Ile Gly Asp Asp Asn
            580                 585                 590
```

-continued

```
Thr Gly Thr Arg Asn Ala Leu Asn Leu Phe Glu Thr Arg Arg Val Ser
        595                 600                 605

Ser Met Thr Lys Cys Asn Ile Ser Leu Arg Met Arg Gln Pro Ser Pro
    610                 615                 620

Glu Leu Phe Ser Leu Met Tyr Phe Arg Pro Asn Glu Thr Thr Phe Ser
625                 630                 635                 640

Asp Cys Thr Phe Glu Val Leu Pro Tyr Asn Trp Ser Cys Thr Ser Gly
                645                 650                 655

Asn Pro Ile Val Phe Glu Thr Thr Asp Thr Pro Pro Ser Gly Met Arg
            660                 665                 670

Val Arg Phe Pro Lys Ser Ile Ser Phe Thr Leu Pro Ala Gly Ser Asn
        675                 680                 685

Ala Gln Arg Ala Thr Gly Gly Ser Gly Tyr Ser Trp Val Ala Arg Ala
    690                 695                 700

Asp Ala Leu Asp Arg Arg Ser Ile Ser Gly Gln Phe Asp Ala Pro Ala
705                 710                 715                 720

Ser Tyr Ser Gly Ser Ser Asp Gly Lys Leu Ile Gly Ile Gly Trp Gln
                725                 730                 735

Leu Asp Gly Val Gln His Thr Tyr Asp His Asn Val Tyr Leu Gln Asn
            740                 745                 750

Phe Thr

<210> SEQ ID NO 4
<211> LENGTH: 570
<212> TYPE: PRT
<213> ORGANISM: Unknown
<220> FEATURE:
<223> OTHER INFORMATION: E.coli bacteriophage EP75 C-terminal part of
      ORF 167

<400> SEQUENCE: 4

Arg Lys Val Asn Glu Lys Leu Asp Glu Tyr Ala Ser Leu Trp Asp Phe
1               5                   10                  15

His Cys Asp Ser Ser Gly Asn Val Ile Gln Pro Gly Leu Ser Thr Asp
            20                  25                  30

Ser Arg Gln Tyr Ile Gln Asn Ala Val Asp Ala Ile Ser Asp Ala Gly
        35                  40                  45

Gly Gly Thr Leu Val Ile Pro Val Gly Tyr Thr Trp Tyr Leu Asn Ser
    50                  55                  60

Thr Asp Pro Ala Ser Gly His Ser Gly Ile Ile Gln Leu Lys Ser Asn
65                  70                  75                  80

Val Asn Ile Gln Ile Glu Gly Thr Ile Lys Ile Gly Pro Ala Leu Ala
                85                  90                  95

Ser Ser Ser Phe Gln Ile Phe Val Gly Phe Asp Asn Gly Ser Pro Ala
            100                 105                 110

Ala Ser Gly Asn Leu Asn Asn Cys His Ile Tyr Thr Asn Gly Asn Gly
        115                 120                 125

Thr Ile Asp Phe Gly Gly Tyr Asp Phe Asp Asn Thr Ser Gln Leu Arg
    130                 135                 140

Asn Gly Ile Ala Phe Gly Lys Ser Tyr Asn Cys Ser Val Ser Arg Ile
145                 150                 155                 160

Ile Phe Gln Asn Gly Asp Ile Thr Trp Ala Val Thr Thr Gly Trp Asn
                165                 170                 175

Gly Tyr Gly Ser Asp Cys Val Val Arg Lys Cys Arg Phe Ile Asn Leu
            180                 185                 190
```

Ile Gln Ser Asn Asn Ala Asp His Ser Thr Val Tyr Ile Asn Cys
        195                 200                 205

Pro Tyr Ser Gly Val Glu Gly Cys Thr Phe Arg Ala Ser Ser Thr Arg
210                 215                 220

Ala Gln Met Ile Ala Cys Thr Val Glu Leu His Gln His Asp Thr Trp
225                 230                 235                 240

Tyr Arg Asp Ser Phe Ile Glu Gly Tyr Val Arg Gly Cys Tyr Ile Ala
                245                 250                 255

Leu His Gly Val Glu Ala Ala Gly Ala Gly Thr Tyr Ile Tyr Asn Ala
                260                 265                 270

Val Val Ser Gly Val Thr Gly Asp Ile Ser Gly Gln Ala Ile Ile Leu
        275                 280                 285

Ala Ala Gly Pro Asp Ser Val Thr Thr Thr His Ile Asn Gly Val Ser
290                 295                 300

Val Glu Asn Cys Arg Ile Thr Ala Gly Asn Gln Ala Gly Met Cys Ser
305                 310                 315                 320

Phe Ile Asp Phe Phe Gln Asp Ser Asn Ser Asp Ser Ser Gln Tyr Leu
                325                 330                 335

Ile Asn His Val Thr Val Lys Gly Cys Ser Phe Ile Val Asp Arg Asn
                340                 345                 350

Arg Ala Leu Ser Ala Ala Ile Thr Ile Asn Gly Ser Ile Gln Gly Ile
                355                 360                 365

Thr Phe Gln Asp Asn Phe Phe Asp Val Lys Gln Ala Met Val Ser Glu
        370                 375                 380

Leu Pro Ser Gly Lys Thr Val Gln Leu Val Arg Phe Asn Trp Asp Glu
385                 390                 395                 400

Ser Asn Ile Ile Gly Asp Asp Asn Thr Gly Thr Arg Asn Ala Leu Asn
                405                 410                 415

Leu Phe Glu Thr Arg Arg Val Ser Ser Met Thr Lys Cys Asn Ile Ser
                420                 425                 430

Leu Arg Met Arg Gln Pro Ser Pro Glu Leu Phe Ser Leu Met Tyr Phe
        435                 440                 445

Arg Pro Asn Glu Thr Thr Phe Ser Asp Cys Thr Phe Glu Val Leu Pro
450                 455                 460

Tyr Asn Trp Ser Cys Thr Ser Gly Asn Pro Ile Val Phe Glu Thr Thr
465                 470                 475                 480

Asp Thr Pro Pro Ser Gly Met Arg Val Arg Phe Pro Lys Ser Ile Ser
                485                 490                 495

Phe Thr Leu Pro Ala Gly Ser Asn Ala Gln Arg Ala Thr Gly Gly Ser
                500                 505                 510

Gly Tyr Ser Trp Val Ala Arg Ala Asp Ala Leu Asp Arg Arg Ser Ile
        515                 520                 525

Ser Gly Gln Phe Asp Ala Pro Ala Ser Tyr Ser Gly Ser Ser Asp Gly
        530                 535                 540

Lys Leu Ile Gly Ile Gly Trp Gln Leu Asp Gly Val Gln His Thr Tyr
545                 550                 555                 560

Asp His Asn Val Tyr Leu Gln Asn Phe Thr
                565                 570

<210> SEQ ID NO 5
<211> LENGTH: 708
<212> TYPE: PRT
<213> ORGANISM: Unknown
<220> FEATURE:

<223> OTHER INFORMATION: E.coli bacteriophage EP75 ORF 169.1

<400> SEQUENCE: 5

| | | | | | | | | | | | | | | |
|---|---|---|---|---|---|---|---|---|---|---|---|---|---|---|
| Met | Ile | Ser | Gln | Phe | Asn | Gln | Pro | Arg | Gly | Ser | Thr | Ser | Ile | Glu | Val |
| 1 | | | | 5 | | | | | 10 | | | | | 15 | |

Met Ile Ser Gln Phe Asn Gln Pro Arg Gly Ser Thr Ser Ile Glu Val
1               5                   10                  15

Asn Lys Gln Ser Ile Ala Arg Asn Phe Gly Val Lys Glu Asp Glu Val
                20                  25                  30

Ile Tyr Phe Thr Ala Gly Ile Asp Leu Ser Gly Phe Lys Val Ile Tyr
            35                  40                  45

Asp Glu Ser Thr Gln Arg Ala Tyr Ser Leu Pro Ser Gly Ile Val Ser
        50                  55                  60

Gly Thr Thr Ala Ile Ser Leu Asn Glu Gln Ala Ile Leu Thr His Ser
65                  70                  75                  80

Ser Gly Ser Val Asp Leu Gly Glu Leu Ala Val Ser Arg Glu Glu Tyr
                85                  90                  95

Val Thr Leu Pro Gly Ser Phe Asn Phe Gly His Thr Ile Asn Val Lys
            100                 105                 110

Asn Glu Leu Leu Val His Asp Asp Lys Lys Tyr Arg Trp Asp Gly Ser
        115                 120                 125

Leu Pro Lys Thr Val Asp Ala Gly Ser Thr Pro Glu Thr Ser Gly Gly
130                 135                 140

Val Gly Leu Gly Ala Trp Leu Ser Val Gly Asp Ala Ala Phe Arg Gln
145                 150                 155                 160

Glu Ala Asn Lys Lys Phe Lys Tyr Ser Val Lys Leu Ser Asp Tyr Ser
                165                 170                 175

Thr Leu Gln Asp Ala Ala Thr Ala Ala Val Asp Gly Leu Leu Ile Asp
            180                 185                 190

Ile Asn Tyr Asn Phe Thr Asp Gly Glu Ser Val Asp Phe Gly Gly Lys
        195                 200                 205

Thr Leu Thr Ile Asn Cys Lys Ala Lys Phe Ile Gly Asp Gly Ala Leu
210                 215                 220

Ile Phe Asn Asn Met Gly Pro Gly Ser Val Ile Asn Gln Pro Phe Met
225                 230                 235                 240

Glu Ser Lys Thr Thr Pro Trp Val Ile Phe Pro Trp Asp Ala Asp Gly
                245                 250                 255

Lys Trp Ile Thr Asp Ala Ala Leu Val Ala Ala Thr Leu Lys Gln Ser
            260                 265                 270

Lys Ile Glu Gly Tyr Gln Pro Gly Val Asn Asp Trp Val Lys Phe Pro
        275                 280                 285

Gly Leu Glu Ala Leu Leu Pro Gln Asn Val Lys Asp Gln His Ile Thr
290                 295                 300

Ala Thr Leu Asp Ile Arg Ser Ala Ser Arg Val Glu Ile Arg Asn Ala
305                 310                 315                 320

Gly Gly Leu Met Ala Ala Tyr Leu Phe Arg Ser Cys His Cys Lys
                325                 330                 335

Val Ile Asp Ser Asp Ser Ile Ile Gly Gly Lys Asp Gly Ile Ile Thr
            340                 345                 350

Phe Glu Asn Leu Ser Gly Asp Trp Gly Leu Gly Asn Tyr Val Ile Gly
        355                 360                 365

Gly Arg Val His Tyr Gly Ser Gly Ser Gly Val Gln Phe Leu Arg Asn
370                 375                 380

Asn Gly Gly Glu Ser His Asn Gly Gly Val Ile Gly Val Thr Ser Trp
385                 390                 395                 400

-continued

```
Arg Ala Gly Glu Ser Gly Phe Lys Thr Tyr Gln Gly Ser Val Gly Gly
                405                 410                 415

Gly Thr Ala Arg Asn Tyr Asn Leu Gln Phe Arg Asp Ser Val Ala Leu
            420                 425                 430

Ser Pro Val Trp Asp Gly Phe Asp Leu Gly Ser Asp Pro Gly Met Ala
        435                 440                 445

Pro Glu Pro Asp Arg Pro Gly Asp Leu Pro Val Ser Glu Tyr Pro Phe
    450                 455                 460

His Gln Leu Pro Asn Asn His Leu Val Asp Asn Ile Leu Val Met Asn
465                 470                 475                 480

Ser Leu Gly Val Gly Leu Gly Met Asp Gly Arg Gly Gly Tyr Val Ser
                485                 490                 495

Asn Val Thr Val Gln Asp Cys Ala Gly Ala Gly Met Leu Ala His Thr
            500                 505                 510

Tyr Asn Arg Val Phe Ser Asn Ile Thr Val Ile Asp Cys Asn Tyr Leu
        515                 520                 525

Asn Phe Asp Ser Asp Gln Ile Ile Ile Gly Asp Cys Ile Val Asn
    530                 535                 540

Gly Ile Lys Ala Ala Gly Ile Lys Pro Gln Pro Ser Asn Gly Leu Val
545                 550                 555                 560

Ile Ser Ala Pro Asn Ser Thr Ile Ser Gly Leu Val Gly Asn Val Pro
                565                 570                 575

Pro Asp Lys Ile Leu Val Gly Asn Leu Leu Asp Pro Val Leu Gly Gln
            580                 585                 590

Ser Arg Val Ile Gly Phe Asn Ser Asp Thr Ala Glu Leu Ala Leu Arg
        595                 600                 605

Ile Asn Lys Leu Ser Ala Thr Leu Asp Ser Gly Ala Leu Arg Ser His
    610                 615                 620

Leu Asn Gly Ser Ala Gly Ser Gly Ser Ala Trp Thr Glu Leu Thr Ala
625                 630                 635                 640

Leu Ser Gly Ser Thr Pro Asn Ala Val Ser Leu Lys Val Asn Arg Gly
                645                 650                 655

Asp Tyr Lys Thr Thr Glu Leu Pro Ile Ser Gly Thr Val Leu Pro Asp
            660                 665                 670

Glu Gly Val Leu Asp Ile Asn Thr Met Ser Tyr Leu Asp Ala Gly
        675                 680                 685

Ala Leu Trp Ala Leu Ile Arg Leu Pro Asp Gly Ser Lys Thr Arg Met
    690                 695                 700

Lys Leu Ser Val
705

<210> SEQ ID NO 6
<211> LENGTH: 926
<212> TYPE: PRT
<213> ORGANISM: Unknown
<220> FEATURE:
<223> OTHER INFORMATION: E.coli bacteriophage EP335 ORF 12

<400> SEQUENCE: 6

Met Ile Val Tyr Asn Asn Gln Ala Pro Ser Ala Val Asn Asn Val Gly
1               5                   10                  15

Gln Phe Gly Ala Thr Glu Gly Ser Ile Gly Ala Tyr Lys Gln Ala Ala
            20                  25                  30

Glu Tyr Ala Ala Asp Ser Lys Tyr Trp Ala Leu Leu Ala Glu Ser Lys
        35                  40                  45
```

```
Phe Gly Thr Val Asp Asp Leu Ile Ala Gln Val Glu Ile Leu Tyr Lys
     50                  55                  60

Gln Gly Val Leu Leu Lys Glu Asp Ile Glu Asp Leu Lys Gln Asp Phe
 65                  70                  75                  80

Ile Ala Gln Asp Ala Arg Leu Met Asn Leu Ile Ala Gln Thr Asn Ala
                 85                  90                  95

Ala Val Ala Asp Ala Asn Asn Ala Val Ala Leu Ile Asn Gln Lys Leu
                100                 105                 110

Val Glu Val Gln Arg Gln Leu Asp Ile Leu Leu Gly Met Thr Val Thr
                115                 120                 125

Val Thr Thr Leu Pro Pro Gly Ser Glu Ala Thr Gly Ser Phe Asn Ser
    130                 135                 140

Gln Thr Gly Glu Ile Lys Leu Gly Ile Pro Glu Gly Glu Lys Gly Ala
145                 150                 155                 160

Asp Gly Ser Val Thr Asp Leu Ser Thr Ala Pro Thr Gly Thr Pro Glu
                165                 170                 175

Leu Gly Asp Ile Gly Phe Tyr Val Asp Lys Asp Asn Thr Val His
                180                 185                 190

Lys Thr Ser Leu Glu Ala Ile Ala Asn Leu Ile Pro Ser Val Arg Ser
                195                 200                 205

Val Ser Ile Asn Gly Pro Ala Leu Asp Gly Glu Val Ala Leu Thr
    210                 215                 220

Ile Asn Lys Glu Thr Val Gly Leu Gly Asn Val Leu Asn Val Ala Gln
225                 230                 235                 240

Tyr Ser Arg Gln Glu Ile Asn Asp Lys Phe Asp Lys Thr Thr Lys Thr
                245                 250                 255

Tyr Gln Ser Lys Ala Glu Ala Asp Ala Asp Ala Gln Phe Arg Gln Val
                260                 265                 270

Gly Glu Lys Val Leu Val Trp Asp Ser Thr Lys Tyr Glu Phe Tyr Thr
                275                 280                 285

Val Ala Ala Asn Lys Thr Leu Thr Pro Val Lys Thr Glu Gly Arg Ile
    290                 295                 300

Leu Thr Val Asn Ser Arg Ala Pro Asp Ser Thr Gly Asn Ile Asp Ile
305                 310                 315                 320

Thr Ile Pro Thr Gly Asn Pro Ser Leu Tyr Leu Gly Glu Met Val Met
                325                 330                 335

Phe Pro Tyr Asp Pro Ala Lys Thr Val Ser Tyr Pro Gly Val Leu Pro
                340                 345                 350

Ala Asp Gly Arg Leu Val Pro Lys Ala Asn Ala Asp Leu Gly Pro
                355                 360                 365

Ser Leu Val Ser Gly Gln Leu Pro Val Val Ser Glu Thr Glu Trp Gln
    370                 375                 380

Ala Gly Ala Arg Gln Tyr Phe Ser Trp Gly Lys Leu Ala Asp Gly Ile
385                 390                 395                 400

Asn Asp Ala Asp Ser Thr Asn Phe Ile Asn Ile Arg Leu Pro Asp Trp
                405                 410                 415

Thr Gly Gly Glu Ala Ile Arg Ser Pro Asp Ser Asp Lys Asp Thr Asn
                420                 425                 430

Tyr Lys Gly Arg Val Leu Ser Gln Val Pro Tyr Ile Val Thr Val Asn
                435                 440                 445

Gly Lys Ala Pro Asp Asp Thr Asn Gly Asn Val Leu Thr Ala Ala
    450                 455                 460

Asn Val Gly Ala Ala Ser Ser Gly Ala Asn Ser Asp Ile Thr Ser Leu
```

```
              465                 470                 475                 480
Asn Gly Leu Thr Thr Pro Leu Ser Val Ala Gln Gly Thr Gly Val
                485                 490                 495

Thr Asp Ile Gly Ser Leu Arg Arg Ala Ala Leu Val Gln Gly Val Leu
            500                 505                 510

Cys Asn Asp Gln Ala Gly Pro Gln Ser Tyr Asn Ser Tyr Arg Ser Pro
                515                 520                 525

Asn Gly Glu Tyr Ala Phe Lys Val Asp Asn Ser Gly Leu Val Ala Ser
            530                 535                 540

Ile Asn Ala Gly Thr Glu Val Val Pro Phe Ala Ile Glu Ser Gly
545                 550                 555                 560

Gly Thr Gly Ala Thr Thr Leu Asn Asp Ala Arg Ile Ser Leu Asn Leu
                565                 570                 575

Glu Arg Phe Leu Gln Pro Ser Asn Glu Thr Ile Val Met Ala Pro Ser
                580                 585                 590

Lys Ser Ser Tyr Leu Thr Ile Ser Asp Thr Ser Trp Gly Ala Tyr Ser
            595                 600                 605

Ser Ser Asp Ser Ser Trp Arg Ala Leu Gly Ile Gly Gln Gly Gly Thr
            610                 615                 620

Gly Ala Thr Ser Glu Ala Ala Arg Val Asn Leu Lys Val Asp Lys
625                 630                 635                 640

Leu Val Gln Ser Ser Thr Asp Thr Lys Leu Leu Asp Gly Ser Gly Glu
                645                 650                 655

His Thr Phe Phe Ile Thr Asp Ala Asp Trp Gly Tyr Phe Asn Asn Ser
                660                 665                 670

Asp Ser Ser Arg Ile Ala Leu Pro Val Ile Ser Gly Thr Gly Gly
            675                 680                 685

Lys Thr Pro Ala Glu Gly Ser Glu Lys Leu Gly Ala Met His Tyr Gln
            690                 695                 700

Tyr Gly Gln Ser Thr Phe Tyr Gly Ser Glu Asp Leu Pro Thr Gly Ile
705                 710                 715                 720

Gly Phe Tyr Ser Gln Asp Val Ser Pro Phe Pro Gly Gly Asn Gly Ala
                725                 730                 735

Pro Tyr Ser Tyr Ala Glu Ile Met Thr Ile Ser Glu Gly Gly Arg Gly
                740                 745                 750

Gly Asn Trp Ser Gln Ile Gly Phe Ser Thr Ile Thr Lys Gln Ala Pro
            755                 760                 765

Arg Tyr Arg Gln Arg Thr Asn Asp Pro Ala Leu Ile Thr Asn Trp Arg
            770                 775                 780

Asp Phe Leu Val Arg Asp Leu Asn Thr Thr Val Asp Val Asn Gly Phe
785                 790                 795                 800

Val Lys Ile Ala Ser Pro Ile Val Lys Leu Lys Pro Asp Gly Ser Ser
                805                 810                 815

Glu Val Asn Asp Gln Ala Gln Gly Val Ile Thr Glu Arg Leu Asp Val
                820                 825                 830

Gly Val Tyr Lys Ile Ser Gly Val Leu Gly Phe Asn Ser Asp Pro Ser
            835                 840                 845

Trp Gly Gly Asn Gly Gly Phe Ser Ile Pro Gln Asn Ser Asn Gly
            850                 855                 860

Leu Pro Leu Leu Trp Val Asp Tyr Glu Val Asp Glu Ile Gly Asp Ile
865                 870                 875                 880

Thr Leu Lys Thr Tyr His Arg Val His Ser Gly Val Pro Ser Phe Ala
                885                 890                 895
```

```
Ser Asn Glu Lys Glu Gly Val Val Asp Gly Glu Pro Val Asp Ile Pro
            900                 905                 910

Glu Gly Arg Trp Val Asp Leu Arg Val Glu Met Pro Thr Glu
        915                 920                 925

<210> SEQ ID NO 7
<211> LENGTH: 450
<212> TYPE: PRT
<213> ORGANISM: Unknown
<220> FEATURE:
<223> OTHER INFORMATION: E.coli bacteriophage EP335 C-terminal part of
      ORF 12

<400> SEQUENCE: 7

Ile Thr Ser Leu Asn Gly Leu Thr Thr Pro Leu Ser Val Ala Gln Gly
1               5                   10                  15

Gly Thr Gly Val Thr Asp Ile Gly Ser Leu Arg Arg Ala Ala Leu Val
            20                  25                  30

Gln Gly Val Leu Cys Asn Asp Gln Ala Gly Pro Gln Ser Tyr Asn Ser
        35                  40                  45

Tyr Arg Ser Pro Asn Gly Glu Tyr Ala Phe Lys Val Asp Asn Ser Gly
50                  55                  60

Leu Val Ala Ser Ile Asn Ala Gly Thr Glu Glu Val Val Pro Phe Ala
65                  70                  75                  80

Ile Glu Ser Gly Gly Thr Gly Ala Thr Thr Leu Asn Asp Ala Arg Ile
                85                  90                  95

Ser Leu Asn Leu Glu Arg Phe Leu Gln Pro Ser Asn Glu Thr Ile Val
            100                 105                 110

Met Ala Pro Ser Lys Ser Ser Tyr Leu Thr Ile Ser Asp Thr Ser Trp
        115                 120                 125

Gly Ala Tyr Ser Ser Ser Asp Ser Ser Trp Arg Ala Leu Gly Ile Gly
130                 135                 140

Gln Gly Gly Thr Gly Ala Thr Ser Glu Ala Ala Ala Arg Val Asn Leu
145                 150                 155                 160

Lys Val Asp Lys Leu Val Gln Ser Ser Thr Asp Thr Lys Leu Leu Asp
                165                 170                 175

Gly Ser Gly Glu His Thr Phe Phe Ile Thr Asp Ala Asp Trp Gly Tyr
            180                 185                 190

Phe Asn Asn Ser Asp Ser Ser Arg Ile Ala Leu Pro Val Ile Ser Gly
        195                 200                 205

Gly Thr Gly Gly Lys Thr Pro Ala Glu Gly Ser Glu Lys Leu Gly Ala
210                 215                 220

Met His Tyr Gln Tyr Gly Gln Ser Thr Phe Tyr Gly Ser Glu Asp Leu
225                 230                 235                 240

Pro Thr Gly Ile Gly Phe Tyr Ser Gln Asp Val Ser Pro Phe Pro Gly
                245                 250                 255

Gly Asn Gly Ala Pro Tyr Ser Tyr Ala Glu Ile Met Thr Ile Ser Glu
            260                 265                 270

Gly Gly Arg Gly Gly Asn Trp Ser Gln Ile Gly Phe Ser Thr Ile Thr
        275                 280                 285

Lys Gln Ala Pro Arg Tyr Arg Gln Arg Thr Asn Asp Pro Ala Leu Ile
290                 295                 300

Thr Asn Trp Arg Asp Phe Leu Val Arg Asp Leu Asn Thr Thr Val Asp
305                 310                 315                 320

Val Asn Gly Phe Val Lys Ile Ala Ser Pro Ile Val Lys Leu Lys Pro
```

```
                    325                 330                 335
Asp Gly Ser Ser Glu Val Asn Asp Gln Ala Gln Gly Val Ile Thr Glu
            340                 345                 350

Arg Leu Asp Val Gly Val Tyr Lys Ile Ser Gly Val Leu Gly Phe Asn
            355                 360                 365

Ser Asp Pro Ser Trp Gly Asn Gly Gly Phe Ser Ile Pro Gln
            370                 375                 380

Asn Ser Asn Gly Leu Pro Leu Leu Trp Val Asp Tyr Glu Val Asp Glu
385                 390                 395                 400

Ile Gly Asp Ile Thr Leu Lys Thr Tyr His Arg Val His Ser Gly Val
            405                 410                 415

Pro Ser Phe Ala Ser Asn Glu Lys Glu Gly Val Val Asp Gly Glu Pro
            420                 425                 430

Val Asp Ile Pro Glu Gly Arg Trp Val Asp Leu Arg Val Glu Met Pro
            435                 440                 445

Thr Glu
    450

<210> SEQ ID NO 8
<211> LENGTH: 729
<212> TYPE: PRT
<213> ORGANISM: Unknown
<220> FEATURE:
<223> OTHER INFORMATION: E.coli bacteriophage EP335 ORF 13

<400> SEQUENCE: 8

Met Ser Arg Glu Leu Met Pro Lys Ser Gly Ile Met Met Pro His Val
1               5                   10                  15

Val Ile Asn Arg Asp Ala Ala Val Gly Val Ser Thr Val Asp Gly
            20                  25                  30

Val Ala Gly Ala Val Asn Leu Thr Asp Lys Tyr Leu Gln Lys Thr Asp
            35                  40                  45

Ala Ala Ser Thr Tyr Leu Thr Arg Ala Glu Gly Ala Thr Lys Thr Phe
        50                  55                  60

Val Thr Asp Ala Ile Gly Pro Ile Met Ser Gly Ala Leu Phe Lys Asp
65                  70                  75                  80

Asp Pro Val Val Ala Asn Asp Val Ala Phe Arg Ser Gly Gly Ala Asn
                85                  90                  95

Gly Val Glu Ser Val Asp Met Ile Lys Val Thr Pro Glu Asn Thr Ile
            100                 105                 110

Lys Leu Gly Ser Tyr Ala Ser Ser Val Gln Gly Val Glu Ile His Ser
            115                 120                 125

Ala Gly Arg Leu Gln Val Asp Gln Asn Asp Ser Gly Val Glu Thr
        130                 135                 140

Lys Tyr Pro Val Tyr Ser Lys Arg Tyr Arg Pro Glu Ile Glu Asp Leu
145                 150                 155                 160

Pro Phe Ala Ala Ile Gly Ser Tyr Val Lys Asp Ser Lys Gly Arg Thr
                165                 170                 175

Ile Gly Val Thr Arg Thr Gly Ile Asn Ser Asp Ile Lys Gln Leu Thr
            180                 185                 190

Gln Lys Val Thr Phe Thr Gln Pro Val Thr Val Ala Asp Gly Val Gly
            195                 200                 205

Asp Tyr Asp Ala Val Thr Met Arg Gln Leu Arg Asn Ser Gly Gly Gly
        210                 215                 220

Ser Gly Gly Pro Thr Met Ser Gly Ile Ser Asn Phe Gly Ile Gly Asp
```

```
        225                 230                 235                 240
Phe His Leu Arg Asp Ser Arg Ala Phe Ile Pro Ala Phe Glu Val Val
                245                 250                 255

Ser Asp Gly Gln Leu Leu Asn Arg Ala Asp Tyr Pro Asp Leu Trp Ala
                260                 265                 270

Tyr Ala Gln Leu Leu Thr Pro Ile Ser Asp Ala Ala Trp Leu Ala Asp
                275                 280                 285

Ala Gln Gln Arg Gly Lys Tyr Ser Thr Gly Asp Gly Thr Thr Thr Phe
                290                 295                 300

Arg Val Pro Asp Arg Asn Gly Val Gln Ala Gly Ser Leu Lys Glu Leu
305                 310                 315                 320

Phe Ala Arg Gly Asp Gly Asn Ser Ser Asn Gly Met Met Tyr
                325                 330                 335

Asp Ala Ala Leu Pro Asn Ile Val Gly Tyr Thr Ala His Thr Leu Leu
                340                 345                 350

Thr Ala Ser Ser Gln Gly Gln Val Ala Thr Asp Gly Ala Phe Thr
                355                 360                 365

Ser Thr Thr Ser Thr Gln Gly Val Trp Pro Val Ser Gly Gly Gly Gly
                370                 375                 380

Leu Tyr Thr Asn Ile Arg Phe Asp Ala Asn Gln Ser Asp Pro Thr Tyr
385                 390                 395                 400

Gly Arg Tyr Gly Ile Thr Ser Asn Val Ile Pro Arg Asn Phe Ile Gly
                405                 410                 415

Val Trp Thr Ile Arg Ala His Gly Gly Phe Thr Ala Ala Asn Thr Ser
                420                 425                 430

Trp Ser Val Ile Asp Ser Asp Ser Thr Glu Pro Ala Ser Gly Thr Val
                435                 440                 445

Val Arg Gly Gly Ser Val Lys Ser Glu Tyr Lys Ile Gly Thr Ser Pro
                450                 455                 460

Lys Tyr Gln Ala Tyr Leu Gln Ala Tyr Gly Lys Ile Gly Gly Leu Ala
465                 470                 475                 480

Ile Asp Arg Gly Ala Val Leu Ser Asn Gly Val Gln Glu Trp Phe Phe
                485                 490                 495

Asn Gln Asp Gly Thr Leu Tyr Phe Pro Asp Ala Glu Thr Gln Ile Gly
                500                 505                 510

Thr Leu Arg Ser Asp Gly Ala Leu His Ile Ser Ala Tyr Val Arg Pro
                515                 520                 525

Lys Asp Val Val Asn Pro Leu Asn Ser Val Gly Val Ala Ala Ser
530                 535                 540

Glu Arg Asn Ala Val Arg Met Ile Asn Tyr Ala Asn Val Pro Glu Gly
545                 550                 555                 560

Gly Tyr Ile Asn Ser Val Gly Gly Asp Trp Tyr Asp Gly Asn Trp Met
                565                 570                 575

Leu Gly Gly Val Arg Ser Gly Thr Thr Ala Leu Asp Arg Ala Gln Leu
                580                 585                 590

Asn Ile Leu Asn Gly Ile Gly Ser Ser Ala Ser Tyr Ile Phe Gly Ser
                595                 600                 605

Asp Gly Ile Ala Arg Cys Gln Glu Trp Arg Ser Thr Ser Asp Glu Arg
                610                 615                 620

Ile Lys Ser Asn Ile Glu Arg Ile Ser Asp Pro Leu Ser Lys Met Lys
625                 630                 635                 640

Asn Ile Lys Gly Val Thr Trp Val Leu Glu Thr Asn Gly Ser Val Gly
                645                 650                 655
```

```
Tyr Gly Phe Ile Ala Gln Asp Val Glu Lys Asp Phe Pro Glu Ala Val
            660                 665                 670

Ser Glu Ile Lys Ala Ser Pro Val Thr Leu Arg Asp Gly Ser Val Leu
            675                 680                 685

Asp Asn Val Lys Ser Val Asn Thr Ser Gly Val Ala Ala Leu His
            690                 695                 700

His Glu Ala Ile Leu Glu Leu Met Lys Gln Val Glu Asp Leu Lys Lys
705                 710                 715                 720

Glu Val Ser Glu Leu Lys Ser Ser Lys
            725

<210> SEQ ID NO 9
<211> LENGTH: 450
<212> TYPE: PRT
<213> ORGANISM: Unknown
<220> FEATURE:
<223> OTHER INFORMATION: E.coli bacteriophage EP335 C-terminal part of
      ORF 13

<400> SEQUENCE: 9

Ile Ser Asp Ala Ala Trp Leu Ala Asp Ala Gln Gln Arg Gly Lys Tyr
1               5                   10                  15

Ser Thr Gly Asp Gly Thr Thr Phe Arg Val Pro Asp Arg Asn Gly
            20                  25                  30

Val Gln Ala Gly Ser Leu Lys Glu Leu Phe Ala Arg Gly Asp Gly Gly
            35                  40                  45

Asn Ser Ser Asn Asn Gly Met Met Tyr Asp Ala Ala Leu Pro Asn Ile
50                  55                  60

Val Gly Tyr Thr Ala His Thr Leu Leu Thr Ala Ser Ser Ser Gln Gly
65                  70                  75                  80

Gln Val Ala Thr Asp Gly Ala Phe Thr Ser Thr Ser Thr Gln Gly
            85                  90                  95

Val Trp Pro Val Ser Gly Gly Gly Leu Tyr Thr Asn Ile Arg Phe
            100                 105                 110

Asp Ala Asn Gln Ser Asp Pro Thr Tyr Gly Arg Tyr Gly Ile Thr Ser
            115                 120                 125

Asn Val Ile Pro Arg Asn Phe Ile Gly Val Trp Thr Ile Arg Ala His
            130                 135                 140

Gly Gly Phe Thr Ala Ala Asn Thr Ser Trp Ser Val Ile Asp Ser Asp
145                 150                 155                 160

Ser Thr Glu Pro Ala Ser Gly Thr Val Val Arg Gly Gly Ser Val Lys
            165                 170                 175

Ser Glu Tyr Lys Ile Gly Thr Ser Pro Lys Tyr Gln Ala Tyr Leu Gln
            180                 185                 190

Ala Tyr Gly Lys Ile Gly Gly Leu Ala Ile Asp Arg Gly Ala Val Leu
            195                 200                 205

Ser Asn Gly Val Gln Glu Trp Phe Phe Asn Gln Asp Gly Thr Leu Tyr
            210                 215                 220

Phe Pro Asp Ala Glu Thr Gln Ile Gly Thr Leu Arg Ser Asp Gly Ala
225                 230                 235                 240

Leu His Ile Ser Ala Tyr Val Arg Pro Lys Asp Val Val Asn Pro
            245                 250                 255

Leu Asn Ser Val Gly Val Ala Ala Ser Glu Arg Asn Ala Val Arg Met
            260                 265                 270

Ile Asn Tyr Ala Asn Val Pro Glu Gly Gly Tyr Ile Asn Ser Val Gly
```

```
                275                 280                 285
Gly Asp Trp Tyr Asp Gly Asn Trp Met Leu Gly Gly Val Arg Ser Gly
    290                 295                 300

Thr Thr Ala Leu Asp Arg Ala Gln Leu Asn Ile Leu Asn Gly Ile Gly
305                 310                 315                 320

Ser Ser Ala Ser Tyr Ile Phe Gly Ser Asp Gly Ile Ala Arg Cys Gln
                325                 330                 335

Glu Trp Arg Ser Thr Ser Asp Glu Arg Ile Lys Ser Asn Ile Glu Arg
            340                 345                 350

Ile Ser Asp Pro Leu Ser Lys Met Lys Asn Ile Lys Gly Val Thr Trp
            355                 360                 365

Val Leu Glu Thr Asn Gly Ser Val Gly Tyr Gly Phe Ile Ala Gln Asp
    370                 375                 380

Val Glu Lys Asp Phe Pro Glu Ala Val Ser Glu Ile Lys Ala Ser Pro
385                 390                 395                 400

Val Thr Leu Arg Asp Gly Ser Val Leu Asp Asn Val Lys Ser Val Asn
            405                 410                 415

Thr Ser Gly Val Ala Ala Ala Leu His His Glu Ala Ile Leu Glu Leu
            420                 425                 430

Met Lys Gln Val Glu Asp Leu Lys Lys Glu Val Ser Glu Leu Lys Ser
            435                 440                 445

Ser Lys
    450
```